United States Patent
Chaffee et al.

(10) Patent No.: US 7,776,869 B2
(45) Date of Patent: Aug. 17, 2010

(54) HETEROARYL-SUBSTITUTED ALKYNE COMPOUNDS AND METHOD OF USE

(75) Inventors: Stuart C. Chaffee, Cambridge, MA (US); Brian K. Albrecht, Cambridge, MA (US); Brian L. Hodous, Cambridge, MA (US); Matthew W. Martin, Arlington, MA (US); David C. McGowan, Woluwe Street Pierre (BE); Erin F. DiMauro, Cambridge, MA (US); Gade Reddy, Newbury Park, CA (US); Victor J. Cee, Mansfield, MA (US); Philip R. Olivieri, Medford, MA (US); Anthony Reed, Oxnard, CA (US); Karina Romero, Cambridge, MA (US)

(73) Assignee: Amgen Inc., Thousand Oaks, CA (US)

( * ) Notice: Subject to any disclaimer, the term of this patent is extended or adjusted under 35 U.S.C. 154(b) by 809 days.

(21) Appl. No.: 11/251,490

(22) Filed: Oct. 14, 2005

(65) Prior Publication Data
US 2006/0217380 A1 Sep. 28, 2006

Related U.S. Application Data

(60) Provisional application No. 60/620,100, filed on Oct. 18, 2004.

(51) Int. Cl.
| C07D 239/38 | (2006.01) |
| C07D 239/42 | (2006.01) |
| A61K 31/505 | (2006.01) |
| A61K 31/506 | (2006.01) |
| A61P 35/00 | (2006.01) |

(52) U.S. Cl. .................. 514/269; 514/275; 544/299; 544/309; 544/317; 544/320; 544/321; 544/323; 544/324

(58) Field of Classification Search .......... 544/299, 544/309, 317, 320, 321, 323, 324; 514/269, 514/275
See application file for complete search history.

(56) References Cited

U.S. PATENT DOCUMENTS

| 6,440,965 B1 | 8/2002 | Kelley et al. |
| 6,635,641 B2 | 10/2003 | Bender et al. |

FOREIGN PATENT DOCUMENTS

| WO | WO-94/14780 A1 * | 7/1994 |
| WO | WO 02/08205 | 1/2001 |
| WO | WO 01/53274 | 7/2001 |
| WO | WO 01/81331 | 11/2001 |
| WO | WO 02/18353 A2 | 3/2002 |
| WO | WO 02/068409 | 9/2002 |
| WO | WO 03/014111 | 2/2003 |
| WO | WO 03/024448 A2 | 3/2003 |
| WO | WO 2004/058776 | 7/2004 |
| WO | WO 2004/062601 | 7/2004 |
| WO | WO 2005/060970 A1 | 7/2005 |

OTHER PUBLICATIONS

Wolft Manfred E. "Burger's Medicinal Chemistry, 5ed, Part 1", John Wiley & Sons, 1995, pp. 975-977.*
Banker, G.S. et al, "Modern Pharmaceutics, 3ed.", Marcel Dekker, New York. 1996. pp. 451 and 596.*
West, Anthony R., Solid State Chemistry and its Applications, Wiley, New York, 1988, pp. 358 & 365.*
Vippagunta et al., Advanced Drug Delivery Reviews 48: 3-26, 2001.*
Cecil Textbook of Medicine, edited by Bennet, J.C., and Plum F., 20th edition, vol. 1, 1004-1010, 1996.*
Michelle De Palma et al., Trends in Immunology, vol. 28, No. 12, 519-524, 2007.*
Augustin, H.G., The British Journal of Radiology, 76, $3-$10, 2003.*
Fox et al., Breast Cancer Research 9, 216+, 2007, online version pp. 1-11.*
Fabbro et al. Pharmacology & therapeutics 93, 79-98, 2002.*
Mass, R. D., Int. J. Radiation Oncology Bio. Phys.vol. 58(3): 932-940, 2004.*
Abram, et al., "Src Family Tyrosine Kinases and Growth Factor Signaling", *Experimental Cell Research*, 254, 1-13 (2000).
Anderson, et al., "Involvement of the Protein Tyrosine Kinase p56$^{lck}$ in T Cell Signaling and Thymocyte Development", *Adv Immunol.*, 56, 151-178 (1994).
Appleby, et al., "Defective T Cell Receptor Signaling in Mice Lacking the Thymic Isoform of p56$^{fyn}$", *Cell*, 70, 751-763 (1992).
Boehm, et al., "Antiangiogenic Therapy of Experimental Cancer Does Not Induce Acquired Drug Resistance", *Letters to Nature*, 390. 404-407 (1997).
Bolen, et al., "Leukocyte Protein Tyrosine Kinases: Potential Targets for Drug Discovery", *Annu. Rev. Immunol.*, 15, 371-404 (1997).
Bolen, Joseph B., "Nonreceptor Tyrosine Protein Kinases", *Oncogene*, 8, 2025-2031 (1993).

(Continued)

*Primary Examiner*—Venkataraman Balasubramanian
(74) *Attorney, Agent, or Firm*—G. Prabhakar Reddy

(57) ABSTRACT

The present invention comprises a new class of compounds useful for the prophylaxis and treatment of protein kinase mediated diseases, including inflammation, cancer and related conditions. The compounds have a general Formula I

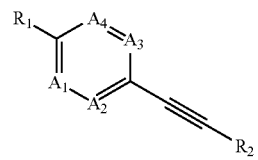

wherein $A^1$, $A^2$, $A^3$, $A^4$, $R^1$ and $R^2$ are defined herein. Accordingly, the invention also comprises pharmaceutical compositions comprising the compounds of the invention, methods for the prophylaxis and treatment of kinase mediated diseases using the compounds and compositions of the invention, and intermediates and processes useful for the preparation of compounds of the invention.

15 Claims, No Drawings

OTHER PUBLICATIONS

Connell, et al., "Patent Focus on Cancer Chemotherapeutics. II Angiogenesis Agents: Apr. 2000-Sep. 2000", *Exp. Opin. Ther. Patents*, 11, 77-114 (2001).

Goldman, et al., "Defective Expression of p56lck in an Infant with Severe Combined Immunodeficiency", *J. Clin. Invest.*, 102(2), 421-429 (1998).

Gomtsyan, et al., "Design, Synthesis, and Structure-Activity Relationship of 6-Alkynylpyrimidines as Potent Adenosine Kinase Inhibitors", *J. Med. Chem.*, 45, 3639-3648 (2002).

Kane, et al., "Signal Transduction by the TCR for Antigen", *Current Opinion in Immunology*, 12, 242-249 (2000).

Paul, et al., "Src Deficiency or Blockade of Src Activity in Mice Provides Cerebral Protection Following Stroke", *Nature Medicine*, 7(2), 222-227 (2001).

Soriano, et al., "Targeted Disruption of the c-src Proto-Oncogene Leads to Osteopetrosis in Mice", *Cell*, 64, 693-702 (1991).

Turner, et al., "Signalling Through the High Affinity IgE Receptor FcεRI", *Nature*, 402, B24-B30 (1999).

Vicentini, et al., "Fgr Deficiency Results in Defective Eosinophil Recruitment to the Lung During Allergic Airway Inflammation", *The Journal of Immunology*, 6446-6454 (2002).

\* cited by examiner

HETEROARYL-SUBSTITUTED ALKYNE COMPOUNDS AND METHOD OF USE

This application claims the benefit of U.S. Provisional Application No. 60/620,100 filed Oct. 18, 2004, which is incorporated by reference herein.

FIELD OF THE INVENTION

The invention generally relates to the field of pharmaceutical agents and, more specifically, to compounds, intermediates, methods for making the compounds and intermediates, compositions, uses and methods for modulating protein kinases and for treating protein kinase-mediated diseases.

BACKGROUND OF THE INVENTION

Protein kinases represent a large family of enzymes, which catalyze the phosphorylation of target protein substrates. The phosphorylation is usually a transfer reaction of a phosphate group from ATP to the protein substrate. Common points of attachment for the phosphate group to the protein substrate include, for example, a tyrosine, serine or threonine residue. For example, protein tyrosine kinases (PTKs) are enzymes, which catalyze the phosphorylation of specific tyrosine residues in cellular proteins. Examples of kinases in the protein kinase family include, without limitation, ab1, Akt, bcr-ab1, Blk, Brk, Btk, c-kit, c-Met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, Tie, Tie-2, TRK, Yes, and Zap70. Due to their activity in numerous cellular processes, protein kinases have emerged as important therapeutic targets.

Protein kinases play a central role in the regulation and maintenance of a wide variety of cellular processes and cellular function. For example, kinase activity acts as molecular switches regulating cell proliferation, activation, and/or differentiation. Uncontrolled or excessive kinase activity has been observed in many disease states including benign and malignant proliferation disorders as well as diseases resulting from inappropriate activation of the immune system (autoimmune disorders), allograft rejection, and graft vs host disease. In addition, endothelial cell specific receptor PTKs, such as VEGF-2 and Tie-2, mediate the angiogenic process and are involved in supporting the progression of cancers and other diseases involving uncontrolled vascularization.

Angiogenesis is the process of developing new blood vessels, particularly capillaries, from pre-existing vasculature and is an essential component of embryogenesis, normal physiological growth, repair, and tumor expansion. Angiogenesis remodels small vessels into larger conduit vessels, a physiologically important aspect of vascular growth in adult tissues. Vascular growth is required for beneficial processes such as tissue repair, wound healing, recovery from tissue ischemia and menstrual cycling.

Certain diseases and/or pathological conditions develop as a result of, or are known to be associated with, the regulation and/or deregulation of angiogenesis. For example, ocular neovascularisation such as retinopathies (including diabetic retinopathy), age-related macular degeneration, psoriasis, hemangioblastoma, hemangioma, and arteriosclerosis have been found to be caused, in part, due the loss of regulation and/or maintenance of vascular growth. Inflammatory diseases such as a rheumatoid or rheumatic inflammatory disease, and especially arthritis (including rheumatoid arthritis) where new capillary blood vessels invade the joint and destroy cartilage, have been associated with angiogenesis. In addition, chronic inflammatory disorders such as chronic asthma, arterial or post-transplantational atherosclerosis, endometriosis, and neoplastic diseases including so-called solid tumors and liquid tumors (for example, leukemias), have been found to be linked to the regulation and control of angiogenesis.

The involvement of angiogenesis in major diseases has led to the identification and development of various targets for inhibiting angiogenesis. These targets relate to various receptors, enzymes, and other proteins in the angiogenic process or cascade of events leading to angiogenesis, such as, for example, activation of endothelial cells by an angiogenic signal, synthesis and release of degradative enzymes, endothelial cell migration, proliferation of endothelial cells, and formation of capillary tubules.

One target identified in the cascade of events leading to angiogenesis is the Tie receptor family. The Tie-1 and Tie-2 receptors are single-transmembrane, tyrosine kinase receptors (Tie stands for tyrosine kinase receptors with immunoglobulin and EGF homology domains). Tie-2 is an endothelial cell specific receptor tyrosine kinase, which is involved in angiogenic processes, such as vessel branching, sprouting, remodeling, maturation and stability. Tie-2 is the first mammalian receptor for which both agonist ligand(s) (for example, Angiopoietin-1 ("Ang1") which binds to and stimulates phosphorylation and signal transduction of Tie-2), and context dependent agonist/antagonist ligand(s) (for example, Angiopoietin-2 ("Ang2")) have been identified. Knock out and transgenic manipulation of the expression of Tie-2 and its ligands indicates that tight spacial and temporal control of Tie-2 signaling is important for the proper development of new vascularization.

Biological models suggest that the stimulation of Tie-2 by the Ang1 ligand is directly involved in the branching, sprouting and outgrowth of new vessels, and recruitment and interaction of periendothelial support cells important in maintaining vessel integrity and inducing quiescence. The absence of Ang1 stimulation of Tie-2 or the inhibition of Tie-2 autophosphorylation by Ang2, which is produced at high levels at sites of vascular regression, may cause a loss in vascular structure and matrix contacts resulting in endothelial death, especially in the absence of growth/survival stimuli.

Recently, upregulation of Tie-2 expression has been found in the vascular synovial pannus of arthritic joints of humans, consistent with the role in inappropriate neovasculariation. This finding suggests that Tie-2 plays a role in the progression of rheumatoid arthritis. Point mutations producing constitutively activated forms of Tie-2 have been identified in association with human venous malformation disorders. Tie-2 inhibitors would, therefore, be useful in treating such disorders, as well as in other instances of improper neovasacularization. However, with the recent recognition of Ang3 and Ang4 as additional Tie-2 binding ligands, targeting a Tie-2 ligand-receptor interaction as an anti-angiogenic therapeutic approach is less favorable. Accordingly, a Tie-2 receptor kinase inhibition approach has become the strategy of choice.

Angiogenesis is regarded as an absolute prerequisite for tumors that grow beyond a diameter of about 1-2 mm. Up to this size, oxygen and nutrients may be supplied to the tumor cells by diffusion. Every tumor, regardless of its origin and its cause, is thus dependent on angiogenesis for its growth after it has reached a certain size.

Three principal mechanisms play an important part in the activity of angiogenesis inhibitors against tumors: 1) Inhibition of the growth of vessels, especially capillaries, into vascular resting tumors, with the result that there is no net tumor growth owing to the balance that is achieved between cell death and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells which normally line the vessels. See R. Connell and J. Beebe, Exp. Opin. Ther. Patents, 11:77-114 (2001).

The inhibition of vascular growth in this context has also shown beneficial effects in preclinical animal models. For example, inhibition of angiogenesis by blocking vascular endothelial growth factor or its receptor has resulted in inhibition of tumor growth and in retinopathy. Also, the development of pathological pannus tissue in rheumatoid arthritis involves angiogenesis and might be blocked by inhibitors of angiogenesis.

The ability to stimulate vascular growth has potential utility for treatment of ischemia-induced pathologies such as myocardial infarction, coronary artery disease, peripheral vascular disease, and stroke. The sprouting of new vessels and/or the expansion of small vessels in ischemic tissues prevents ischemic tissue death and induces tissue repair. Regulating angiogenesis by inhibiting certain recognized pathways in this process would, therefore, be useful in treating diseases, such as ocular neovascularization, including retinopathy, age-related macular degeneration, psoriasis, hemangioblastoma, hemangioma, arteriosclerosis, inflammatory disease rheumatoid arthritis, chronic inflammatory disorders such as chronic asthma, arterial or post-transplantational atherosclerosis, endometriosis, and neoplastic diseases such as leukemias, otherwise known to be associated with deregulated angiogenesis. Treatment of malaria and related viral diseases may also be mediated by HGF and cMet.

Recent work on the relationship between inhibition of angiogenesis and the suppression or reversion of tumor progression shows great promise in the treatment of cancer (Nature, 390:404-407 (1997)), especially the use of multiple angiogenesis inhibitors compared to the effect of a single inhibitor.

Non-receptor tyrosine kinases represent a collection of cellular enzymes, which lack extracellular activity and transmembrane sequences. Examples of non-receptor tyrosine kinases identified include over twenty-four individual kinases, comprising eleven (11) subfamilies (Src, Frk, Btk, Csk, Abl, Zap70, Fes/Fps, Fak, jak, Ack, and LIMK). Src is thought to be the largest family including Src, Lck, Fyn(B), Fyn(T), Lyn, Yes, Hck, Fgr and Blk (for review see: Bolen, J B, and Brugge, J S Annu. Rev. Immunol, 15, 371, 1997). The Src subfamily has been linked to oncogenesis and immune responses (See Bohlen, Oncogene, 8:2025-2031, 1993). These kinases have also been found to be involved in cellular signaling pathways in numerous pathogenic conditions, including cancer, psoriasis, and other hyper-proliferative disorders or hyper-immune responses. Thus, it would be useful to inhibit the activity of non-receptor kinases as well.

Members of the Src-family of tyrosine kinases, in particular, have been shown to be important in cell signal transduction as it relates to inflammatory response and inflammation-related conditions. Gene disruption studies suggest that inhibition of some members of the src family of kinases would potentially lead to a therapeutic benefit. Src(−/−) mice have abnormalities in bone remodeling or osteopetrosis (Soriano, P. Cell 1991, 64, 693), suggesting that inhibition of this kinase might be useful in diseases of bone resorption, such as osteoporosis. Lck(−/−) mice have defects in T cell maturation and activation (Anderson, S J et al. Adv. Immunol. 1994, 56, 151), suggesting that inhibition of this kinase might be useful in diseases of T cell mediated inflammation. In addition, human patients have been identified with mutations affecting Lck kinase activity (Goldman, F D et al. J. Clin. Invest. 1998, 102, 421). These patients suffer from a severe combined immunodeficiency disorder (SCID).

T cells play a pivotal role in the regulation of immune responses and are important for establishing immunity to pathogens. In addition, T cells are often activated during inflammatory autoimmune diseases, such as rheumatoid arthritis, inflammatory bowel disease, type I diabetes, multiple sclerosis, Sjogren's disease, myasthenia gravis, psoriasis, and lupus. T cell activation is also an important component of transplant rejection, allergic reactions, and asthma.

T cells are activated by specific antigens through the T cell receptor (TCR), which is expressed on the cell surface. This activation triggers a series of intracellular signaling cascades mediated by enzymes expressed within the cell (Kane, L P et al. Current Opinion in Immunol. 12, 242, 2000). These cascades lead to gene regulation events that result in the production of cytokines, like interleukin-2 (IL-2). IL-2 is a necessary cytokine in T cell activation, leading to proliferation and amplification of specific immune responses.

Src-family kinases are also important for signaling downstream of other immune cell receptors. Fyn, like Lck, is involved in TCR signaling in T cells (Appleby, M W et al. Cell, 70, 751, 1992). Hck and Fgr are involved in Fcγ receptor signaling leading to neutrophil activation (Vicentini, L. et al. J. Immunol. 2002, 168, 6446). Lyn and Src also participate in Fcγ receptor signaling leading to release of histamine and other allergic mediators (Turner, H. and Kinet, J-P Nature 1999, 402, B24). These-findings suggest that Src family kinase inhibitors may be useful in treating allergic diseases and asthma.

Src kinases are also activated in tumors including sarcoma, melanoma, breast, and colon cancers suggesting that Src kinase inhibitors may be useful anti-cancer agents (Abram, C L and Courtneidge, S A Exp. Cell Res., 254, 1, 2000). Src kinase inhibitors have also been reported to be effective in an animal model of cerebral ischemia (R. Paul et al. Nature Medicine, 7, 222, 2001), suggesting that Src kinase inhibitors may be effective at limiting brain damage following stroke.

Many classes of compounds have been disclosed to modulate or, more specifically, inhibit kinase activity for use to treat kinase-related conditions or other disorders. For example, the PCT publication, WO 01/81311, published on Nov. 1, 2001, describes substituted benzoic acid amides and use thereof for the inhibition of angiogenisis; U.S. Pat. No. 6,440,965, issued Aug. 27, 2002, describes substituted pyrimidine derivatives and their use in the treatment of neurodegenerative or neurological disorders of the central nervous system; PCT publication, WO 02/08205, published on Jan. 13, 2001, describes substituted pyrimidines having neurotrophic activity; PCT publication, WO 03/014111, published on Feb. 20, 2003, describes arylpiperazines and arylpiperidines and their use as metalloproteinase inhibiting agents; PCT publication, WO 03/024448, published on Mar. 27, 2003, describes compounds as inhibitors of histone deacetylase enzymatic activity; PCT publication, WO 04/058776, published on Jul. 15, 2004, describes compounds which possess anti-angiogenic activity; and PCT publication, WO 04/062601, published on Jul. 29, 2004, describes compounds as anti-bacterial agents for generally treating infections caused by gram-negative bacteria.

BRIEF DESCRIPTION OF THE INVENTION

The present invention provides new heteroaryl-substituted alkyne compounds useful in treating pathological conditions and/or disease states related to kinase activity. Particularly, the compounds are useful for treating various diseases, such as cancer, inflammation and related disorders and conditions including rheumatoid arthritis. The compounds are useful by virtue of their ability to regulate active angiogenesis, cell-signal transduction and related pathways, for example, through kinase modulation. The compounds provided by the invention, including stereoisomers, tautomers, solvates, pharmaceutically acceptable salts, derivatives or prodrugs thereof, are defined by general Formula I

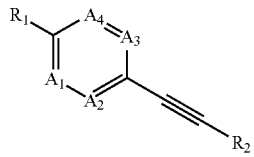

wherein $A^1$, $A^2$, $A^3$, $A^4$, $R^1$ and $R^2$ are as described below.

The invention also provides procedures for making compounds of Formula I, as well as intermediates useful in such procedures.

The compounds provided by the invention are capable of modulating various kinase activity. For example, in one embodiment, the compounds are capable of modulating one or both of Tie-2 or Lck kinase enzymes. In particular, the compounds are capable of inhibiting the activity of Tie-2, and Lck.

To this end, the invention further provides for the use of these compounds for therapeutic, prophylactic, acute and/or chronic treatment of Tie-2 and/or Lck kinase mediated diseases, such as those described herein. For example, the invention provides the use and preparation of a medicament, containing one or more of the compounds, useful to attenuate, alleviate, or treat disorders through inhibition of Tie-2 and/or Lck. These compounds are also useful in the treatment of an angiogenesis- or T-cell activation- or proliferation-mediated disease or condition. Accordingly, these compounds are useful in the manufacture of anti-cancer and anti-inflammation medicaments. In one embodiment, the invention provides a pharmaceutical composition comprising an effective dosage amount of a compound of Formula I in association with a least one pharmaceutically acceptable carrier, adjuvant or diluent.

Further, the invention provides a method of treating kinase mediated disorders, such as treating angiogenesis related or T-cell activation related disorders in a subject inflicted with, or susceptible to, such disorder. The method comprises administering to the subject an effective dosage amount of a compound of Formula I. In other embodiments, the invention provides methods of reducing tumor size, blood flow to and from a tumor, and treating or alleviating various inflammatory responses, including arthritis, organ transplantation or rejection, and many others as described herein.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, heteroaryl-substituted alkyne compounds useful for treating angiogenesis- and/or T-cell proliferation-related disorders, including cancer and inflammation are provided. The compounds, including stereoisomers, tautomers, solvates, pharmaceutically acceptable salts, derivatives or prodrugs thereof, are defined by general Formula I:

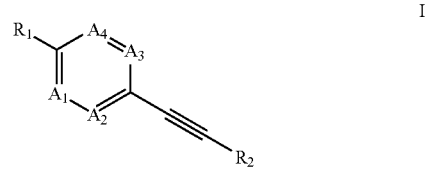

wherein
$A^1$ is $CR^3$ or N;
$A^2$ is $CR^4$ or N;
$A^3$ is $CR^5$ or N;
$A^4$ is $CR^6$ or N;
provided that at least one of $A^1$, $A^2$, $A^3$ and $A^4$ is N and no more than three of $A^1$, $A^2$, $A^3$ and $A^4$ are N;

$R^1$ is $NR^7R^7$, $NR^7R^8$, $SR^7$, $OR^8$; $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$;

$R^2$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein said ring system is substituted independently with one or more substituents of $R^{10}$, $R^{11}$, $R^{15}$, $NR^{10}R^{10}$, $NR^{10}R^{11}$, $OR^{10}$, $SR^{10}$, $OR^{11}$, $SR^{11}$, $C(O)R^{10}$, $C(S)R^{10}$, $C(NCN)R^{10}$, $C(O)R^{11}$, $C(S)R^{11}$, $C(NCN)R^{11}$, $C(O)C(O)R^{10}$, $OC(O)R^{10}$, $COOR^{10}$, $C(O)SR^{10}$, $C(O)C(O)R^{11}$, $OC(O)R^{11}$, $COOR^{11}$, $C(O)SR^{11}$, $C(O)NR^{10}R^{10}$, $C(S)NR^{10}R^{10}$, $C(O)NR^{10}R^{11}$, $C(S)NR^{10}R^{11}$, $OC(O)NR^{10}R^{11}$, $NR^{10}C(O)R^{10}$, $NR^{10}C(O)R^{11}$, $NR^{10}C(S)R^{10}$, $NR^{10}C(S)R^{11}$, $NR^{10}C(O)NR^{10}R^{10}$, $NR^{10}C(O)NR^{10}R^{11}$, $NR^{10}C(S)NR^{10}R^{10}$, $NR^{10}C(S)NR^{10}R^{11}$, $NR^{10}(COOR^{10})$, $NR^{10}(COOR^{11})$, $NR^{10}C(O)C(O)R^{10}$, $NR^{10}C(O)C(O)R^{11}$, $NR^{10}C(O)C(O)NR^{10}R^{11}$, $S(O)_2R^{10}$, $S(O)_2R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$, provided that at least one substituent on said ring system is $C(O)_2R^{10}$, $C(O)_2R^{11}$, $C(O)C(O)R^{10}$, $OC(O)R^{10}$, $COOR^{10}$, $C(O)SR^{10}$, $C(O)C(O)R^{11}$, $OC(O)R^{11}$, $COOR^{11}$, $C(O)SR^{11}$, $C(O)NR^{10}R^{10}$, $C(S)NR^{10}R^{10}$, $C(O)NR^{10}R^{11}$, $C(S)NR^{10}R^{11}$, $OC(O)NR^{10}R^{11}$, $NR^{10}C(O)R^{10}$, $NR^{10}C(O)R^{11}$, $NR^{10}C(S)R^{10}$, $NR^{10}C(S)R^{11}$, $NR^{10}C(O)NR^{10}R^{10}$, $NR^{10}C(O)NR^{10}R^{11}$, $NR^{10}C(S)NR^{10}R^{10}$, $NR^{10}C(S)NR^{10}R^{11}$, $NR^{10}(COOR^{10})$, $NR^{10}(COOR^{11})$, $NR^{10}C(O)C(O)R^{10}$, $NR^{10}C(O)C(O)R^{11}$, $NR^{10}C$ (O)C(O)NR$^{10}$R$^{11}$, S(O)$_2$R$^{10}$, S(O)$_2$R$^{11}$, S(O)$_2$NR$^{10}$R$^{10}$, S(O)$_2$NR$^{10}$R$^{11}$, NR$^{10}$S(O)$_2$NR$^{10}$R$^{11}$, NR$^{10}$S(O)$_2$R$^{10}$ or NR$^{10}$S(O)$_2$R$^{11}$;

R$^3$ is H, halo, haloalkyl, NO$_2$, CN, OR$^7$, SR$^7$, NR$^7$R$^7$, NR$^7$R$^8$, C(O)R$^7$, COOR$^7$, C(O)NR$^7$R$^7$, C(O)NR$^7$R$^8$, NR$^7$C(O)NR$^7$R$^7$, NR$^7$C(O)NR$^7$R$^8$, OC(O)NR$^7$R$^8$, S(O)$_2$R$^7$, S(O)$_2$NR$^7$R$^7$, S(O)$_2$NR$^7$R$^8$, NR$^7$S(O)$_2$R$^7$, NR$^7$S(O)$_2$R$^8$, C$_{1-10}$-alkyl, C$_{2-10}$-alkenyl, C$_{2-10}$-alkynyl, C$_{3-10}$-cycloalkyl or C$_{4-10}$-cycloalkenyl, each of the C$_{1-10}$-alkyl, C$_{2-10}$-alkenyl, C$_{2-10}$-alkynyl, C$_{3-10}$-cycloalkyl and C$_{4-10}$-cycloalkenyl optionally comprising 1-4 heteroatoms selected from N, O and S and optionally substituted with 1-5 substituents of R$^8$ or R$^9$;

alternatively R$^1$ and R$^3$ taken together with the atoms to which they are attached form a partially or fully unsaturated 5- or 6-membered ring of carbon atoms optionally including 1-3 heteroatoms selected from O, N, or S, and the ring optionally substituted independently with 1-5 substituents of R$^8$ or R$^9$;

R$^4$ is H, halo, haloalkyl, NO$_2$, CN, NR$^7$R$^7$, OR$^7$; SR$^7$, C(O)R$^7$, C$_{1-10}$-alkyl, C$_{2-10}$-alkenyl, C$_{2-10}$-alkynyl or C$_{3-10}$-cycloalkyl, each of the C$_{1-10}$-alkyl, C$_{2-10}$-alkenyl, C$_{2-10}$-alkynyl and C$_{3-10}$-cycloalkyl optionally comprising 1-4 heteroatoms selected from N, O and S and optionally substituted with 1-5 substituents of R$^9$;

alternatively R$^3$ and R$^4$ taken together with the atoms to which they are attached form a partially or fully unsaturated 5- or 6-membered ring of carbon atoms optionally including 1-3 heteroatoms selected from O, N, or S, and the ring optionally substituted independently with 1-3 substituents of R$^8$ or R$^9$ R$^5$ is H, halo, haloalkyl, NO$_2$, CN, NR$^7$R$^7$, OR$^7$; SR$^7$, C(O)R$^7$, C$_{1-10}$-alkyl, C$_{2-10}$-alkenyl, C$_{2-10}$-alkynyl or C$_{3-10}$-cycloalkyl, each of the C$_{1-10}$-alkyl, C$_{2-10}$-alkenyl, C$_{2-10}$-alkynyl and C$_{3-10}$-cycloalkyl optionally comprising 1-4 heteroatoms selected from N, O and S and optionally substituted with 1-5 substituents of R$^9$;

R$^6$ is H, halo, haloalkyl, NO$_2$, CN, SR$^7$, OR$^7$, C(O)R$^7$, COOR$^7$, OC(O)R$^7$, NR$^7$R$^7$, NR$^7$R$^8$, C(O)NR$^7$R$^7$, C(O)NR$^7$R$^8$, NR$^7$C(O)R$^7$, NR$^7$C(O)NR$^7$R$^8$, S(O)NR$^7$R$^8$, S(O)$_2$NR$^7$R$^8$, NR$^7$S(O)NR$^7$R$^8$, NR$^7$C$_{1-10}$-alkyl, C$_{2-10}$-alkenyl, C$_{2-10}$-alkynyl, C$_{3-10}$-cycloalkyl or C$_{4-10}$-cycloalkenyl, each of the C$_{1-10}$-alkyl, C$_{2-10}$-alkenyl, C$_{2-10}$-alkynyl, C$_{3-10}$-cycloalkyl and C$_{4-10}$-cycloalkenyl optionally comprising 1-4 heteroatoms selected from N, O and S and optionally substituted with 1-5 substituents of R$^8$ or R$^9$;

alternatively R$^1$ and R$^6$ taken together with the atoms to which they are attached form a partially or fully unsaturated 5- or 6-membered ring of carbon atoms optionally including 1-3 heteroatoms selected from O, N, or S, and the ring optionally substituted independently with 1-5 substituents of R$^8$ or R$^9$;

alternatively R$^5$ and R$^6$ taken together with the atoms to which they are attached form a partially or fully unsaturated 5- or 6-membered ring of carbon atoms optionally including 1-3 heteroatoms selected from O, N, or S, and the ring optionally substituted independently with 1-3 substituents of R$^8$ or R$^9$;

R$^7$ is H, C$_{1-10}$-alkyl, C$_{2-10}$-alkenyl, C$_{2-10}$-alkynyl, C$_{3-10}$-cycloalkyl or C$_{4-10}$-cycloalkenyl, each of the C$_{1-10}$-alkyl, C$_{2-10}$-alkenyl, C$_{2-10}$-alkynyl, C$_{3-10}$-cycloalkyl and C$_{4-10}$-cycloalkenyl optionally comprising 1-4 heteroatoms selected from N, O and S and optionally substituted with 1-5 substituents of NR$^8$R$^9$, NR$^9$R$^9$, OR$^8$, SR$^8$, OR$^9$, SR$^9$, C(O)R$^8$, OC(O)R$^8$, COOR$^8$, C(O)R$^9$, OC(O)R$^9$, COOR$^9$, C(O)NR$^8$R$^9$, C(O)NR$^9$R$^9$, NR$^9$C(O)R$^8$, NR$^9$C(O)R$^9$, NR$^9$C(O)NR$^8$R$^9$, NR$^9$C(O)NR$^9$R$^9$, NR$^9$(COOR$^8$), NR$^9$(COOR$^9$), OC(O)NR$^8$R$^9$, OC(O)NR$^9$R$^9$, S(O)$_2$R$^8$, S(O)$_2$R$^9$, S(O)$_2$NR$^8$R$^9$, NR$^9$S(O)$_2$NR$^8$R$^9$, NR$^9$S(O)$_2$NR$^9$R$^9$, NR$^9$S(O)$_2$R$^8$, NR$^9$S(O)$_2$R$^9$, R$^8$ or R$^9$;

R$^8$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of R$^9$, oxo, NR$^9$R$^9$, OR$^9$; SR$^9$, C(O)R$^9$ or a partially or fully saturated or unsaturated 5-6 membered ring of carbon atoms optionally including 1-3 heteroatoms selected from O, N, or S, and optionally substituted independently with 1-5 substituents of R$^9$;

alternatively, R$^7$ and R$^8$ taken together form a saturated or partially or fully unsaturated 5-6 membered ring of carbon atoms optionally including 1-3 heteroatoms selected from O, N, or S, and said ring optionally substituted independently with 1-5 substituents of R$^9$;

R$^9$ is H, halo, haloalkyl, CN, OH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a saturated or partially or fully unsaturated 5-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring of said ring system is optionally substituted independently with 1-5 substituents of halo, haloalkyl, CN, NO$_2$, NH$_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

R$^{10}$ is H, halo, haloalkyl, CN, NO$_2$, C$_{1-10}$-alkyl, C$_{2-10}$-alkenyl, C$_{2-10}$-alkynyl, C$_{3-10}$-cycloalkyl or C$_{4-10}$-cycloalkenyl, each of the C$_{1-10}$-alkyl, C$_{2-10}$-alkenyl, C$_{2-10}$-alkynyl, C$_{3-10}$-cycloalkyl and C$_{4-10}$-cycloalkenyl optionally comprising 1-4 heteroatoms selected from N, O and S and optionally substituted with 1-5 substituents of R$^{11}$, R$^{12}$ or R$^{16}$, NR$^{11}$R$^{12}$, NR$^{12}$R$^{12}$, OR$^{11}$, SR$^{11}$, OR$^{12}$, SR$^{12}$, C(O)R$^{11}$, OC(O)R$^{11}$, COOR$^{11}$, C(O)R$^{12}$, OC(O)R$^{12}$, COOR$^{12}$, C(O)NR$^{11}$R$^{12}$, NR$^{12}$C(O)R$^{11}$, C(O)NR$^{12}$R$^{12}$, NR$^{12}$C(O)R$^{12}$, NR$^{12}$C(O)NR$^{11}$R$^{12}$, NR$^{12}$C(O)NR$^{12}$R$^{12}$, NR$^{12}$(COOR$^{11}$), NR$^{12}$(COOR$^{12}$), OC(O)NR$^{11}$R$^{12}$, OC(O)NR$^{12}$R$^{12}$, S(O)$_2$R$^{11}$, S(O)$_2$R$^{12}$, S(O)$_2$NR$^{11}$R$^{12}$, S(O)$_2$NR$^{12}$R$^{12}$, NR$^{12}$S(O)$_2$NR$^{11}$R$^{12}$, NR$^{12}$S(O)$_2$NR$^{12}$R$^{12}$, NR$^{12}$S(O)$_2$R$^{11}$, NR$^{12}$S(O)$_2$R$^{12}$, NR$^{12}$S(O)$_2$R$^{11}$ or NR$^{12}$S(O)$_2$R$^{12}$;

R$^{11}$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of R$^{12}$, R$^{13}$, R$^{14}$ or R$^{16}$;

alternatively, R$^{10}$ and R$^{11}$ taken together form a partially or fully saturated or unsaturated 5-6 membered ring of carbon atoms optionally including 1-3 heteroatoms selected from O, N, or S, and the ring optionally substituted independently with 1-5 substituents of R$^{12}$, R$^{13}$, R$^{14}$ or R$^{16}$;

R$^{12}$ is H, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, $C_{1-10}$-alkoxyl or $C_{1-10}$-thioalkyl, each of which is optionally substituted independently with 1-5 substituents of $R^{13}$, $R^{14}$, $R^{15}$ or $R^{16}$;

$R^{13}$ is $NR^{14}R^{15}$, $NR^{15}R^{15}$, $OR^{14}$; $SR^{14}$, $OR^{15}$; $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2$ $NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is a partially or fully saturated or unsaturated 5-8 membered or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-5 substituents of $R^{16}$;

$R^{16}$ is H, halo, haloalkyl, CN, OH, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, oxo, acetyl, benzyl, phenyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl;

and provided that (1) when said at least one substituent on said $R^2$ ring system is $C(O)NR^{10}R^{10}$ or $C(O)NR^{10}R^{11}$, then $R^{10}$ and $R^{11}$, independently, are not —$CH_2$-L-Q or —$C(C_{1-6}$ alkyl)$(C_{1-6}$alkyl)-L-Q, wherein L is —O—, —NH—, —NHC(O)—, —NHC(O)N—, —NHC(=NH)N— or —$CO_2$— and Q is H, substituted or unsubstituted $C_{1-6}$alkyl, substituted or unsubstituted aryl, substituted or unsubstituted heterocyclyl, substituted or unsubstituted heteraryl or $C_{1-6}$alkyl substituted with aryl, heterocyclyl or heteroaryl; or (2) when said $R^2$ is a phenyl ring substituted with $C(O)NR^{10}R^{10}$ or $C(O)NR^{10}R^{11}$ meta to the alkynyl group of Formula I, then either (a) $R^1$ is not halogen, $C_{1-6}$alkyl, $C_{1-6}$alkoxyl or hydroxyl or (b) where $R^1$ and $R^3$ taken together with the atoms to which they are attached form a partially or fully unsaturated 5- or 6-membered ring of carbon atoms optionally including 1-3 heteroatoms selected from O, N, or S, said ring is not substituted with halogen, $C_{1-6}$alkyl, $C_{1-6}$alkoxyl or hydroxyl substituents.

In another embodiment, the compounds of Formula I include N as $A^1$, in conjunction with any of the above or below embodiments.

In another embodiment, the compounds of Formula I include N as $A^4$, in conjunction with any of the above or below embodiments.

In another embodiment, the compounds of Formula I include N, independently, as both $A^1$ and $A^4$, in conjunction with any of the above or below embodiments.

In another embodiment, the compounds of Formula I include compounds wherein $A^1$ is N, $A^2$ is $CR^4$, $A^3$ is $CR^5$ and $A^4$ is $CR^6$, in conjunction with any of the above or below embodiments.

In another embodiment, the compounds of Formula I include compounds wherein $A^1$ is $CR^3$, $A^2$ is $CR^4$, $A^3$ is $CR^5$ and $A^4$ is N, in conjunction with any of the above or below embodiments.

In another embodiment, the compounds of Formula I include compounds wherein each of $A^2$ and $A^3$, independently, is N, $A^1$ is $CR^3$ and $A^4$ is $CR^6$, in conjunction with any of the above or below embodiments.

In another embodiment, the compounds of Formula I include compounds wherein each of $A^1$ and $A^2$, independently, is N, $A^3$ is $CR^5$ and $A^4$ is $CR^6$, in conjunction with any of the above or below embodiments.

In another embodiment, the compounds of Formula I include compounds wherein each of $A^1$ and $A^4$, independently, is N, $A^2$ is $CR^4$ and $A^3$ is $CR^5$, in conjunction with any of the above or below embodiments.

In another embodiment, the compounds of Formula I include N as $A^1$, N as $A^4$, and a substituted 5-6 membered monocyclic aryl or heteroaryl ring system, or a 8-12 membered bicyclic aryl or heteroaryl ring system, said ring system including 1-3 heteroatoms if monocyclic or 1-6 heteroatoms if bicyclic, said heteroatoms selected from O, N and S as $R^3$, in conjunction with any of the above or below embodiments.

In another embodiment, the compounds of Formula I include phenyl, naphthyl, pyridyl, pyrimidinyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, dihydrobenzofuranyl, benzothiophenyl or benzimidazolyl as the substituted ring system of $R^2$ in the embodiment above, in conjunction with any of the above or below embodiments.

In another embodiment, the compounds of Formula I in the embodiment immediately above include $C(O)R^{10}$, $COOR^{10}$, $C(O)R^{11}$, $COOR^{11}$, $C(O)NR^{10}R^{10}$, $C(S)NR^{10}R^{10}$, $C(O)NR^{10}R^{11}$, $C(S)NR^{10}R^{11}$, $NR^{10}R^{11}$, $NR^{10}C(O)R^{10}$, $NR^{10}C(S)R^{10}$, $NR^{10}C(O)R^{11}$, $NR^{10}C(S)R^{11}$, $NR^{10}C(O)NR^{10}R^{10}$, $NR^{10}C(O)NR^{10}R^{11}$, $NR^{10}C(S)NR^{10}R^{10}$, $NR^{10}C(S)NR^{10}R^{11}$, $NR^{10}(COOR^{10})$, $NR^{10}(COOR^{11})$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$ as a substituent on $R^2$, taken in conjunction with any of the above or below embodiments.

In another embodiment, the compounds are generally defined by Formula I above, wherein $A^1$ and $A^4$, independently, are N;

$A^2$ is $CR^4$;

$A^3$ is $CR^5$;

$R^1$ is $NR^7R^7$, $NR^7R^8$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2R^7$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$;

$R^2$ is a phenyl, naphthyl, pyridyl, pyrimidinyl, pyridazinyl, pyrazinyl, triazinyl, quinolinyl, isoquinolinyl, quinazolinyl, isoquinazolinyl, phthalazinyl, aza-phthalazinyl, thiophenyl, furyl, pyrrolyl, imidazolyl, pyrazolyl, triazolyl, thiazolyl, thiadiazolyl, oxazolyl, isoxazolyl, oxadiazolyl, isothiazolyl, indolyl, isoindolyl, benzofuranyl, dihydrobenzofuranyl, benzothiophenyl or benzimidazolyl ring system, said ring system substituted independently with 1-5 substituents of $R^{10}$, $R^{11}$, $R^{15}$, $NR^{10}R^{10}$, $NR^{10}R^{11}$, $OR^{10}$, $SR^{10}$, $OR^{11}$, $SR^{11}$, $C(O)R^{10}$, $C(S)R^{10}$, $C(NCN)R^{10}$, $C(O)R^{11}$, $C(S)R^{11}$, $C(NCN)R^{11}$, $C(O)C(O)R^{10}$, $OC(O)R^{10}$, $COOR^{10}$, $C(O)SR^{10}$, $C(O)C(O)R^{11}$, $OC(O)R^{11}$, $COOR^{11}$, $C(O)SR^{11}$, $C(O)NR^{10}R^{10}$, $C(S)NR^{10}R^{10}$, $C(O)NR^{10}R^{11}$, $C(S)NR^{10}R^{11}$, $OC(O)NR^{10}R^{11}$, $NR^{10}C(O)R^{10}$, $NR^{10}C(O)R^{11}$, $NR^{10}C(S)R^{10}$, $NR^{10}C(S)R^{11}$, $NR^{10}C(O)NR^{10}R^{10}$, $NR^{10}C(O)NR^{10}R^{11}$, $NR^{10}C(S)NR^{10}R^{10}$, $NR^{10}C(S)NR^{10}R^{11}$, $NR^{10}(COOR^{10})$, $NR^{10}(COOR^{11})$, $NR^{10}C(O)C(O)R^{10}$, $NR^{10}C(O)C(O)R^{11}$, $NR^{10}C(O)C(O)NR^{10}R^{11}$, $S(O)_2R^{10}$, $S(O)_2R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$, provided that (1) one substituent is $C(O)R^{10}$, $COOR^{10}$, $C(O)R^{11}$, $COOR^{11}$, $C(O)NR^{10}R^{10}$, $C(S)NR^{10}R^{10}$, $C(O)NR^{10}R^{11}$, $C(S)NR^{10}R^{11}$, $NR^{10}R^{11}$, $NR^{10}C(O)R^{10}$, $NR^{10}C(S)R^{10}$, $NR^{10}C(O)R^{11}$, $NR^{10}C(S)R^{11}$, $NR^{10}C(S)NR^{10}R^{10}$, $NR^{10}C(S)NR^{10}R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$;

$R^4$ is H, halo, haloalkyl, $NO_2$, CN, $NR^7R^7$, $OR^7$, $SR^7$, $C(O)R^7$, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally comprising 1-4 heteroatoms selected from N, O and S and optionally substituted with 1-3 substituents of $R^9$;

$R^5$ is H, halo, haloalkyl, $NO_2$, CN, $NR^7R^7$, $OR^7$; $SR^7$, $C(O)R^7$, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally comprising 1-4 heteroatoms selected from N, O and S and optionally substituted with 1-3 substituents of $R^9$;

$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-3 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^9$, oxo, $NR^9R^9$, $OR^9$; $SR^9$, $C(O)R^9$ or a partially or fully saturated or unsaturated 5-6 membered ring of carbon atoms optionally including 1-3 heteroatoms selected from O, N, or S, and optionally substituted independently with 1-3 substituents of $R^9$;

alternatively, $R^7$ and $R^8$ taken together form a saturated or partially or fully unsaturated 5-6 membered ring of carbon atoms optionally including 1-3 heteroatoms selected from O, N, or S, and the ring optionally substituted independently with 1-3 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H, halo, haloalkyl, CN, $NO_2$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^{11}$, $R^{12}$ or $R^{16}$, $NR^{11}R^{12}$, $NR^{12}R^{12}$, $OR^{11}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, $NR^{12}(COOR^{12})$, $OC(O)NR^{11}R^{12}$, $OC(O)NR^{12}R^{12}$, $S(O)_2R^{11}$, $S(O)_2R^{12}$, $S(O)_2NR^{11}R^{12}$, $S(O)_2NR^{12}R^{12}$, $NR^{12}R^{12}S(O)_2NR^{11}R^{12}$, $NR^{12}S(O)_2NR^{12}R^{12}$, $NR^{12}S(O)_2R^{11}$, $NR^{12}S(O)_2R^{12}$, $NR^{12}S(O)R^{11}$ or $NR^{12}S(O)_2R^{12}$;

$R^{11}$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^{12}$, $R^{13}$, $R^{14}$ or $R^{16}$;

alternatively, $R^{10}$ and $R^{11}$ taken together form a partially or fully saturated or unsaturated 5-6 membered ring of carbon atoms optionally including 1-3 heteroatoms selected from O, N, or S, and the ring optionally substituted independently with 1-5 substituents of $R^{12}$, $R^{13}$, $R^{14}$ or $R^{16}$;

$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-5 substituents of $R^{13}$, $R^{14}$, $R^{15}$ or $R^{16}$;

$R^{13}$ is $NR^{14}R^{15}$, $NR^{15}R^{15}$, $OR^{14}$; $SR^{14}$, $OR^{15}$; $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is a partially or fully saturated or unsaturated 5-8 membered or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-5 substituents of $R^{16}$;

$R^{16}$ is H, halo, haloalkyl, CN, OH, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, oxo, acetyl, benzyl, phenyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl;

and provided that (1) when said at least one substituent on said $R^2$ ring system is $C(O)NR^{10}R^{10}$ or $C(O)NR^{10}R^{11}$, then $R^{10}$ and $R^{11}$, independently, are not —$CH_2$-L-Q or —$C(C_{1-6}$alkyl)($C_{1-6}$alkyl)-L-Q, wherein L is —O—, —NH—, —NHC(O)—, —NHC(O)N—, —NHC(=NH)N— or —$CO_2$— and Q is H, substituted or unsubstituted $C_{1-6}$alkyl, substituted or unsubstituted aryl, substituted or unsubstituted heterocyclyl, substituted or unsubstituted heteraryl or $C_{1-6}$alkyl substituted with aryl, heterocyclyl or heteroaryl; (2) where the sole substituent on said $R^2$ ring system is $R^{10}$, said substituent is not $C_1$-alkyl-$C(O)NR^{11}R^{12}$, $C_1$-alkyl-$NR^{12}C(O)R^{11}$, $C_1$-alkyl-$C(O)NR^{12}R^{12}$ or $C_1$-alkyl-$NR^{12}C(O)R^{12}$, wherein the $C_1$-alkyl portion is $CH_2$ or substituted with $C_{1-6}$-alkyl or cycloalky; or (3) when said $R^2$ is a phenyl ring substituted with $C(O)NR^{10}R^{10}$ or $C(O)NR^{10}R^{11}$ meta to the alkynyl group of Formula I, then either (a) $R^1$ is not halogen, $C_{1-6}$alkyl, $C_{1-6}$alkoxyl or hydroxyl or (b) where $R^1$ and $R^3$ taken together with the atoms to which they are attached form a partially or fully unsaturated 5- or 6-membered ring of carbon atoms optionally including 1-3 heteroatoms selected from O, N, or S, said ring is not substituted with halogen, $C_{1-6}$alkyl, $C_{1-6}$alkoxyl or hydroxyl substituents.

In another embodiment, the compounds of the embodiment immediately above, are generally defined by Formula I above, wherein $R^1$ is $R^7$, $NR^7R^7$, $NR^7R^8$, $SR^7$, $C(O)R^7$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $C(O)NR^7R^8$, $C(S)NR^7R^8$, $NR^7C(O)NR^7R^8$, $NR^7C(S)NR^7R^8$, $S(O)_2R^7$, $S(O)_2NR^7R^7$, $NR^7S(O)_2NR^7R^7$, $NR^7S(O)_2R^7$, $S(O)_2NR^7R^8$ or $NR^7S(O)_2NR^7R^8$;

$R^2$ is a phenyl, naphthyl, pyridyl, pyrimidinyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, dihydrobenzofuranyl, benzothiophenyl or benzimidazolyl ring system, said ring system substituted independently with 1-3 substituents of $R^{10}$, $R^{11}$, $R^{15}$, $NR^{10}R^{10}$, $NR^{10}R^{11}$, $OR^{10}$, $SR^{10}$, $OR^{11}$, $SR^{11}$, $C(O)R^{10}$, $C(S)R^{10}$, $C(NCN)R^{10}$, $C(O)R^{11}$, $C(S)R^{11}$, $C(NCN)R^{11}$, $C(O)C(O)R^{10}$, $OC(O)R^{10}$, $COOR^{10}$, $C(O)SR^{10}$, $C(O)C(O)R^{11}$, $OC(O)R^{11}$, $COOR^{11}$, $C(O)SR^{11}$, $C(O)NR^{10}R^{10}$, $C(S)NR^{10}R^{10}$, $C(O)NR^{10}R^{11}$, $C(S)NR^{10}NR^{11}$, $OC(O)NR^{10}R^{11}$, $NR^{10}C(O)R^{10}$, $NR^{10}C(O)R^{11}$, $NR^{10}C(S)R^{10}$, $NR^{10}C(S)R^{11}$, $NR^{10}C(O)NR^{10}R^{10}$, $NR^{10}C(O)NR^{10}R^{11}$, $NR^{10}C(S)NR^{10}R^{10}$, $NR^{10}C(S)NR^{10}R^{11}$, $NR^{10}(COOR^{10})$, $NR^{10}(COOR^{11})$, $NR^{10}C(O)C(O)R^{10}$, $NR^{10}C(O)C(O)R^{11}$, $NR^{10}C(O)C(O)NR^{10}R^{11}$, $S(O)_2R^{10}$, $S(O)_2R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$, provided that one substituent is $C(O)R^{11}$, $COOR^{11}$, $C(O)NR^{10}R^{11}$, $C(S)NR^{10}R^{11}$, $NR^{10}R^{11}$, $NR^{10}C(O)R^{11}$, $NR^{10}C(S)R^{11}$, $NR^{10}C(O)NR^{10}R^{11}$, $NR^{10}C(S)NR^{10}R^{11}$, $NR^{10}(COOR^{11})$, $S(O)_2NR^{10}R^{11}$, $NR^{10}S(O)_2NR^{10}R^{11}$ or $NR^{10}S(O)_2R^{11}$;

$R^4$ is H, halo, haloalkyl, $NO_2$, CN, $NH_2$, N—$C_{1-10}$-alkyl, N—$C_{1-10}$-dialkyl, O—$C_{1-10}$-alkyl, S—$C_{1-10}$-alkyl, $C_{1-10}$-alkyl, $C_{2-10}$-alkenyl, $C_{2-10}$-alkynyl or $C_{3-10}$-cycloalkyl;

$R^5$ is H, halo, haloalkyl, $NO_2$, CN, $NH_2$, N—$C_{1-10}$-alkyl, N—$C_{1-10}$-dialkyl, O—$C_{1-10}$-alkyl, S—$C_{1-10}$-alkyl, $C_{1-10}$-alkyl, $C_{2-10}$-alkenyl, $C_{2-10}$-alkynyl or $C_{3-10}$-cycloalkyl;

$R^7$ is H, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally comprising 1-4 heteroatoms selected from N, O and S and optionally substituted with 1-3 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is a ring system of phenyl, naphthyl, pyridyl, pyrimidinyl, pyrrolidinyl, piperidinyl, piperazinyl, triazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, furyl, dihydrofuryl, tetrahydrofuryl, pyrrolyl, imidazolyl, triazolyl, thiazolyl, oxazolyl, isoxazolyl, isothiazolyl, indolyl, isoindolyl, indolinyl, benzofuranyl, dihydrobenzofuranyl, benzothiophenyl or benzimidazolyl, said ring system optionally substituted independently with 1-3 substituents of $R^9$, oxo, $NR^9R^9$, $OR^9$; $SR^9$, $C(O)R^9$ or a partially or fully saturated or unsaturated 5-6 membered ring of carbon atoms optionally including 1-3 heteroatoms selected from O, N, or S, and optionally substituted independently with 1-3 substituents of $R^9$;

alternatively, $R^7$ and $R^8$ taken together form a saturated or partially or fully unsaturated 5-6 membered ring of carbon atoms optionally including 1-3 heteroatoms selected from O, N, or S, and the ring optionally substituted independently with 1-3 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{1-10}$-alkoxyl, $C_{1-10}$-thioalkoxyl or a ring system of phenyl, naphthyl, pyridyl, pyrimidinyl, pyrrolidinyl, piperidinyl, piperazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, furyl, dihydrofuryl, tetrahydrofuryl, pyrrolyl, imidazolyl, thiazolyl, oxazolyl, isoxazolyl, isothiazolyl, indolyl, isoindolyl, indolinyl, benzofuranyl, dihydrobenzofuranyl, benzothiophenyl and benzimidazolyl, each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring system optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H, halo, haloalkyl, CN, $NO_2$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^{11}$, $R^{12}$ or $R^{16}$, $NR^{11}R^{12}$, $NR^{12}R^{12}$, $OR^{11}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, $NR^{12}(COOR^{12})$, $OC(O)NR^{11}R^{12}$, $OC(O)NR^{12}R^{12}$, $S(O)_2R^{11}$, $S(O)_2R^{12}$, $S(O)_2NR^{11}R^{12}$, $S(O)^2NR^{12}R^{12}$, $NR^{12}S$ (O)$_2$NR$^{11}$R$^{12}$, NR$^{12}$S(O)$_2$NR$^{12}$R$^{12}$, NR$^{12}$S(O)$_2$R$^{11}$, NR$^{12}$S(O)$_2$R$^{12}$, NR$^{12}$S(O)$_2$R$^{11}$ or NR$^{12}$S(O)$_2$R$^{12}$;

R$^{11}$ is a ring system of phenyl, naphthyl, pyridyl, pyrimidinyl, triazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, furyl, dihydrofuryl, tetrahydrofuryl, pyrrolyl, imidazolyl, triazolyl, thiazolyl, oxazolyl, isoxazolyl, isothiazolyl, indolyl, isoindolyl, indolinyl, benzofuranyl, dihydrobenzofuranyl, benzothiophenyl or benzimidazolyl, said ring system optionally substituted independently with 1-5 substituents of R$^{12}$, R$^{13}$, R$^{14}$ or R$^{16}$;

alternatively, R$^{10}$ and R$^{11}$ taken together form a partially or fully saturated or unsaturated 5-6 membered ring of carbon atoms optionally including 1-3 heteroatoms selected from O, N, or S, and the ring optionally substituted independently with 1-5 substituents of R$^{12}$, R$^{13}$, R$^{14}$ or R$^{16}$;

R$^{12}$ is H, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl or C$_{1-10}$-thioalkyl, each of which is optionally substituted independently with 1-5 substituents of R$^{13}$, R$^{14}$, R$^{15}$ or R$^{16}$;

R$^{13}$ is NR$^{14}$R$^{15}$, NR$^{15}$R$^{15}$, OR$^{14}$, SR$^{14}$, OR$^{15}$, SR$^{15}$, C(O)R$^{14}$, OC(O)R$^{14}$, COOR$^{14}$, C(O)R$^{15}$, OC(O)R$^{15}$, COOR$^{15}$, C(O)NR$^{14}$R$^{15}$, C(O)NR$^{15}$R$^{15}$, NR$^{14}$C(O)R$^{14}$, NR$^{15}$C(O)R$^{14}$, NR$^{14}$C(O)R$^{15}$, NR$^{15}$C(O)R$^{15}$, NR$^{15}$C(O)NR$^{14}$R$^{15}$, NR$^{15}$C(O)NR$^{15}$R$^{15}$, NR$^{15}$(COOR$^{14}$), NR$^{15}$(COOR$^{15}$), OC(O)NR$^{14}$R$^{15}$, OC(O)NR$^{15}$R$^{15}$, S(O)$_2$R$^{14}$, S(O)$_2$R$^{15}$, S(O)$_2$ NR$^{14}$R$^{15}$, S(O)$_2$NR$^{15}$R$^{15}$, NR$^{14}$S(O)$_2$NR$^{14}$R$^{15}$, NR$^{15}$S(O)$_2$NR$^{15}$R$^{15}$, NR$^{14}$S(O)$_2$R$^{14}$ or NR$^{15}$S(O)$_2$R$^{15}$;

R$^{14}$ is a partially or fully saturated or unsaturated 5-8 membered or a saturated or partially or fully saturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of R$^{15}$ or R$^{16}$;

R$^{15}$ is H or C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl or C$_{1-10}$-thioalkoxyl, each of which is optionally substituted independently with 1-5 substituents of R$^{16}$; and R$^{16}$ is H, halo, haloalkyl, CN, OH, NO$_2$, NH$_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, oxo, acetyl, benzyl, phenyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, NO$_2$, NH$_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

In another embodiment, the compounds of the embodiment immediately above, are generally defined by Formula I above, wherein R$^1$ is NH$_2$ or NCH$_3$, in conjunction with any of the above or below embodiments.

In another embodiment, the compounds are generally defined by Formula I above, wherein A$^2$ is CH;

A$^3$ is CH;

R$^1$ is NR$^7$R$^7$, NR$^7$R$^8$, SR$^7$, C(O)R$^7$, COOR$^7$, C(O)NR$^7$R$^7$, NR$^7$C(O)R$^7$, NR$^7$C(O)NR$^7$R$^7$, NR$^7$(COOR$^7$), C(O)NR$^7$R$^8$, NR$^7$C(O)R$^8$, NR$^7$C(O)NR$^7$R$^8$, NR$^7$(COOR$^8$), S(O)$_2$R$^7$, S(O)$_2$NR$^7$R$^7$, NR$^7$S(O)$_2$NR$^7$R$^7$, NR$^7$S(O)$_2$R$^7$, S(O)$_2$NR$^7$R$^8$, NR$^7$S(O)$_2$NR$^7$R$^8$ or NR$^7$S(O)$_2$R$^8$;

R$^2$ is a phenyl, naphthyl, pyridyl, pyrimidinyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, dihydrobenzofuranyl, benzothiophenyl or benzimidazolyl ring system, said ring system substituted independently with 1-3 substituents of R$^{10}$, R$^{11}$, R$^{15}$, NR$^{10}$R$^{10}$, NR$^{10}$R$^{11}$, OR$^{10}$, SR$^{10}$, OR$^{11}$, SR$^{11}$, C(O)R$^{10}$, C(S)R$^{10}$, C(NCN)R$^{10}$, C(O)R$^{11}$R$^{11}$, C(S)R$^{11}$, C(NCN)R$^{11}$, C(O)C(O) R$^{10}$, OC(O)R$^{10}$, COOR$^{10}$, C(O)SR$^{10}$, C(O)C(O)R$^{11}$, OC(O) R$^{11}$, COOR$^{11}$, C(O)SR$^{11}$, C(O)NR$^{10}$R$^{10}$, C(S)NR$^{10}$R$^{10}$, C(O)NR$^{10}$R$^{11}$, C(S)NR$^{10}$R$^{11}$, OC(O)NR$^{10}$R$^{11}$, NR$^{10}$C(O) R$^{10}$, NR$^{10}$C(O)R$^{11}$, NR$^{10}$C(S)R$^{10}$, NR$^{10}$C(S)R$^{11}$, NR$^{10}$C(O) NR$^{10}$R$^{10}$, NR$^{10}$C(O)NR$^{10}$R$^{11}$, NR$^{10}$C(S)NR$^{10}$R$^{10}$, NR$^{10}$C (S)NR$^{10}$R$^{11}$, NR$^{10}$(COOR$^{10}$), NR$^{10}$(COOR$^{11}$), NR$^{10}$C(O)C (O)R$^{10}$, NR$^{10}$C(O)C(O)R$^{11}$, NR$^{10}$C(O)C(O)NR$^{10}$R$^{11}$, S(O)$_2$ R$^{10}$, S(O)$_2$R$^{11}$, S(O)$_2$NR$^{10}$R$^{10}$, S(O)$_2$NR$^{10}$R$^{11}$, NR$^{10}$S(O)$_2$ NR$^{10}$R$^{11}$, NR$^{10}$S(O)$_2$R$^{10}$ or NR$^{10}$S(O)$_2$R$^{11}$, provided that one substituent is C(O)NR$^{10}$R$^{10}$, C(S)NR$^{10}$R$^{10}$, C(O) NR$^{10}$R$^{11}$, C(S)NR$^{10}$R$^{11}$, NR$^{10}$R$^{11}$, NR$^{10}$C(O)R$^{10}$, NR$^{10}$C (S)R$^{10}$, NR$^{10}$C(O)R$^{11}$, NR$^{10}$C(S)R$^{11}$, NR$^{10}$C(S)NR$^{10}$R$^{10}$, NR$^{10}$C(S)NR$^{10}$R$^{11}$, S(O)$_2$NR$^{10}$R$^{10}$, S(O)$_2$NR$^{10}$R$^{11}$, NR$^{10}$S (O)$_2$NR$^{10}$R$^{11}$, NR$^{10}$S(O)$_2$R$^{10}$ or NR$^{10}$S(O)$_2$R$^{11}$;

R$^7$ is H, C$_{1-10}$-alkyl or C$_{3-10}$-cycloalkyl, each of the C$_{1-10}$-alkyl and C$_{3-10}$-cycloalkyl optionally comprising 1-2 heteroatoms selected from N, O and S and optionally substituted with 1-3 substituents of R$^9$;

R$^8$ is a phenyl, naphthyl, pyridyl, pyrimidinyl, pyrrolidinyl, piperidinyl, piperazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, furyl, dihydrofuryl, tetrahydrofuryl, pyrrolyl, imidazolyl, thiazolyl, oxazolyl, isoxazolyl, isothiazolyl, indolyl, isoindolyl, indolinyl, benzofuranyl, dihydrobenzofuranyl, benzothiophenyl or benzimidazolyl ring system, said ring system optionally substituted independently with 1-3 substituents of R$^9$, oxo, NR$^9$R$^9$, OR$^9$; SR$^9$, C(O)R$^9$ or a partially or fully saturated or unsaturated 5-6 membered ring of carbon atoms optionally including 1-3 heteroatoms selected from O, N, or S, and optionally substituted independently with 1-3 substituents of R$^9$;

alternatively, R$^7$ and R$^8$ taken together form a 5-6 membered ring selected from pyrrolidine, piperidine, morpholine and piperazine, the ring optionally substituted independently with 1-3 substituents of R$^9$;

R$^9$ is H, halo, haloalkyl, CN, OH, NO$_2$, NH$_2$, acetyl, C$_{1-10}$-alkyl, C$_{2-10}$-alkenyl, C$_{2-10}$-alkynyl, C$_{3-10}$-cycloalkyl, C$_{1-10}$-alkylamino-, C$_{1-10}$-dialkylamino-, C$_{1-10}$-alkoxyl, C$_{1-10}$-thioalkoxyl or a ring system of phenyl, naphthyl, pyridyl, pyrimidinyl, pyrrolidinyl, piperidinyl, piperazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, furyl, dihydrofuryl, tetrahydrofuryl, pyrrolyl, imidazolyl, thiazolyl, oxazolyl, isoxazolyl, isothiazolyl, indolyl, isoindolyl, indolinyl, benzofuranyl, dihydrobenzofuranyl, benzothiophenyl and benzimidazolyl, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and ring system is optionally substituted independently with 1-3 substituents of halo, haloalkyl, CN, NO$_2$, NH$_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally comprising 1-4 heteroatoms selected from N, O and S and optionally substituted with 1-3 substituents of $R^{11}$, $R^{12}$ or $R^{16}$, $NR^{11}R^{12}$, $NR^{12}R^{12}$, $OR^{11}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, $NR^{12}(COOR^{12})$, $OC(O)NR^{11}R^{12}$, $OC(O)NR^{12}R^{12}$, $S(O)_2R^{11}$, $S(O)_2R^{12}$, $S(O)_2NR^{11}R^{12}$, $S(O)_2NR^{12}R^{12}$, $NR^{12}S(O)_2NR^{11}R^{12}$, $NR^{12}S(O)_2NR^{12}$; $NR^{12}S(O)_2R^{11}$, $NR^{12}S(O)_2R^{12}$, $NR^{12}S(O)_2R^{11}$ or $NR^{12}S(O)_2R^{12}$;

$R^{11}$ is a phenyl, naphthyl, pyridyl, pyrimidinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, thiophenyl, furyl, pyrrolyl, imidazolyl, thiazolyl, oxazolyl, isoxazolyl, isothiazolyl, indolyl, isoindolyl, indolinyl, benzofuranyl, dihydrobenzofuranyl, benzothiophenyl or benzimidazolyl ring system, said ring system optionally substituted independently with 1-3 substituents of $R^{12}$, $R^{13}$, $R^{14}$ or $R^{16}$;

alternatively, $R^{10}$ and $R^{11}$ taken together form a partially or fully saturated or unsaturated 5-6 membered ring of carbon atoms optionally including 1-3 heteroatoms selected from O, N, or S, said ring optionally substituted independently with 1-3 substituents of $R^{12}$, $R^{13}$, $R^{14}$ or $R^{16}$;

$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-3 substituents of $R^{31}$, $R^{14}$, $R^{15}$ or $R^{16}$;

$R^{13}$ is $NR^{14}R^{15}$, $NR^{15}R^{15}$, $OR^{14}$; $SR^{14}$, $OR^{15}$; $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is phenyl, naphthyl, pyridyl, pyrimidinyl, pyrrolidinyl, piperidinyl, piperazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, furyl, dihydrofuryl, tetrahydrofuryl, pyrrolyl, imidazolyl, thiazolyl, oxazolyl, isoxazolyl, isothiazolyl, indolyl, isoindolyl, indolinyl, benzofuranyl, dihydrobenzofuranyl, benzoxazinyl, benzodioxazinyl, benzothiophenyl and benzimidazolyl, each of which is optionally substituted independently with 1-5 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-5 substituents of $R^{16}$; and $R^{16}$ is H, halo, haloalkyl, CN, OH, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, oxo, acetyl, benzyl, phenyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

In yet another embodiment, the compounds are generally defined by Formula II

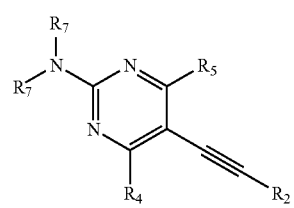

wherein
$R^2$ is

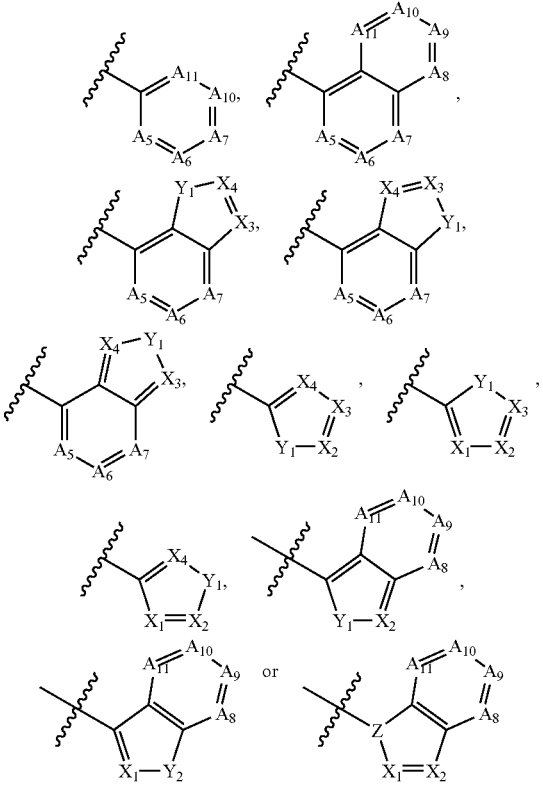

wherein
one of $A^6$ and $A^7$ is $CR^{3a}$ and the other of $A^6$ and $A^7$ is $CR^{3b}$ or N;
each of $A^5$, $A^8$, $A^9$, $A^{10}$ and $A^{11}$ is, independently, $CR^{3b}$ or N;
$X^2$ is $CR^{3a}$;
each of $X^1$, $X^3$ and $X^4$ is, independently, $CR^{3b}$ or N;
$Y^1$ is $CR^{3b}R^{3c}$, $NR^{3c}$, O or S;
$Y^2$ is $CR^{3a}R^{3b}$ or $NR^{3a}$; and Z is CH or N;

$R^{3a}$ is $OC(O)R^{10}$, $COOR^{10}$, $OC(O)R^{11}$, $COOR^{11}$, $C(O)SR^{10}$, $C(O)SR^{11}$, $C(O)NR^{10}R^{10}$, $C(S)NR^{10}R^{10}$, $C(O)NR^{10}R^{11}$, $C(S)NR^{10}R^{11}$, $NR^{10}R^{11}$, $NR^{10}C(O)R^{10}$, $NR^{10}C(S)R^{10}$, $NR^{10}C(O)R^{11}$, $NR^{10}C(S)R^{11}$, $NR^{10}C(S)NR^{10}R^{10}$, $NR^{10}C(S)NR^{10}R^{11}$, $OC(O)NR^{10}R^{11}$, $S(O)_2R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$;

$R^{3b}$ is H, halo, haloalkyl, CN, $NO_2$, $NH_2$, $C_{1-10}$-alkyl, $C_{2-10}$-alkenyl, $C_{2-10}$-alkynyl or $C_{3-10}$-cycloalkyl; and $R^{3c}$ is H, CN or $C_{1-10}$-alkyl;

$R^4$ is H, halo, haloalkyl, $NO_2$, CN, OH, O—$C_{1-10}$-alkyl, $NH_2$, $C_{1-10}$-alkyl, $C_{2-10}$-alkenyl, $C_{2-10}$-alkynyl or $C_{3-10}$-cycloalkyl;

$R^5$ is H, halo, haloalkyl, $NO_2$, CN, OH, $NH_2$, O—$C_{1-10}$-alkyl, $C_{1-10}$-alkyl, $C_{2-10}$-alkenyl, $C_{2-10}$-alkynyl or $C_{3-10}$-cycloalkyl;

Each $R^7$, independently, is H, $R^8$, $C_{1-10}$-alkyl, $C_{2-10}$-alkenyl or $C_{2-10}$-alkynyl, each of which is optionally substituted with 1-3 substituents of $NR^8R^9$, $NR^9R^9$, $OR^8$, $SR^8$, $OR^9$, $SR^9$, $C(O)R^8$, $C(O)R^9$, $C(O)NR^8R^9$, $C(O)NR^9R^9$, $S(O)_2R^8$, $S(O)_2NR^8R^9$, $S(O)_2R^9$, $S(O)_2NR^9R^9$, $R^8$ or $R^9$;

alternatively, $NR^7R^7$ form a 5-6 membered heterocyclic ring selected from pyrrolidine, piperidine, morpholine and piperazine, the ring optionally substituted independently with 1-3 substituents of $R^9$;

$R^8$ is a ring system selected from phenyl, naphthyl, pyridyl, piperazinyl, triazinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, pyranyl, dioxozinyl, cyclopropyl, cyclobutyl, cyclopentyl, cyclohexyl and cycloheptyl, said ring system optionally substituted independently with 1-3 substituents of $R^9$, oxo, $NR^9R^9$, $OR^9$, $SR^9$, $C(O)R^9$, phenyl, pyridyl, piperidyl, piperazinyl, morpholinyl or pyrrolidinyl;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a ring system selected from phenyl, naphthyl, pyridyl, piperazinyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring system optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamine, isopropylamine, dipropylamine, diisopropylamine, benzyl or phenyl;

$R^{10}$ is H, halo, haloalkyl, CN, $NO_2$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^{11}$, $R^{12}$ or $R^{16}$, $NR^{11}R^{12}$, $NR^{12}R^{12}$, $OR^{11}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, $NR^{12}(COOR^{12})$, $OC(O)NR^{11}R^{12}$, $OC(O)NR^{12}R^{12}$, $S(O)_2R^{11}$, $S(O)_2R^{12}$, $S(O)_2NR^{11}R^{12}$, $S(O)_2NR^{12}R^{12}$, $NR^{12}S(O)_2$ $NR^{11}R^{12}$, $NR^{12}S(O)_2NR^{12}R^{12}$, $NR^{12}S(O)_2R^{11}$, $NR^{12}S(O)_2R^{12}$, $NR^{12}S(O)_2R^{11}$ or $NR^{12}S(O)_2R^{12}$;

$R^{11}$ is a phenyl, naphthyl, 5,6,7,8-tetrahydronaphthyl, dihydro-indenyl, pyridyl, pyrimidinyl, triazinyl, quinolinyl, tetrahydroquinolinyl, oxo-tetrahydroquinolinyl, isoquinolinyl, oxo-tetrahydroisoquinolinyl, tetrahydroisoquinolinyl, quinazolinyl, isoquinazolinyl, thiophenyl, furyl, tetrahydrofuranyl, pyrrolyl, pyrazolyl, thieno-pyrazolyl, tetrahydropentapyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazopyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl or cycloheptyl ring system, said ring system optionally substituted independently with 1-3 substituents of $R^{12}$, $R^{13}$, $R^{14}$ or $R^{16}$;

alternatively, $R^{10}$ and $R^{11}$ taken together form a partially or fully saturated or unsaturated 5-6 membered ring of carbon atoms optionally including 1-3 heteroatoms selected from O, N, or S, and the ring optionally substituted independently with 1-3 substituents of $R^{12}$, $R^{13}$, $R^{14}$ or $R^{16}$;

$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-3 substituents of $R^{13}$, $R^{14}$, $R^{15}$ or $R^{16}$;

$R^{13}$ is $NR^{14}R^{15}$, $NR^{15}R^{15}$, $OR^{14}$, $SR^{14}$, $OR^{15}$, $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is phenyl, pyridyl, pyrimidinyl, thiophenyl, furyl, tetrahydrofuryl, pyrrolyl, pyrazolyl, thieno-pyrazolyl, imidazolyl, triazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, isoindolyl, indazolyl, benzofuranyl, benzothiophenyl, benzimidazolyl, pyrrolidinyl, pyrazolinyl, morpholinyl, piperidinyl, piperazinyl, 2,3-dihydro-1,4-benzoxazinyl, 1,3-benzodioxolyl, cyclopropyl, cyclobutyl, azetidinyl, cyclopentyl and cyclohexyl, each of which is optionally substituted independently with 1-3 substituents of $R^{15}$ is or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-3 substituents of $R^{16}$; and $R^{16}$ is H, halo, haloalkyl, CN, OH, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, oxo, acetyl, benzyl, phenyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

In another embodiment, the compounds are defined by Formula II above, wherein:

$R^2$ is

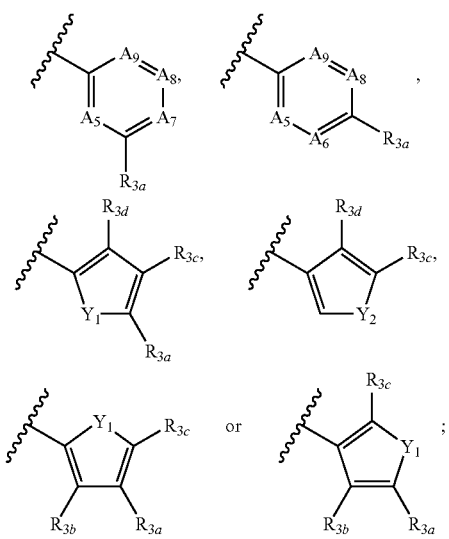

wherein
each of $A^5$, $A^6$, and $A^7$ is, independently, $CR^{3b}$ or N;
$A^8$ is $CR^{3c}$ or N; and
$A^9$ is $CR^{3d}$ or N;
$Y^1$ is O or S;
$Y^2$ is $NR^{3a}$;

$R^{3a}$ is $COOR^{10}$, $COOR^{11}$, $C(O)SR^{10}$, $C(O)SR^{11}$, $C(O)NR^{10}R^{10}$, $C(S)NR^{10}R^{10}$, $C(O)NR^{10}R^{11}$, $C(S)NR^{10}R^{11}$, $NR^{10}R^{11}$, $NR^{10}C(O)R^{10}$, $NR^{10}C(S)R^{10}$, $NR^{10}C(O)R^{11}$, $NR^{10}C(S)R^{11}$, $NR^{10}C(S)NR^{10}R^{10}$, $NR^{10}C(S)NR^{10}R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$;

$R^{3b}$ is H, halo, haloalkyl, CN, $NO_2$, $NH_2$, $C_{1-10}$-alkyl, $C_{2-10}$-alkenyl, $C_{2-10}$-alkynyl or $C_{3-10}$-cycloalkyl; $R^{3c}$ is H, halo, haloalkyl, CN, $NO_2$, $NH_2$, $C_{1-10}$-alkyl, $C_{2-10}$-alkenyl, $C_{2-10}$-alkynyl or $C_{3-10}$-cycloalkyl;

$R^{3c}$ is H, halo, haloalkyl, CN, $NO_2$, $NH_2$, $C_{1-10}$-alkyl, $C_{2-10}$-alkenyl, $C_{2-10}$-alkynyl or $C_{3-10}$-cycloalkyl;

$R^{3d}$ is H, halo, haloalkyl, CN, $NO_2$, $NH_2$, $C_{1-10}$-alkyl, $C_{2-10}$-alkenyl, $C_{2-10}$-alkynyl or $C_{3-10}$-cycloalkyl; and alternatively, $R^{3c}$ and $R^{3d}$ taken together with the atoms to which they are attached form a phenyl or tetrahydrofuranyl ring system, optionally substituted with 1-3 substituents of halo, haloalkyl, CN, $NO_2$, $NH_2$, $C_{1-10}$-alkyl, $C_{2-10}$-alkenyl, $C_{2-10}$-alkynyl or $C_{3-10}$-cycloalkyl;

$R^4$ is H, $C_{1-10}$-alkyl or O—$C_{1-10}$-alkyl;
$R^5$ is H, $C_{1-10}$-alkyl or O—$C_{1-10}$-alkyl;
$R^7$ is H or $C_{1-10}$-alkyl;
$R^8$ is H or $C_{1-10}$-alkyl;

$R^{10}$ is H, halo, haloalkyl, CN, $NO_2$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^{11}$, $R^{12}$ or $R^{16}$, $NR^{11}R^{12}$, $NR^{12}R^{12}$, $OR^{11}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, $NR^{12}(COOR^{12})$, $OC(O)NR^{11}R^{12}$, $OC(O)NR^{12}R^{12}$, $S(O)_2R^{11}$, $S(O)_2R^{12}$, $S(O)_2NR^{11}R^{12}$, $S(O)_2NR^{12}R^{12}$, $NR^{12}S(O)_2NR^{11}R^{12}$, $NR^{12}S(O)_2NR^{12}R^{12}$, $NR^{12}S(O)_2R^{11}$, $NR^{12}S(O)_2R^{12}$, $NR^{12}S(O)_2R^{11}$ or $NR^{12}S(O)_2R^{12}$;

$R^{11}$ is a phenyl, naphthyl, 5,6,7,8-tetrahydronaphthyl, dihydro-indenyl, pyridyl, pyrimidinyl, triazinyl, quinolinyl, tetrahydroquinolinyl, oxo-tetrahydroquinolinyl, isoquinolinyl, oxo-tetrahydroisoquinolinyl, tetrahydroisoquinolinyl, quinazolinyl, isoquinazolinyl, thiophenyl, furyl, tetrahydrofuranyl, pyrrolyl, pyrazolyl, thieno-pyrazolyl, tetrahydropentapyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazopyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl or cycloheptyl ring system, said ring system optionally substituted independently with 1-3 substituents of $R^{12}$, $R^{13}$, $R^{14}$ or $R^{16}$;

alternatively, $R^{10}$ and $R^{11}$ taken together form a partially or fully saturated or unsaturated 5-6 membered ring of carbon atoms optionally including 1-3 heteroatoms selected from O, N, or S, and the ring optionally substituted independently with 1-3 substituents of $R^{12}$, $R^{13}$, $R^{14}$ or $R^{16}$;

$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-3 substituents of $R^{13}$, $R^{14}$, $R^{15}$ or $R^{16}$;

$R^{13}$ is $NR^{14}R^{15}$, $NR^{15}R^{15}$, $OR^{14}$, $SR^{14}$, $OR^{15}$, $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2$ $NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is phenyl, pyridyl, pyrimidinyl, thiophenyl, furyl, tetrahydrofuryl, pyrrolyl, pyrazolyl, thieno-pyrazolyl, imidazolyl, triazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, isoindolyl, indazolyl, benzofuranyl, benzothiophenyl, benzimidazolyl, pyrrolidinyl, pyrazolinyl, morpholinyl, piperidinyl, piperazinyl, 2,3-dihydro-1,4-benzoxazinyl, 1,3-benzodioxolyl, cyclopropyl, cyclobutyl, azetidinyl, cyclopentyl and cyclohexyl, each of which is optionally substituted independently with 1-3 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-5 substituents of $R^{16}$; and $R^{16}$ is H, halo, haloalkyl, CN, OH, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, oxo, acetyl, benzyl, phenyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

In another embodiment, the compounds are generally defined by Formula II, wherein:
$R^2$ is

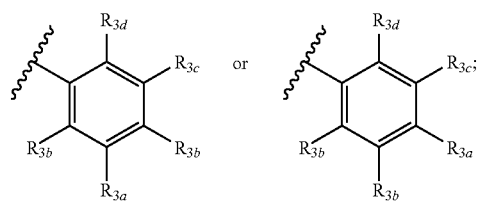

wherein
$R^{3a}$ is $COOR^{10}$, $COOR^{11}$, $C(O)SR^{10}$, $C(O)SR^{11}$, $C(O)NR^{10}R^{10}$, $C(O)NR^{10}R^{11}$, $NR^{10}R^{11}$, $NR^{10}C(O)R^{10}$, $NR^{10}C(O)R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$;

each of $R^{3b}$, $R^{3c}$ and $R^{3d}$, independently, is H, F, Cl, Br, I, $CF_3$, $CF_2CF_3$, $OCF_3$, $OCF_2CF_3$, CN, $NO_2$, $NH_2$, methyl, ethyl, propyl, isopropyl, n-butyl, sec-butyl, tert-butyl, acetylenyl, cyclopropyl, cyclobutyl, cyclopentyl, cyclohexyl, OH, methoxyl, ethoxyl, propoxyl, SH, thiomethyl or thioethyl;

each of $R^4$ and $R^5$, independently, is H, F, Cl, Br, I, $CF_3$, $CF_2CF_3$, $OCF_3$, CN, methyl, ethyl, propyl, isopropyl, n-butyl, sec-butyl, tert-butyl, OH, methoxyl, ethoxyl, propoxyl;

each $R^7$, independently, is H, $C(O)R^8$, $COOR^8$, $C(O)R^9$, $COOR^9$, $C(O)NR^8R^9$, $C(O)NR^9R^9$, $S(O)_2R^8$, $S(O)_2NR^8R^9$, $S(O)_2R^9$, $S(O)_2NR^9R^9$, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally comprising 1-4 heteroatoms selected from N, O and S and optionally substituted with one or more substituents of $NR^8R^9$, $NR^9R^9$, $OR^8$, $SR^8$, $OR^9$, $SR^9$, $C(O)R^8$, $C(O)R^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is a phenyl, naphthyl, pyridyl, piperazinyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl or cycloheptyl ring system, said ring system optionally substituted independently with 1-3 substituents of $R^9$, oxo, $NR^9R^9$, $OR^9$; $SR^9$, $C(O)R^9$, phenyl, pyridyl, piperidyl, piperazinyl or morpholinyl;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{1-10}$-alkoxyl, $C_{1-10}$-thioalkoxyl or a ring system selected from phenyl, naphthyl, pyridyl, piperazinyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl and dioxozinyl, each of the $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{1-10}$-alkoxyl, $C_{1-10}$-thioalkoxyl and ring system optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamine, isopropylamine, dipropylamine, diisopropylamine, benzyl or phenyl;

$R^{10}$ is H, methyl, ethyl, propyl, isopropyl, n-butyl, sec-butyl, tert-butyl, acetylenyl, cyclopropyl, cyclobutyl, cyclopentyl, cyclohexyl, OH, methoxyl, ethoxyl, propoxyl, SH, thiomethyl or thioethyl; each of which is optionally substituted with one or more substituents of $R^{11}$, $R^{12}$ or $R^{16}$;

$R^{11}$ is a phenyl, naphthyl, 5,6,7,8-tetrahydronaphthyl, dihydro-indenyl, pyridyl, pyrimidinyl, triazinyl, quinolinyl, tetrahydroquinolinyl, oxo-tetrahydroquinolinyl, isoquinolinyl, oxo-tetrahydroisoquinolinyl, tetrahydroisoquinolinyl, quinazolinyl, isoquinazolinyl, thiophenyl, furyl, tetrahydrofuranyl, pyrrolyl, pyrazolyl, thieno-pyrazolyl, tetrahydropentapyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazopyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl or cycloheptyl ring system, said ring system optionally substituted independently with 1-3 substituents of $R^{12}$, $R^{13}$, $R^{14}$ or $R^{16}$;

alternatively, $R^{10}$ and $R^{11}$ taken together form a partially or fully saturated or unsaturated 5-6 membered ring of carbon atoms optionally including 1-3 heteroatoms selected from O, N, or S, and the ring optionally substituted independently with 1-3 substituents of $R^{12}$, $R^{13}$, $R^{14}$ or $R^{16}$;

$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-3 substituents of $R^{13}$, $R^{14}$, $R^{15}$ or $R^{16}$;

$R^{13}$ is $NR^{14}R^{15}$, $NR^{15}R^{15}$, $OR^{14}$; $SR^{14}$, $OR^{15}$; $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is phenyl, pyridyl, pyrimidinyl, thiophenyl, furyl, tetrahydrofuryl, pyrrolyl, pyrazolyl, thieno-pyrazolyl, imidazolyl, triazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, isoindolyl, indazolyl, benzofuranyl, benzothiophenyl, benzimidazolyl, pyrrolidinyl, pyrazolinyl, morpholinyl, piperidinyl, piperazinyl, 2,3-dihydro-1,4-benzoxazinyl, 1,3-benzodioxolyl, cyclopropyl, cyclobutyl, azetidinyl, cyclopentyl and cyclohexyl, each of which is optionally substituted independently with 1-3 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-3 substituents of $R^{16}$; and $R^{16}$ is H, halo, haloalkyl, CN, OH, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, oxo, acetyl, benzyl, phenyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

In another embodiment, the compounds are generally defined by Formula II

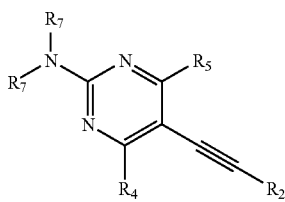

wherein $R^2$ is a phenyl, naphthyl, pyridyl, pyrimidinyl, pyridazinyl, pyrazinyl, triazinyl, thiophenyl, furyl, pyrrolyl, imidazolyl, triazolyl, thiazolyl, oxazolyl, isoxazolyl, isothiazolyl, indolyl or isoindolyl ring system, said ring system substituted independently with 0-3 substituents of $R^{10}$, $R^{11}$ or $R^{15}$ and one substituent, meta or para to the point of attachment of the alkyne on the $R^2$ ring, is $NR^{10}C(O)NR^{10}R^{10}$, $NR^{10}C(O)NR^{10}R^{11}$, $NR^{10}(COOR^{10})$ or $NR^{10}(COOR^{11})$;

$R^7$ is H, $C_{1-10}$-alkyl or $C_{3-10}$-cycloalkyl, each of the $C_{1-10}$-alkyl and $C_{3-10}$-cycloalkyl optionally comprising 1-2 heteroatoms selected from N, O and S and optionally substituted with 1-3 substituents of $R^9$;

$R^8$ is a phenyl, naphthyl, pyridyl, pyrimidinyl, pyrrolidinyl, piperidinyl, piperazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, furyl, dihydrofuryl, tetrahydrofuryl, pyrrolyl, imidazolyl, thiazolyl, oxazolyl, isoxazolyl, isothiazolyl, indolyl, isoindolyl, indolinyl, benzofuranyl, dihydrobenzofuranyl, benzothiophenyl or benzimidazolyl ring system, said ring system optionally substituted independently with 1-3 substituents of $R^9$, oxo, $NR^9R^9$, $OR^9$; $SR^9$, $C(O)R^9$ or a partially or fully saturated or unsaturated 5-6 membered ring of carbon atoms optionally including 1-3 heteroatoms selected from O, N, or S, and optionally substituted independently with 1-3 substituents of $R^9$;

alternatively, $R^7$ and $R^8$ taken together form a 5-6 membered ring selected from pyrrolidine, piperidine, morpholine and piperazine, the ring optionally substituted independently with 1-3 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{1-10}$-alkoxyl, $C_{1-10}$-thioalkoxyl or a ring system of phenyl, naphthyl, pyridyl, pyrimidinyl, pyrrolidinyl, piperidinyl, piperazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, furyl, dihydrofuryl, tetrahydrofuryl, pyrrolyl, imidazolyl, thiazolyl, oxazolyl, isoxazolyl, isothiazolyl, indolyl, isoindolyl, indolinyl, benzofuranyl, dihydrobenzofuranyl, benzothiophenyl and benzimidazolyl, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally comprising 1-4 heteroatoms selected from N, O and S and optionally substituted with 1-3 substituents of $R^{11}$, $R^{12}$ or $R^{16}$, $NR^{11}R^{12}$, $NR^{12}R^{12}$, $OR^{11}$, $SR^{11}$, $OR^{12}$, $SR^{12}$, $C(O)R^{11}$, $OC(O)R^{11}$, $COOR^{11}$, $C(O)R^{12}$, $O(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, $NR^{12}(COOR^{12})$, $OC(O)NR^{11}R^{12}$, $OC(O)NR^{12}R^{12}$, $S(O)_2R^{11}$, $S(O)_2R^{12}$, $S(O)_2NR^{11}R^{12}$, $S(O)_2NR^{12}R^{12}$, $NR^{12}S(O)_2NR^{11}R^{12}$, $NR^{12}S(O)_2NR^{12}R^{12}$, $NR^{12}S(O)_2R^{11}$, $NR^{12}S(O)_2R^{12}$, $NR^{12}S(O)_2R^{11}$ or $NR^{12}S(O)_2R^{12}$;

$R^{11}$ is a phenyl, naphthyl, pyridyl, pyrimidinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, thiophenyl, furyl, pyrrolyl, imidazolyl, thiazolyl, oxazolyl, isoxazolyl, isothiazolyl, indolyl, isoindolyl, indolinyl, benzofuranyl, dihydrobenzofuranyl, benzothiophenyl or benzimidazolyl ring system, said ring system optionally substituted independently with 1-3 substituents of $R^{12}$, $R^{13}$, $R^{14}$ or $R^{16}$;

alternatively, $R^{10}$ and $R^{11}$ taken together form a partially or fully saturated or unsaturated 5-6 membered ring of carbon atoms optionally including 1-3 heteroatoms selected from O, N, or S, said ring optionally substituted independently with 1-3 substituents of $R^{12}$, $R^{13}$, $R^{14}$ or $R^{16}$;

$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-3 substituents of $R^{13}$, $R^{14}$, $R^{15}$ or $R^{16}$;

$R^{13}$ is $NR^{14}R^{15}$, $NR^{15}R^{15}$, $OR^{14}$; $SR^{14}$, $OR^{15}$; $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}(COOR^{15})$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is phenyl, naphthyl, pyridyl, pyrimidinyl, pyrrolidinyl, piperidinyl, piperazinyl, quinolinyl, isoquinolinyl, tetrahydroquinolinyl, tetrahydroisoquinolinyl, quinazolinyl, isoquinazolinyl, tetrahydroquinazolinyl, tetrahydroisoquinazolinyl, morpholinyl, thiophenyl, furyl, dihydrofuryl, tetrahydrofuryl, pyrrolyl, imidazolyl, thiazolyl, oxazolyl, isoxazolyl, isothiazolyl, indolyl, isoindolyl, indolinyl, benzofuranyl, dihydrobenzofuranyl, benzoxazinyl, benzodioxazinyl, benzothiophenyl and benzimidazolyl, each of which is optionally substituted independently with 1-5 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-5 substituents of $R^{16}$; and $R^{16}$ is H, halo, haloalkyl, CN, OH, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, oxo, acetyl, benzyl, phenyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

In another embodiment, the compounds are generally defined by Formula I wherein $A^1$ and $A^4$, independently, are N;

$A^2$ is $CR^4$;

$A^3$ is $CR^5$;

$R^1$ is $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2R^7$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$;

$R^2$ is a phenyl, naphthyl, pyridyl, pyrimidinyl, pyridazinyl, pyrazinyl, triazinyl, quinolinyl, isoquinolinyl, quinazolinyl, isoquinazolinyl, phthalazinyl, aza-phthalazinyl, thiophenyl, furyl, pyrrolyl, imidazolyl, pyrazolyl, triazolyl, thiazolyl, thiadiazolyl, oxazolyl, isoxazolyl, oxadiazolyl, isothiazolyl, indolyl, isoindolyl, benzofuranyl, dihydrobenzofuranyl, benzothiophenyl or benzimidazolyl ring system, said ring system substituted independently with 1-5 substituents of $R^{10}$, $R^{11}$, $R^{15}$, $NR^{10}R^{10}$, $NR^{10}R^{11}$, $OR^{10}$, $SR^{10}$, $OR^{11}$, $SR^{11}$, $C(O)R^{10}$, $C(S)R^{10}$, $C(NCN)R^{10}$, $C(O)R^{11}$, $C(S)R^{11}$, $C(NCN)R^{11}$, $C(O)C(O)R^{10}$, $OC(O)R^{10}$, $COOR^{10}$, $C(O)SR^{10}$, $C(O)C(O)R^{11}$, $OC(O)R^{11}$, $COOR^{11}$, $C(O)SR^{11}$, $C(O)NR^{10}R^{10}$, $C(S)NR^{10}R^{10}$, $C(O)NR^{10}R^{11}$, $C(S)NR^{10}R^{11}$, $OC(O)NR^{10}R^{11}$, $NR^{10}C(O)R^{10}$, $NR^{10}C(O)R^{11}$, $NR^{10}C(S)R^{10}$, $NR^{10}C(S)R^{11}$, $NR^{10}C(O)NR^{10}R^{10}$, $NR^{10}C(O)NR^{10}R^{11}$, $NR^{10}C(S)NR^{10}R^{10}$, $NR^{10}C(S)NR^{10}R^{11}$, $NR^{10}(COOR^{10})$, $NR^{10}(COOR^{11})$, $NR^{10}C(O)C(O)R^{10}$, $NR^{10}C(O)C(O)R^{11}$, $NR^{10}C(O)C(O)NR^{10}R^{11}$, $S(O)_2R^{10}$, $S(O)_2R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$, provided that (1) one substituent is $C(O)R^{10}$, $COOR^{10}$, $C(O)R^{11}$, $COOR^{11}$, $C(O)NR^{10}R^{10}$, $C(S)NR^{10}R^{10}$, $C(O)NR^{10}R^{11}$, $C(S)NR^{10}R^{11}$, $NR^{10}C(O)R^{10}$, $NR^{10}C(S)R^{10}$, $NR^{10}C(O)R^{11}$, $NR^{10}C(S)R^{11}$, $NR^{10}C(O)NR^{10}R^{10}$, $NR^{10}C(O)NR^{10}R^{11}$, $NR^{10}(COOR^{10})$, $NR^{10}(COOR^{11})$, $NR^{10}C(S)NR^{10}R^{11}$, $NR^{10}C(S)NR^{10}R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$;

$R^4$ is H, halo, haloalkyl, $NO_2$, CN, $NR^7R^7$, $OR^7$, $SR^7$, $C(O)R^7$, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally comprising 1-4 heteroatoms selected from N, O and S and optionally substituted with 1-3 substituents of $R^9$;

$R^5$ is H, halo, haloalkyl, $NO_2$, CN, $NR^7R^7$, $OR^7$; $SR^7$, $C(O)R^7$, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally comprising 1-4 heteroatoms selected from N, O and S and optionally substituted with 1-3 substituents of $R^9$;

$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-3 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^9$, oxo, $NR^9R^9$, $OR^9$; $SR^9$, $C(O)R^9$ or a partially or fully saturated or unsaturated 5-6 membered ring of carbon atoms optionally including 1-3 heteroatoms selected from O, N, or S, and optionally substituted independently with 1-3 substituents of $R^9$;

alternatively, $R^7$ and $R^8$ taken together form a saturated or partially or fully unsaturated 5-6 membered ring of carbon atoms optionally including 1-3 heteroatoms selected from O, N, or S, and the ring optionally substituted independently with 1-3 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H, halo, haloalkyl, CN, $NO_2$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^{11}$, $R^{12}$ or $R^{16}$, $NR^{11}R^{12}$, $NR^{12}R^{12}$, $OR^{12}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, $NR^{12}(COOR^{12})$, $OC(O)NR^{11}R^{12}$, $OC(O)NR^{12}R^{12}$, $S(O)_2R^{11}$, $S(O)_2R^{12}$, $S(O)_2NR^{11}R^{12}$, $S(O)_2NR^{12}R^{12}$, $NR^{12}S(O)_2$ $NR^{11}R^{12}$, $NR^{12}S(O)_2NR^{12}R^{12}$, $NR^{12}S(O)R^{11}$, $NR^{12}S(O)_2$ $R^{12}$, $NR^{12}S(O)_2R^{11}$ or $NR^{12}S(O)_2R^{12}$;

$R^{11}$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^{12}$, $R^{13}$, $R^{14}$ or $R^{16}$;

alternatively, $R^{10}$ and $R^{11}$ taken together form a partially or fully saturated or unsaturated 5-6 membered ring of carbon atoms optionally including 1-3 heteroatoms selected from O, N, or S, and the ring optionally substituted independently with 1-5 substituents of $R^{12}$, $R^{13}$, $R^{14}$ or $R^{16}$;

$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-5 substituents of $R^{13}$, $R^{14}$, $R^{15}$ or $R^{16}$;

$R^{13}$ is $NR^{14}R^{15}$, $NR^{15}R^{15}$, $OR^{14}$; $SR^{14}$, $OR^{15}$; $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2$ $NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is a partially or fully saturated or unsaturated 5-8 membered or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-5 substituents of $R^{16}$;

$R^{16}$ is H, halo, haloalkyl, CN, OH, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, oxo, acetyl, benzyl, phenyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl;

and provided that (1) when said at least one substituent on said $R^2$ ring system is $C(O)NR^{10}R^{10}$ or $C(O)NR^{10}R^{11}$, then $R^{10}$ and $R^{11}$, independently, are not —$CH_2$-L-Q or —$C(C_{1-6}$alkyl$)(C_{1-6}$alkyl$)$-L-Q, wherein L is —O—, —NH—, —NHC(O)—, —NHC(O)N—, —NHC(=NH)N— or —$CO_2$— and Q is H, substituted or unsubstituted $C_{1-6}$alkyl, substituted or unsubstituted aryl, substituted or unsubstituted heterocyclyl, substituted or unsubstituted heteraryl or $C_{1-6}$alkyl substituted with aryl, heterocyclyl or heteroaryl; or (2) when said $R^2$ is a phenyl ring substituted with $C(O)NR^{10}R^{10}$ or $C(O)NR^{10}R^{11}$ meta to the point of attachment of the alkynyl group on $R^2$ of Formula I, then either (a) $R^1$ is not halogen, $C_{1-6}$alkyl, $C_{1-6}$alkoxyl or hydroxyl or (b) where $R^1$ and $R^3$ taken together with the atoms to which they are attached form a partially or fully unsaturated 5- or 6-membered ring of carbon atoms optionally including 1-3 heteroatoms selected from O, N, or S, said ring is not substituted with halogen, $C_{1-6}$alkyl, $C_{1-6}$alkoxyl or hydroxyl substituents.

In another embodiment, the compounds are generally defined by Formula I herein, wherein Each of $A^1$, $A^2$, $A^3$, $A^4$, $R^1$ are as defined in any of the embodiments above, and $R^2$ is a partially or fully saturated 6-12 membered bicyclic or 7-14 membered tricyclic ring system, said ring system formed of carbon atoms and including 1-6 heteroatoms if bicyclic or 1-9 heteroatoms if tricyclic, said heteroatoms selected from O, N, or S, wherein said ring system is substituted independently with one or more substituents of $R^{10}$, $R^{11}$, $R^{15}$, $NR^{10}R^{10}$, $NR^{10}R^{11}$, $OR^{10}$, $SR^{10}$, $OR^{11}$, $SR^{11}$, $C(O)R^{10}$, $C(S)R^{10}$, $C(NCN)R^{10}$, $C(O)R^{11}$, $C(S)R^{11}$, $C(NCN)R^{11}$, $C(O)C(O)R^{10}$, $OC(O)R^{10}$, $COOR^{10}$, $C(O)SR^{10}$, $C(O)C(O)R^{11}$, $OC(O)R^{11}$, $COOR^{11}$, $C(O)SR^{11}$, $C(O)NR^{10}R^{10}$, $C(S)NR^{10}R^{10}$, $C(O)NR^{10}R^{11}$, $C(S)NR^{10}R^{11}$, $OC(O)NR^{10}R^{11}$, $NR^{10}C(O)R^{10}$, $NR^{10}C(O)R^{11}$, $NR^{10}C(S)R^{10}$, $NR^{10}C(S)R^{11}$, $NR^{10}C(O)NR^{10}R^{10}$, $NR^{10}C(O)NR^{10}R^{11}$, $NR^{10}C(S)NR^{10}R^{10}$, $NR^{10}C(S)NR^{10}R^{11}$, $NR^{10}(COOR^{10})$, $NR^{10}(COOR^{11})$, $NR^{10}C(O)C(O)R^{10}$, $NR^{10}C(O)C(O)R^{11}$, $NR^{10}C(O)C(O)NR^{10}R^{11}$, $S(O)_2R^{10}$, $S(O)_2R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$, provided that (1) one substituent is $C(O)R^{10}$, $COOR^{10}$, $C(O)R^{11}$, $COOR^{11}$, $C(O)NR^{10}R^{10}$, $C(S)NR^{10}R^{10}$, $C(O)NR^{10}R^{11}$, $C(S)NR^{10}R^{11}$, $NR^{10}C(O)R^{10}$, $NR^{10}C(S)R^{10}$, $NR^{10}C(O)R^{11}$, $NR^{10}C(S)R^{11}$, $NR^{10}C(O)NR^{10}R^{10}$, $NR^{10}C(O)NR^{10}R^{11}$, $NR^{10}(COOR^{10})$, $NR^{10}(COOR^{11})$, $NR^{10}C(S)NR^{10}R^{10}$, $NR^{10}C(S)NR^{10}R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$, in conjunction with any of the above or below embodiments.

For example, in the embodiment immediately above, $R^2$ may be a quinolinyl, isoquinolinyl, quinazolinyl, isoquinazolinyl, phthalazinyl, aza-phthalazinyl, benzothiophenyl, benzofuryl, benzopyrazolyl, benzotriazolyl, benzothiazolyl, benzothiadiazolyl, benzoxazolyl, benzisoxazolyl, benzoxadiazolyl, benzisothiazolyl, indolyl, isoindolyl, dihydrobenzofuranyl or benzimidazolyl ring system.

In another embodiment, the compounds are generally defined by Formula III

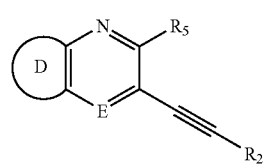

III wherein

D is

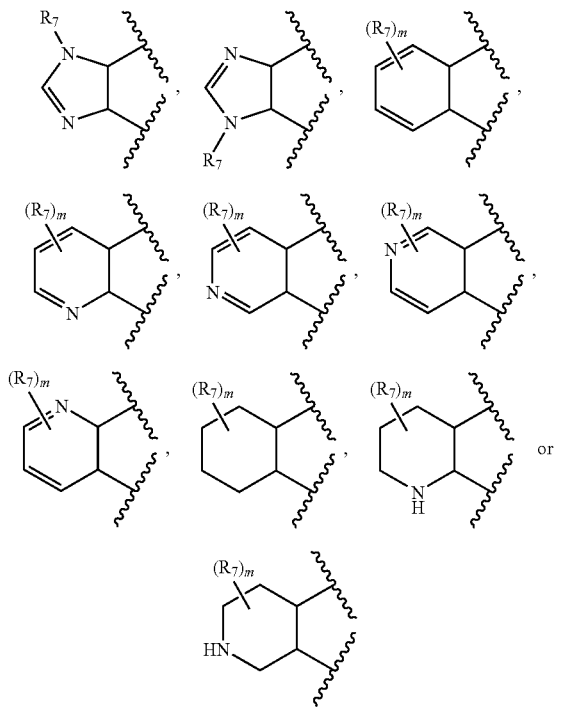

wherein m is 0, 1, 2 or 3;

E is $CR^4$ or N;

$R^2$ is

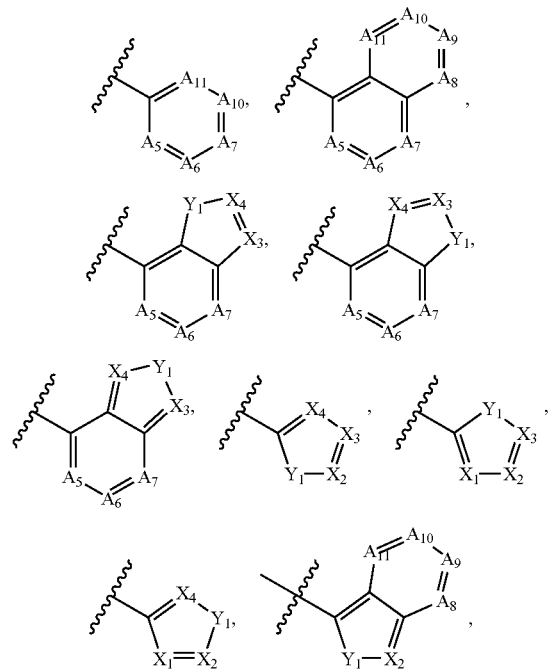

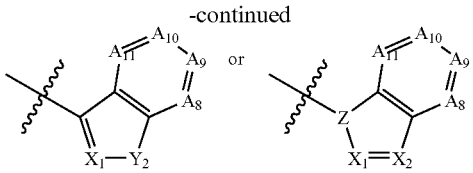

wherein
one of $A^6$ and $A^7$ is $CR^{3a}$ and the other of $A^6$ and $A^7$ is $CR^{3b}$ or N;
each of $A^5$, $A^8$, $A^9$, $A^{10}$ and $A^{11}$ is, independently, $CR^{3b}$ or N;
$X^2$ is $CR^{3a}$;
each of $X^1$, $X^3$ and $X^4$ is, independently, $CR^{3b}$ or N;
$Y^1$ is $CR^{3b}R^{3c}$, $NR^{3c}$, O or S;
$Y^2$ is $CR^{3a}R^{3b}$ or $NR^{3a}$; and
Z is CH or N;
$R^{3a}$ is $C(O)OC_{1-3}$-alkyl$R^{11}$, $OC(O)R^{11}$, $COOR^{11}$, $C(O)SC_{1-3}$-alkyl$R^{11}$, $C(O)SR^{11}$, $C(O)N(R^{10})C_{1-3}$-alkyl$R^{11}$, $C(S)N(R^{10})C_{1-3}$-alkyl$R^{11}$, $C(O)NR^{10}R^{11}$, $C(S)NR^{10}R^{11}$, $NR^{10}C(O)C_{1-3}$-alkyl$R^{11}$, $NR^{10}C(S)C_{1-3}$-alkyl$R^{11}$, $NR^{10}C(O)R^{11}$, $NR^{10}C(S)R^{11}$, $NR^{10}C(O)N(R^{10})C_{1-3}$-alkyl$R^{11}$, $NR^{10}C(O)NR^{10}R^{11}$, $NR^{10}C(S)N(R^{10})C_{1-3}$-alkyl$R^{11}$, $NR^{10}C(S)NR^{10}R^{11}$, $NR^{10}C(O)OC_{1-3}$-alkyl$R^{11}$, $NR^{10}(COOR^{11})$, $OC(O)NR^{10}R^{11}$, $S(O)_2N(R^{10})C_{1-3}$-alkyl$R^{11}$, $S(O)_2NR^{10}R^{11}$, $NR^{10}S(O)_2NR^{10}R^{11}$, $NR^{10}S(O)_2C_{1-3}$-alkyl$R^{11}$ or $NR^{10}S(O)_2R^{11}$;
$R^{3b}$ is H, halo, haloalkyl, CN, $NO_2$, $NH_2$, $C_{1-10}$-alkyl, $C_{2-10}$-alkenyl, $C_{2-10}$-alkynyl or $C_{3-10}$-cycloalkyl; and
$R^{3c}$ is H, CN or $C_{1-10}$-alkyl;
$R^4$ is H, halo, haloalkyl, $NO_2$, CN, OH, O—$C_{1-10}$-alkyl, $NH_2$, $C_{1-10}$-alkyl, $C_{2-10}$-alkenyl, $C_{2-10}$-alkynyl or $C_{3-10}$-cycloalkyl;
$R^5$ is H, halo, haloalkyl, $NO_2$, CN, OH, $NH_2$, O—$C_{1-10}$-alkyl, $C_{1-10}$-alkyl, $C_{2-10}$-alkenyl, $C_{2-10}$-alkynyl or $C_{3-10}$-cycloalkyl;
Each $R^7$, independently, is H, $R^8$, $C_{1-10}$-alkyl, $C_{2-10}$-alkenyl or $C_{2-10}$-alkynyl, each of which is optionally substituted with 1-3 substituents of $NR^8R^9$, $NR^9R^9$, $OR^8$, $SR^8$, $OR^9$, $SR^9$, $C(O)R^8$, $C(O)R^9$, $C(O)NR^8R^9$, $C(O)NR^9R^9$, $S(O)_2R^8$, $S(O)_2NR^8R^9$, $S(O)_2R^9$, $S(O)_2NR^9R^9$, $R^8$ or $R^9$;
$R^8$ is a ring system selected from phenyl, pyridyl, piperazinyl, thiophenyl, furyl, pyrrolyl, imidazolyl, triazolyl, thiazolyl, oxazolyl, isoxazolyl, isothiazolyl, pyrrolidinyl, oxazolinyl, isoxazolinyl, thiazolinyl, pyrazolinyl, morpholinyl, piperidinyl, pyranyl, dioxozinyl, cyclopropyl, cyclobutyl, cyclopentyl, cyclohexyl and cycloheptyl, said ring system optionally substituted independently with 1-3 substituents of $R^9$, oxo, $NR^9R^9$, $OR^9$, $SR^9$ or $C(O)R^9$;
$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$alkoxyl, $C_{1-10}$-thioalkoxyl or a ring system selected from phenyl, naphthyl, pyridyl, piperazinyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring system optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamine, isopropylamine, dipropylamine, diisopropylamine, benzyl or phenyl;

$R^{10}$ is H, CN, $NO_2$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^{11}$, $R^{12}$ or $R^{16}$, $NR^{11}R^{12}$, $NR^{12}R^{12}$, $OR^{11}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, $NR^{12}(COOR^{12})$, $OC(O)NR^{11}R^{12}$, $OC(O)NR^{12}R^{12}$, $S(O)_2R^{11}$, $S(O)_2R^{12}$, $S(O)_2NR^{11}R^{12}$, $S(O)_2NR^{12}R^{12}$, $NR^{12}S(O)_2NR^{11}R^{12}$, $NR^{12}S(O)_2NR^{12}R^{12}$, $NR^{12}S(O)_2R^{11}$, $NR^{12}S(O)_2R^{12}$, $NR^{12}S(O)_2R^{11}$ or $NR^{12}S(O)R^{12}$;

$R^{11}$ is a phenyl, naphthyl, 5,6,7,8-tetrahydronaphthyl, dihydro-indenyl, pyridyl, pyrimidinyl, triazinyl, quinolinyl, tetrahydroquinolinyl, oxo-tetrahydroquinolinyl, isoquinolinyl, oxo-tetrahydroisoquinolinyl, tetrahydroisoquinolinyl, quinazolinyl, isoquinazolinyl, thiophenyl, furyl, tetrahydrofuranyl, pyrrolyl, pyrazolyl, thieno-pyrazolyl, tetrahydropentapyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, 2,3-dihydroindolyl, isoindolyl, indazolyl, benzofuranyl, benzothiophenyl, benzimidazolyl, imidazopyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl or cycloheptyl ring system, said ring system optionally substituted independently with 1-3 substituents of $R^{12}$, $R^{13}$, $R^{14}$ or $R^{16}$;

alternatively, $R^{10}$ and $R^{11}$ taken together form a partially or fully saturated or unsaturated 5-6 membered ring of carbon atoms optionally including 1-3 heteroatoms selected from O, N, or S, and the ring optionally substituted independently with 1-3 substituents of $R^{12}$, $R^{13}$, $R^{14}$ or $R^{16}$;

$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-3 substituents of $R^{13}$, $R^{14}$, $R^{15}$ or $R^{16}$;

$R^{13}$ is $NR^{14}R^{15}$, $NR^{15}R^{15}$, $OR^{14}$; $SR^{14}$, $OR^{15}$; $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2 NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is phenyl, pyridyl, pyrimidinyl, thiophenyl, furyl, tetrahydrofuryl, pyrrolyl, pyrazolyl, thieno-pyrazolyl, imidazolyl, triazolyl, thiazolyl, thiadiazolyl, benzothiazolyl, oxazolyl, oxadiazolyl, benzoxazolyl, benzoxadiazolyl, isoxazolyl, isothiazolyl, indolyl, azaindolyl, isoindolyl, indazolyl, benzofuranyl, benzothiophenyl, benzimidazolyl, pyrrolidinyl, pyrazolinyl, morpholinyl, piperidinyl, piperazinyl, 2,3-dihydro-1,4-benzoxazinyl, 1,3-benzodioxolyl, cyclopropyl, cyclobutyl, azetidinyl, cyclopentyl and cyclohexyl, each of which is optionally substituted independently with 1-3 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-3 substituents of $R^{16}$; and $R^{16}$ is H, halo, haloalkyl, CN, OH, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, oxo, acetyl, benzyl, phenyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

In other embodiments, Formulas I, II and III include various of the exemplary compounds described in the Experimentals Methods section hereinbelow.

Definitions

The following definitions should assist in understanding the invention described herein.

The terms "agonist" and "agonistic" when used herein refer to or describe a molecule which is capable of, directly or indirectly, substantially inducing, promoting or enhancing biological activity of a biological molecule, such as an enzyme or receptor, including Tie-2 and Lck.

The term "comprising" is meant to be open ended, including the indicated component(s), but not excluding other elements.

The term "H" denotes a single hydrogen atom. This radical may be attached, for example, to an oxygen atom to form a hydroxyl radical.

The term "$C_{\alpha-\beta}$alkyl", when used either alone or within other terms such as "haloalkyl" and "alkylamino", embraces linear or branched radicals having $\alpha$ to $\beta$ number of carbon atoms (such as $C_1$-$C_{10}$).

The term "alkyl" radicals include "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. The term "alkylenyl" embraces bridging divalent alkyl radicals such as methylenyl and ethylenyl.

The term "alkenyl", when used alone or in combination, embraces linear or branched radicals having at least one carbon-carbon double bond in a moiety having between two and ten carbon atoms. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "alkynyl", when used alone or in combination, denotes linear or branched radicals having at least one carbon-carbon triple bond and having two to ten carbon atoms.

Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "alkoxy" or "alkoxyl", when used alone or in combination, embraces linear or branched oxygen-containing radicals each having alkyl portions of one or more carbon atoms. The term alkoxy radicals include "lower alkoxy" radicals having one to six carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy.

The term "aryl", when used alone or in combination, means a carbocyclic aromatic moiety containing one, two or even three rings wherein such rings may be attached together in a fused manner. Every ring of an "aryl" ring-system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be subisitituted, such as with 1 to 5 substituents including lower alkyl, hydroxyl, halo, haloalkyl, nitro, cyano, alkoxy and lower alkylamino, and the like. Phenyl substituted with —O—CH$_2$—O— or —O—CH$_2$—CH$_2$—O— forms an aryl benzodioxolyl substituent.

The term "carbocyclic", also referred to herein as "cycloalkyl", when used alone or in combination, means a partially or fully saturated ring moiety containing one ("monocyclic"), two ("bicyclic") or even three ("tricyclic") rings wherein such rings may be attached together in a fused manner and formed from carbon atoms. Examples of saturated carbocyclic radicals include saturated 3 to 6-membered monocyclic groups such as cyclopropane, cyclobutane, cyclopentane and cyclohexane.

The term "cycloalkenyl", when used alone or in combination, means a partially or fully saturated cycloalkyl containing one, two or even three rings in a structure having at least one carbon-carbon double bond in the structure. Examples of cycloalkenyl groups include C$_3$-C$_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms and, for example, lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "ring system" refers generally to a moiety comprising one or more rings collectively having the delineated number of atoms, the atoms being carbon or, where indicated, a heteroatom such as nitrogen, oxygen or sulfur. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl or heteroaryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and saturated heterocyclyl include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-azafluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "aminocarbonyl" denotes an amide group of the formula —C(=O)NH$_2$.

The term "alkylthio" embraces radicals containing a linear or branched alkyl radical, of one to ten-carbon atoms, attached to a divalent sulfur atom. An example of "alkylthio", is methylthio, (CH$_3$S—).

The term "haloalkylthio" embraces radicals containing a haloalkyl radical, of one to ten carbon atoms, attached to a divalent sulfur atom. An example of "haloalkylthio" is trifluoromethylthio.

The term "aminoalkyl" embraces linear or branched alkyl radicals having one to about ten carbon atoms any one of which may be substituted with one or more amino radicals. Examples of aminoalkyl radicals include "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. Examples of alkylaminoalkyl radicals include "lower alkylaminoalkyl" radicals having alkyl radicals of one to six carbon atoms. Suitable alkylaminoalkyl radicals may be mono or dialkyl substituted, such as N-methylaminomethyl, N,N-dimethylaminoethyl, N,N-diethylaminomethyl and the like.

The term "alkylaminoalkoxy" embraces alkoxy radicals substituted with alkylamino radicals. Examples of alkylaminoalkoxy radicals include "lower alkylaminoalkoxy" radicals having alkoxy radicals of one to six carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "Formula I" includes any sub formulas, such as Formula II. Similarly, the terms "Formula II" and "Formula III" include any sub formulas.

The term "pharmaceutically-acceptable" when used with reference to a compound of Formulas I-III is intended to refer to a form of the compound that is safe for administration. For example, a salt form, a solvate, a hydrate or derivative form of a compound of Formula I, II or III, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I-III are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I-III may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I-III include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I, II or III.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, hydrobromic acid, citric acid, sulphuric acid and phosphoric acid and such organic acids as oxalic acid, stearic and, salicylic acid, pamoic acid, gluconic acid, ethanesulfonic acid, methanesulfonic acid, toluenesulfonic acid, tartaric acid, fumaric acid, medronic acid, napsylic acid, maleic acid, succinic acid and citric acid. Other examples include salts with alkali metals or alkaline earth metals such as sodium, potassium, calcium or magnesium, or with organic bases.

Additional examples of such salts can be found in Berge et al., J. Pharm. Sci., 66, 1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling-point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "derivative" is broadly construed herein, and intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate a kinase enzyme.

The term "pharmaceutically-acceptable derivative" as used herein, denotes a derivative which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formulas I-III. A "pharmaceutically-acceptable prodrug" as used herein, denotes a prodrug which is pharmaceutically acceptable. Pharmaceutically acceptable modifications to the compounds of Formulas I-III are readily appreciated by those of ordinary skill in the art.

The compound(s) of Formula I, II or III may be used to treat a subject by administering the compound(s) as a pharmaceutical composition. To this end, the compound(s) can be combined with one or more carriers, diluents or adjuvants to form a suitable composition, which is described in more detail herein.

The term "carrier", as used herein, denotes any pharmaceutically acceptable additive, excipient, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. As such, this term is not limited to a single unit dosage, to be effective. Accordingly, it is contemplated herein that an "effective dosage amount" may include more than one unit dosage to be administered to the subject. For example, the subject may be prescribed, or requested by qualifie medical staff, to ingest 2 tablets, which comprise a compound of the invention, to obtain an effective dosage amount.

The term "leaving groups" generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxysuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

The term "angiogenesis" is defined as any alteration of an existing vascular bed or the formation of new vasculature which benefits tissue perfusion. This includes the formation of new vessels by sprouting of endothelial cells from existing blood vessels or the remodeling of existing vessels to alter size, maturity, direction and/or flow properties to improve blood perfusion of tissue.

The terms "cancer" and "cancerous" when used herein refer to or describe the physiological condition in mammals that is typically characterized by unregulated cell growth. Examples of cancer include, without limitation, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers which are found to be accompanied by unregulated levels of Tie-2, and similar kinases, in the subject.

General Synthetic Procedures

The present invention further comprises procedures for the preparation of a compound of Formulas I-III. The compounds of Formulas I-III can be synthesized according to the procedures described in the following Schemes 1-6, wherein the substituents are generally as defined for Formulas I-III above, except where further noted. The synthetic methods described below are merely exemplary, and the compounds of the invention may be synthesized by alternate routes as appreciated by persons of ordinary skill in the art.

The following list of abbreviations used throughout the specification represent the following and should assist in understanding the invention:

ACN, MeCN—acetonitrile
BSA—bovine serum albumin
$Cs_2CO_3$—cesium carbonate
$CHCl_3$—chloroform
$CH_2Cl_2$, DCM—dichloromethane, methylene chloride
CuBr—copper bromide
CuI—copper iodide
DIBAL—diisobutylaluminum hydride
DIC—1,3-diisopropylcarbodiimide
DIEA, $(iPr)_2NEt$—diisopropylethylamine
DME—dimethoxyethane
DMF—dimethylformamide
DMAP—4-dimethylaminopyridine
DMSO—dimethylsulfoxide
EDC—1-(3-dimethylaminopropyl)-3-ethylcarbodiimide
$Et_2O$—diethyl ether
EtOAc—ethyl acetate
FBS—fetal bovine serum
G, gm—gram
h, hr—hour
$H_2$—hydrogen
HATU—O-(7-azabenzotriazol-1-yl)-N,N,N',N'-tetramethyluroniumhexafluorophosphate
HBr—hydrobromic acid
HCl—hydrochloric acid
HOBt—1-hydroxybenzotriazole hydrate
HPLC—high pressure liquid chromatography
IPA, IpOH—isopropyl alcohol
$K_2CO_3$—potassium carbonate
KI—potassium iodide
$MgSO_4$—magnesium sulfate
MeOH—methanol
$N_2$—nitrogen
$NaCNBH_3$—sodium cyanoborohydride
$NaHCO_3$—sodium bicarbonate
NaH—sodium hydride
$NaOCH_3$—sodium methoxide
NaOH—sodium hydroxide
$Na_2SO_4$—sodium sulfate
$NH_4Cl$—ammonium chloride
$NH_4OH$—ammonium hydroxide
NMP—N-methylpyrrolidinone
$P(t-bu)_3$—tri(tert-butyl)phosphine
PBS—phospate buffered saline
Pd/C—palladium on carbon
$Pd(PPh_3)_4$—palladium(0)triphenylphosphine tetrakis
$PdCl_2(PPh_3)_2$—palladiumdichloro-diphenylphosphine
$Pd(OAc)_2$—palladium acetate
PyBop—benzotriazol-1-yl-oxy-tripyrrolidino-phosphonium hexafluorophosphate
RT—room temperature
TBTU—O-benzotriazol-1-yl-N,N,N',N'-tetramethyluronium tetrafluoroborate
TEA, $Et_3N$—triethylamine
TFA—trifluoroacetic acid
THF—tetrahydrofuran

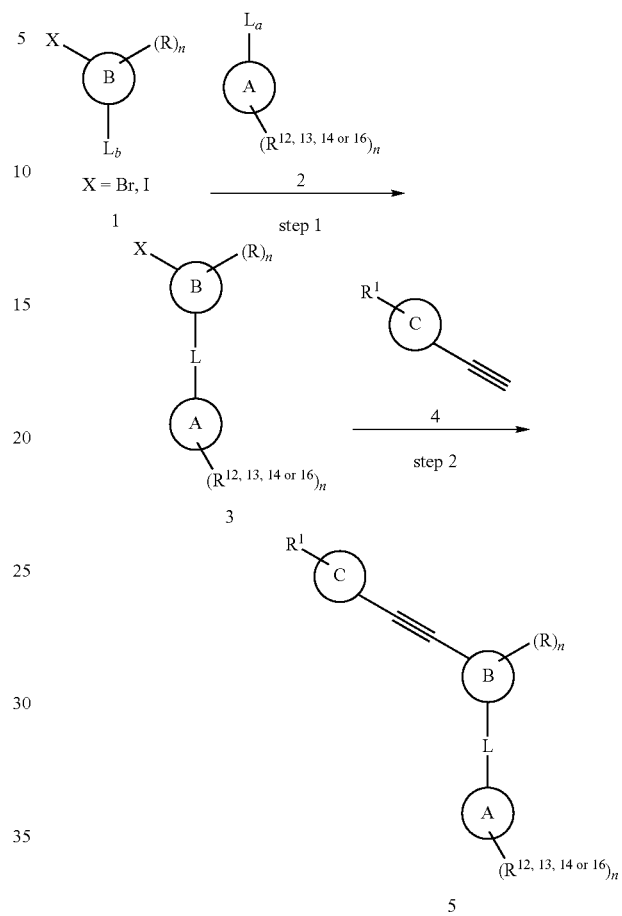

Scheme 1

A heteroaryl-substituted alkynes 5 can be prepared according to the method generally described in Scheme 1, wherein the heteroaryl is designated as C, while A and B are independent ring systems, respectively, and "L" is a linker connecting ring A to ring B. As shown, a halogen-substituted B ring system 1, having a linker portion $L_b$ can be reacted with a substituted A ring system 2 having a corresponding linker portion $L_a$. Linker portions $L_a$ and $L_b$ are capable of reacting with one another to form compound 3 having the desired linker "L". "L" may be any linker generally defined by the $R^2$ substitutions in Formulas I, II and III, and particularly, it includes, without limitation, an amide, a urea, a thiourea, a thioamide, a carbamate, an anhydride, a sulfonamide and the like, allowing for spacer atoms either between ring B and L and/or between ring A and L, as described in Scheme 3 below. Accordingly, various desirable linker "L"s can be formed from suitable linker portions $L_a$ and $L_b$, respectively.

Halogen-B-A intermediates 3 can be coupled to suitable heteroaryl-substituted alkynes 4 using conventional metallation chemistry methods, such as those disclosed by Stephen Buchwald. For example, compound 3 where X=iodide can be coupled to an alkyne 4 in the presence of palladium and copper under suitable basic solution conditions. Generally, suitable palladium reagents include $PdCl_2(PPh_3)_2$, and the like. Suitable solvents include polar solvents such as ACN or DMF and suitable bases include weak tertiary amine bases such as TEA. Suitable reaction conditions may involve heating the reaction to a suitable temperature to allow complete coupling between the halogen-intermediate 3 and alkyne 4.

The acetylide 6 can then be reacted with a desired heteroaryl halide 7 to yield the desired heteroaryl-substituted alkyne 5.

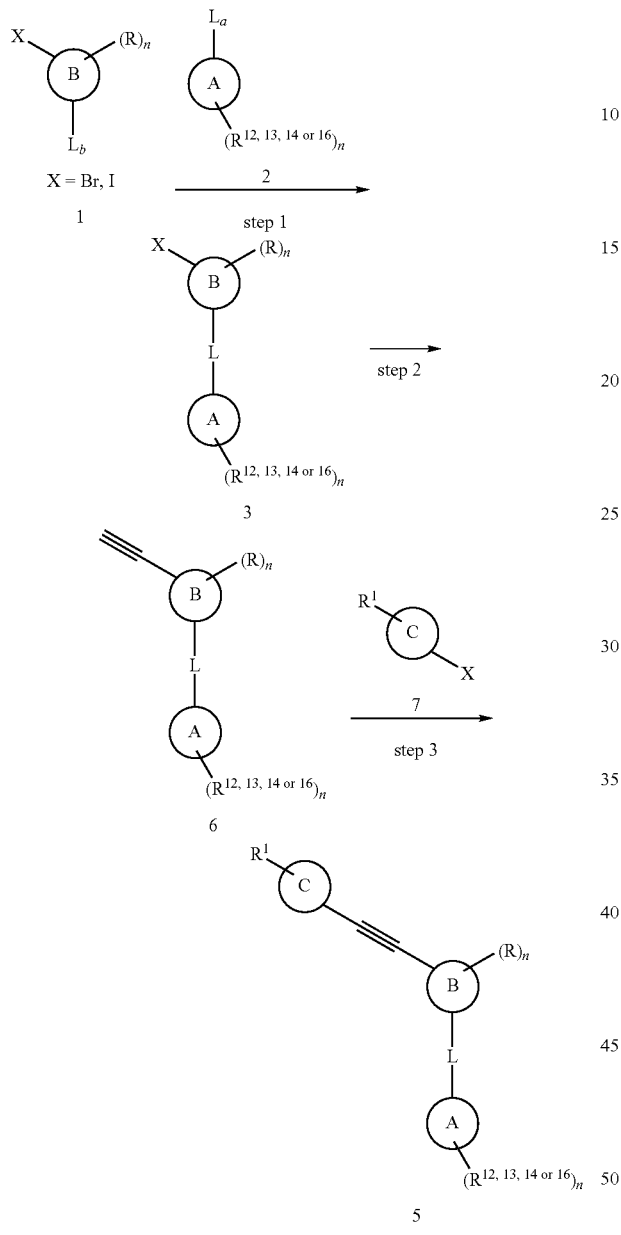

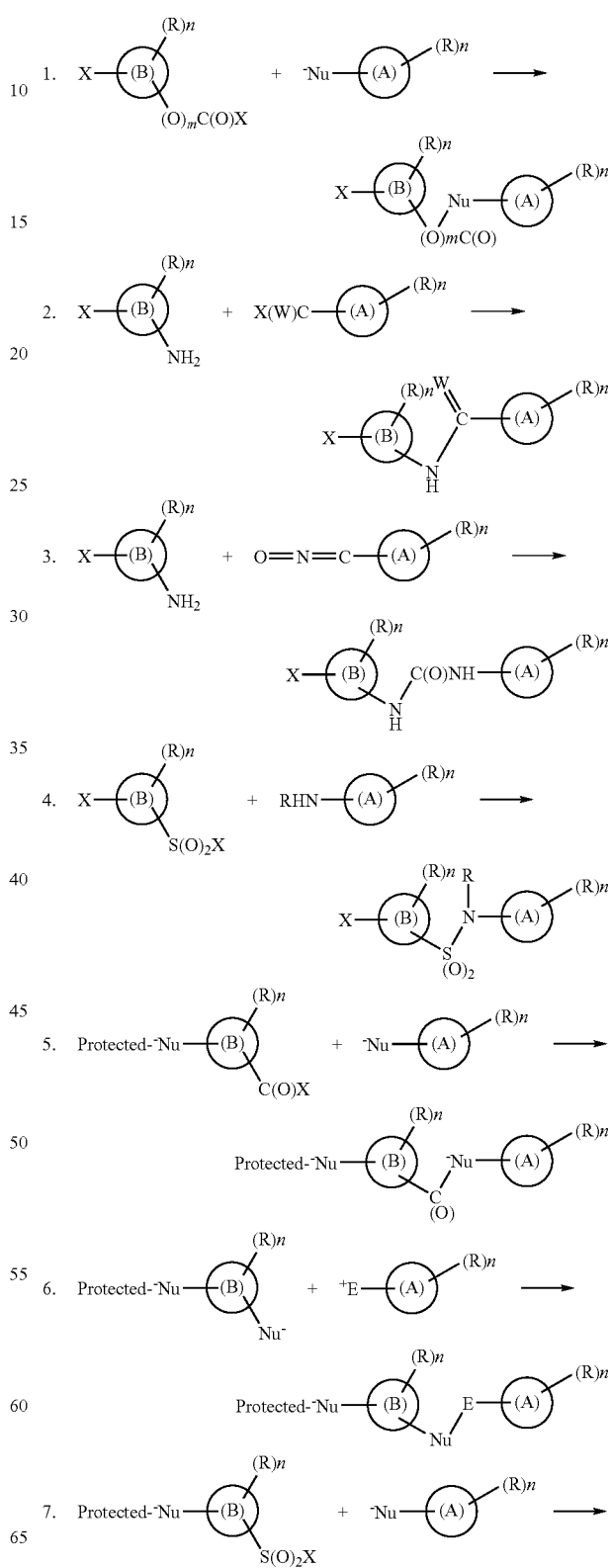

Alternatively, heteroaryl-substituted alkynes 5 can be prepared according to the method generally described in Scheme 2. As shown and described in scheme 1, a halogen-substituted B ring system-linked-A ring system intermediate 3 can be made. The halogen group of compound 3 can be converted to the corresponding acetylide 6, as shown in step 2, by reaction with a suitable acetylene donor, such as a silyl acetylide, under suitable reactions conditions. Such reactions generally take place with suitable metal catalysts, such as palladium and copper. The reaction may proceed under ambient temperature, or may require heat, depending upon the particular intermediate 3, acetylene reagent, concentration of reagents, solvent, and other factors, as appreciated by persons of ordinary skill in the art.

-continued

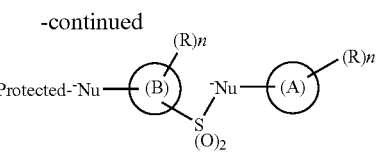

R[2] ring system, generally designated and referred to in Scheme 3, and throughout the specification, as the "B" ring may be substituted with various substitutions including R[11] ring systems, generally designated and referred to in Scheme 3, and throughout the specification, as the "A" ring system, by various coupling methods as described in Scheme 3. Each of the seven sub-schemes, numbered 1-7 above and described below, utilize the following meanings for $(R)_n$, X, Nu⁻, E⁺, W and m: $(R)_n$ refers to n number of R[10], R[11] and R[16] substitutions wherein n is an integer from 0-9; X refers generally to a "leaving group" such as a halide (bromine, chlorine, iodine or fluorine), alkylsulfonate and other known groups (also see definitions herein); Nu⁻ refers generally to a nucleophilic species such as a primary or secondary amine, an oxygen, a sulfur or a anionic carbon species—examples of nucleophiles include, without limitation, amines, hydroxides, alkoxides and the like; E⁺ refers generally to an electrophilic species, such as the carbon atom of a carbonyl, which is susceptible to nucleophilic attack or readily eliminates—examples of suitable electrophilic carbonyl species include, without limitation, acid halides, mixed anhydrides, aldehydes, carbamoyl-chlorides, sulfonyl chlorides, acids activated with activating reagents such as TBTU, HBTU, HATU, HOBT, BOP, PyBOP, carbodiimides (DCC, EDC and the like), pentafluo-rophenyl, and other electrophilic species including halides, isocyanates, daizonium ions and the like; W is either O or S; and m is either 0 or 1.

The coupling of rings B and A, as shown as products in sub-schemes 1-7, can be brought about using various conventional methods to link rings B and A together. For example, an amide or a sulfonamide linkage, as shown in sub-schemes 2 and 4, and 5 and 7 where the Nu– is an amine, respectively, can be made utilizing an amine on either the B or A rings and an acid chloride or sulfonyl chloride on the other of either the B or A rings. The reaction proceeds generally in the presence of a suitable solvent and/or base. Suitable solvents include, without limitation, generally non-nucleophilic, a solvent such as toluene, $CH_2Cl_2$, THF, DMF, DMSO, N,N-dimethylaceta-mide and the like, including solvent combinations thereof. The solvent may range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH, boro-hydrides, cyanoborohydrides and the like, alkoxides such as $NaOCH_3$, and the like. The base itself may also serve as a solvent. The reaction may optionally be run neat, i.e., without any base and/or solvent. These coupling reactions are generally fast and conversion occurs typically in ambient conditions. However, depending upon the particular substrate, concentration and other stoichiometric factors, such reactions may require heat, as appreciated by those skilled in the art.

Similarly, carbamates as illustrated in sub-scheme 1 where Nu– is an amine, anhydrides as illustrated in sub-scheme 1 where Nu– is an oxygen, reverse amides as generally illustrated in sub-scheme 6 where Nu– is an amine and E+ is an acid chloride, ureas as illustrated in sub-scheme 3, thioamides and thioureas where the respective carbonyl oxygen is a sulfur, thiocarbamates where the respective carbonyl oxygen and/or carbamate oxygen is a sulfur, and the like. While the above methods are so described, they are not exhaustive, and other methods for linking rings A and B together may be utilized as appreciated by those skilled in the art.

Although sub-schemes 1-7 are illustrated as having the nucleophilic and electrophilic coupling groups, such as the amino group and acid chloride groups illustrated in sub-scheme 2, directly attached to the substrate, either the A or B ring, in question, the invention is not so limited. It is contemplated herein that these nucleophilic and/or electrophilic coupling groups may be tethered from their respective ring. For example, the amine group on the B ring, and/or the acid halide group on the A ring, as illustrated in sub-scheme 2, may be removed from direct attachment to the ring by a one or more atom spacer, such as by a methylene, ethylene, propylene spacer or the like. As appreciated by those skilled in the art, such spacer may or may not affect the coupling reactions described above, and accordingly, such reaction conditions may need to be modified to affect the desired transformation.

The coupling methods described in sub-schemes 1-7 of scheme 3 are also applicable for coupling desired A rings to desired C-B intermediates, to synthesize desired compounds of Formulas I, II and III. For example, a halo-B-$NH_2$ ring may first be coupled to a heteroaryl-substituted alknye intermediate 4 (scheme 1, also referred to as the C ring) to form the C-B intermediate. The B ring amine group of this C-B intermediate may then be converted to an isocyanate, for example, or any other desired group for coupling the A ring via the desired linker. Further, the B ring amine may be protected, such as with BOC-ON, while further substituents are coupled to the B ring and/or the C ring, prior to coupling the C-B intermediate to an A ring (see Scheme 5 below).

Scheme 4

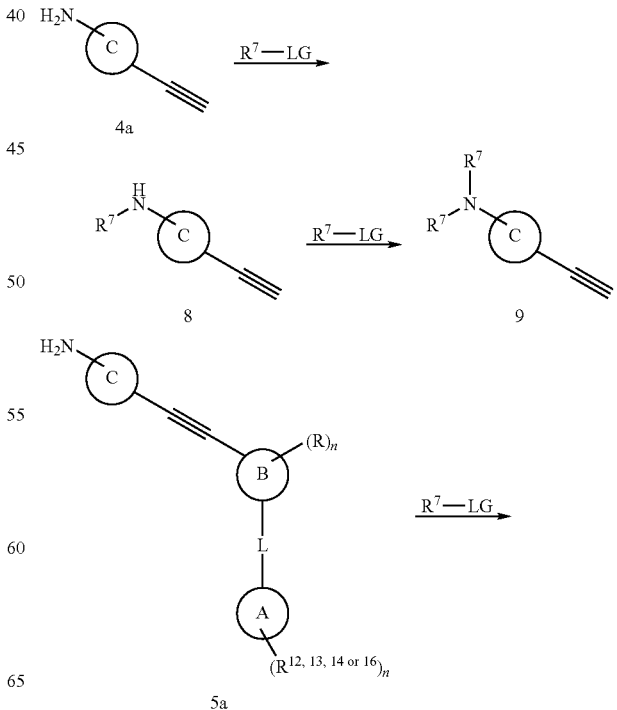

-continued

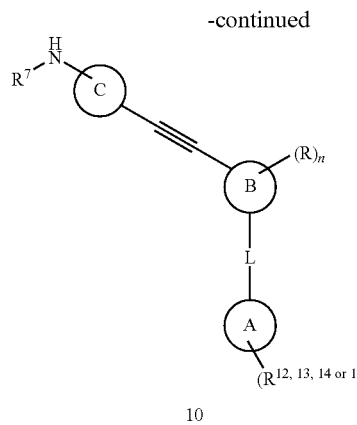

10

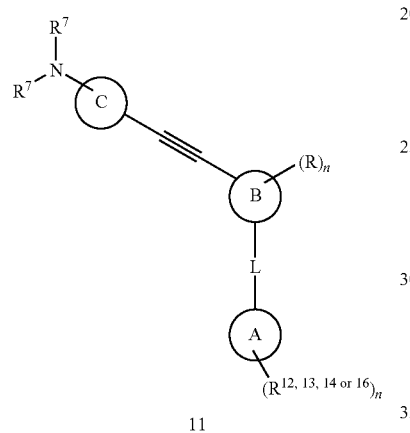

11

Various $R^7$ substitutions and/or $R^8$ substitutions (not shown) can be installed in the C ring portion, at a desired location on the C ring of the compounds of Formulas I, II and III, with or without the B-A ring system attached, as described in Scheme 4. For instance, compounds 8, 9, 10 and 11 may be made by the method described in Scheme 4. As shown, amino substitutions $R^7$ may be made by reacting the amino heteroaryl substituted alkyne compound 4a with a desired R group having a leaving group ("LG"), suitable for reaction with an aryl NH$_2$. For example, a methyl group may be covalently bound to the amine via reaction with methyl iodide. Similarly, a 2-dimethylamino substitution may be obtained via excess methyl iodide, or similar methylating reagent. Base may or may nor be needed, as appreciated by those skilled in the art. Similarly, amide or sulfonamide linkers may be obtained where $R^7$ (or $R^8$) is an activated carbonyl or sulfonyl species, such as an acid or sulfonyl chloride and the like. The acetylene group on compound 4a may need to be protected such as with a silyl group or the like, to prevent reaction at that site during the reaction to install the $R^7$ and/or $R^8$ groups, and later deprotected to couple the desired C ring system to the desired B-A ring system, utilizing methods described in Scheme 3. Such is readily appreciated by those skilled in the art. Such protection may or may not be necessary while functionalizing an amino group off of the C ring in compound 10, depending upon the particular substitutions on rings A and B.

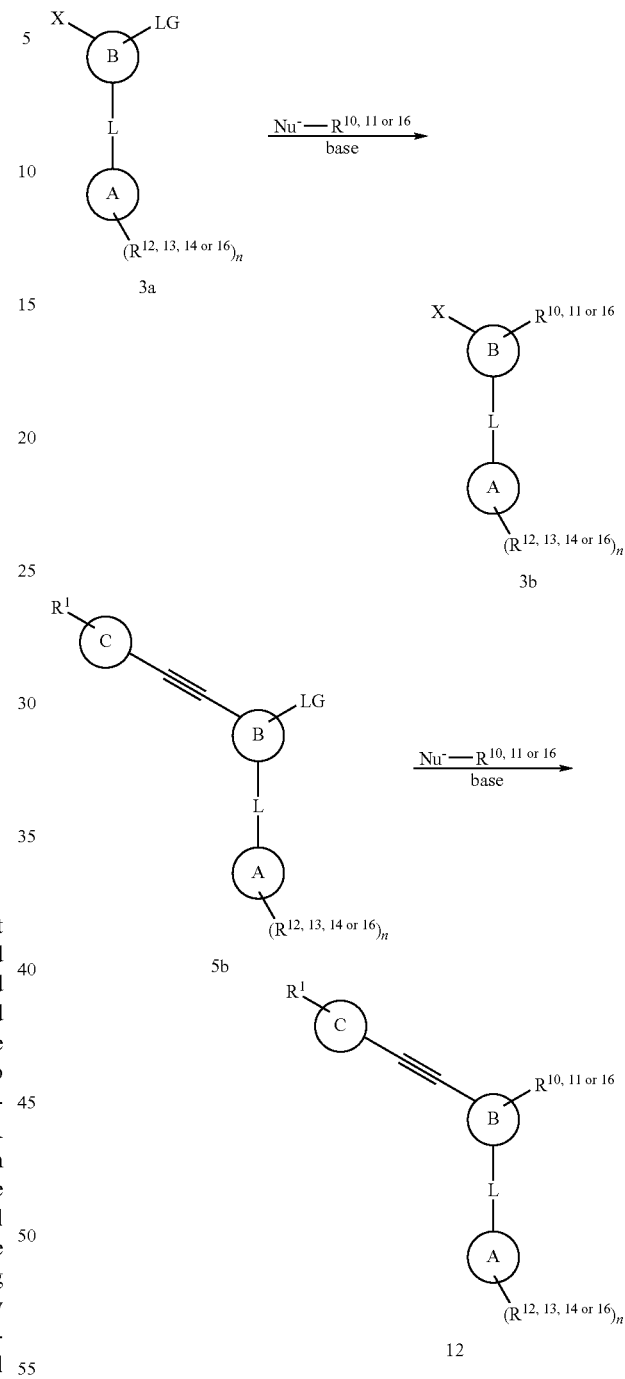

Various $R^{10}$, $R^{11}$ and $R^{16}$ substitutions, as shown on compounds 3b and 12, can be installed on the B ring of Formulas I-III, with or without the C ring system attached, as described in Scheme 5. For instance, compounds 3b and 12 may be made by the method described in Scheme 5. As shown, iodinated compounds 3a (X=I) and compounds 5b may contain suitable leaving groups, such as a fluoride, at a desired position on the B ring for substitution. Intermediates 3a and 5b may be reacted with desirable nucleophilic R groups ($R^{10}$, $R^{11}$ and $R^{16}$ substitutions), such as alkoxides, amines and the like, in the presence of a suitable base, such as a hydride or borohydride, to covalently bind the R group to the B ring. Alternatively, the B ring may have a nucleophile (not shown), such as a hydroxide or an amine, which may be further functionalized as desired via standard chemical methodology, as appreciated by those skilled in the art.

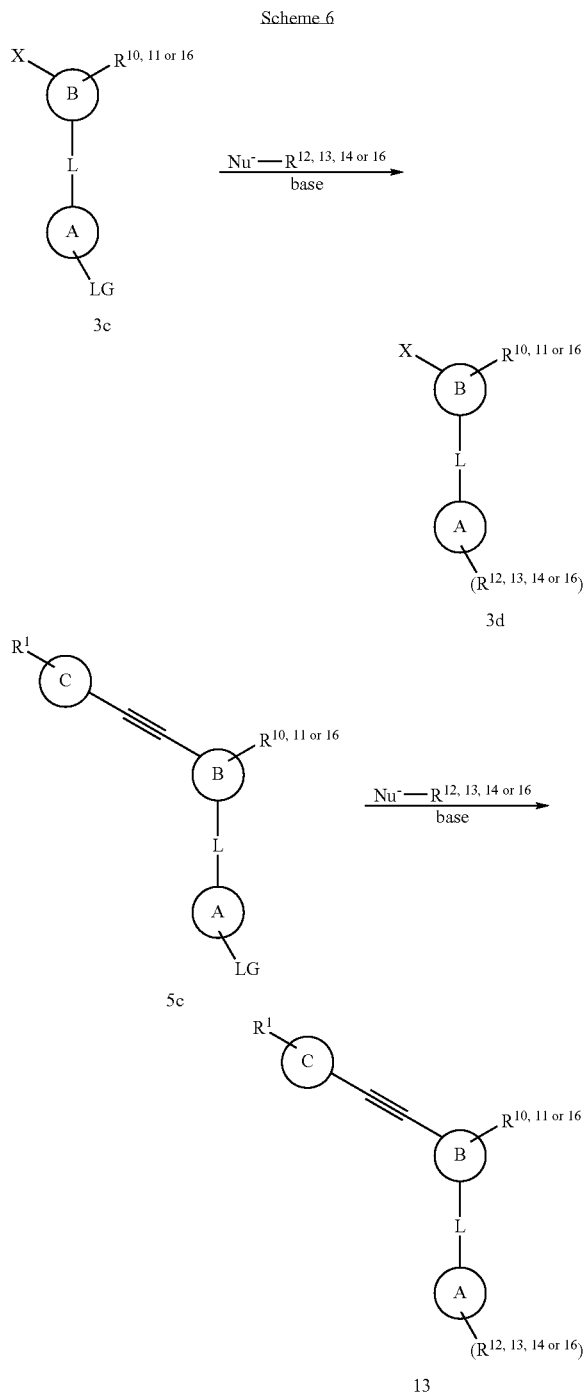

Scheme 6

Various $R^{12}$, $R^{13}$, $R^{14}$ and $R^{16}$ substitutions, as shown on compounds 3d and 13, can be installed on the A ring of Formulas I-III, with or without the C ring system attached, as described in Scheme 6. For instance, compounds 3d and 13 may be made by the method described in Scheme 6. As shown, iodinated (X=I; or amino-protected, which is not shown) aryl B ring compounds 3c, and compounds 5c may contain suitable leaving groups on the A ring, such as a halide, sulfonate, activated acid, anhydride, ester, hydroxide and the like, at a desired position for substitution. Intermediates 3c and 5c may be reacted with desirable nucleophilic R groups ($R^{12}$, $R^{13}$, $R^{14}$ and $R^{16}$ substitutions), such as alkoxides, amines and the like, in the presence of a suitable base, such as a tertiary amine base, carbonate or bicarbonate bases, hydride or borohydride bases, hydroxide and alkoxide bases, and stronger bases as necessary, to covalently bind the R group to the A ring. Other R groups such as aryl rings, acetylene groups, and the like may be attached utilizing Suzuki methods or other metal chemistry as appreciated by the skilled artisan. Alternatively, the A ring may have a nucleophile, such as a hydroxide or an amine, which may be further functionalized as desired via standard chemical methodology, as appreciated by those skilled in the art.

To enhance the understanding and appreciation of the present invention, the following exemplary methods and specific examples (starting reagents, intermediates and compounds of Formulas I, II and III) are set forth. It should be appreciated that these methods and examples are merely for illustrative purposes only and are not to be construed as limiting the scope of this invention in any manner.

Analytical Methods:

Unless otherwise indicated, all HPLC analyses were run on a Agilent Model 1100 system with an Agilent Technologies Zorbax SB-$C_8$(5μ) reverse phase column (4.6×150 mm; Part no. 883975-906) run at 30° C. with a flow rate of about 1.50 mL/min. The mobile phase used solvent A ($H_2O$/0.1% TFA) and solvent B (ACN/0.1% TFA) with a 11 min gradient from 5% to 100% ACN. The gradient was followed by a 2 min. return to 5% ACN and about a 2.5 min. re-equilibration (flush).

LC-MS Method:

Samples were run on an Agilent model-1100 LC-MSD system with an Agilent Technologies XDB-$C_8$ (3.5μ) reverse phase column (4.6×75 mm) at 30° C. The flow rate was constant and ranged from about 0.75 mL/min to about 1.0 mL/min.

The mobile phase used a mixture of solvent A ($H_2O$/0.1% HOAc) and solvent B (ACN/0.1% HOAc) with a 9 min time period for a gradient from 10% to 90% solvent B. The gradient was followed by a 0.5 min period to return to 10% solvent B and a 2.5 min 10% solvent B re-equilibration (flush) of the column.

Preparative HPLC Method:

Where indicated, compounds of interest were purified via reverse phase HPLC using a Gilson workstation utilizing one of the following two columns and methods:

(A) Using a 50×100 mm column (Waters, Exterra, C18, 5 microns) at 50 mL/min. The mobile phase used was a mixture of solvent A ($H_2O$/10 mM ammonium carbonate at pH about 10, adjusted with conc. $NH_4OH$) and solvent B (85:15 ACN/water, 10 mM ammonium carbonate at pH of about 10 adjusted with conc. $NH_4OH$). Each purification run utilized a 10 minute gradient from 40% to 100% solvent B followed by a 5 minute flow of 100% solvent B. The gradient was followed by a 2 min return to 40% solvent B.

(B) Using a 20×50 mm column at 20 mL/min. The mobile phase used was a mixture of solvent A ($H_2O$/0.1% TFA) and solvent B (ACN/0.1% TFA) with a 10 min gradient from 5% to 100% solvent B. The gradient is followed by a 2 min return to 5% ACN.

Proton NMR Spectra:

Unless otherwise indicated, all $^1$H NMR spectra were run on a Varian series Mercury 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method. Compounds having an isotopic atom, such as bromine and the like, are reported according to the detected isotopic pattern, as appreciated by those skilled in the art.

The following examples represent various starting materials and intermediates, which should assist in better understanding and appreciating the exemplary methods of synthesizing compounds of Formulas I, II and III.

Various experimental methods have been employed to synthesize compounds of Formulas I-III, as more generally described in schemes 1-6 above, and further described in more detail by the representative examples below.

Experimental Method A1

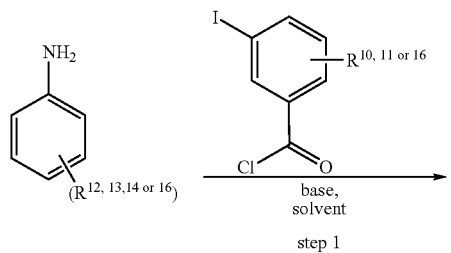

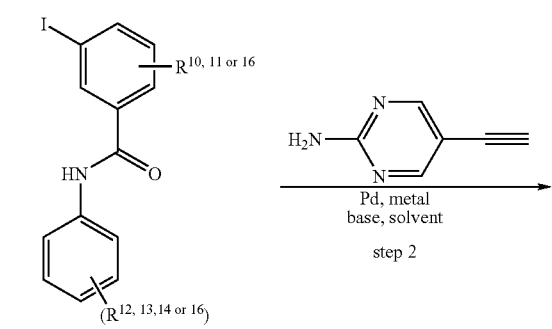

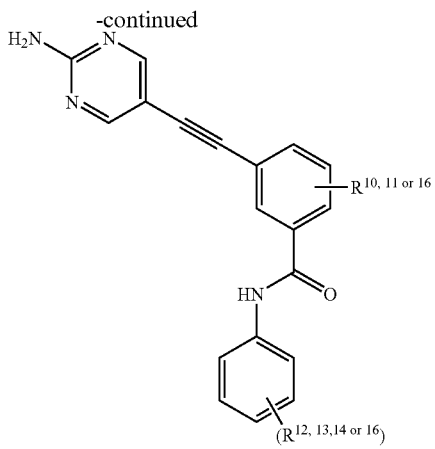

Example 1

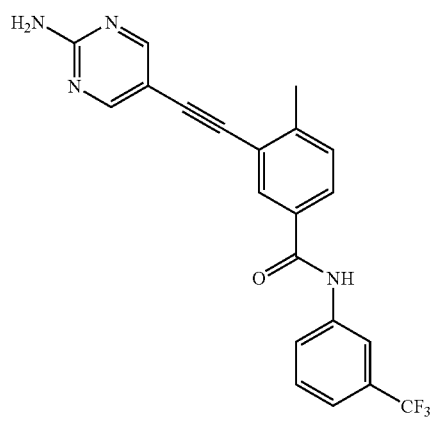

Synthesis of 3-(2-(2-aminopyrimidin-5-yl)ethynyl)-4-methyl-N-(3-(trifluoromethyl)phenyl)benzamide Step 1. Preparation of 3-iodo-4-methyl-N-(3-(trifluoromethyl)phenyl)benzamide 3-Iodo-4-methylbenzoic acid (2.0 g, 7.6 mmol) was taken up in SOCl$_2$ (4 mL). The resulting slurry was allowed to reflux for 2 h upon which time the reaction was concentrated under reduced pressure to afford the corresponding acid chloride, which was used without further purification. The off white acid-chloride solid was taken up in CH$_2$Cl$_2$ (70 mL) followed by the addition of DIEA (1.5 mL, 8.4 mmol) and 3-(trifluoromethyl)aniline (0.86 mL, 6.9 mmol). The mixture was allowed to stir at room temperature for 3 h. The reaction mixture was diluted with CH$_2$Cl$_2$ (70 mL) and washed with aq. HCl (1M, 25 mL), sat. aq. NaHCO$_3$ (25 mL), brine (25 mL), dried over anhydrous sodium sulfate, filtered and concentrated under reduced pressure to afford 3-iodo-4-methyl-N-(3-(trifluoromethyl)phenyl)benzamide as an off white solid. MS m/z=406 [M+H]$^+$. Calc'd for C$_{15}$H$_{11}$F$_3$INO: 405.

Step 2: Preparation of 3-(2-(2-aminopyrimidin-5-yl)ethynyl)-4-methyl-N-(3-(trifluoromethyl)phenyl)benzamide To a sealable tube containing 5-ethynylpyrimidin-2-amine (172 mg, 1.44 mmol), PdCl$_2$(PPh$_3$)$_2$ (25 mg, 0.036 mmol), 3-iodo-4-methyl-N-(3-(trifluoromethyl)phenyl)benzamide (292 mg, 0.72 mmol) was added MeCN (10 mL) and Et$_3$N (3 mL) followed by CuI (6.8 mg, 0.036 mmol). The tube was sealed and heated at 90° C. for 1 h. The reaction was allowed to cool to room temperature and concentrated under reduced pressure. The resulting brown solid was reconstituted in MeOH:CH$_2$Cl$_2$ (1:1, 10 mL) and silica gel was added and reconcentrated. The silica-gel combined crude mixture was purified via automated flash chromatography (silica gel, 0 to 5% MeOH in CH$_2$Cl$_2$, gradient elution) to afford 3-(2-(2-aminopyrimidin-5-yl)ethynyl)-4-methyl-N-(3-(trifluoromethyl)phenyl)benzamide. MS m/z=397 [M+H]$^+$. Calc'd for C$_{21}$H$_{15}$F$_3$N$_4$O: 396

Example 2

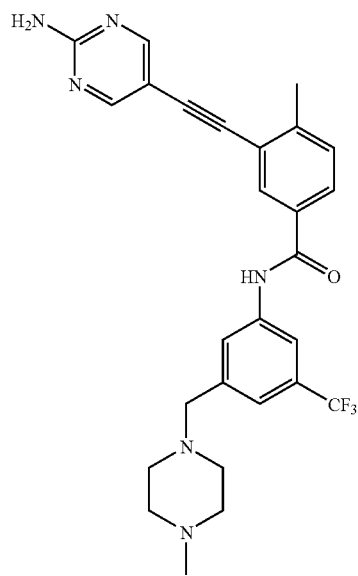

Synthesis of 3-(2-(2-aminopyrimidin-5-yl)ethynyl)-4-methyl-N-(3-((4-methylpiperazin-1-yl)methyl)-5-(trifluoromethyl)phenyl)benzamide

Step 1: Preparation of 3-iodo-4-methyl-N-(3-((4-methylpiperazin-1-yl)methyl)-5-(trifluoromethyl)phenyl)benzamide To a solution of 3-((4-methylpiperazin-1-yl)methyl)-5-(trifluoromethyl)-benzenamine (0.274 g, 1 mmol) in CH$_2$Cl$_2$ (3 mL) at room temperature was added 3-iodo-4-methylbenzoyl chloride (0.267 g, 0.95 mmol). The mixture was allowed to stir for 20 h. The reaction was concentrated under reduced pressure, and purified via column chromatography (0 to 20% methanol in dichloromethane) to afford 3-iodo-4-methyl-N-(3-((4-methylpiperazin-1-yl)methyl)-5-(trifluoromethyl)phenyl)benzamide. MS m/z=518. Calc'd for C$_{24}$H$_{18}$ClF$_3$N$_4$O: 517.33.

Step 2: Preparation of 3-(2-(2-aminopyrimidin-5-yl)ethynyl)-4-methyl-N-(3-((4-methylpiperazin-1-yl)methyl)-5-(trifluoromethyl)phenyl)benzamide Aryl iodide (0.113 g, 0.22 mmol), 2-amino-5-ethynylpyrimidine (0.53 g, 0.44 mmol), Palladium dichloro-bis-triphenylphosphine (0.008 g, 0.011 mmol), and copper(I) iodide were placed into a vial. Acetonitrile (10 mL) and triethylamine (2 mL) were added, and the mixture was heated with stirring at 90 C for 1 hour. The misture was cooled to room temperature, concentrated under reduced pressure and adsorbed onto silica gel. Flash chromatography of the pre-absorbed mixture (eluting with 0 to 20% methanol in dichloromethane) afforded 3-(2-(2-aminopyrimidin-5-yl)ethynyl)-4-methyl-N-(3-((4-methylpiperazin-1-yl)methyl)-5-(trifluoromethyl)phenyl)benzamide as a yellow semi-solid. MS m/z=509. Calc'd for C$_{24}$H$_{18}$ClF$_3$N$_4$O: 508.54.

Example 2a

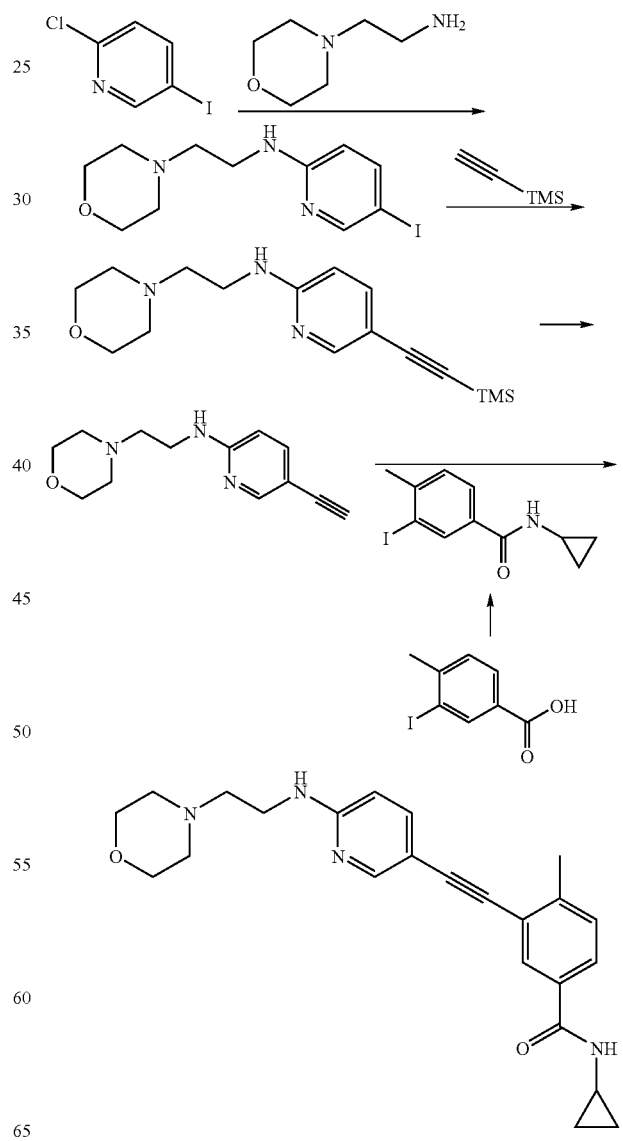

Synthesis of N-cyclopropyl-4-methyl-3-(2-(6-(2-morpholinoethylamino)pyridin-3-yl)ethynyl)benzamide

Step 1: 5-iodo-N-(2-morpholinoethyl)pyridin-2-amine

2-Chloro-5-iodopyridine (2.21 g, 9.25 mmol) was dissolved in 2-morpholinoethanamine (10 mL) and placed in the microwave for 30 min. at about 180° C. The reaction mixture was diluted with 100 mL EtOAc, washed with 50 mL saturated, aqueous NaHCO$_3$, and dried over anhydrous Na$_2$SO$_4$. After purification by chromatography, the title compound was obtained. MS (ES+): 334 (M+H)$^+$.

Step 2: N-(2-morpholinoethyl)-5-(2-(trimethylsilyl)ethynyl)pyridin-2-amine

5-Iodo-N-(2-morpholinoethyl)pyridin-2-amine (0.82 g, 2.46 mmol), TMS acetylene (1.70 mL, 12.3 mmol), and triethylamine (0.69 mL, 4.92 mmol) were dissolved in dioxane (20 mL) and with nitrogen for about 15 min. Tetrakis(triphenylphosphine)palladium (142 mg, 0.12 mmol) and copper (I) iodide (47 mg, 0.25 mmol) were added before the reaction mixture was heated to 80° C. for 3.5 h. The reaction mixture was diluted with 100 mL EtOAc, washed with 50 mL saturated, aqueous NaHCO$_3$, and dried over anhydrous Na$_2$SO$_4$. After purification by chromatography, the title compound was obtained. MS (ES+): 304 (M+H)$^+$.

Step 3: 5-ethynyl-N-(2-morpholinoethyl)pyridin-2-amine

N-(2-morpholinoethyl)-5-(2-(trimethylsilyl)ethynyl)pyridin-2-amine (2.0 g, 6.60 mmol) was dissolved in methanol (30 mL) before it was cooled to 0° C. and potassium carbonate (1.0 g, 7.26 mmol) added. The reaction mixture was stirred for 1 h at ambient temperature, then diluted with 50 mL EtOAc, washed with 20 mL saturated, aqueous NaHCO$_3$, and dried over anhydrous Na$_2$SO$_4$ to give the title compound. MS (ES+): 232 (M+H)$^+$.

Step 4: N-cyclopropyl-3-iodo-4-methylbenzamide

To 3-iodo-4-methylbenzoic acid (3.5 g, 13 mmol) was added thionyl chloride (10 mL) before heating the mixture to reflux for 1.5 h. The reaction mixture was concentrated in vacuo, and dissolved in DCM (50 mL) and Hünigs base (4.6 mL, 27 mmol). After the addition of cyclopropylamine (1.87 mL, 27 mmol) at −78° C., the reaction mixture was stirred at ambient Temp. for about 3 h. The mixture was diluted with 100 mL DCM, washed with 20 mL saturated, aqueous NaHCO$_3$ and 20 mL 3 N HCl, and dried over anhydrous Na$_2$SO$_4$. The solid obtained was suspended in EtOAc and filtered to give the title compound. MS (ES+): 302 (M+H)$^+$.

Step 5: N-cyclopropyl-4-methyl-3-(2-(6-(2-morpholinoethylamino)pyridin-3-yl)ethynyl)benzamide 5-Ethynyl-N-(2-morpholinoethyl)pyridin-2-amine (0.54 g, 2.36 mmol), N-cyclopropyl-3-iodo-4-methylbenzamide (0.71 g, 2.36 mmol), and triethylamine (0.49 mL, 3.54 mmol) were dissolved in dioxane (10 mL) before these were sparged with nitrogen for 15 min.; palladium dichloro-bis-triphenylphosphine (83 mg, 0.12 mmol) and copper (I) iodide (45 mg, 0.24 mmol) were added before the reaction mixture was heated to 90° C. for 6 h. The reaction mixture was diluted with 100 mL EtOAc, washed with 50 mL saturated, aqueous NaHCO$_3$, and dried over anhydrous Na$_2$SO$_4$. After purification by chromatography, the title compound was obtained as a yellow oil. MS (ES+): 406 (M+H)$^+$.

The following Examples 3-75 were prepared by a method similar to that described in Experimental Method A1 and Examples 1, 2 and 2a.

| Example No. | Structure | Method | MW | MS Data M + 1 | MS Data M − 1 |
|---|---|---|---|---|---|
| 3 | 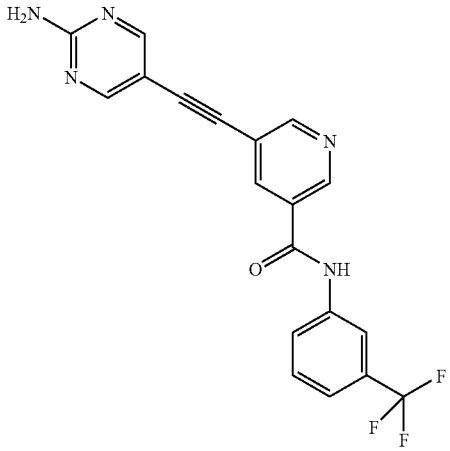 | A1 | 383.33 | 384 | |

-continued

| Example No. | Structure | Method | MW | MS Data M + 1 | MS Data M − 1 |
|---|---|---|---|---|---|
| 4 | 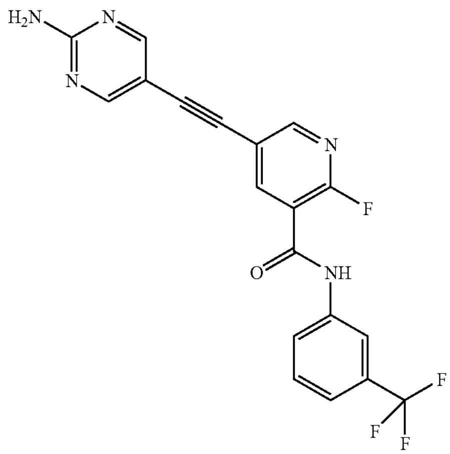 | A1 | 400.33 | 401 | |
| 5 | 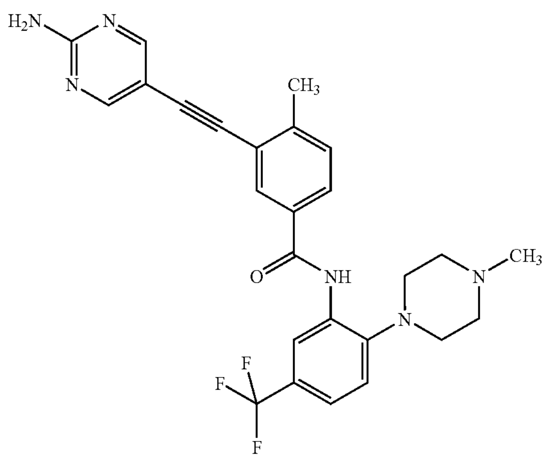 | A1 | 494.52 | 495 | |
| 6 | 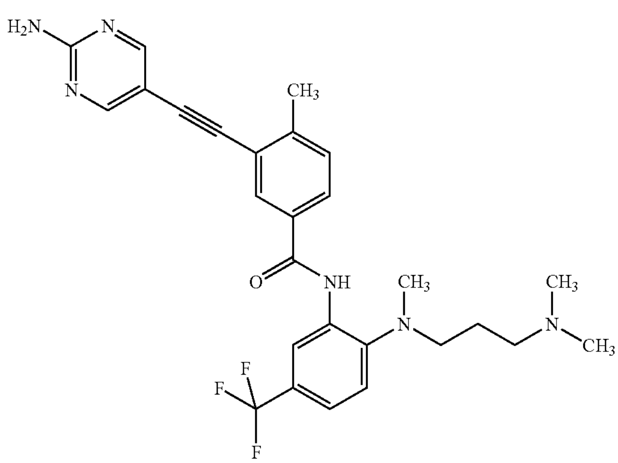 | A1 | 510.56 | 511 | |

-continued

| Example No. | Structure | Method | MW | MS Data M + 1 | MS Data M − 1 |
|---|---|---|---|---|---|
| 7 | 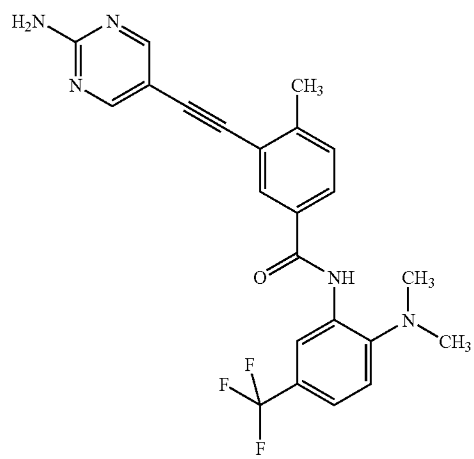 | A1 | 439.44 | 440 | |
| 8 | 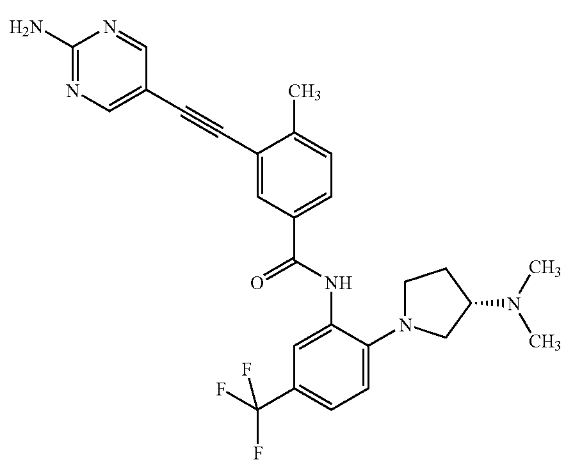 | A1 | 508.55 | 509 | |
| 9 | 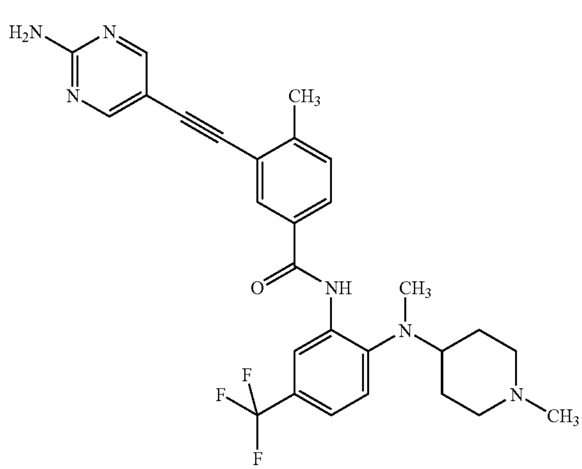 | A1 | 522.57 | 523 | |

-continued

| Example No. | Structure | Method | MW | MS Data M + 1 | MS Data M − 1 |
|---|---|---|---|---|---|
| 10 | 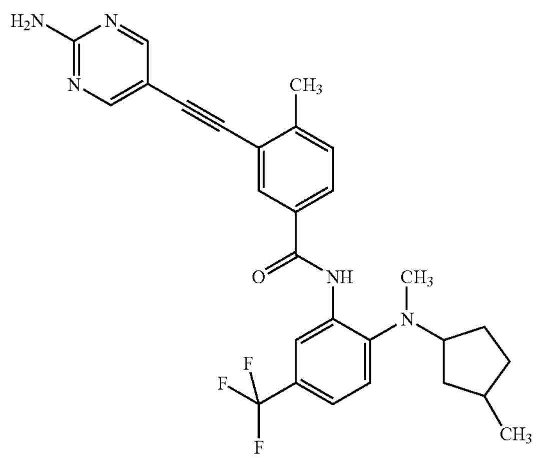 | A1 | 508.5 | 509 | |
| 11 | 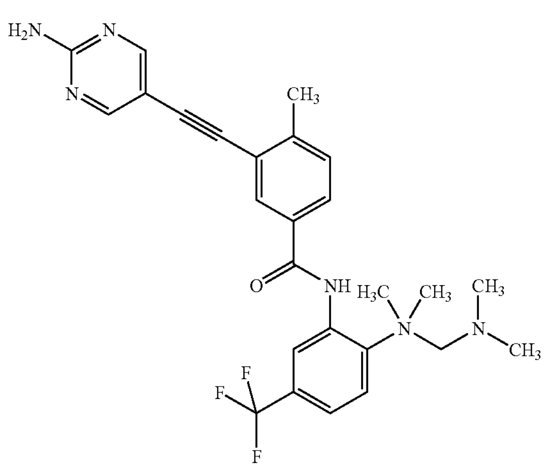 | A1 | 495.55 | 496 | |

-continued

| Example No. | Structure | Method | MW | MS Data M + 1 | MS Data M − 1 |
|---|---|---|---|---|---|
| 12 | 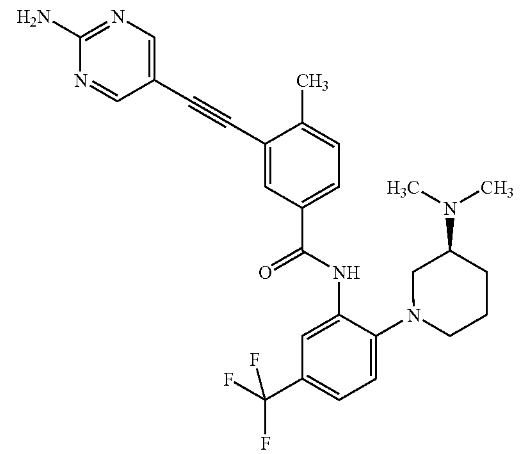 | A1 | 522.57 | 523 | |
| 13 | | A1 | 512.5 | 513 | |

-continued

| Example No. | Structure | Method | MW | MS Data M + 1 | MS Data M − 1 |
|---|---|---|---|---|---|
| 14 | 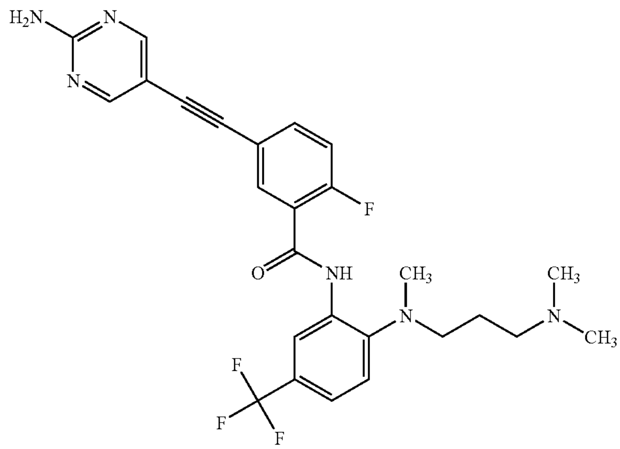 | A1 | 514.52 | 515 | |
| 15 | 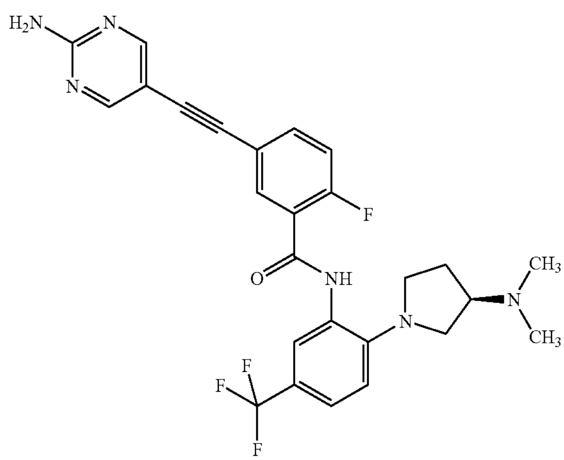 | A1 | 512.51 | 513 | |
| 16 | 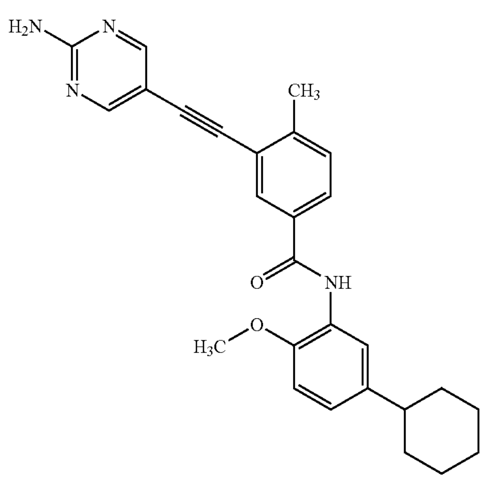 | A1 | 440.54 | 441 | |

| Example No. | Structure | Method | MW | MS Data M + 1 | MS Data M − 1 |
|---|---|---|---|---|---|
| 17 | 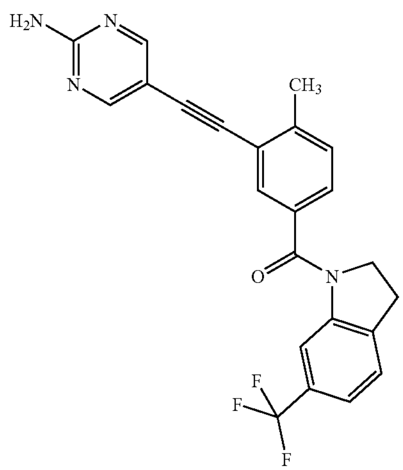 | A1 | 422.41 | 423 | |
| 18 | 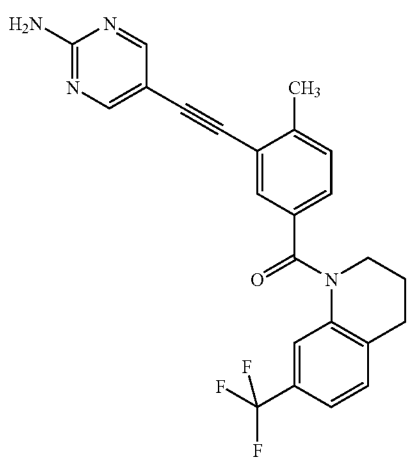 | A1 | 436.44 | 437 | |
| 19 | 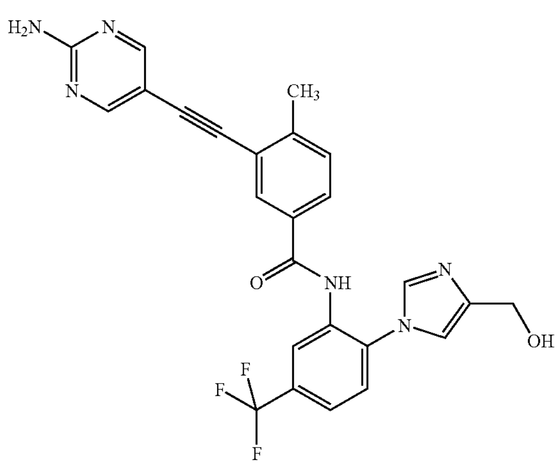 | A1 | 492.46 | 493 | |

-continued

| Example No. | Structure | Method | MW | MS Data M + 1 | MS Data M − 1 |
|---|---|---|---|---|---|
| 20 | 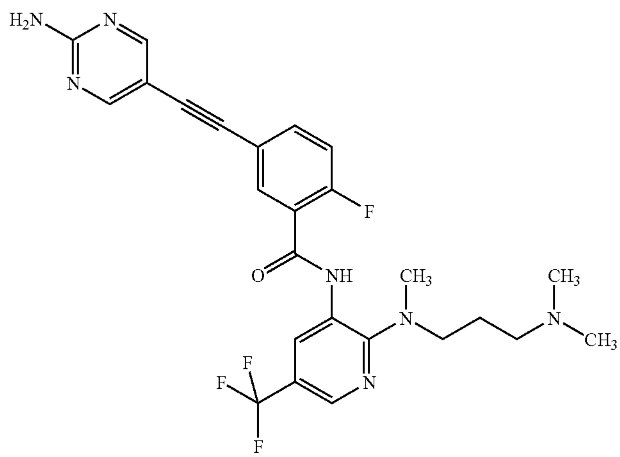 | A1 | 515.51 | 516 | |
| 21 | 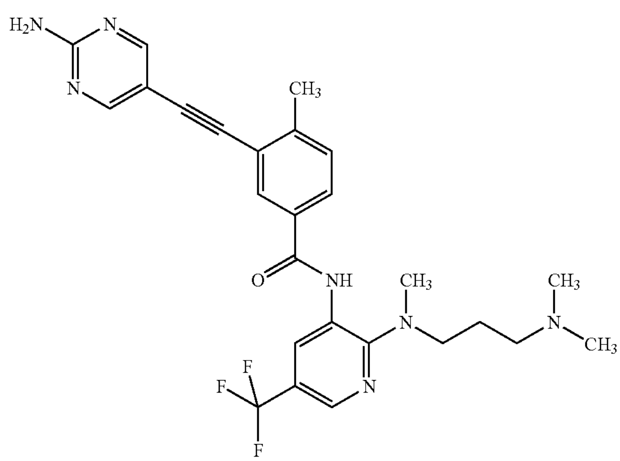 | A1 | 511.55 | 512 | |
| 22 | 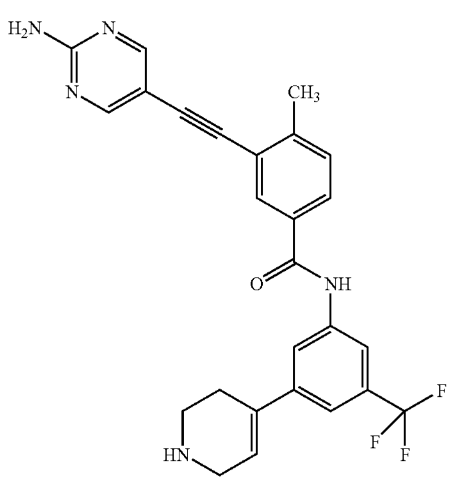 | A1 | 477.49 | 478 | |

| Example No. | Structure | Method | MW | MS Data M + 1 | MS Data M − 1 |
|---|---|---|---|---|---|
| 23 | 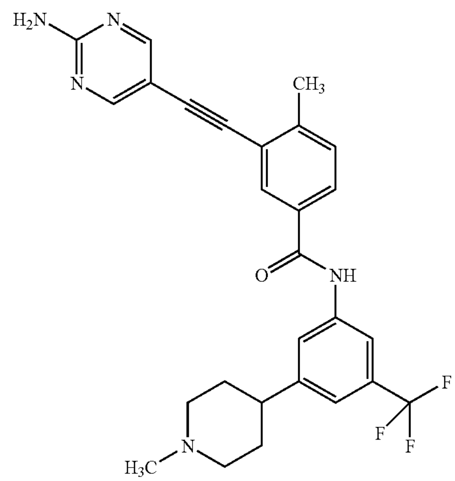 | A1 | 493.53 | 494 | |
| 24 | 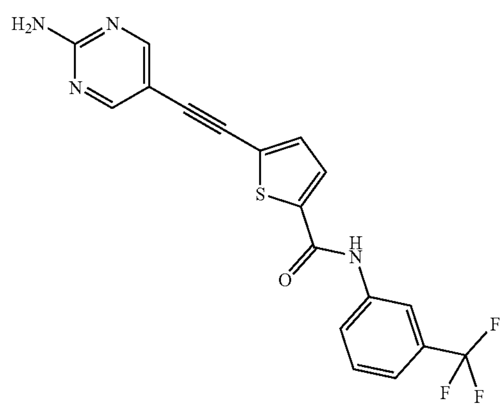 | A1 | 388.37 | 389 | |
| 25 | 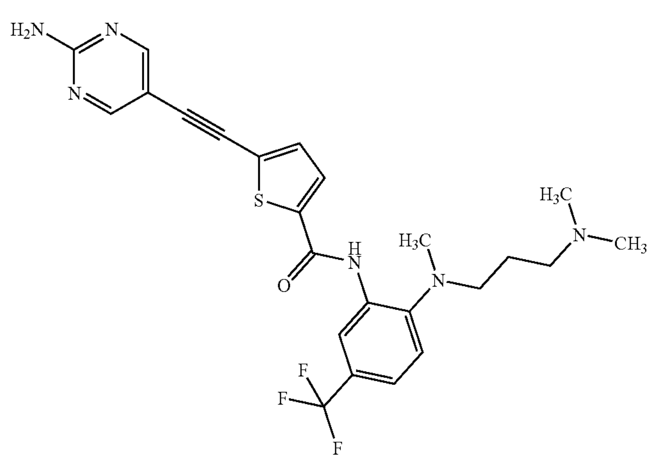 | A1 | 502.56 | 503 | |

-continued

| Example No. | Structure | Method | MW | MS Data M + 1 | MS Data M − 1 |
|---|---|---|---|---|---|
| 26 | (structure) | A1 | 384.48 | 385 | |
| 27 | (structure) | A1 | 498.67 | 500 | |
| 28 | (structure) | A1 | 490.67 | 491 | |

-continued

| Example No. | Structure | Method | MW | MS Data M + 1 | MS Data M − 1 |
|---|---|---|---|---|---|
| 29 | 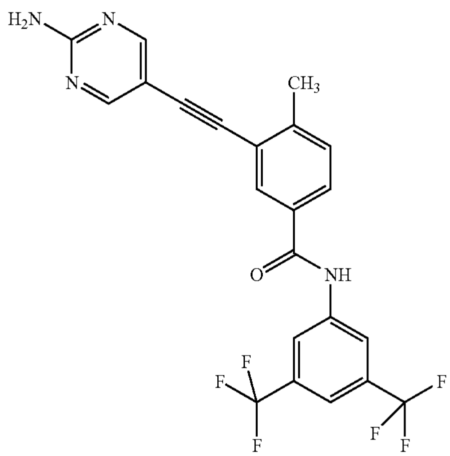 | A1 | 464.37 | 465 | |
| 30 | 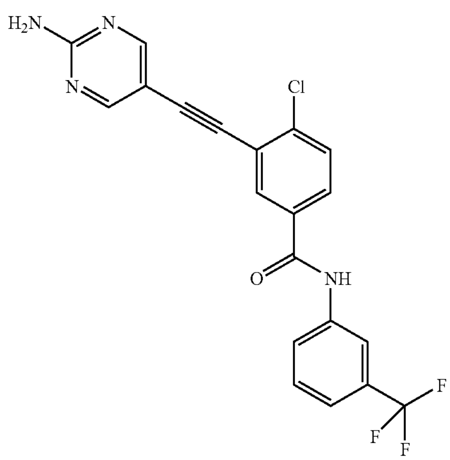 | A1 | 416.79 | 47 | |
| 31 | 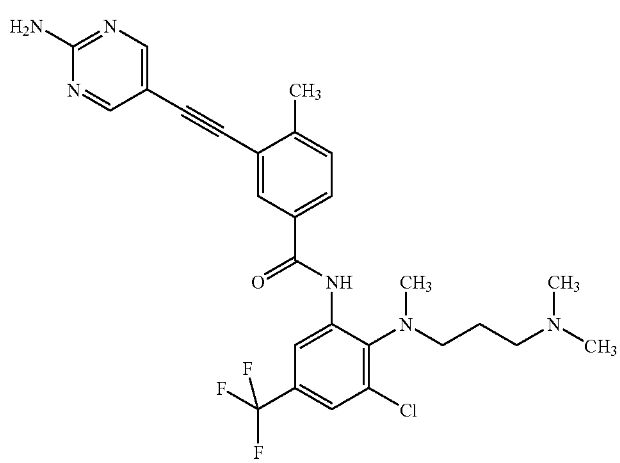 | A1 | 545.01 | 545 | |

-continued
| Example No. | Structure | Method | MW | MS Data M + 1 | MS Data M − 1 |
|---|---|---|---|---|---|
| 32 | 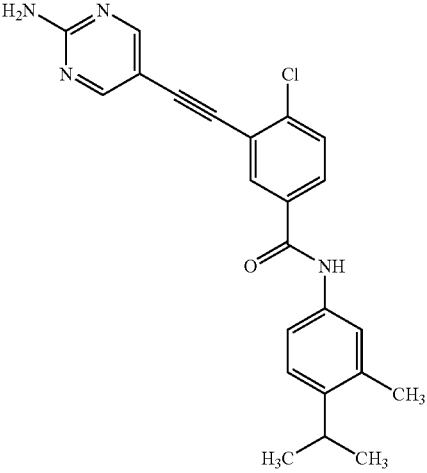 | A1 | 404.9 | 405 | |
| 33 | 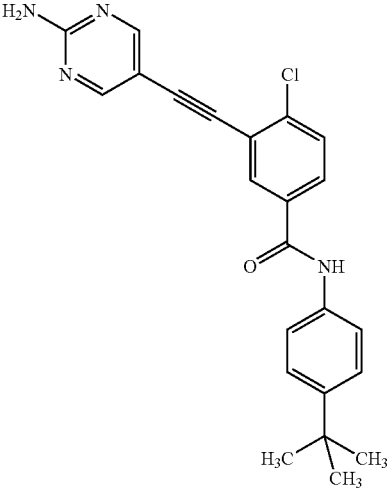 | A1 | 404.9 | 405 | |
| 34 | 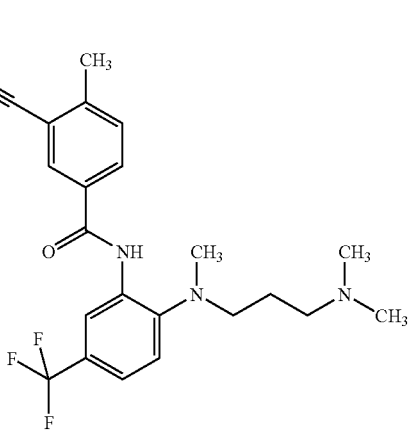 | A1 | 524.59 | 525 | |

| Example No. | Structure | Method | MW | MS Data M + 1 | MS Data M − 1 |
|---|---|---|---|---|---|
| 35 | 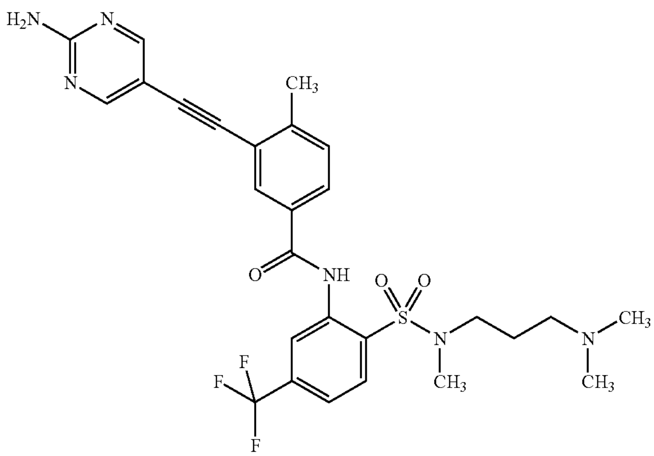 | A1 | 574.63 | 575 | |
| 36 | 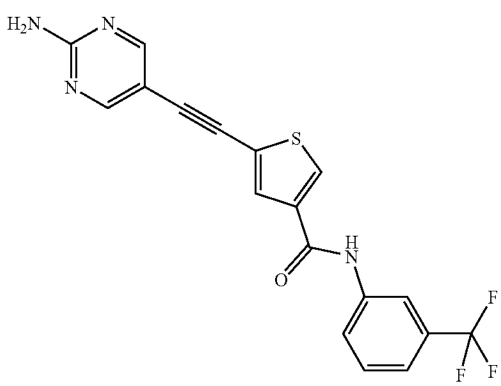 | A1 | 388.37 | 389 | |
| 37 | 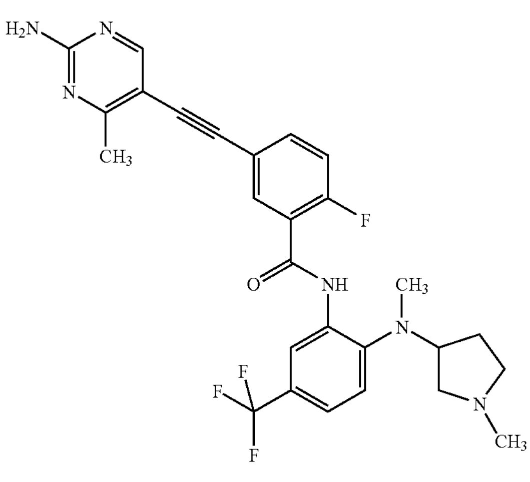 | A1 | 526.5 | 527 | |

| Example No. | Structure | Method | MW | MS Data M + 1 | MS Data M − 1 |
|---|---|---|---|---|---|
| | (structure) | | | | |
| 38 | (structure) | A1 | 477.01 | | 47 |
| 39 | (structure) | A1 | 430.82 | | 429 |

-continued

| Example No. | Structure | Method | MW | MS Data M + 1 | MS Data M − 1 |
|---|---|---|---|---|---|
| 40 | 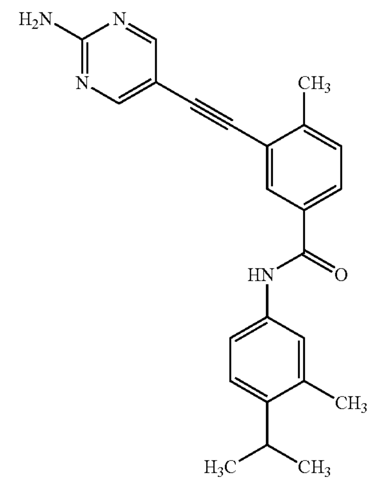 | A1 | 384.48 | | 383 |
| 41 | 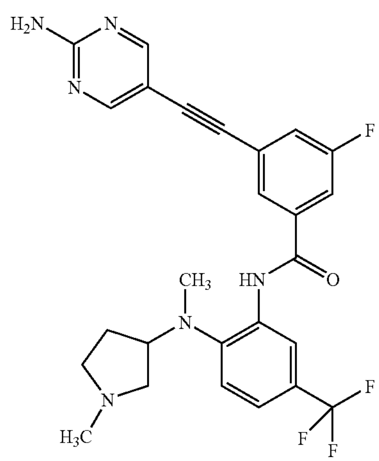 | A1 | 512.5 | 513 | |

-continued

| Example No. | Structure | Method | MW | MS Data M + 1 | MS Data M − 1 |
|---|---|---|---|---|---|
| 42 | 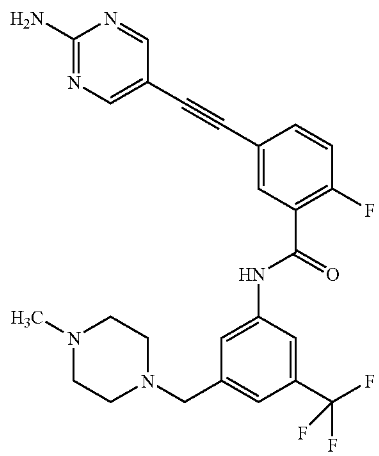 | A1 | 512.51 | 513 | |
| 43 | 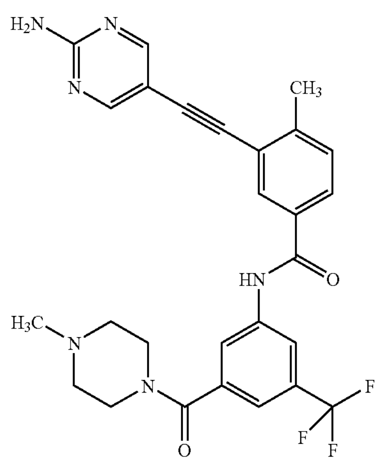 | A1 | 522.53 | 523 | |
| 44 | 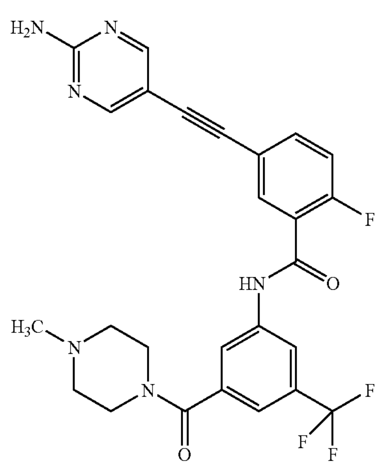 | A1 | 526.49 | 527 | |

-continued

| Example No. | Structure | Method | MW | MS Data M + 1 | MS Data M − 1 |
|---|---|---|---|---|---|
| 45 | 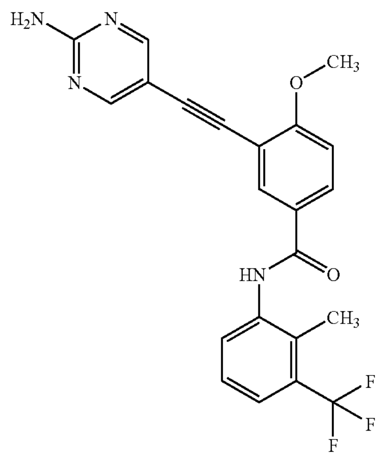 | A1 | 426.4 | | 425 |
| 46 | 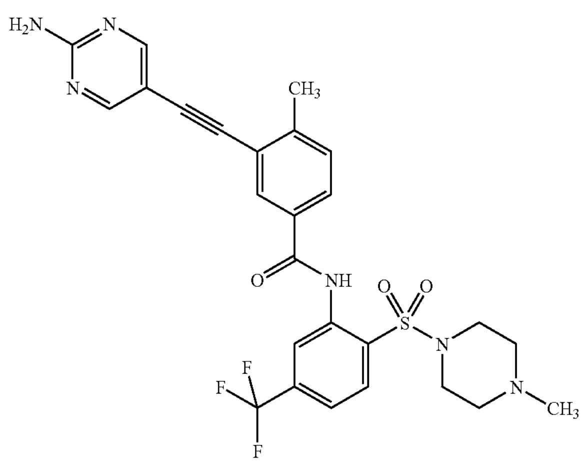 | A1 | 558.58 | 559 | |
| 47 | 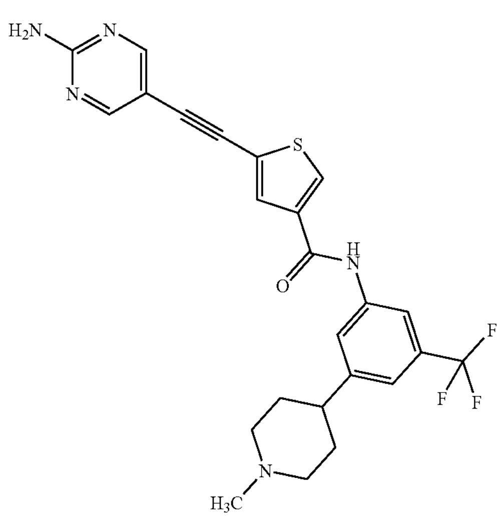 | A1 | 485.53 | 486 | |

-continued

| Example No. | Structure | Method | MW | MS Data M + 1 | MS Data M − 1 |
|---|---|---|---|---|---|
| 48 | 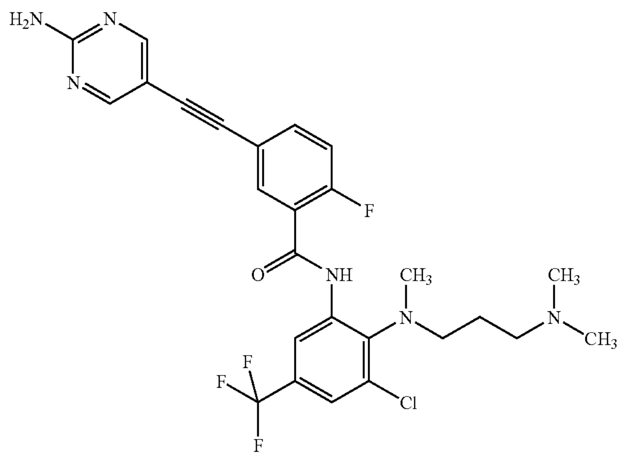 | A1 | 548.97 | 549 | |
| 49 | 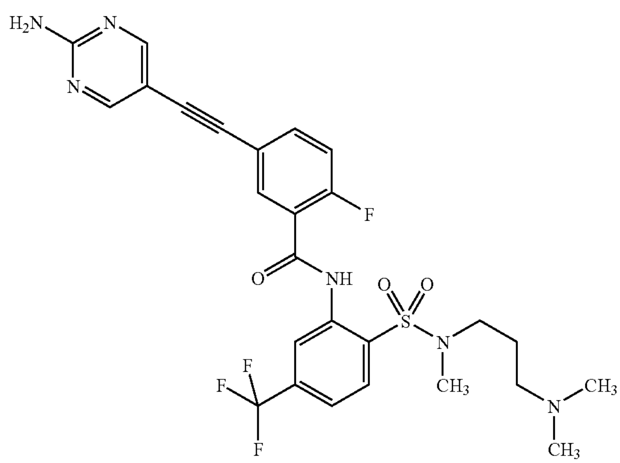 | A1 | 578.59 | 579 | |
| 50 | 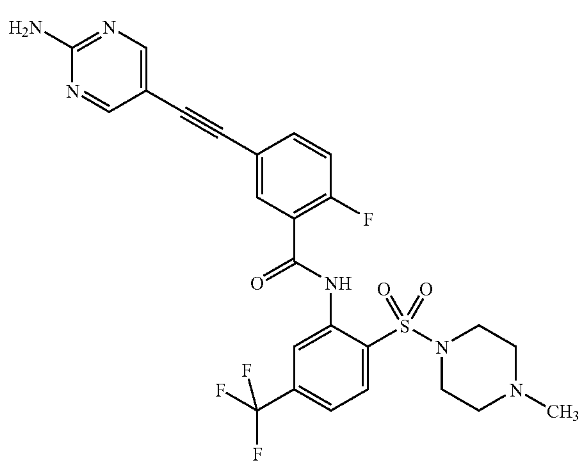 | A1 | 562.55 | 563 | |

-continued

| Example No. | Structure | Method | MW | MS Data M + 1 | MS Data M − 1 |
|---|---|---|---|---|---|
| 51 | 2-amino-pyrimidin-5-yl-ethynyl-(4-methylphenyl)-N-(2-methyl-3-trifluoromethylphenyl)benzamide | A1 | 410.4 | | 409 |
| 52 | 2-amino-pyrimidin-5-yl-ethynyl-(4-methylphenyl)-N-(3-trifluoromethoxyphenyl)benzamide | A1 | 412.37 | | 411 |
| 53 | 2-amino-pyrimidin-5-yl-ethynyl-(4-methoxyphenyl)-N-(3-trifluoromethoxyphenyl)benzamide | | 428.37 | | 427 |

-continued

| Example No. | Structure | Method | MW | MS Data M + 1 | MS Data M − 1 |
|---|---|---|---|---|---|
| 54 | 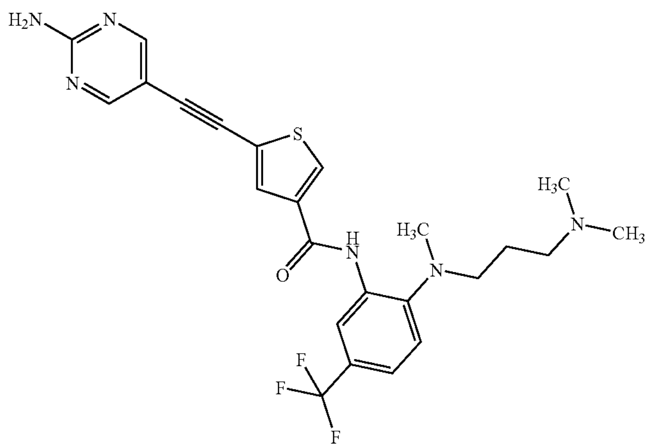 | A1 | 502.56 | 503 | |
| 55 | 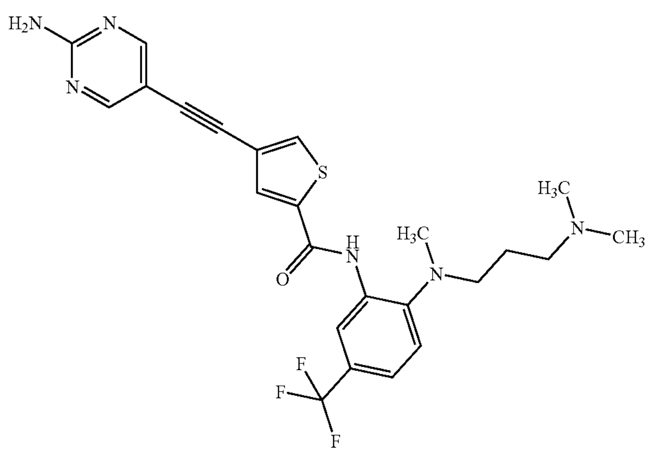 | A1 | 502.56 | 503 | |
| 56 | 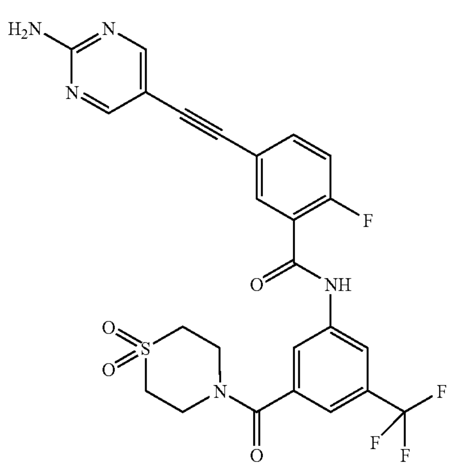 | A1 | 561.51 | 562 | |

-continued

| Example No. | Structure | Method | MW | MS Data M + 1 | MS Data M − 1 |
|---|---|---|---|---|---|
| 57 | 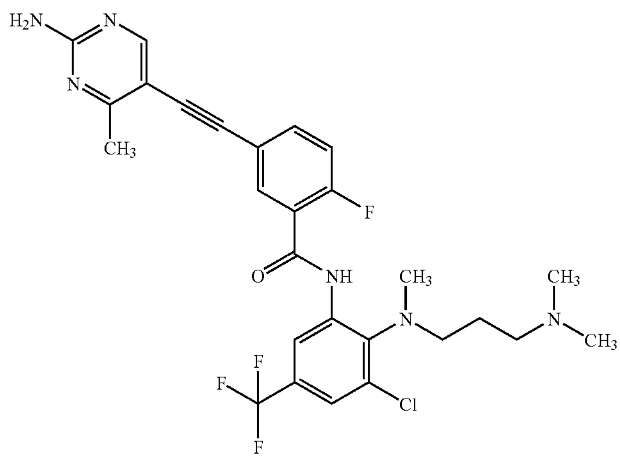 | A1 | 563 | 563 | |
| 58 | 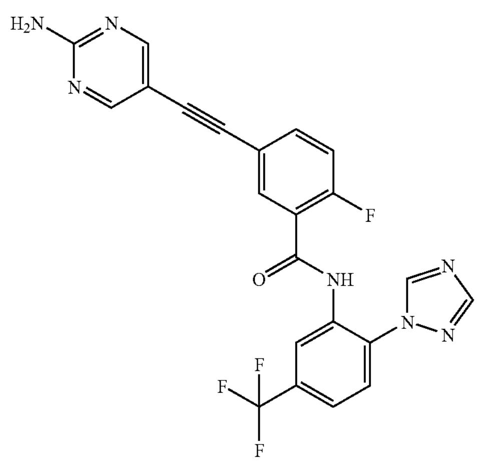 | A1 | 467.38 | 468 | |
| 59 | 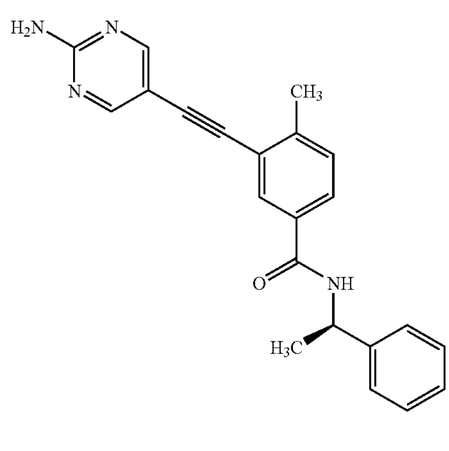 | A1 | 356.43 | 357 | |

-continued

| Example No. | Structure | Method | MW | MS Data M + 1 | MS Data M − 1 |
|---|---|---|---|---|---|
| 60 | 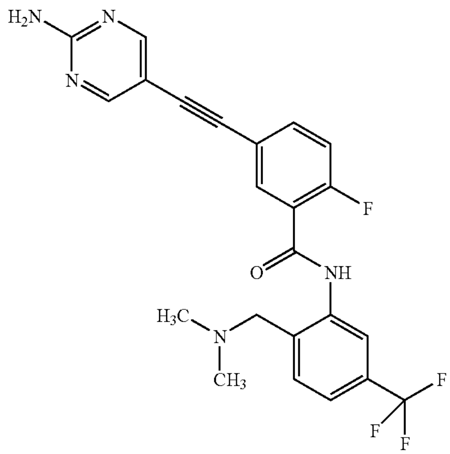 | A1 | 457.43 | 458 | |
| 61 | 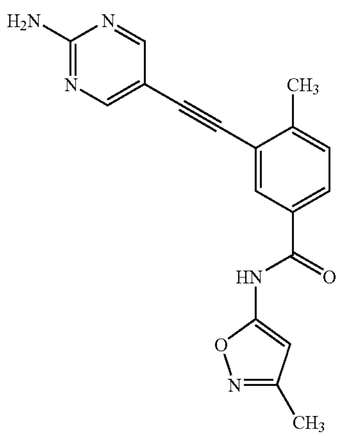 | A1 | 333.35 | | 332 |
| 62 | 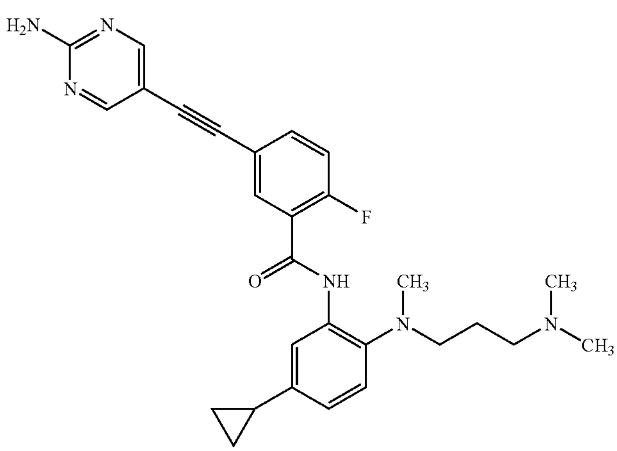 | A1 | 486.59 | 487 | |

-continued

| Example No. | Structure | Method | MW | MS Data M + 1 | MS Data M − 1 |
|---|---|---|---|---|---|
| 63 | 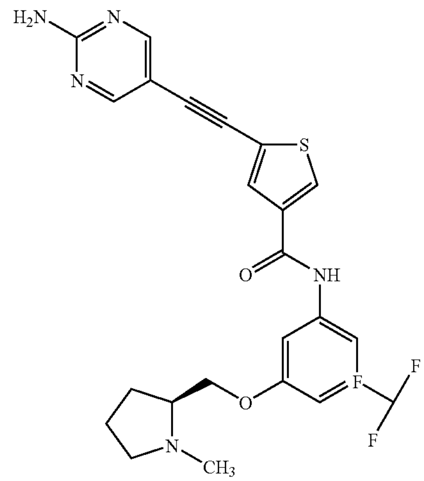 | A1 | 501.53 | 502 | |
| 64 | 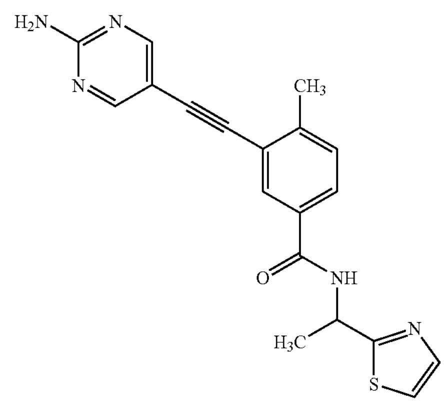 | A1 | 363.4 | 364 | |

-continued

| Example No. | Structure | Method | MW | MS Data M + 1 | MS Data M − 1 |
|---|---|---|---|---|---|
| 65 | 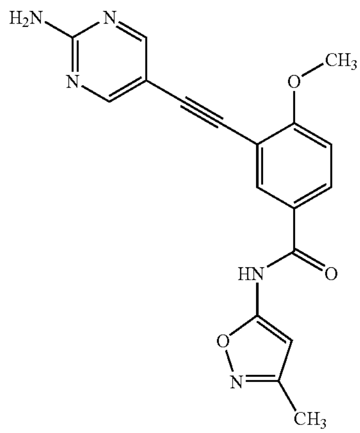 | A1 | 349.35 | | 348 |
| 66 | 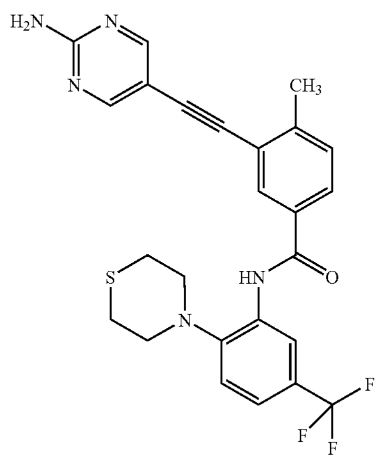 | A1 | 497.54 | 48 | |
| 67 | 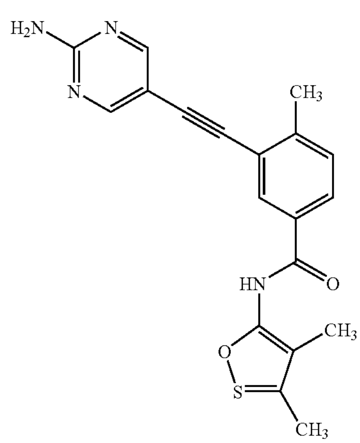 | A1 | 347.38 | | 346 |

-continued

| Example No. | Structure | Method | MW | MS Data M + 1 | MS Data M − 1 |
|---|---|---|---|---|---|
| 68 | 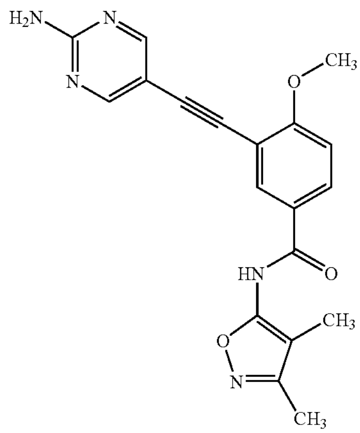 | A1 | 363.38 | | 362 |
| 69 | 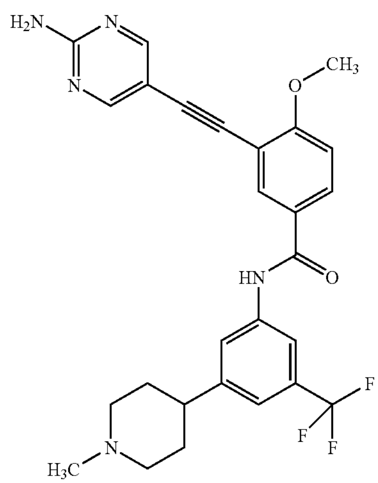 | A1 | 509.53 | | 508 |
| 70 | 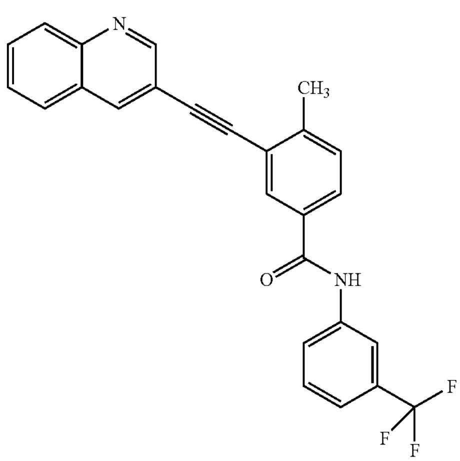 | A1 | 430.43 | 431 | |

-continued

| Example No. | Structure | Method | MW | MS Data M + 1 | MS Data M − 1 |
|---|---|---|---|---|---|
| 71 | 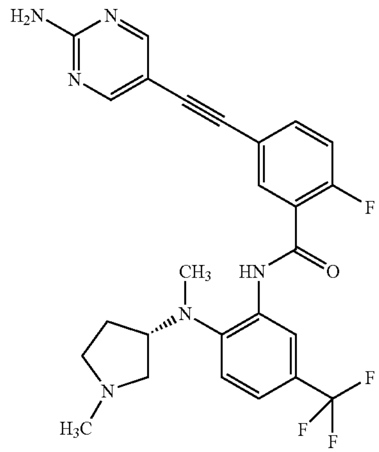 | A1 | 512.51 | 513 | |
| 72 | 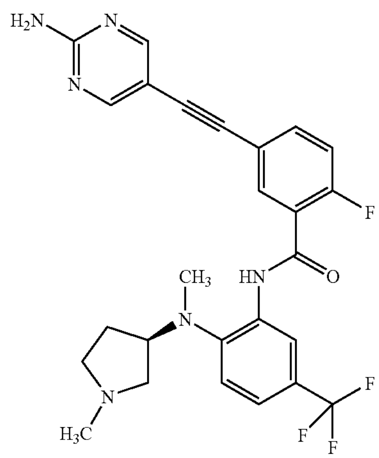 | A1 | 512.51 | 513 | |
| 73 | 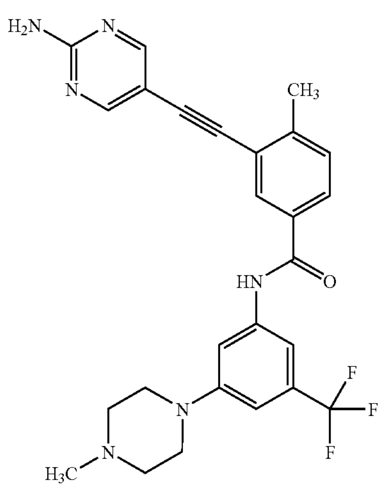 | A1 | 494.52 | | 493 |

| Example No. | Structure | Method | MW | MS Data M + 1 | MS Data M − 1 |
|---|---|---|---|---|---|
| 74 | 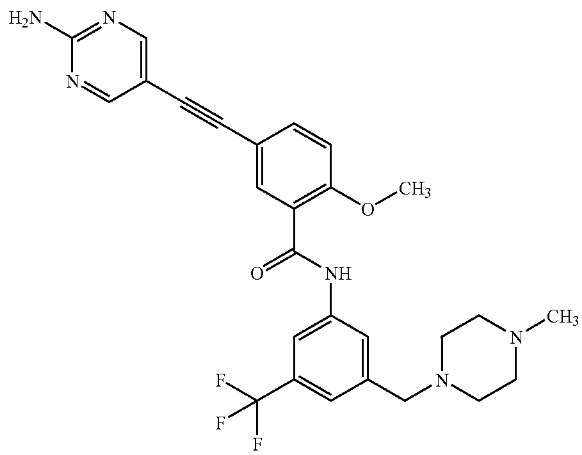 | A1 | 524.54 | 525 | |
| 75 | 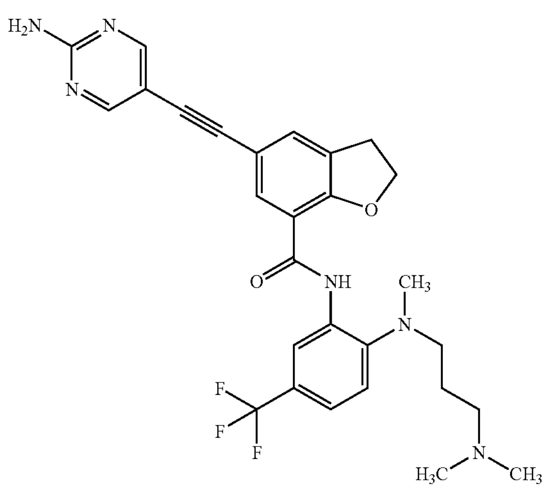 | A1 | 538.57 | 539 | |

The following Examples 76-77 were prepared by a method (Method A2) similar to that described in Experimental Method A1 and Example 2, utilizing a conventional acid to amine coupling reagent, such as HOBT, HATU, HBTU, pentafluorophenyl ester and the like, in step 1.

| Example No. | Structure | Method | MW | MS Data M + 1 | MS Data M − 1 |
|---|---|---|---|---|---|
| 76 | 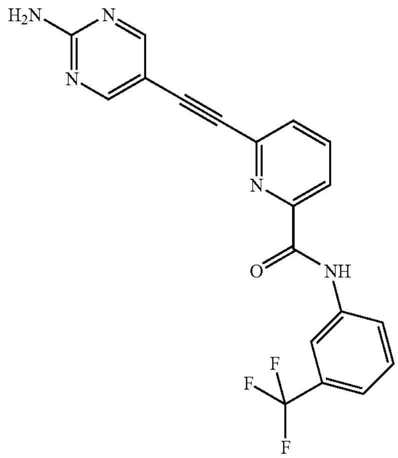 | A1 | 383.33 | 384 | |
| 77 | 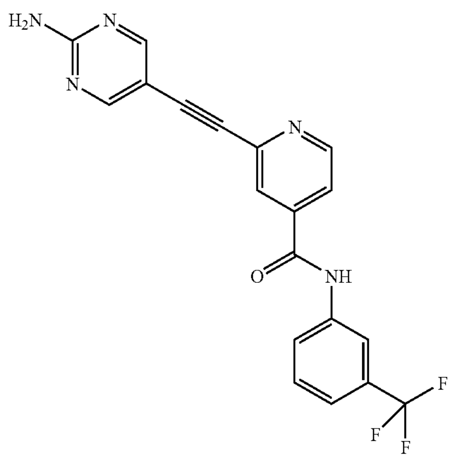 | A1 | 383.33 | 384 | |
Experimental Method A3
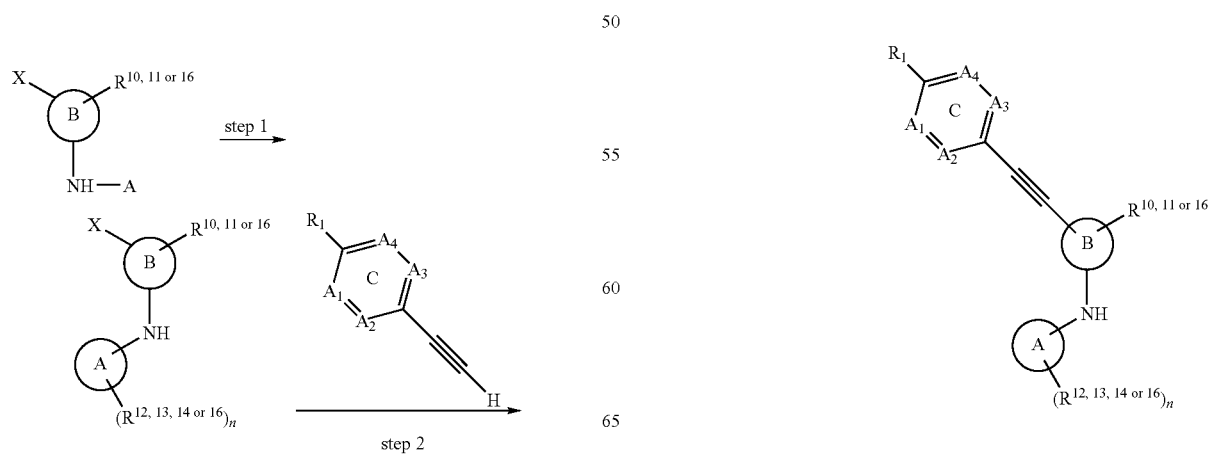

Example 77-V

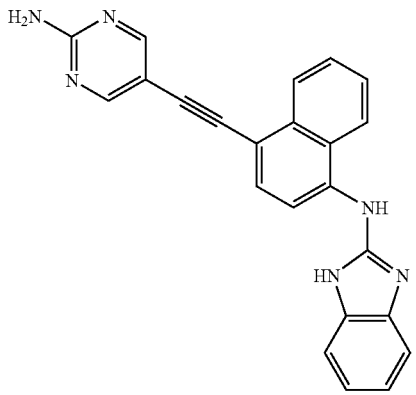

N-(4-(2-(2-aminopyrimidin-5-yl)ethynyl)naphthalen-1-yl)-1H-benzo[d]imidazol-2-amine

Step 1: 1-bromo-4-isothiocyanatonaphthalene

To a solution of 1-bromo-4-aminonapthalene (2.6 g, 12 mmol) in dichloromethane (45 mL) was added di(1H-imidazol-1-yl)methanethione (2.1 g, 12 mmol). The reaction was allowed to stir for 16 h, at which point the reaction was concentrated to give a gray solid. The solid was slurried in 50% EtOAc/hexanes and filtered through a pad of silica gel, rinsing with 400 mL 50% EtOAc/hexanes. The solution was concentrated to give 1-bromo-4-isothiocyanatonaphthalene as a gray solid, which was used without further purification.

Step 2: N-4-bromonaphthalen-1-yl)-1H-benzo[d]imidazol-2-amine

A slurry of 1-bromo-4-isothiocyanatonaphthalene (1.0 g, 3.8 mmol), o-phenylene diamine (0.45 g, 4.2 mmol), and polymer-supported carbodiimide (9.0 g, 11 mmol, 1.27 mmol/g) in 72 mL THF was heated to 70° C. with a water-cooled reflux condenser for 3 h. The reaction was filtered, rinsing with dichloromethane. The solution was concentrated to a yellow solid, suspended in dichloromethane, and filtered, rinsing with a small quantity of diethyl ether to give N-(4-bromonaphthalen-1-yl)-1H-benzo[d]imidazol-2-amine as a white solid. MS m/z=338 [M+1]$^+$. Calc'd for $C_{17}H_{12}BrN_3$: 337

Step 3 N-(4-(2-(2-aminopyrimidin-5-yl)ethynyl)naphthalen-1-yl)-1H-benzo[d]imidazol-2-amine The title compound was prepared in a manner to that described in experimental procedure A1 step 2. MS m/z=377 [M+1]$^+$. Calc'd for $C_{23}H_{16}N_6$: 376

Example 77-V-1

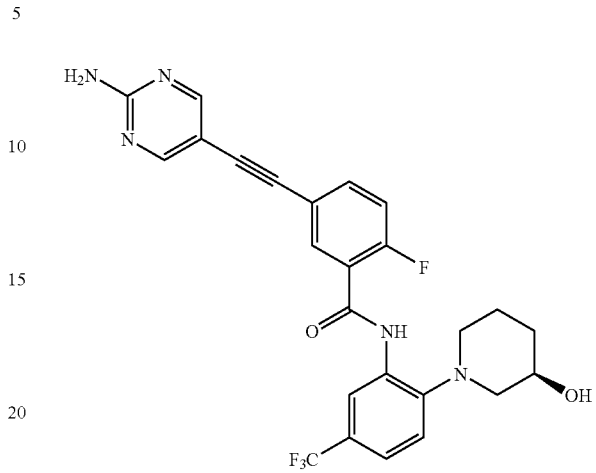

Synthesis of (R)-5-(2-(2-aminopyrimidin-5-yl)ethynyl)-2-fluoro-N-(2-(3-hydroxypiperidin-1-yl)-5-(trifluoromethyl)phenyl)benzamide

Step 1: Preparation of (R)-1-(2-nitro-4-(trifluoromethyl)phenyl)piperidin-3-ol To a 100-mL round bottom flask (RBF) was added (R)-piperidin-3-ol hydrochloride (1.29 g, 9.37 mmol), sodium bicarbonate (2.76 g, 32.8 mmol), THF and 1-fluoro-2-nitro-4-(trifluoromethyl)benzene (1.31 ml, 9.37 mmol). The yellow mixture was heated to 75° C. with a water-cooled reflux condenser and allowed to stir 14 h. The reaction was filtered through a glass frit, rinsing with EtOAc, and concentrated in vacuo to give (R)-1-(2-nitro-4-(trifluoromethyl)phenyl)piperidin-3-ol as an orange oil.

Step 2: Preparation of (R)-3-(tert-butyldimethylsilyloxy)-1-(2-nitro-4-(trifluoromethyl)phenyl)piperidine To a solution of (R)-1-(2-nitro-4-(trifluoromethyl)phenyl)piperidin-3-ol (3.35 g, 11.5 mmol) and imidazole (1.02 g, 15.0 mmol) in DMF at ambient temperature under nitrogen was added tert-butyldimethylsilylchloride (1.91 g, 12.7 mmol). The reaction was allowed to stir for 24 h, at which point additional 0.3 g tert-butyldimethylsilylchloride was added. The reaction was allowed to stir for an additional 14 h, and was then poured into Et$_2$O/saturated aqueous NaHCO$_3$. The organic layer was washed 2×H$_2$O, 1×brine, dried over anhydrous MgSO$_4$, filtered and concentrated to a yellow oil. The crude material was treated with hexanes and adsorbed onto silica gel and passed through a Redi-Sep® pre-packed silica gel column (80 g) eluting with 0-20% EtOAc/hexane. The product-containing fractions were concentrated to afford (R)-3-(tert-butyldimethylsilyloxy)-1-(2-nitro-4-(trifluoromethyl)phenyl)piperidine as a yellow oil. MS m/z=405 [M+H]$^+$. Calc'd for $C_{18}H_{27}F_3N_2O_3Si$: 404.

Step 3: Preparation of (R)-2-(3-(tert-butyldimethylsilyloxy)piperidin-1-yl)-5-(trifluoromethyl)benzenamine A 200 mL RBF was charged with (R)-3-(tert-butyldimethylsilyloxy)-1-(2-nitro-4-(trifluoromethyl)phenyl)piperidine (4.10 g, 10.1 mmol) and palladium, 10 wt. % on activated carbon wet (0.179 ml, 2.03 mmol) under nitrogen. MeOH was added via syringe, and the atmosphere replaced with hydrogen via one or more balloons. The reaction was stirred rapidly for 60 h. The reaction was flushed with nitrogen, filtered through celite rinsing with 100 mL MeOH, and concentrated in vacuo. The crude material was treated with hexanes and passed through a Redi-Sep® pre-packed silica gel column (80 g) eluting with 0-40% EtOAc/hexane. The product-containing fractions were concentrated to afford (R)-2-(3-(tert-butyldimethylsilyloxy)piperidin-1-yl)-5-(trifluoromethyl)benzenamine as a brown oil. MS m/z=375 [M+H]$^+$. Calc'd for $C_{18}H_{29}F_3N_2OSi$: 374.

Step 4: Preparation of (R)-N-(2-(3-(tert-butyldimethylsilyloxy)piperidin-1-yl)-5-(trifluoromethyl)phenyl)-2-fluoro-5-iodobenzamide In a vial, (R)-2-(3-(tert-butyldimethylsilyloxy)piperidin-1-yl)-5-(trifluoromethyl)benzenamine (0.517 g, 1.4 mmol) was taken up in THF. Triethylamine (0.29 ml, 2.1 mmol) and 2-fluoro-5-iodobenzoyl chloride (0.43 g, 1.5 mmol) were added. The vial was sealed and the reaction stirred for 48 h. The reaction mixture was poured into EtOAc/1N NaOH. The organic layer was dried over anhydrous sodium sulfate and concentrated in vacuo. The crude material was treated with hexanes and passed through a Redi-Sep® pre-packed silica gel column (40 g) eluting with 0-10% EtOAc/hexane. The product-containing fractions were concentrated to afford (R)-N-(2-(3-(tert-butyldimethylsilyloxy)piperidin-1-yl)-5-(trifluoromethyl)phenyl)-2-fluoro-5-iodobenzamide as a white foam.

Step 5: Preparation of (R)-5-(2-(2-aminopyrimidin-5-yl)ethynyl)-N-(2-(3-(tert-butyldimethylsilyloxy)piperidin-1-yl)-5-(trifluoromethyl)phenyl)-2-fluorobenzamide In a 16×120 mm resealable pyrex tube, 5-ethynylpyrimidin-2-amine (0.080 g, 0.67 mmol), (R)-N-(2-(3-(tert-butyldimethylsilyloxy)piperidin-1-yl)-5-(trifluoromethyl)phenyl)-2-fluoro-5-iodobenzamide (0.210 g, 0.34 mmol), Bis(triphenylphosphine)palladium(II) dichloride (0.012 g, 0.017 mmol), and Copper(I) iodide (0.0032 g, 0.017 mmol) were taken up in CH$_3$CN and Triethylamine (0.71 ml, 5.1 mmol) was added, and the tube was flushed with nitrogen. The tube was sealed and the reaction heated to 70° C. overnight. The reaction was cooled, and transferred to a 50 mL RBF with EtOAc. The mixture was concentrated in vacuo, and the resulting solid was treated with 10% MeOH in CH$_2$Cl$_2$ and adsorbed onto 1.5 g silica gel and passed through a Redi-Sep®D pre-packed silica gel column (40 g) eluting with 0-60% EtOAc/hexane. The product-containing fractions were concentrated to afford (R)-5-(2-(2-aminopyrimidin-5-yl)ethynyl)-N-(2-(3-(tert-butyldimethylsilyloxy)piperidin-1-yl)-5-(trifluoromethyl)phenyl)-2-fluorobenzamide as an off-white solid.

Step 6: Preparation of (R)-5-(2-(2-aminopyrimidin-5-yl)ethynyl)-2-fluoro-N-(2-(3-hydroxypiperidin-1-yl)-5-(trifluoromethyl)phenyl)

To a yellow solution of (R)-5-(2-(2-aminopyrimidin-5-yl)ethynyl)-N-(2-(3-(tert-butyldimethylsilyloxy)piperidin-1-yl)-5-(trifluoromethyl)phenyl)-2-fluorobenzamide (0.162 g, 0.264 mmol) was added tetrabutylammonium fluoride, 1.0 M in THF (0.688 ml, 2.38 mmol). The reaction was allowed to stir for 6 h, at which point it was found by TLC analysis to be complete. The reaction was diluted with EtOAc and washed once with brine. The organic layer was dried over anhydrous sodium sulfate and concentrated in vacuo to give a yellow oil, which was purified by silica gel chrmatography, 0-10% MeOH/MC to give (R)-5-(2-(2-aminopyrimidin-5-yl)ethynyl)-2-fluoro-N-(2-(3-hydroxypiperidin-1-yl)-5-(trifluoromethyl)phenyl)benzamide as an off-white solid. MS m/z=500 [M+H]$^+$. Calc'd for $C_{25}H_{21}F_4N_5O_2$: 499.

Example 77-V-2

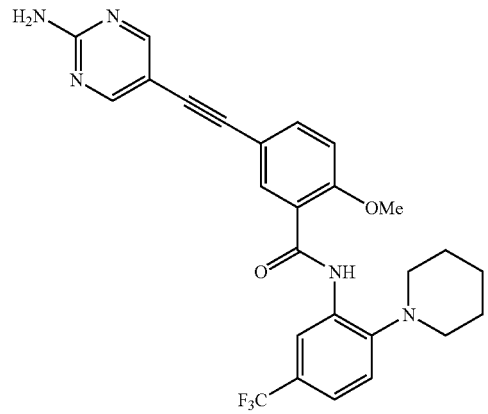

Synthesis of 5-(2-(2-aminopyrimidin-5-yl)ethynyl)-2-methoxy-N-(2-(piperidin-1-yl)-5-(trifluoromethyl)phenyl)benzamide A mixture of 5-(2-(2-aminopyrimidin-5-yl)ethynyl)-2-fluoro-N-(2-(piperidin-1-yl)-5-(trifluoromethyl)phenyl)benzamide (0.14 g, 0.29 mmol) and NaOMe (0.5 M solution in methanol, 2.0 mL, 1.0 mmol) in a sealed tube was heated to reflux. After 16 h, the reaction was cooled and partitioned between EtOAc and brine. The organic layer was dried over anhydrous sodium sulfate, filtered, and concentrated. The material was purified by preparative TLC, eluting with 30% acetone/dichloromethane to give 5-(2-(2-aminopyrimidin-5-yl)ethynyl)-2-methoxy-N-(2-(piperidin-1-yl)-5-(trifluoromethyl)phenyl)benzamide as a white solid. MS m/z=496 [M+H]$^+$. Calc'd for $C_{26}H_{24}F_3N_5O_2$: 495.

Example 77-V-3

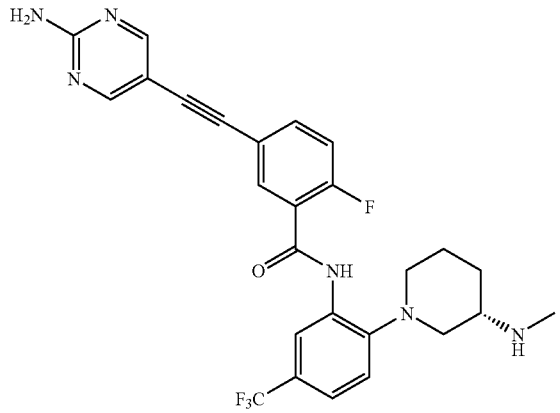

Synthesis of (S)-5-(2-(2-aminopyrimidin-5-yl)ethynyl)-2-fluoro-N-(2-(3-(methylamino)piperidin-1-yl)-5-(trifluoromethyl)phenyl)benzamide

Step 1: Preparation of (S)-tert-butyl methyl(1-(2-nitro-4-(trifluoromethyl)phenyl)piperidin-3-yl)carbamate To an orange solution of (S)-tert-butyl 1-(2-nitro-4-(trifluoromethyl)phenyl)piperidin-3-ylcarbamate (1.50 g, 3.9 mmol) in DMF at 0 deg. C. was added sodium hydride, 60% dispersion in mineral oil (0.19 g, 4.8 mmol). Bubbling was observed, and the solution became darker orange. After about 20 min, iodomethane (0.30 ml, 4.8 mmol) was added dropwise via syringe. The orange mixture was allowed to warm to room temperature over 30 min. Water was added, followed by diethyl ether. The organics were washed 1×H$_2$O, 1×brine, dried over anhydrous Na$_2$SO$_4$, filtered, and concentrated to give (S)-tert-butyl methyl(1-(2-nitro-4-(trifluoromethyl)phenyl)piperidin-3-yl)carbamate as an orange semi-solid which was used without further purification. MS m/z=404 [M+H]$^+$. Calc'd for C$_{18}$H$_{24}$F$_3$N$_3$O$_4$: 403.

Step 2: Preparation of (S)-tert-butyl 1-(2-amino-4-(trifluoromethyl)phenyl)piperidin-3-yl(methyl)carbamate To a 100 mL RBF was added (S)-tert-butyl methyl(1-(2-nitro-4-(trifluoromethyl)phenyl)piperidin-3-yl)carbamate (1.75 g, 4.34 mmol) and palladium, 10 wt. % on activated carbon wet (0.923 g, 0.868 mmol) under nitrogen. MeOH was added via syringe, and the atmosphere was purged with hydrogen from a balloon. The reaction was allowed to stir rapidly under hydrogen for 8 h. The flask was purged with nitrogen, filtered through celite, rinsing with 100 mL MeOH, and concentrated to give (S)-tert-butyl 1-(2-amino-4-(trifluoromethyl)phenyl)piperidin-3-yl(methyl)carbamate as a gray solid. MS m/z=374 [M+H]$^+$. Calc'd for C$_{18}$H$_{26}$F$_3$N$_3$O$_2$: 373.

Step 3: Preparation of (S)-tert-butyl 1-(2-(2-fluoro-5-iodobenzamido)-4-(trifluoromethyl)phenyl)piperidin-3-yl(methyl)carbamate In a vial, (S)-tert-butyl 1-(2-amino-4-(trifluoromethyl)phenyl)piperidin-3-yl(methyl)carbamate (0.500 g, 1.3 mmol) was taken up in CH2Cl2. The solution was cooled to 0 deg. C. and Triethylamine (0.24 ml, 1.7 mmol) and 2-fluoro-5-iodobenzoyl chloride (0.42 g, 1.5 mmol) were added. The tube was sealed and the reaction stirred for 2 h. The reaction mixture was poured into EtOAc/1N NaOH. The organic layer was dried over anhydrous sodium sulfate and concentrated in vacuo. The resulting off-white-foam (S)-tert-butyl 1-(2-(2-fluoro-5-iodobenzamido)-4-(trifluoromethyl)phenyl)piperidin-3-yl(methyl)carbamate was used without further purification. MS m/z=622 [M+H]$^+$. Calc'd for C$_{25}$H$_{28}$F$_4$IN$_3$O$_3$: 621.

Step 4: Preparation of (S)-tert-butyl 1-(2-(5-(2-(2-aminopyrimidin-5-yl)ethynyl)-2-fluorobenzamido)-4-(trifluoromethyl)phenyl)piperidin-3-yl(methyl)carbamate In a 25-mL RBF (S)-tert-butyl 1-(2-(2-fluoro-5-iodobenzamido)-4-(trifluoromethyl)phenyl)piperidin-3-yl(methyl)carbamate (0.496 g, 0.80 mmol), 5-ethynylpyrimidin-2-amine (0.19 g, 1.6 mmol), Bis(triphenylphosphine)palladium (II) dichloride (0.028 g, 0.040 mmol), and Copper(I) iodide (0.0076 g, 0.040 mmol) were taken up in CH$_3$CN and Triethylamine (1.7 ml, 12 mmol) was added, and the tube was flushed with nitrogen. The tube was sealed and the reaction heated to 70 deg. C. for 16 h. The reaction was cooled and transfered to a larger flask with EtOAc and concentrated in vacuo. The solid was adsorbed onto 4 g silica gel from 10% MeOH/MC purified by Isco {Redi-Sep® pre-packed silica gel column (80 g); eluent 0-75% EtOAc/hexanes over 30 min}. Product-containing fractions were concentrated to afford (S)-tert-butyl 1-(2-(5-(2-(2-aminopyrimidin-5-yl)ethynyl)-2-fluorobenzamido)-4-(trifluoromethyl)phenyl)piperidin-3-yl(methyl)carbamate as a orange foam. MS m/z=613 [M+H]$^+$. Calc'd for C$_{31}$H$_{32}$F$_4$N$_6$O$_3$: 612.

Step 5: Preparation of (S)-5-(2-(2-aminopyrimidin-5-yl)ethynyl)-2-fluoro-N-(2-(3-(methylamino)piperidin-1-yl)-5-(trifluoromethyl)phenyl)benzamide To a yellow solution of (S)-tert-butyl 1-(2-(5-(2-(2-aminopyrimidin-5-yl)ethynyl)-2-fluorobenzamido)-4-(trifluoromethyl)phenyl)piperidin-3-yl(methyl)carbamate (0.397 g, 0.65 mmol) in 3 mL dioxane at 0 deg. C. was added hydrogen chloride 4.0 M in dioxane (1.6 ml, 6.5 mmol). The reaction was allowed to warm to ambient temp, as the clump, which formed would not go into solution. 3 mL of CH$_2$Cl$_2$, was added followed by 5 mL MeOH to give a homogenous yellow solution. After 30 min, the solution was concentrated in vacuo to give a yellow solid, which was treated with 1N NaOH and EtOAc. The organic layer was washed twice with 1N NaOH, dried over anhyd. Na$_2$SO$_4$, filtered, and concentrated in vacuo to give (S)-5-(2-(2-aminopyrimidin-5-yl)ethynyl)-2-fluoro-N-(2-(3-(methylamino)piperidin-1-yl)-5-(trifluoromethyl)phenyl)benzamide as a light yellow solid. MS m/z=513 [M+H]$^+$. Calc'd for C$_{26}$H$_{24}$F$_4$N$_6$O: 512.

Example 77-V-4

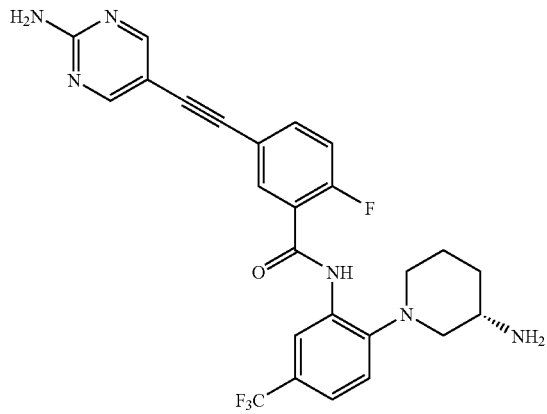

Synthesis of (S)-N-(2-(3-aminopiperidin-1-yl)-5-(trifluoromethyl)phenyl)-5-(2-(2-aminopyrimidin-5-yl)ethynyl)-2-fluorobenzamide The title compound was synthesized in a manner analogous to that described in Example 77-V-3. MS m/z=499 [M+H]$^+$. Calc'd for $C_{25}H_{22}F_4N_6O$: 498.

Experiental Method B

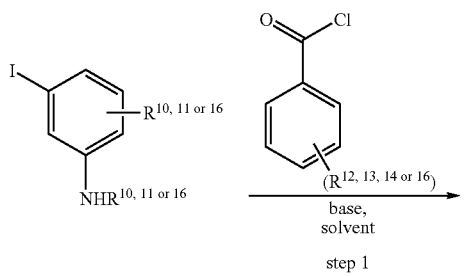

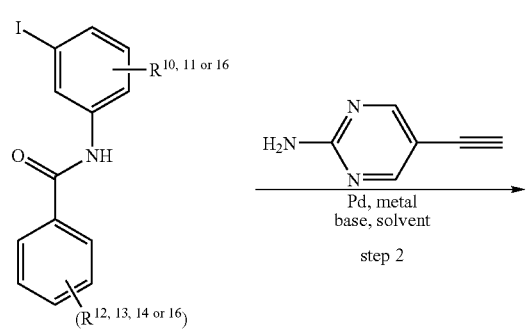

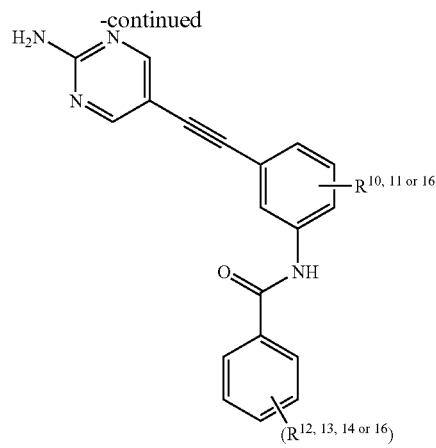

Example 78

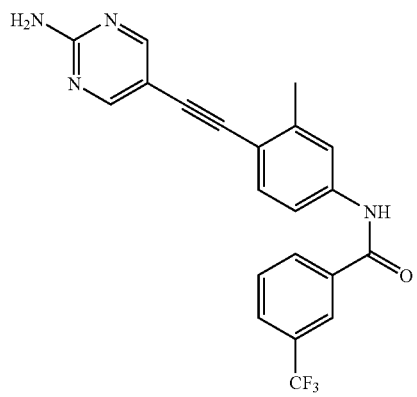

Synthesis of N-(4-(2-(2-aminopyrimidin-5-yl)ethynyl)-3-methylphenyl)-3-(trifluoromethyl)benzamide Step 1: Preparation of N-(4-iodo-3-methylphenyl)-3-(trifluoromethyl)benzamide To a solution of 4-iodo-3-methyl aniline (200 mg, 0.86 mmol) and $^i$Pr$_2$NEt (0.19 mL, 0.95 mmol) in CH$_2$Cl$_2$ (10 mL) was added 3-(trifluoromethyl)benzoyl chloride (0.133 mL, 0.90 mmol). The mixture was allowed to stir at room temperature for 0.5 h at which time it was diluted with CH$_2$Cl$_2$ (20 mL). The organic layer was washed with aq. HCl (10 mL, 1 M), 9% aq. Na$_2$CO$_3$ (10 mL), brine, dried over anhydrous sodium sulfate, filtered and concentrated under reduced pressure. The resulting oil was used without further purification.

Step 2: N-(4-(2-(2-aminopyrimidin-5-yl)ethynyl)-3-methylphenyl)-3-(trifluoromethyl)benzamide The title compound was prepared in a manner similar to that described Experimental Method A1, Example 1-step 2. MS m/z=397 [M+H]$^+$. Calc'd for $C_{21}H_{15}F_3N_4O$: 396

The following Examples 79-80 were prepared by a method similar to that described in Experimental Method B and Example 78.

| Example No. | Structure | Method | MW | MS Data M + 1 | MS Data M − 1 |
|---|---|---|---|---|---|
| 79 | 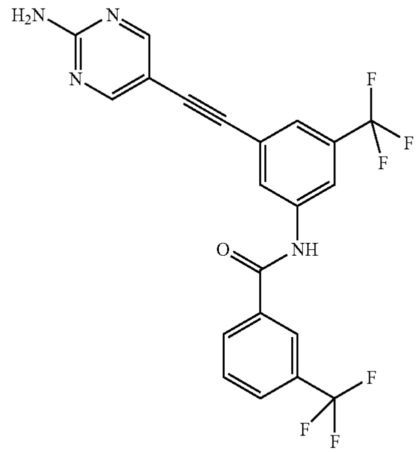 | B1 | 450.34 | 451 | |
| 80 | 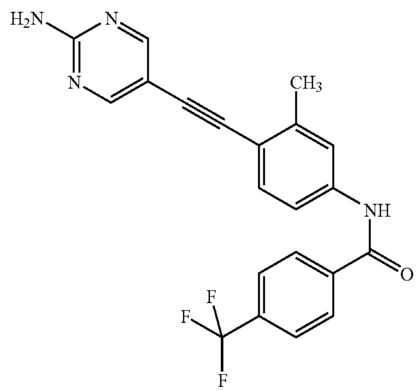 | B1 | 396.37 | 397 | |
Experimental Method C1
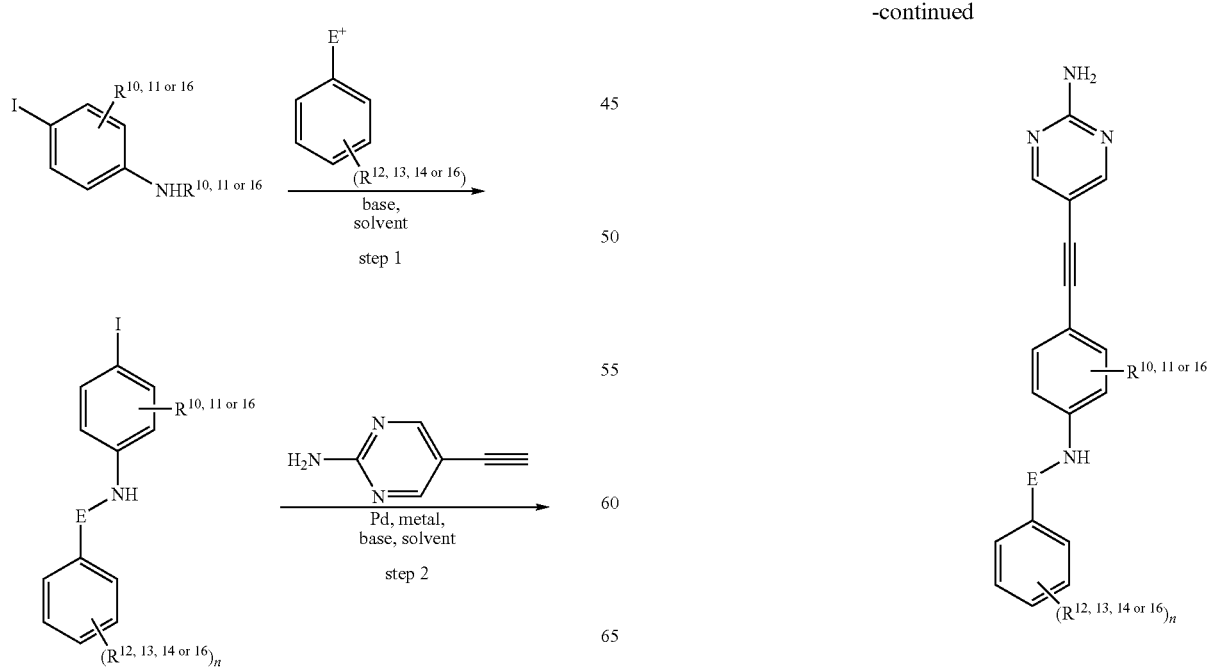

Example 81

Synthesis of 1-(4-(2-(2-aminopyrimidin-5-yl)ethynyl)-3-methylphenyl)-3-(3-(trifluoromethyl)phenyl) urea

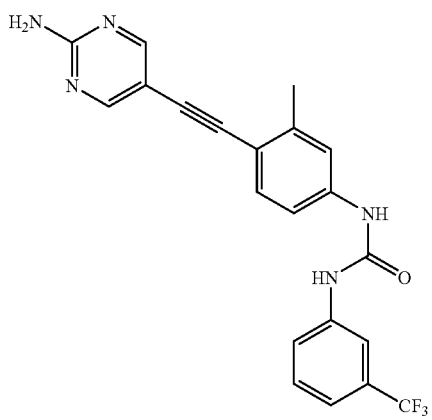

Step 1: 1-(4-iodo-3-methylphenyl)-3-(3-(trifluoromethyl)phenyl)urea

To a solution of 4-iodo-3-methylaniline (200 mg, 0.86 mmol) in benzene (5 mL) in a sealable tube was added 1-isocyanato-3-(trifluoromethyl)benzene (0.133 mL, 0.94 mL; "E" is an electrophilic group disussed in scheme 3, and here is an isocyanate). The tube was sealed and heated at 90° C. for 4 h. The mixture was allowed to cool to room temperature before filtering. The off white solid was washed with additional benzene (10 mL) and used without further purification.

Step 2: 1-(4-(2-(2-aminopyrimidin-5-yl)ethynyl)-3-methylphenyl)-3-(3-(trifluoromethyl)phenyl)urea The title compound was prepared in a manner similar to that described Experimental Method A1, Example 1-step 2. MS m/z=412 [M+H]$^+$. Calc'd for $C_{21}H_{16}F_3N_5O$: 411

The following Example 82 was prepared by a method similar to that described in Experimental Method C1 and Example 81.

| Example No. | Structure | Method | MW | MS Data M + 1 | MS Data M − 1 |
|---|---|---|---|---|---|
| 82 | 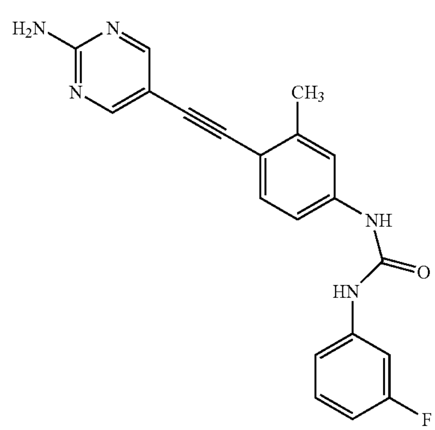 | C1 | 361.38 | 362 | |

Experimental Method D

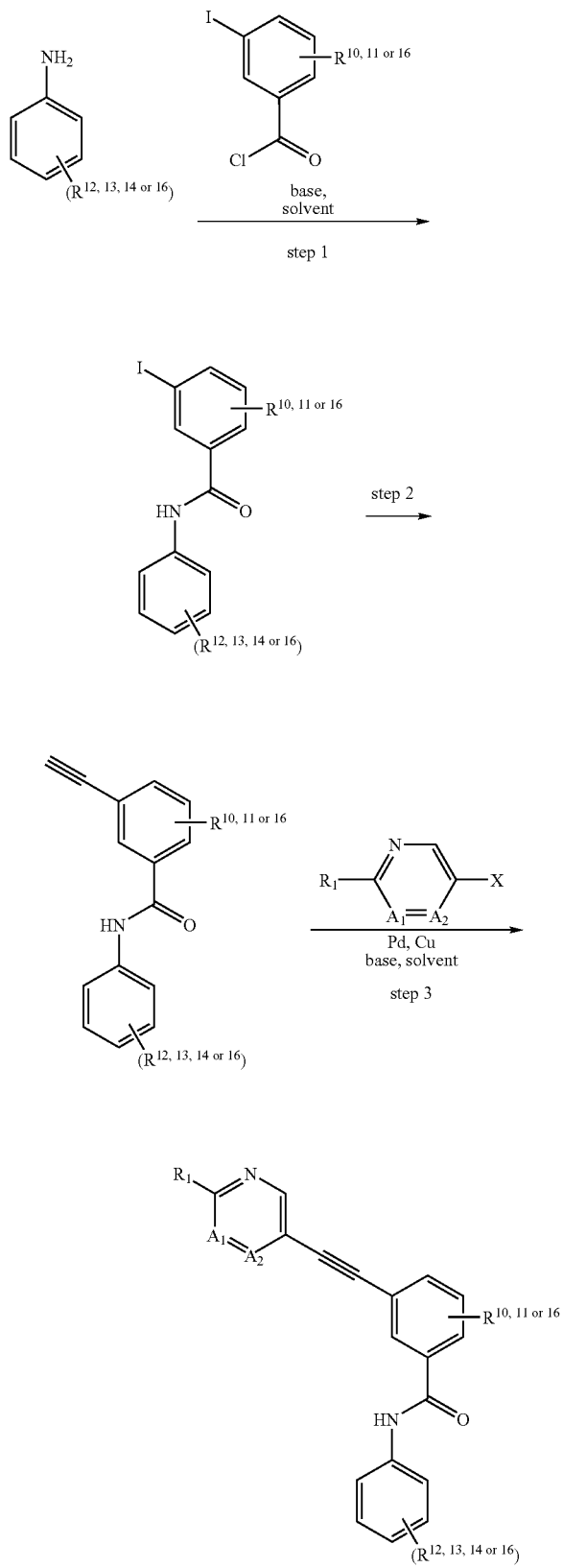

Example 83

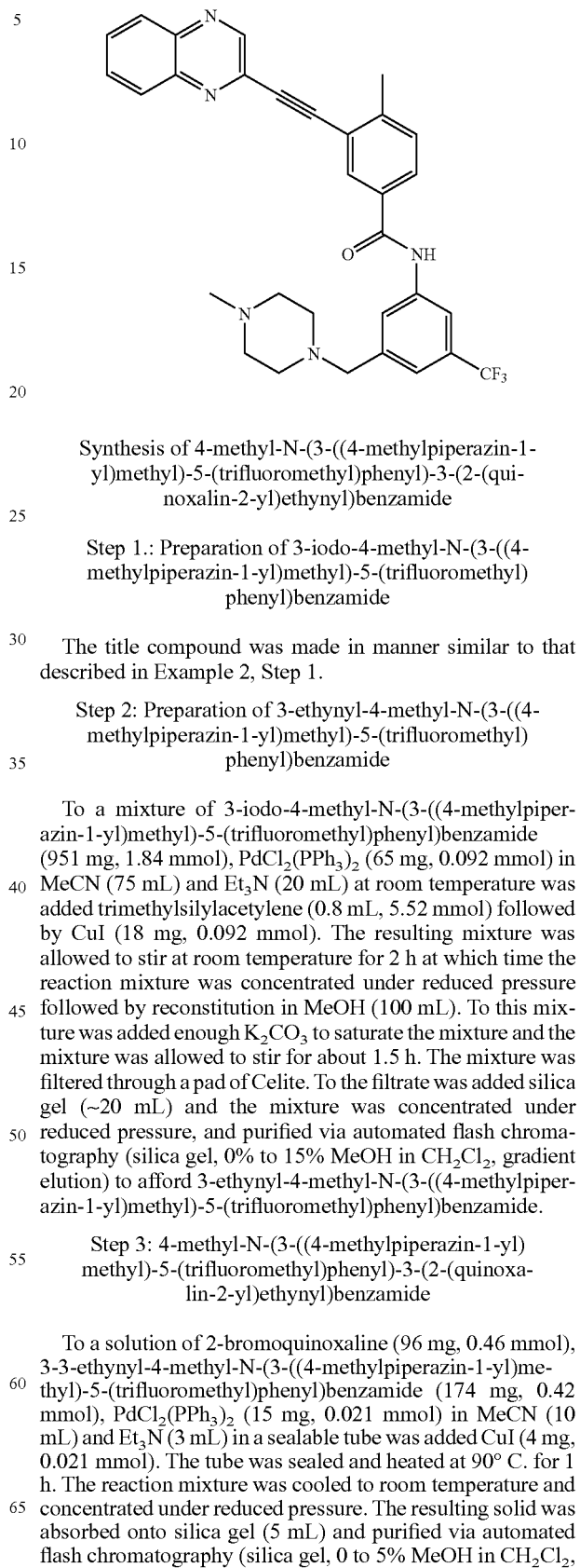

Synthesis of 4-methyl-N-(3-((4-methylpiperazin-1-yl)methyl)-5-(trifluoromethyl)phenyl)-3-(2-(quinoxalin-2-yl)ethynyl)benzamide Step 1.: Preparation of 3-iodo-4-methyl-N-(3-((4-methylpiperazin-1-yl)methyl)-5-(trifluoromethyl)phenyl)benzamide The title compound was made in manner similar to that described in Example 2, Step 1.

Step 2: Preparation of 3-ethynyl-4-methyl-N-(3-((4-methylpiperazin-1-yl)methyl)-5-(trifluoromethyl)phenyl)benzamide To a mixture of 3-iodo-4-methyl-N-(3-((4-methylpiperazin-1-yl)methyl)-5-(trifluoromethyl)phenyl)benzamide (951 mg, 1.84 mmol), $PdCl_2(PPh_3)_2$ (65 mg, 0.092 mmol) in MeCN (75 mL) and $Et_3N$ (20 mL) at room temperature was added trimethylsilylacetylene (0.8 mL, 5.52 mmol) followed by CuI (18 mg, 0.092 mmol). The resulting mixture was allowed to stir at room temperature for 2 h at which time the reaction mixture was concentrated under reduced pressure followed by reconstitution in MeOH (100 mL). To this mixture was added enough $K_2CO_3$ to saturate the mixture and the mixture was allowed to stir for about 1.5 h. The mixture was filtered through a pad of Celite. To the filtrate was added silica gel (~20 mL) and the mixture was concentrated under reduced pressure, and purified via automated flash chromatography (silica gel, 0% to 15% MeOH in $CH_2Cl_2$, gradient elution) to afford 3-ethynyl-4-methyl-N-(3-((4-methylpiperazin-1-yl)methyl)-5-(trifluoromethyl)phenyl)benzamide.

Step 3: 4-methyl-N-(3-((4-methylpiperazin-1-yl)methyl)-5-(trifluoromethyl)phenyl)-3-(2-(quinoxalin-2-yl)ethynyl)benzamide To a solution of 2-bromoquinoxaline (96 mg, 0.46 mmol), 3-3-ethynyl-4-methyl-N-(3-((4-methylpiperazin-1-yl)methyl)-5-(trifluoromethyl)phenyl)benzamide (174 mg, 0.42 mmol), $PdCl_2(PPh_3)_2$ (15 mg, 0.021 mmol) in MeCN (10 mL) and $Et_3N$ (3 mL) in a sealable tube was added CuI (4 mg, 0.021 mmol). The tube was sealed and heated at 90° C. for 1 h. The reaction mixture was cooled to room temperature and concentrated under reduced pressure. The resulting solid was absorbed onto silica gel (5 mL) and purified via automated flash chromatography (silica gel, 0 to 5% MeOH in $CH_2Cl_2$, gradient elution) to afford 4-methyl-3-(2-(quinolin-3-yl)ethynyl)-N-(3-(trifluoromethyl)phenyl)benzamide. MS m/z=544 [M+H]$^+$. Calc'd for $C_{31}H_{28}F_3N_5O$: 543

The following Examples 84-92 were prepared by a method similar to that described in Experimental Method D and Example 83.

| Example No. | Structure | Method | MW | MS Data M + 1 | MS Data M − 1 |
|---|---|---|---|---|---|
| 84 | 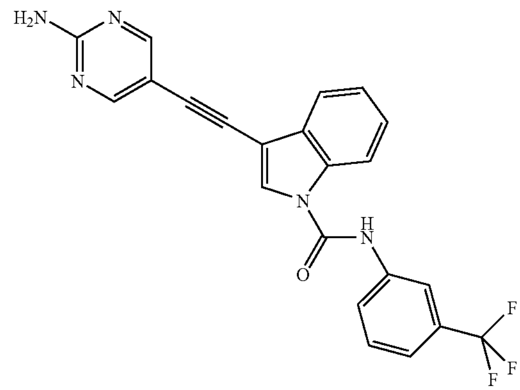 | D1 | 421.38 | 422 | |
| 85 | 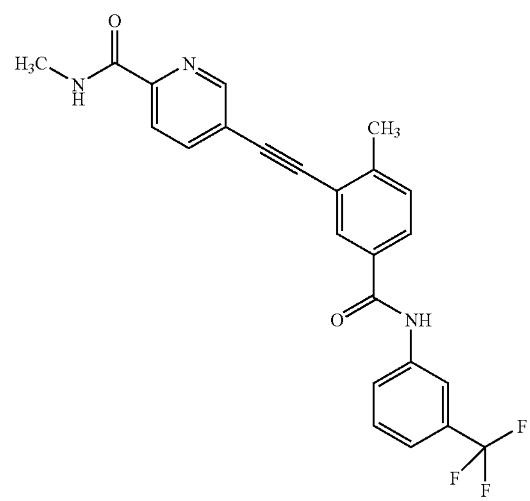 | D1 | 437.42 | 438 | |
| 86 | 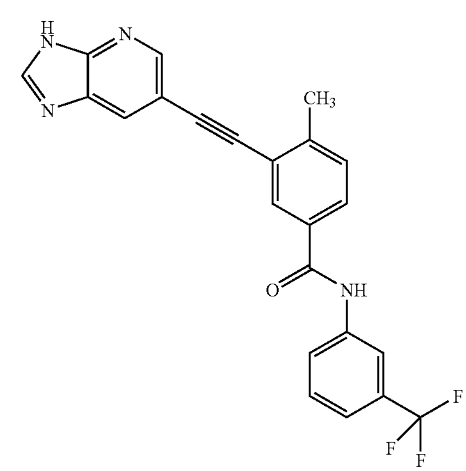 | D1 | 420.39 | 421 | |

-continued

| Example No. | Structure | Method | MW | MS Data M + 1 | MS Data M − 1 |
|---|---|---|---|---|---|
| 87 | 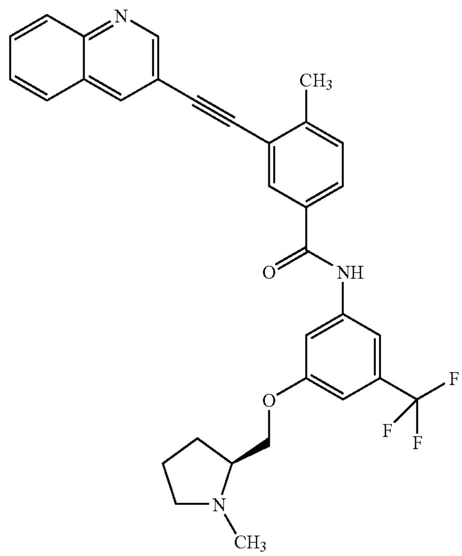 | D1 | 543.59 | 544 | |
| 88 | 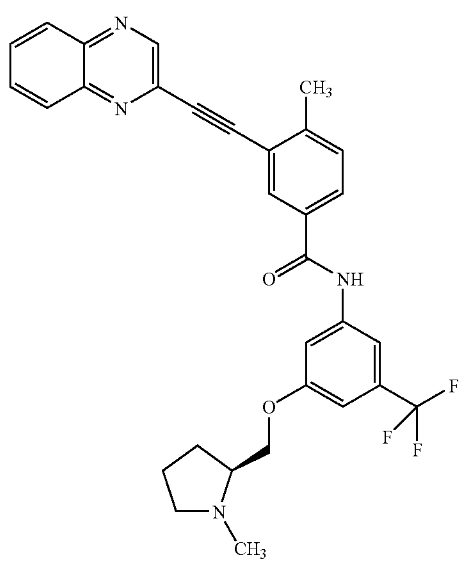 | D1 | 544.57 | 545 | |

-continued

| Example No. | Structure | Method | MW | MS Data M + 1 | MS Data M − 1 |
|---|---|---|---|---|---|
| 89 | 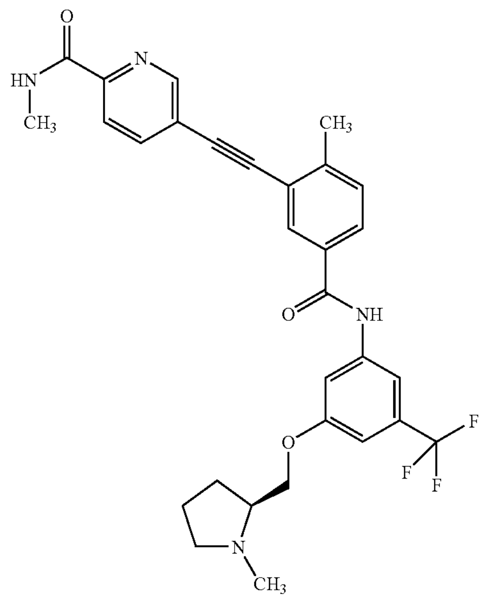 | D1 | 550.58 | 551 | |
| 90 | 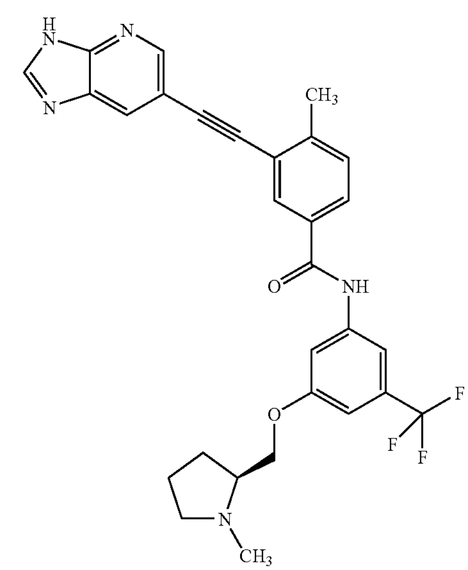 | D1 | 533.55 | 534 | |

-continued

| Example No. | Structure | Method | MW | MS Data M + 1 | MS Data M − 1 |
|---|---|---|---|---|---|
| 91 | 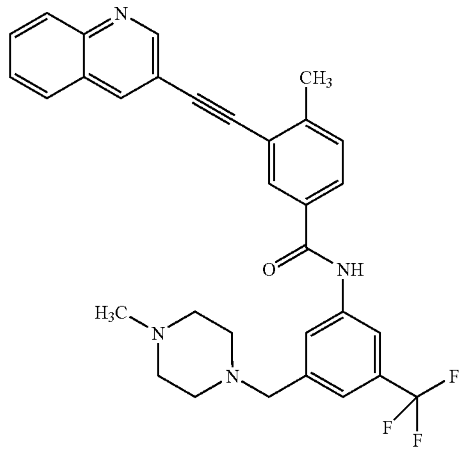 | D1 | 542.6 | 543 | |
| 92 | 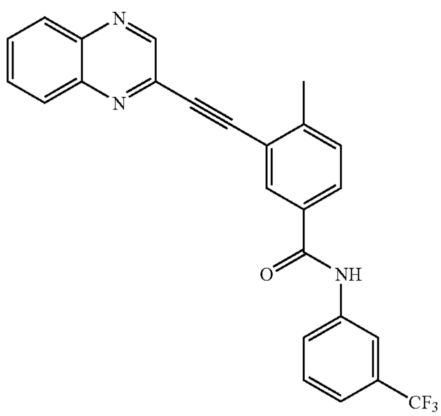 | D1 | 431 | 432 | |

Provided below are exemplary building block starting materials and intermediates, generally not commercially available, which may be utilized in Experimental Methods A-D above. Below are procedures and examples for building various of the exemplary building blocks.

Various different A rings ($R^{11}$ and $R^{14}$ groups), which are contemplated herein, may be made by various methods, as represented by Examples 93-160 below.

Example 93

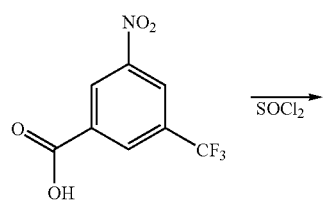

-continued

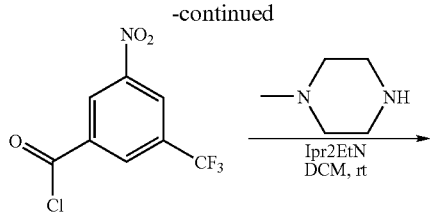

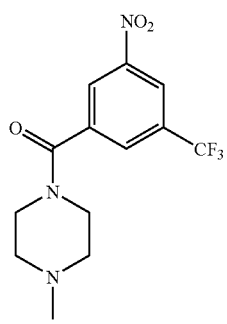

Synthesis of (4-methylpiperazin-1-yl)(3-nitro-5-trifluoromethyl)phenyl)-methanone Step 1: A solution of thionyl chloride (30 ml) and 3-nitro-5-(trifluoromethyl)benzoic acid (10 g) was heated to reflux for 2 h. The reaction mixture was concentrated under reduced pressure and azeotroped with toluene (10 ml—removed under reduced pressure) to afford 3-nitro-5-(trifluoromethyl) benzoyl chloride.

Step 2: To a solution of 3-nitro-5-(trifluoromethyl)benzoyl chloride (2.35 g, 9.3 mmol) in $CH_2Cl_2$ (40 ml) at room temperature was added N-methylpiperazine (1.26 ml, 9.3 mmol) and the mixture was allowed to stir for 30 min. The reaction was concentrated under reduced pressure, taken up in 1 M HCl (50 ml) and the aqueous layer was washed with $Et_2O$ (2×20 ml). The aqueous layer was basified to a pH of about 9 with 6N NaOH and extracted with $Et_2O$ (3×50 ml). The organic extracts were combined and washed with water (1×20 ml) followed by brine (1×20 ml), dried over anhydrous sodium sulfate, filtered and concentrated under reduced pressure to afford (4-methylpiperazin-1-yl)(3-nitro-5-trifluoromethyl)phenyl)-methanone as a tan oil. MS m/z=318 [M+H]$^+$; Calc'd for $C_{13}H_{14}F_3N_3O_3$: 317.3.

Example 94

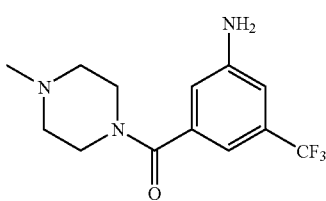

Synthesis of (3-amino-5-(trifluoromethyl)phenyl)(4-methylpiperazin-1-yl)methanone To an argon purged solution of (4-methylpiperazin-1-yl(3-nitro-5-trifluoromethyl)phenyl)-methanone (1.03 g, 3.25 mmol) was added Pd/C (344 mg, 0.32 mmol, 10%). The mixture was placed under an atmosphere of $H_2$ for 5 h. The reaction was purged with argon and filtered through Celite. The filtrate was concentrated under reduced pressure to afford (3-amino-5-(trifluoromethyl)phenyl)(4-methylpiperazin-1-yl)methanone as an off-white solid. MS m/z=288.1 [M+H]$^+$. Calc'd for $C_{13}H_{16}F_3N_3O$: 287.3.

Example 95

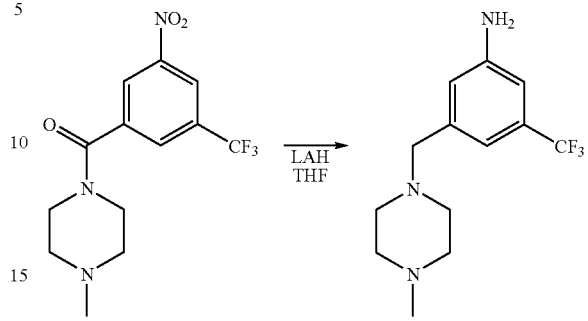

Synthesis of 3-((4-methylpiperazin-1-yl)methyl)-5-(trifluoromethyl)-benzenamine

To LAH (1.84 g, 48.5 mmol) in THF (50 ml) at room temperature was added (4-methylpiperazin-1-yl)(3-nitro-5-trifluoromethyl)phenyl)-methanone (1.54 g, 4.85 mmol) in THF (10 ml). The resulting mixture was refluxed for 5 h. The reaction mixture was cooled to 0° C. at which point water (1.84 ml), 15% aq. NaOH (1.84 ml) and water (3.68 ml) were successively added. The resulting mixture was allowed to stir at room temperature for 1 h. The mixture was filtered through Celite, concentrated under reduced pressure and purified via flash chromatography (silica gel, 0 to 25% MeOH in $CH_2Cl_2$, gradient elution) to afford 3-((4-methylpiperazin-1-yl)methyl)-5-(trifluoromethyl)benzenamine as a colorless oil. MS m/z=274 [M+H]$^+$; Calc'd for $C_{13}H_{16}F_3N_3O$: 273.3.

Example 96

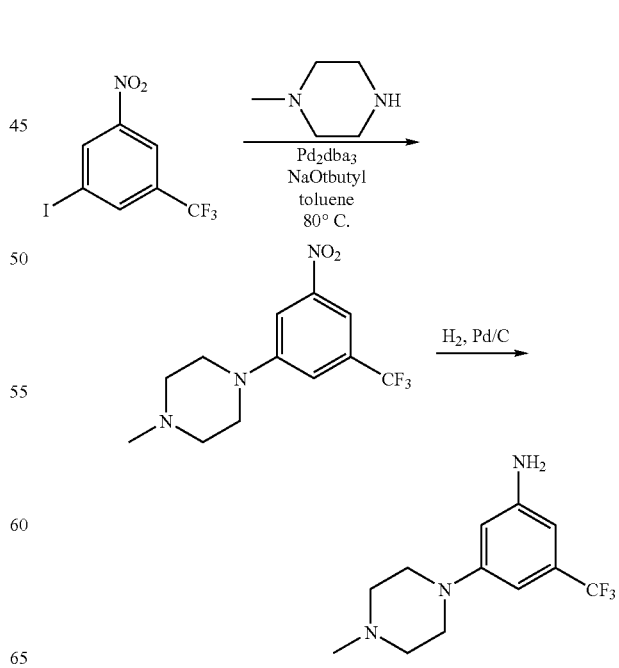

135

Synthesis of 3-(4-methylpiperazin-1-yl)-5-(trifluoromethyl)benzenamine

Step 1: Preparation of 1-methyl-4-(3-nitro-5-(trifluoromethyl)phenyl)piperazine

Into a 50 mL round bottom flask was placed the 1-iodo-3-nitro-5-(trifluoromethyl)benzene (1 g, 3.15 mmol), N-methylpiperazine (0.379 g, 3.78 mmol), bis(dibenzylideneacetone)palladium (0.029 g, 0.0315 mmol), sodium tert-butoxide (0.424 g, 4.416 mmol), 2-dicyclohexyl-2'-(N,N-dimethylamino)biphenyl (0.037 g, 0.094 mmol), and toluene (25 mL). Reaction was heated to 80° C. with stirring for 20 hours. Reaction was cooled to room temperature and water (1 mL) and ethyl acetate (10 mL) were added. The organic layer is separated, concentrated under reduced pressure and purified via silica column eluting with 0 to 20% methanol in dichloromethane. The title compound was obtained as an orange oil.

Step 2. Preparation of 3-(4-methylpiperazin-1-yl)-5-(trifluoromethyl)benzenamine Into a 100 mL round bottom flask under inert atmosphere was placed 1-methyl-4-(3-nitro-5-(trifluoromethyl)phenyl)piperazine (0.736 g, 2.54 mmol), 10% palladium on carbon (90 mg), ethanol (40 mL), and acetic acid (20 mL). The atmosphere was exchanged with hydrogen gas via balloon. The reaction was allowed to stir 3 days at room temperature, then filtered through celite and concentrated under reduced pressure to afford the crude as an orange oil. The crude mixture was purified via silica column chromatography with a solvent solution of 90%/10%/1% ratio of $CH_2Cl_2/CH_3OH/NH_4OH$, to afford the title compound. MS m/z=260 [M+H]$^+$; Calc'd for $C_{12}H_{16}F_3N_3$: 259.3.

Example 97

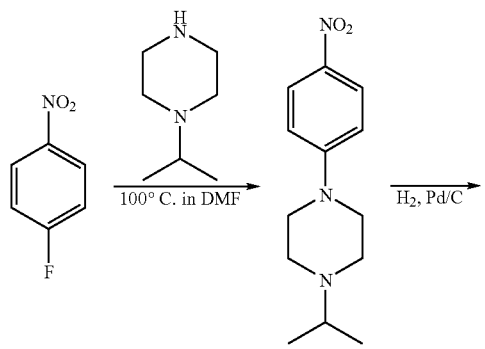

136

Step 1: Synthesis of 1-isopropyl-4-(4-nitrophenyl)piperazine

To a vial was added 4-fluoronitrobenzene (1.41 g, 1.06 mL, 0.01 mol), N,N-diisopropylethylamine (1.92 mL, 0.011 mmol), isopropylpiperazine (1.41 g, 0.011 mmol), and N,N-dimethylformamide (10 mL). Mixture was heated at 100° C. for 48 h in a sealed tube. The reaction mixture was cooled to room temperature and concentrated. The residue was purified via silica gel column chromatography (gradient elution with 0 to 10% methanol in dichloromethane) to afford 1-isopropyl-4-(4-nitrophenyl)piperazine.

Step 2: Synthesis of 4-(4-isopropylpiperazin-1-yl)benzenamine

10% Palladium on carbon (0.05 g) was added to a solution of the nitroaniline (0.001 mol) in ethanol (50 mL) under a $H_2(g)$ atmosphere (via balloon). The reaction mixture stirred at RT overnight and then filtered through celite. The filtrate was concentrated to afford a dark yellow oil, which was purified via silica column chromatography using an isocratic solvent system of 100% (90/10/1) ($CH_2Cl_2/CH_3OH/NH_4OH$) to isolate the title compound. MS m/z=220 [M+H]$^+$; Calc'd for $C_{13}H_{21}N_3$: 219.3.

Example 98

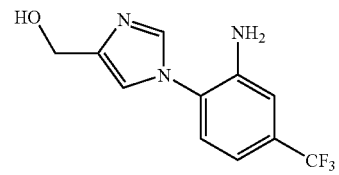

Synthesis of (1-(2-amino-4-(trifluoromethyl)phenyl)-1H-imidazol-4-yl)methanol

Step 1: (1-(2-nitro-4-(trifluoromethyl)phenyl)-1H-imidazol-4-yl)methanol

To a solution of 1-fluoro-2-nitro-4-(trifluoromethyl)benzene (1.04 mL, 7.43 mmol) and (1H-pyrrol-3-yl)methanol hydrochloride salt (1.0 g, 7.43 mmol) in DMF (10 mL) was added $Na_2CO_3$ (2.36 g, 22.3 mmol). The resulting mixture was heated at 70° C. overnight. The mixture was cooled to room temperature and concentrated under reduced pressure. The mixture was reconstituted in EtOAc (50 mL) and washed with 9% aq. $Na_2CO_3$ (10 mL), brine (10 mL), dried over anhydrous sodium sulfate, filtered and concentrated under reduced pressure to afford (1-(2-nitro-4-(trifluoromethyl)phenyl)-1H-imidazol-4-yl)methanol.

Step 2: (1-(2-amino-4-(trifluoromethyl)phenyl)-1H-imidazol-4-yl)methanol

To a solution of (1-(2-nitro-4-(trifluoromethyl)phenyl)-1H-imidazol-4-yl)methanol (167 mg, 0.58 mmol) in EtOH (10 mL) was added a slurry of Raney Nickel (500 mg, washed, wet). The mixture was allowed to stir at room temperature overnight. Upon completion, the reaction mixture was filtered through Celite and concentrated to afford (1-(2-

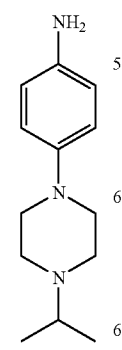

amino-4-(trifluoromethyl)phenyl)-1H-imidazol-4-yl)methanol. MS m/z=258 [M+H]+. Calc'd for $C_{11}H_{10}F_3N_3O$: 257.

Example 99

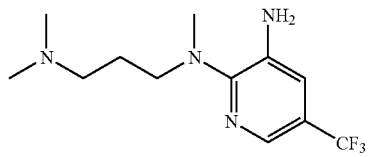

Synthesis of N-(3-(dimethylamino)propyl)-N-2-methyl-5-(trifluoromethyl)pyridine-2,3-diamine Step 1: N-(3-(dimethylamino)propyl)-N-methyl-3-nitro-5-(trifluoromethyl)pyridin-2-amine A solution of 3-nitro-5-(trifluoromethyl)pyridin-2-ol (500 mg, 2.4 mmol), $CHCl_3$ (25 mL), oxalyl chloride (0.42 mL, 4.8 mmol) and DMF (1 drop) was allowed to reflux for 16 h. Once consumption of starting material was complete the reaction was concentrated under reduced pressure. A portion of the crude material (182 mg, 0.8 mmol) was removed and added to a mixture of $N^1,N^1,N^3$-trimethylpropane-1,3-diamine (0.13 mL, 0.88 mmol), $K_2CO_3$ (221 mg, 1.6 mmol) and heated at 90° C. for 10 min. The mixture was concentrated under reduced pressure and reconstituted in $CH_2Cl_2$ (20 mL). The organic layer was washed with water (10 mL), brine (10 mL), dried over anhydrous sodium sulfate, filtered and concentrated under reduced pressure to afford N-(3-(dimethylamino)propyl)-N-methyl-3-nitro-5-(trifluoromethyl)pyridin-2-amine. MS m/z=307 [M+H]+. Calc'd for $C_{12}H_{17}F_3N_4O_2$: 306.

Step 2: $N^2$-(3-(dimethylamino)propyl)-$N^2$-methyl-5-(trifluoromethyl)pyridine-2,3-diamine To a solution of N-(3-(dimethylamino)propyl)-N-methyl-3-nitro-5-(trifluoromethyl)pyridin-2-amine (246 mg, 0.8 mmol) in EtOH was added Raney Nickel (700 mg, wet, washed). The reaction was allowed to stir for 2 h then filtered through a pad of Celite and concentrated under reduced pressure to afford $N^2$-(3-(dimethylamino)propyl)-$N^2$-methyl-5-(trifluoromethyl)pyridine-2,3-diamine. MS m/z=277 [M+H]+. Calc'd for $C_{12}H_{19}F_3N_4$: 276

Example 100

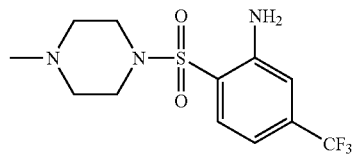

Synthesis of 2-(4-methylpiperazin-1-ylsulfonyl)-5-(trifluoromethyl)benzenamine

Step 1: 1-methyl-4-(2-nitro-4-(trifluoromethyl)phenylsulfonyl)piperazine

To a solution of 2-nitro-4-(trifluoromethyl)benzene-1-sulfonyl chloride (1.0 g, 1.73 mmol) in $CH_2Cl_2$ (50 mL) was added 1-methylpiperazine (0.40 mL, 3.6 mmol). The resulting mixture was allowed to stir at room temperature overnight, then diluted with $CH_2Cl_2$ (30 mL), the organic layer was washed with 9% aq. $Na_2CO_3$ (10 mL) and brine (10 mL). The organic layer was dried over anhydrous sodium sulfate, filtered and concentrated to afford the title compound as a white solid.

Step 2: 2-(4-methylpiperazin-1-ylsulfonyl)-5-(trifluoromethyl)benzenamine 1-methyl-4-(2-nitro-4-(trifluoromethyl)phenylsulfonyl)piperazine was dissolved in EtOH (20 mL) and the solution was purged with argon. Pd/C (365 mg, 0.34 mmol, 10%) was added to the solution, which was stirred for 3 days in an atmosphere of hydrogen gas. The mixture was again purged with argon, filtered through Celite and concentrated under reduced pressure to afford 2-(4-methylpiperazin-1-ylsulfonyl)-5-(trifluoromethyl)benzenamine. MS m/z=324 [M+H]+. Calc'd for $C_{12}H_{16}F_3N_3O_2S$: 323.

Example 101

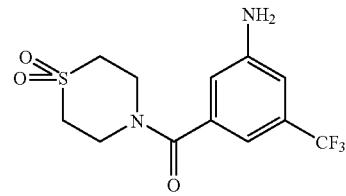

Synthesis of (3-amino-5-(trifluoromethyl)phenyl)(sulfonylmorpholino)methanone

Step 1: (3-nitro-5-(trifluoromethyl)phenyl)(thiomorpholino)methanone

3-Nitro-5-(trifluoromethyl)benzoic acid (2.96 g, 12.6 mmol) was allowed to reflux in thionyl chloride (6 mL) for 6 h. The resulting solution was allowed to cool to room temperature and then concentrated under reduced pressure. The resulting solid was taken up in $CH_2Cl_2$ (20 mL) and $^iPr_2Net$ (2.6 mL, 15.1 mmol) and thiomorpholine (1.4 mL, 13.8 mmol) was added. The reaction was stirred at RT for 1 h and then diluted with $CH_2Cl_2$ (50 mL). The organic layer was washed with aq. HCl (1M, 25 mL), 9% aq. $Na_2CO_3$ (25 mL), brine, dried over anhydrous sodium sulfate, filtered and concentrated under reduced pressure to afford (3-nitro-5-(trifluoromethyl)phenyl)(thiomorpholino)-methanone.

Step 2: (3-nitro-5-(trifluoromethyl)phenyl)(sulfonylmorpholino)-methanone

To a solution of (3-nitro-5-(trifluoromethyl)phenyl)-(thiomorpholino)methanone (1.56 g, 4.88 mmol) in EtOH (50 mL)

was added a solution of ammonium molybdate tetrahydrate (602 mg, 0.49 mmol) and hydrogen peroxide (30%, 4.2 mL, 43.92 mmol). The resulting mixture was allowed to stir overnight. Once the reaction was complete, as observed by TLC (1:1 hexanes:EtOAc), it was poured onto water (100 mL). The aqueous layer was extracted with $CH_2Cl_2$ (3×50 mL). The combined organic layers were washed with water (25 mL), brine (25 mL), dried over anhydrous sodium sulfate, filtered and concentrated under reduced pressure to afford (3-nitro-5-(trifluoromethyl)phenyl)(sulfonylmorpholino)methanone.

Step 3: (3-amino-5-(trifluoromethyl)phenyl)(sulfonylmorpholino)-methanone

To an argon purged solution of (3-nitro-5-(trifluoromethyl)phenyl)-(sulfonylmorpholino)methanone (658 mg, 1.87 mmol) in EtOH (20 mL) was added Pd/C (198 mg, 0.187 mmol, 10%). The resulting mixture was allowed to stir under an atmosphere of hydrogen gas for 3 days. The reaction was purged with argon, filtered through Celite and concentrated under reduced pressure to afford (3-amino-5-(trifluoromethyl)phenyl)-(sulfonylmorpholino)methanone which was used without further purification. MS m/z=323 [M+H]$^+$. Calc'd for $C_{12}H_{13}F_3N_2O_3S$: 322.

Example 102

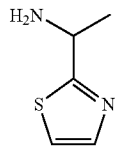

Synthesis of 1-(thiazol-2-yl)ethanamine

The title compound was prepared by a procedure similar to that described in *J. Chem. Soc. Perkin trans.*, 2, 1339, 2000 (also described in PCT Intl. Patent Publication No. WO 2003093238 A1). $NH_4OAc$ (38.54 g, 500 mmol) was added to 1-(thiazol-2-yl)ethanone (5.0 g, 39.3 mmol) in MeOH (100 ml). The mixture was stirred at RT for 15 min. $NaCNBH_4$ (1.76 g, 200 mmol) was added and the mixture was stirred for 4 d. 30 ml 6N HCl was added dropwise with the formation of a solid precipitate. The white solid was isolated by filtration then taken up in $H_2O$ and washed with $Et_2O$. The aqueous solution was then basified to pH of about 10 with NaOH, Extracted with EtOAc and dried over $Na_2SO_4$. Purification by silica chromatography eluting with 5% MeOH/$CH_2Cl_2$ afforded 1-(thiazol-2-yl)ethanamine. MS m/z=129 [M+H]$^+$. Calc'd for $C_5H_8N_2S$: 128

Example 103

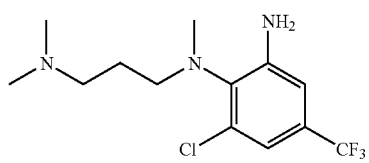

Synthesis of 6-chloro-$N^1$-(3-(dimethylamino)propyl)-$N^1$-methyl-4-(trifluoromethyl)benzene-1,2-diamine A heterogeneous mixture of 1-chloro-2-fluoro-3-nitro-5-(trifluoromethyl)benzene (1.25 mL, 8.2 mmol), $K_2CO_3$ (3.44 g, 24.6 mmol), $N^1,N^1,N^3$-trimethylpropane-1,3-diamine (1.26 mL, 8.61 mmol) and THF were allowed to stir at room temperature for 45 min. The THF was removed under reduced pressure and reconstituted in EtOAc (50 ml). The organic layer was washed with water (20 ml), brine (20 ml), dried over anhydrous sodium sulfate, filtered and concentrated to an oil. The concentrated oil was taken up in EtOH (20 ml) to which Raney nickel (2.5 g wet, washed) was added. The reduction was monitored and after 1 h, another portion of Raney nickel (3.8 g, wet, washed) was added. The reaction was allowed to stir for an additional 30 min., and filtered through Celite, washed with EtOH (10 ml) and concentrated. The crude residue was purified via flash chromatography (silica gel, gradient elution 0 to 25% MeOH in $CH_2Cl_2$) to afford 6-chloro-$N^1$-(3-(dimethylamino)propyl)-$N^1$-methyl-4-(trifluoromethyl)benzene-1,2-diamine as a yellow oil. MS m/z=310.1 [M+H]$^+$. Calc'd for $C_{13}H_{19}ClF_3N_3$: 309.8.

Example 104

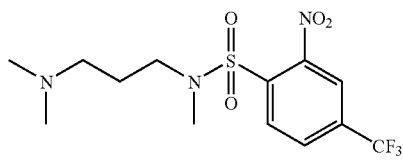

Synthesis of N-(3-(dimethylamino)propyl)-N-methyl-2-nitro-4-(trifluoromethyl)benzenesulfonamide To a solution of 2-nitro-4-(trifluoromethyl)benzene-1-sulfonyl chloride (500 mg, 1.73 mmol) in $CH_2Cl_2$ (5 ml) was added $N^1,N^1,N^3$-trimethylpropane-1,3-diamine (0.26 ml, 1.8 mmol). The resulting mixture was allowed to stir at room temperature for 20 min. Diluted with $CH_2Cl_2$ (30 ml) and washed the organic layer with 9% aq. $Na_2CO_3$ (10 ml) and brine (10 ml). Dried over anhydrous sodium sulfate, filtered and concentrated to a white solid, which was used without further purification. MS m/z=370.1 [M+H]$^+$. Calc'd for $C_{13}H_{18}F_3N_3O_4S$: 369.4.

Example 105

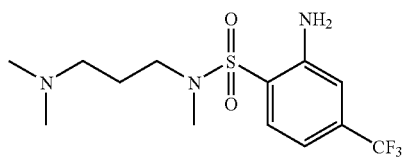

Synthesis of 2-amino-N-(3-(dimethylamino)propyl)-N-methyl-4-(trifluoromethyl)benzenesulfonamide To an argon purged solution of N-(3-(dimethylamino)propyl)-N-methyl-2-nitro-4-(trifluoromethyl)benzenesulfonamide (255 mg, 0.69 mmol) in EtOH (10 ml) was added Pd/C (73 mg, 0.069 mmol, 10%). The reaction mixture was placed under an atmosphere of $H_2$ gas and allowed to stir for 2 h. The reaction mixture was purged with argon and filtered through Celite. The reaction was washed with EtOH (10 ml) and concentrated under reduced pressure to afford 2-amino-N-(3-(dimethylamino)propyl)-N-methyl-4-(trifluoromethyl)benzenesulfonamide as a dark oil. MS m/z=340.1 [M+H]$^+$. Calc'd for $C_{13}H_{20}F_3N_3O_2S$: 339.4.

The following substituted aniline intermediates were prepared in a manner similar to the procedures described in Examples 93-105 and Example 55 of co-pending patent Application Ser. No. 60/569,193:

| Example | Structure | Name | Cal'd MS | M + H$^+$ |
|---|---|---|---|---|
| 106 | 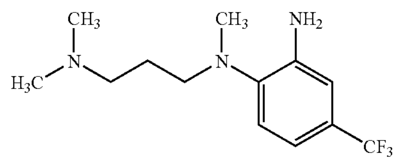 | N1-(3-(dimethylamino)propyl)-N1-methyl-4-(trifluoromethyl)benzene-1,2-diamine: | 275 | 276.1 |
| 107 | 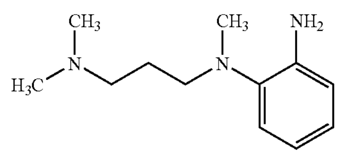 | N1-(3-(dimethylamino)propyl)-N1-methylbenzene-1,2-diamine | 207 | 208 |
| 108 | 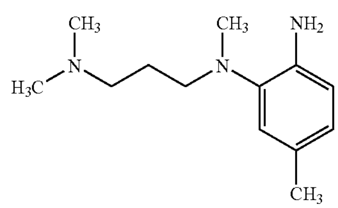 | N1-(3-(dimethylamino)propyl) N1,5-dimethylbenzene-1,2-diamine: | 221 | 222 |
| 109 | 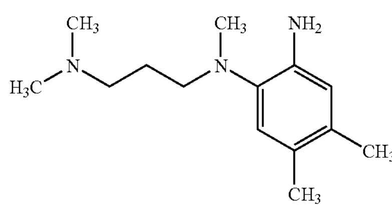 | N1-(3-(dimethylamino)propyl)-N1,4,5-trimethylbenzene-1,2-diamine: | 235 | 236 |
| 110 | 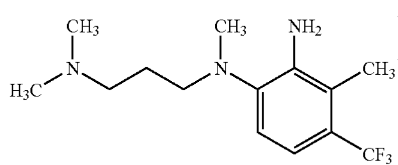 | N1-(3-(dimethylamino)propyl)-N1,3-dimethyl-4-(trifluoromethyl)benzene-1,2-diamine: | 289 | 290 |
| 111 | 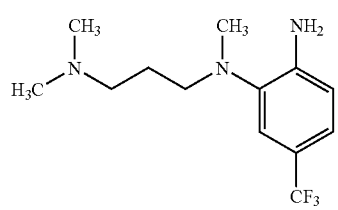 | N1-(3-(dimethylamino)propyl)-N1-methyl-5-(trifluoromethyl)benzene-1,2-diamine: | 275 | 276 |

Example 112

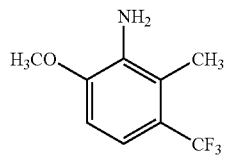

Synthesis of 6-methoxy-2-methyl-3-(trifluoromethyl)benzenamine

Step 1: 1-methoxy-3-methyl-2-nitro-4-(trifluoromethyl)benzene

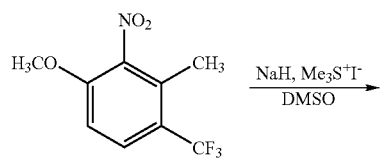

1-methoxy-3-methyl-2-nitro-4-(trifluoromethyl)benzene was prepared by a procedure similar to that described in "Synthesis of 3,6-Disubstituted 2-Nitrotoluenes by Methylation of Aromatic Nitro Compounds with Dimethylsulfonium Methylide", Kitano, Masafumi, Ohashi Naohito, *Synthetic Communications*, 30(23), 4247-4254, 2000. To a suspension of NaH (60% by wt. in mineral oil, 362 mg, 9.04 mmol) and trimethylsulfonium iodide (1.84 g, 9.04 mmol) in DMSO (17 ml) and THF (6.7 ml) was added 4-methoxy-3-nitrobenzotrifluoride (1.00 g, 4.52 mmol) as a solution in DMSO (2.7 ml). The reaction mixture was allowed to stir at 10-20° C. for 5 hrs. The reaction mixture was quenched by addition to ice water. The aqueous layer was separated and extracted with toluene 7 times. The combined organic extracts were washed with brine, dried over MgSO₄, and filtered. The solvent was removed by distillation at reduced pressure. The residue was purified by automated silica gel chromatography (100% hexanes to 98:2 hexanes:ethylacetate) to provide 1-methoxy-3-methyl-2-nitro-4-(trifluoromethyl)benzene.

Step 2: 6-methoxy-2-methyl-3-(trifluoromethyl)benzenamine

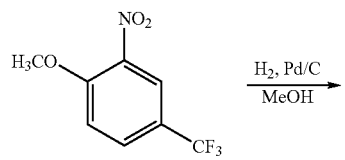

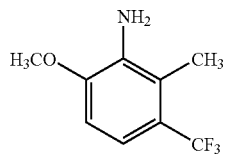

1-methoxy-3-methyl-2-nitro-4-(trifluoromethyl)benzene (258 mg, 1.10 mmol), methanol (11.0 mL), and palladium on carbon (77.4 mg) were combined in a $N_2$-purged round bottom flask. A balloon containing $H_2$ was affixed to the flask, and the solution was saturated with $H_2$ for 2 minutes. The reaction mixture was allowed to stir under $H_2$ atmosphere for 12 hrs. Upon completion, as judged by LCMS, the reaction mixture was filtered through a plug of Celite and the solvent was removed in vacuo to afford 6-methoxy-2-methyl-3-(trifluoromethyl)benzenamine. MS m/z=206 [M+H]⁺. Calc'd for $C_9H_{10}F_3NO$: 205.

Example 113

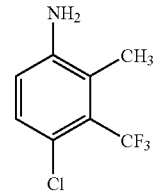

Synthesis of 4-chloro-2-methyl-3-(trifluoromethyl)benzenamine

4-Chloro-2-methyl-3-(trifluoromethyl)benzenamine was prepared by a method similar to that described in "Preparation of Fused Succinimides as Modulators of Nuclear Hormone Receptor Function", Salvati, Mark E. et al., PCT Patent Publication WO 2003062241. MS m/z=210 [M+H]⁺. Calc'd for $C_9H_{10}F_3NO$: 210.

Example 114

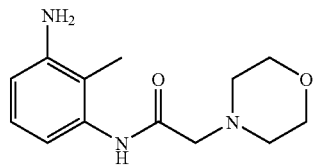

Synthesis of N-(3-amino-2-methylphenyl)-2-morpholinoacetamide

Step 1: 2-bromo-N-(2-methyl-3-nitrophenyl)acetamide

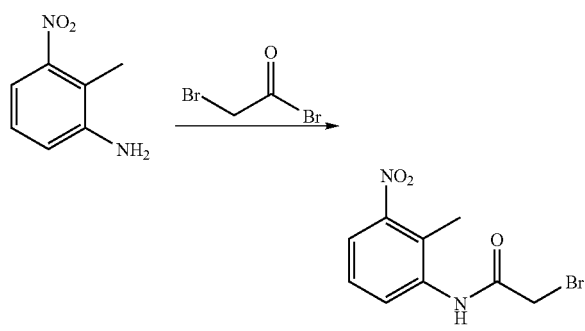

To a solution of 2-methyl-3-nitroaniline (5.0 g, 32.9 mmol) in 120 ml of $CH_2Cl_2$ was added 120 ml of saturated $NaHCO_3$ and bromoacetyl bromide (2.85 ml, 6.6 g, 32.9 mmol). The reaction was stirred at room temperature for 64 hours. The layers were separated, and the organic layer was washed with water, brine and then dried over $MgSO_4$. Solvent evaporation afforded 2-bromo-N-(2-methyl-3-nitrophenyl)acetamide as a yellow solid.

Step 2: N-(2-methyl-3-nitrophenyl)-2-morpholinoacetamide

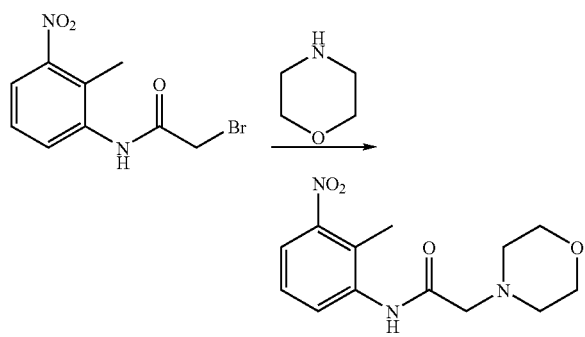

2-Bromo-N-(2-methyl-3-nitrophenyl)acetamide (0.5 g, 1.8 mmol) was dissolved in 15 ml of THF and to this was added morpholine (0.17 g, 2.0 mmol) and diisopropylethylamine (0.71 g, 5.5 mmol). The reaction was stirred at room temperature for 16 hours. The reaction was then partitioned between EtOAc and $H_2O$. The aqueous mixture was extracted with EtOAc, and the combined organic layers were washed with $H_2O$, brine and then dried over $MgSO_4$. Solvent evaporation afforded N-(2-methyl-3-nitrophenyl)-2-morpholinoacetamide as a yellow solid.

Step 3: N-(3-amino-2-ethylphenyl)-2-morpholinoacetamide

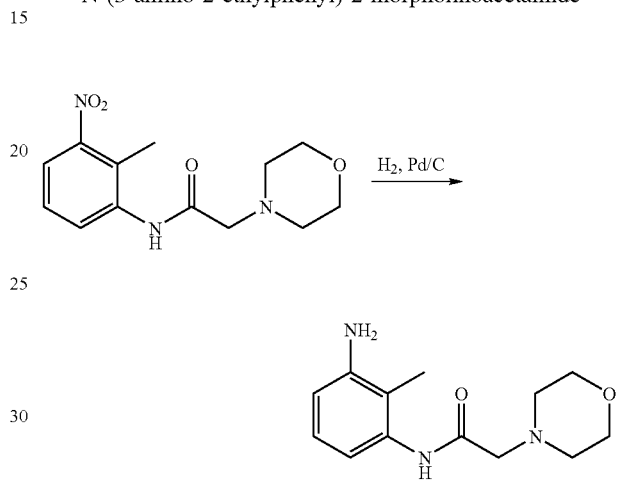

N-(2-Methyl-3-nitrophenyl)-2-morpholinoacetamide (0.25 g, 0.9 mmol) was dissolved in 20 ml of MeOH, and to this was added a slurry of 10% Pd/C (0.025 g) in a minimal amount of EtOH. The reaction vessel was evacuated and purged with $H_2$, and the reaction was stirred at room temperature for 16 hours. The mixture was purged with $N_2$ for 30 minutes and then filtered through a pad of celite. Solvent evaporation afforded N-(3-amino-2-methylphenyl)-2-morpholinoacetamide as a gray solid. MS m/z=250.1 $[M+H]^+$; Calc'd for $C_{13}H_{19}N_3O_2$: 249.

Examples 115-118 were prepared by a method similar to the procedure described in Example 114 above.

| Example | Structure | Name |
| --- | --- | --- |
| 115 | 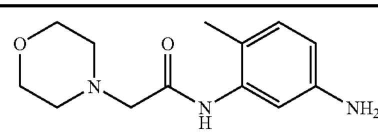 | N-(5-amino-2-methylphenyl)-2-morpholinoacetamide |
| 116 | 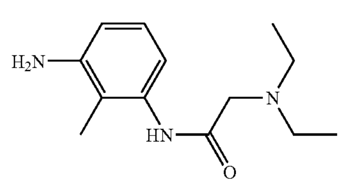 | N-(3-amino-2-methylphenyl_2-(diethylamino)acetamide |

| Example | Structure | Name |
|---|---|---|
| 117 | 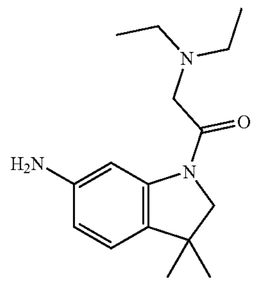 | 1-(6-amino-3,3-dimethylindolin-1-yl)-2-(diethylamino)ethanone |
| 118 | 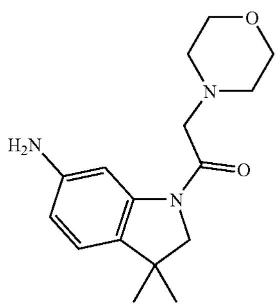 | 1-(6-amino-3,3-dimethylindolin-1-yl)-2-morpholinoethanone |

Example 119

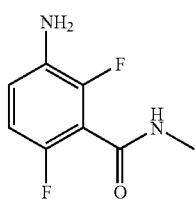

Synthesis of 3-amino-2,6-difluoro-N-methylbenzamide

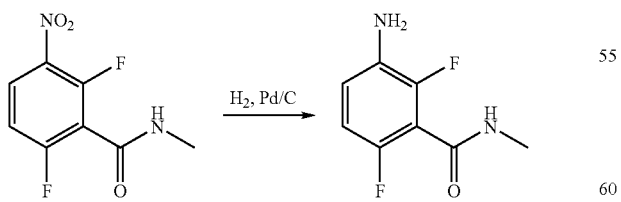

2,6-Difluoro-3-nitrophenylacetamide (0.5 g, 2.3 mmol) was dissolved in 20 ml of MeOH and to this was added a slurry of 10% Pd/C (0.050 g). The reaction vessel was evacuated and purged with $H_2$, and the reaction was stirred at room temperature for 3 hours. The mixture was purged with $N_2$, and then filtered through a pad of celite. Solvent evaporation afforded 3-amino-2,6-difluoro-N-methylbenzamide as a pink solid.

Example 120

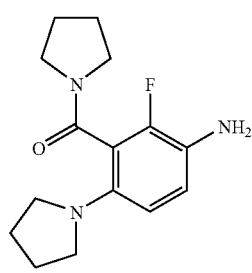

(3-amino-2-fluoro-6-(pyrrolidin-1-yl)phenyl)(pyrrolidin-1-yl)methanone

Example 120 was prepared by a method similar to that described in Example 119 above.

Example 121

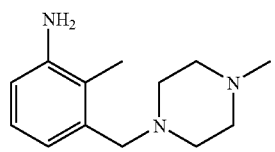

149

Synthesis of 2-methyl-3-((4-methylpiperazin-1-yl)methyl)benzeneamine

Step 1: 1-(2-methyl-3-nitrobenzyl)-4-methylpiperazine

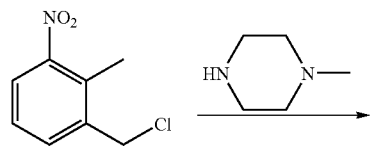

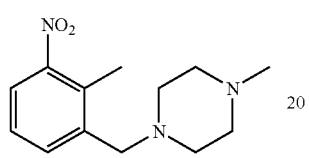

2-Methyl-3-nitrobenzylchloride (1.0 g, 5.4 mmol) was dissolved in 30 ml of THF, and to this was added 1-methylpiperazine (0.65 g, 6.5 mmol) and sodium bicarbonate (2.26 g, 26.9 mmol). The reaction mixture was stirred at 65° C. for 16 hours. The mixture was partitioned between EtOAc and H₂O. The aqueous layer was extracted with EtOAc, and the combined organic layers were washed with saturated NH₄Cl, H₂O, brine and dried over MgSO₄. Solvent evaporation afforded 1-(2-methyl-3-nitrobenzyl)-4-methylpiperazine.

Step 2: 2-methyl-3-((4-methylpiperazin-1-yl)methyl)benzeneamine

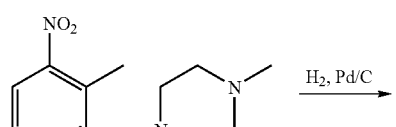

1-(2-Methyl-3-nitrobenzyl)-4-methylpiperazine (1.2 g, 4.8 mmol) was dissolved in 50 ml of MeOH, and to this was added a slurry of 10% Pd/C in a minimal amount of EtOH. The reaction mixture was evacuated and purged with H₂, and then stirred at room temperature for 3 hours. The mixture was purged with N₂ for 30 minutes and then filtered through a pad of celite. Solvent evaporation afforded 2-methyl-3-((4-methylpiperazin-1-yl)methyl)benzeneamine.

150

Example 122

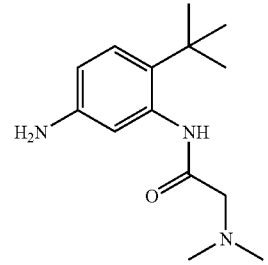

Synthesis of N-(5-amino-2-tert-butylphenyl)-2-dimethylamino)acetamide

Step 1: 2-tert-butyl-5-nitrobenzenamine

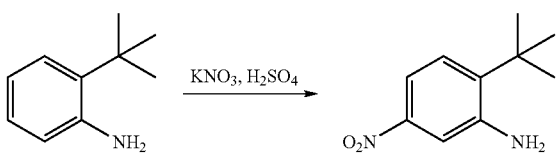

Concentrated sulfuric acid (1 L) was cooled to −10° C. with a dry ice-isopropanol bath in a 2 L 3-necked round bottom flask fitted with a mechanical stirrer and temperature probe. The 2-t-butylaniline (109 g, 730 mmol) was added, giving a clumpy solid. Once the temperature of the mixture was stabilized at −10° C., the potassium nitrate (101 g, 1001 mmol) was added portion wise, as a solid, over a 4-hour period, maintaining the temperature between −20 and −5° C. Once all of the potassium nitrate was added, the reaction was left to stir overnight with gradual warming to room temperature. The reaction was quenched by diluting with water and then extracting three times with EtOAc. The EtOAc extracts were washed multiple times with saturated NaHCO₃, until gas evolution ceased, then with brine. The ethyl acetate extracts were then combined, dried over anhydrous Na₂SO₄, filtered and concentrated under reduced pressure giving a black oil. The oil was eluted through a column of silica gel with EtOAc: hexanes gradient 5-50%. Solvent evaporation afforded 2-tert-butyl-5-nitrobenzenamine as a red solid.

Step 2: 2-bromo-N-(2-tert-butyl-5-nitrophenyl)acetamide

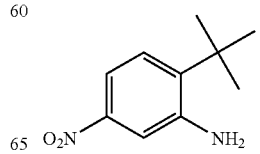 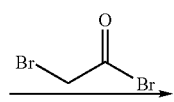

151

-continued

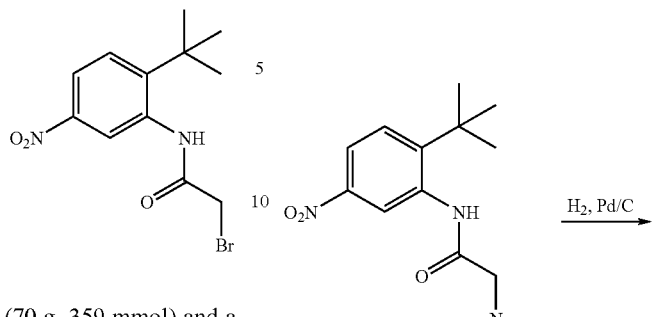

2-tert-Butyl-5-nitrobenzenamine (70 g, 359 mmol) and a catalytic amount of DMAP were dissolved into THF (1.5 L) under $N_2$. Triethylamine (109 g, 1077 mmol) was added and the solution was cooled to 0° C. Bromoacetyl bromide (207 g, 1023 mmol) was then added and the reaction was stirred at room temperature for 16 hours. The reaction was then partially concentrated under reduced pressure, treated with water, and extracted three times with EtOAc. The EtOAc extracts were washed with brine, combined, dried over $Na_2SO_4$ and concentrated to a black oil. This oil was purified using silica chromatography, 95:5:0.5 $CH_2Cl_2$:MeOH: $NH_4OH$, giving 2-bromo-N-(2-tert-butyl-5-nitrophenyl)acetamide as a brown solid.

Step 3: N-(2-tert-butyl-5-nitrophenyl)-2-(dimethylamino)acetamide

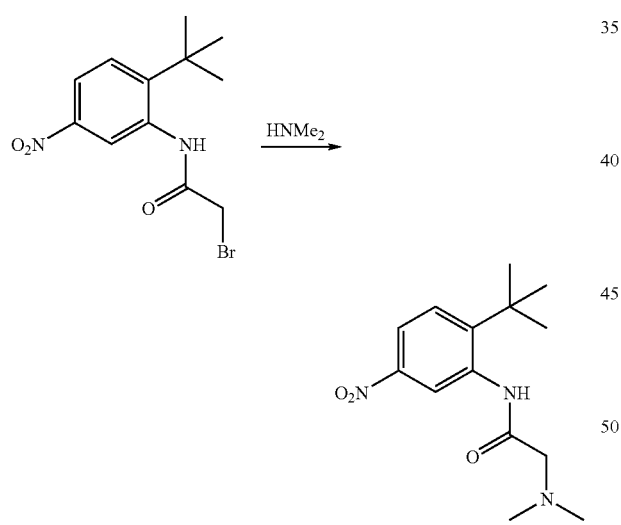

2-Bromo-N-(2-tert-butyl-5-nitrophenyl)acetamide (80 g, 253, mmol) and potassium carbonate (70 g, 506 mmol) were combined in THF (1.75 L), and the mixture was cooled to 0° C. N,N-Dimethylamine (40 ml of a 2 M solution in THF, 800 mmol) was then added to the mixture through an addition funnel over a 30-minute period. The mixture was then stirred at room temperature for 16 hours. The mixture was then filtered and the filtrate was concentrated. The crude material was purified by silica chromatography using 50% EtOAc: hexanes as the eluent to give N-(2-tert-butyl-5-nitrophenyl)-2-(dimethylamino)acetamide as a brown solid.

152

Step 4: N-(5-amino-2-tert-butylphenyl)-2-dimethylamino)acetamide

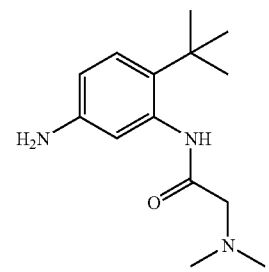

To a solution of N-(2-tert-butyl-5-nitrophenyl)-2-(dimethylamino)acetamide in 1,4-dioxane was added 10% Pd/C as a slurry in a minimal amount of EtOH. The mixture was evacuated and purged with $H_2$, and then stirred at room temperature for 16 hours. The reaction was then purged with $N_2$ and filtered through celite. The filtrate was concentrated and purified using silica chromatography, 97.5:2.5:0.25 to 95:5: 0.5 $CH_2Cl_2$:MeOH:$NH_4OH$, to afford N-(5-amino-2-tert-butylphenyl)-2-dimethylamino)acetamide as a brown solid. MS (m/z)=250.2 (M+H$^+$); Calculated for $C_{14}H_{23}N_3O$: 249.4

Example 123

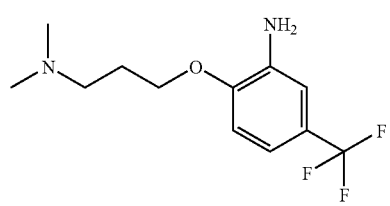

Synthesis of N,N-dimethyl-3-(2-nitro-4-(trifluoromethyl)phenoxy)propan-1-amine

Step 1: 2-(3-(dimethylamino)propoxy)-5-(trifluoromethyl)benzenamine

A suspension of $NaHCO_3$ (3.9 g, 48 mmol), 1-fluoro-2-nitro-4-trifluoromethylbenzene (4.0 g, 19 mmol), and 3-dimethylamino-1-propanol (2.5 ml, 21 mmol) in 38 mL dry THF was heated with a reflux condenser under nitrogen for 12 h. The mixture was filtered through a fritted funnel into a flask. The solution was cooled to 0° C. and was treated with potassium tert-butoxide (2.4 g, 21 mmol) resulting in an orange solution. The solution was warmed to ambient temperature and was allowed to stir for 1 h. The solvent was removed in vacuo, and the resulting brown oil was partitioned between saturated aqueous NaHCO$_3$ and methylene chloride. The aqueous layer was extracted three times with methylene chloride. The combined organic layers were dried with Na$_2$SO$_4$, filtered, and concentrated. The residue was purified by silica gel chromatography (MC/MeOH/conc. NH$_4$OH) to provide the desired compound as an orange oil. MS (m/z): 293.1 (M+H)$^+$. Calc'd for C$_{12}$H$_{15}$F$_3$N$_2$O$_3$: 292.25.

Step 2: N,N-dimethyl-3-(2-nitro-4-(trifluoromethyl) phenoxy)propan-1-amine

To 2-(3-(dimethylamino)propoxy)-5-(trifluoromethyl) benzenamine (1.6 g, 5.5 mmol) was added Pd/C (10%, 0.58 g) under nitrogen. Methanol (18 ml) was added via syringe, and H$_2$ gas was introduced and the mixture stirred vigorously under an atmosphere of H$_2$. After 23 h, the mixture was filtered through celite and concentrated to afford the title compound as a light brown solid. MS (m/z): 263 (M+H)$^+$. Calc'd for C$_{12}$H$_{17}$F$_3$N$_2$O$_3$: 262.27.

Example 124

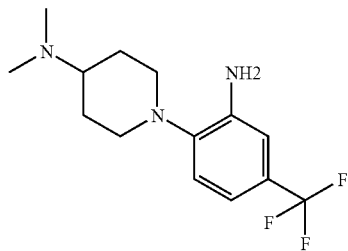

Synthesis of 1-(2-amino-4-(trifluoromethyl)phenyl)-N,N-dimethylpiperidin-4-amine Step 1: 1-benzyl-N,N-dimethylpiperidin-4-amine dihydrochloride To a mixture of 4-amino-1-benzyl piperidine (5.0 g, 26 mmol), NaBH$_3$CN (3.3 g, 53 mmol), AcOH (7.5 ml, 132 mmol) in 130 ml MeOH at 0° C. under nitrogen was added formaldehyde (37 wt % in water, 5.3 mL) as a solution in 15 ml MeOH slowly dropwise via a pressure-equalized addition funnel over 15 min. The resulting clear solution was allowed to warm to room temperature and was allowed to stir for approximately 60 h. The reaction was quenched by the addition of 20 ml saturated aqueous potassium carbonate. The mixture was concentrated in vacuo, and water and EtOAc was added. The organic layer was removed, and the aqueous layer was extracted twice with EtOAc. The combined organic layers were dried with Na$_2$SO$_4$, filtered, and concentrated to give a cloudy oil, which was dissolved in methylene chloride and filtered through a fritted funnel. The solvent was removed to give a waxy solid, which was purified by silica gel chromatography (MC/MeOH/conc. NH$_4$OH). The resulting material was dissolved in diethyl ether, cooled to 0° C. and treated with 20 ml 4N HCl in dioxane. The solvent was removed in vacuo to give the desired product as a white solid. MS (m/z): 219.1 (M+H)$^+$. Calc'd for C$_{14}$H$_{22}$N$_2$: 218.34.

Step 2: N,N-dimethyl-1-(2-nitro-4-(trifluoromethyl) phenyl)piperidin-4-amine

To 1-benzyl-N,N-dimethylpiperidin-4-amine dihydrochloride (6.7 g, 23 mmol) was added Pd/C (10%, 2.4 g) under argon. Methanol (100 ml) was added via syringe, and H$_2$ gas was introduced and the mixture stirred vigorously under an atmosphere of H$_2$. After 48 h, the mixture was flushed with nitrogen, filtered through celite and concentrated to afford a mixture of starting material and N,N-dimethylpiperidin-4-amine dihydrochloride as a white solid. This solid was treated with 1-Fluoro-2-nitro-4-trifluoromethyl-benzene (3.2 ml, 22.9 mmol), triethylamine (12.7 ml, 92 mmol), and 50 ml dry THF. The mixture was heated to 75° C. with a water-cooled reflux condenser for 12 h. The mixture was allowed to cool to ambient temperature, was filtered through a fritted funnel, and concentrated to an orange oil. The residue was purified by silica gel chromatography (MC/MeOH/conc. NH$_4$OH) to give the desired product as an orange oil. MS (m/z): 318.1 (M+H)$^+$. Calc'd for C$_{14}$H$_{18}$F$_3$N$_3$O$_2$: 317.31.

Step 3: 1-(2-amino-4-(trifluoromethyl)phenyl)-N,N-dimethylpiperidin-4-amine

To N,N-dimethyl-1-(2-nitro-4-(trifluoromethyl)phenyl) piperidin-4-amine (3.4 g, 11 mmol) was added Pd/C (10%, 0.57 g) under nitrogen. Methanol (25 mL) was added via syringe, and H$_2$ gas was introduced and the mixture stirred vigorously under an atmosphere of H$_2$. After 96 h, the mixture was flushed with nitrogen, filtered through celite and concentrated. The residue was resubjected to the reaction conditions. After 12 h, the reaction was flushed with nitrogen, filtered through celite and concentrated. The resulting solid was triturated with methanol ten times to give the title compound as a pink solid. MS (m/z): 288.2 (M+H)$^+$. Calc'd for C$_{14}$H$_{20}$F$_3$N$_3$: 287.32.

Example 125

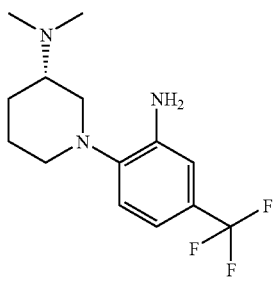

Synthesis of (S)-1-(2-amino-4-(trifluoromethyl)phenyl)-N,N-dimethylpiperidin-3-amine Step 1: (S)-N,N-dimethyl-1-(2-nitro-4-(trifluoromethyl)phenyl)piperidin-3-amine To a light yellow solution of (S)-tert-butyl 3-aminopiperidine-1-carboxylate (0.52 g, 2.6 mmol) in 25 ml MeOH was added sodium cyanoborohydride (0.33 g, 5.2 mmol), AcOH (0.74 ml, 13 mmol), and formaldehyde (37 wt. % solution in water, 1.0 ml). After stirring approximately 12 h, the reaction was quenched by the addition of 5 ml saturated aqueous sodium bicarbonate. The volatile organic solvents were removed in vacuo, and water and EtOAc was added. The organic layer was removed, and the aqueous layer was extracted twice with EtOAc. The combined organic layers were dried with Na$_2$SO$_4$, filtered, and concentrated to give a yellow oil. The resulting material was treated with 4 ml 4N HCl in dioxane at 0° C. After 2 h, the solution was concentrated in vacuo to give a light yellow solid. This solid was treated with 1-Fluoro-2-nitro-4-trifluoromethylbenzene (0.37 ml, 2.6 mmol), sodium bicarbonate (1.0 g, 13 mmol), and 5 ml dry THF. The mixture was heated to 75° C. with a water-cooled reflux condenser for 12 h. The mixture was allowed to cool to ambient temperature, was filtered through a fritted funnel, and concentrated to give the desired product as an orange oil. MS (m/z): 318.0 (M+H)$^+$. Calc'd for C$_{14}$H$_{18}$F$_3$N$_3$O$_2$: 317.31.

Step 2: (S)-1-(2-amino-4-(trifluoromethyl)phenyl)-N,N-dimethylpiperidin-3-amine (S)-N,N-Dimethyl-1-(2-nitro-4-(trifluoromethyl)phenyl) piperidin-3-amine (0.82 g, 2.6 mmol) was reduced with Pd/C (10%, 0.27 g) in 10 ml methanol in a manner similar to Example 124-Step 3 to give the title compound as an orange-red oil. MS (m/z): 288.2 (M+H)$^+$. Calc'd for C$_{14}$H$_{20}$F$_3$N$_3$: 287.32.

Example 126

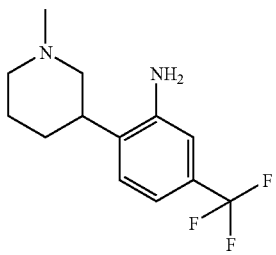

Synthesis of 2-(1-methylpiperidin-3-yl)-5-(trifluoromethyl)benzenamine

Step 1: 3-(2-nitro-4-(trifluoromethyl)phenyl)pyridine

A mixture of pyridin-3-ylboronic acid (0.99 g, 8.1 mmol), 2-bromo-5-(trifluoromethyl)benzenamine (1.2 ml, 8.1 mmol), tetrakis(triphenylphosphine)palladium (0.28 g, 0.24 mmol), sodium carbonate (2.0 M solution in water, 8.0 ml, 16 mmol), 4 ml ethanol, and 20 ml toluene was heated to 90° C. under nitrogen with a water-cooled reflux condenser. After 12 h, mixture was cooled to ambient temperature, and was partitioned between EtOAc and 1N NaOH. The organic layer was washed once with brine, dried with Na$_2$SO$_4$, filtered, and concentrated to give a brown oil, which was further purified by silica gel chromatography (EtOAc/hexanes) to give the desired product as a waxy orange solid. MS (m/z): 269.0 (M+H)$^+$. Calc'd for C$_{12}$H$_7$F$_3$N$_2$O$_2$: 268.19.

Step 2: 2-(1-methylpiperidin-3-yl)-5-(trifluoromethyl)benzenamine

To an orange solution of 3-(2-nitro-4-(trifluoromethyl) phenyl)pyridine (1.4 g, 5.2 mmol) in 2 ml acetone and 1 mL benzene was added iodomethane (1.0 ml, 16 mmol). The solution was allowed to stand for 5 days, and was concentrated in vacuo to give an orange solid. A portion of this material was treated with platinum (IV) oxide (0.11 g, 0.49 mmol) in 5 ml MeOH under an atmosphere of hydrogen for approximately 24 h. The reaction was flushed with nitrogen, filtered through celite, and concentrated. Purification by silica gel chromatography (MC/MeOH/conc. NH$_4$OH) provided the title compound. MS (m/z): 259.0 (M+H)$^+$. Calc'd for C$_{13}$H$_{17}$F$_3$N$_2$: 258.28.

Example 127

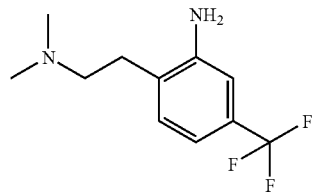

Synthesis of 2-(2-(dimethylamino)ethyl)-5-(trifluoromethyl)benzenamine

The title compound was synthesized in a manner similar to that described in Example 58 of pending U.S. Patent Application No. 60/569,193. MS (m/z): 233.1 (M+H)$^+$. Calc'd for C$_{11}$H$_{15}$F$_3$N$_2$: 232.25.

Example 128

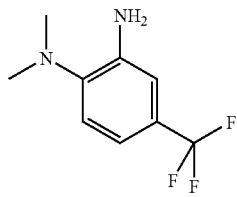

Synthesis of N1,N1-dimethyl-4-(trifluoromethyl) benzene-1,2-diamine

The title compound was synthesized in a manner similar to Example 55 of pending U.S. Patent Application No. 60/569, 193. MS (m/z): 205.1 (M+H)$^+$. Calc'd for C$_9$H$_{11}$F$_3$N$_2$: 204.19.

Example 129

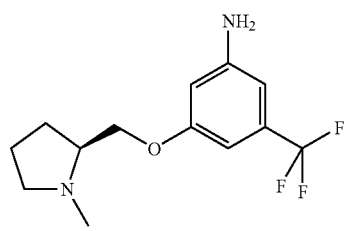

Synthesis of (S)-3-((1-methylpyrrolidin-2-yl)methoxy)-5-(trifluoromethyl)benzenamine The title compound was synthesized by a method similar to that described in WO 2002066470 A1.

Example 130

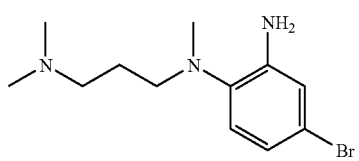

Synthesis of 4-bromo-N-1-(3-(dimethylamino)propyl)-N1-methylbenzene-1,2-diamine

To N-(4-Bromo-2-nitro-phenyl)-N,N',N'-trimethylpropane-1,3-diamine (made by a method similar to that of Example 103—Step 1) (0.54 g, 1.7 mmol) in 20 ml EtOH was added $SnCl_2$ (0.51 g, 2.67 mmol). The mixture was sealed and was heated to 80° C. for 12 h. An additional amount of $SnCl_2$ (0.51 g, 2.67 mmol) was added and heating continued for 12 h. The reaction was cooled to ambient temperature, and was poured into a mixture of EtOAc and saturated aqueous sodium bicarbonate. The mixture was filtered through celite, and the organic layer was removed. The aqueous layer was extracted twice with EtOAc, and the combined organic layers were dried with $Na_2SO_4$, filtered, and concentrated to give a cloudy oil. This material was filtered through silica gel with 90/10/1 dichloromethane/MeOH/conc. $NH_4OH$ and concentrated in vacuo to give the title compound as a red oil. MS ($ES^+$): 285.9 $(M+H)^+$. Calc'd for $C_{12}H_{20}BrN_3$: 286.21.

Examples 131-141 were prepared by methods similar to the procedures described in pending U.S. Patent Application No. 60/569,193.

| Example No | Structure |
|---|---|
| 131 | |
| 132 | |
| 133 | 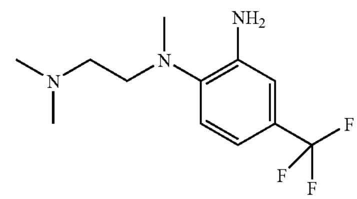 |
| 134 | 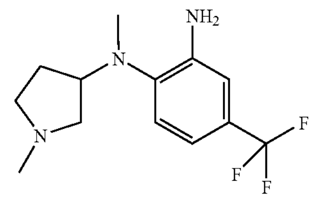 |
| 135 | 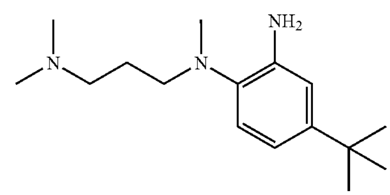 |
| 136 | 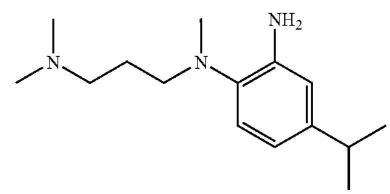 |
| 137 | 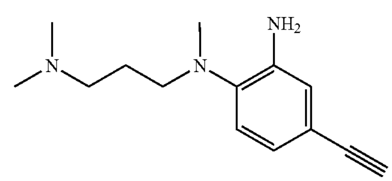 |
| 138 | 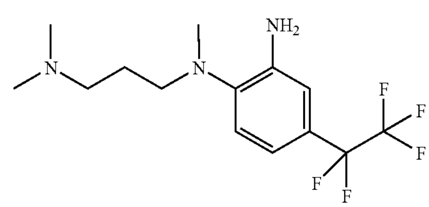 |
| 139 | 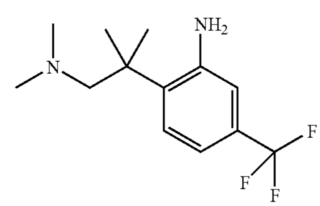 |

| Example No | Structure |
|---|---|
| 140 | 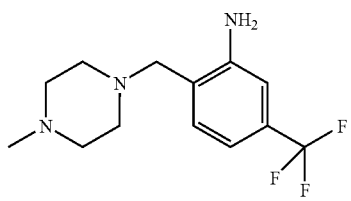 |
| 141 | 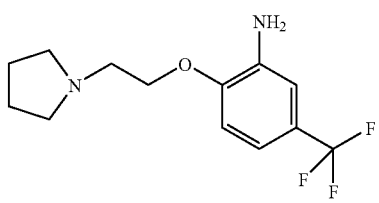 |

Example 142

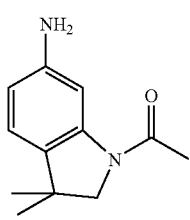

1-(6-amino-3,3-dimethylindolin-1-yl)ethanone

The title compound was prepared according to a procedure described in U.S. Patent Publication No. 2003/0203922.

Example 143

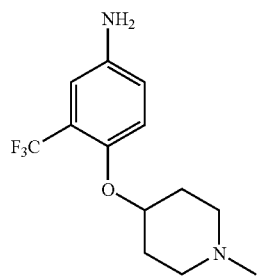

4-(1-methylpiperidin-4-yloxy)-3-(trifluoromethyl)benzenamine

The title compound was synthesized in a manner similar to Example 56 of pending U.S. Patent Application No. 60/569,193.

Example 144

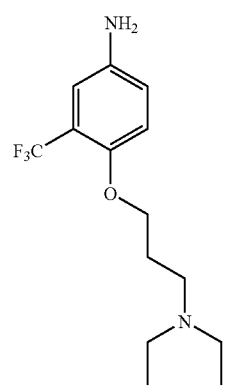

4-(3-(diethylamino)propoxy)-3-(trifluoromethyl)benzenamine

The title compound was synthesized in a manner similar to Example 143 above.

Example 145

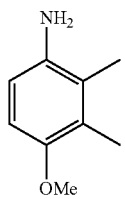

4-methoxy-2,3-dimethylbenzenamine

The title compound was synthesized in a manner similar to Example 143 above.

Example 146

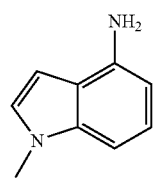

161

1-methyl-1H-indol-4-amine

The title compound was synthesized in a manner similar to Example 143 above.

Example 147

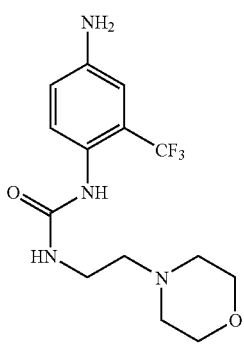

1-(4-amino-2-(trifluoromethyl)phenyl)-3-(2-morpholinoethyl)urea

Step 1: 1-(2-morpholinoethyl)-3-(4-nitro-2-(trifluoromethyl)phenyl)urea

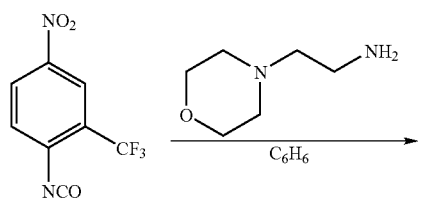

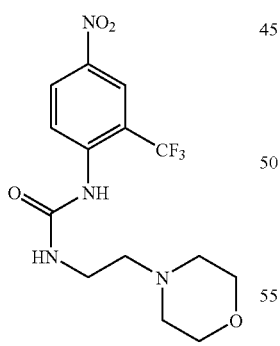

To a solution of 1-isocyanato-4-nitro-2-(trifluoromethyl)benzene (339 µL, 2.21 mmol, 1.0 equiv) in benzene (3.0 mL), was added 2-morpholinoethanamine (316 mg, 2.43 mmol, 1.0 equiv). The resulting precipitant was filtered and washed with hexanes to provide 1-(2-morpholinoethyl)-3-(4-nitro-2-(trifluoromethyl)phenyl)urea, which was advanced without further purification. MS (MH$^+$) 363; Calculated for $C_{14}H_{17}F_3N_4O_4$: 362.1

162

Step 2: 1-(4-amino-2-(trifluoromethyl)phenyl)-3-(2-morpholinoethyl)urea

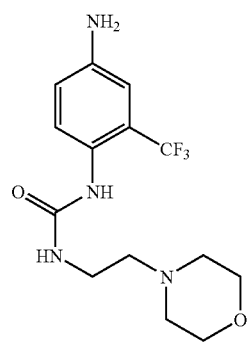

A mixture of 1-(2-morpholinoethyl)-3-(4-nitro-2-(trifluoromethyl)phenyl)urea (651 mg, 1.80 mmol, 1.0 equiv) and 10% Pd/C (20 mg) in EtOAc (25 mL) and MeOH (2 mL) was exposed to an atmosphere of H$_2$ (balloon). Upon completion of the reduction, the reaction mixture was filtered through celite and concentrated in vacuo to afford 1-(4-amino-2-(trifluoromethyl)phenyl)-3-(2-morpholinoethyl)urea, which was advanced without further purification. MS m/z: 333 (M+H$^+$); Calculated for $C_{14}H_{19}F_3N_4O_2$: 332.2

Example 148

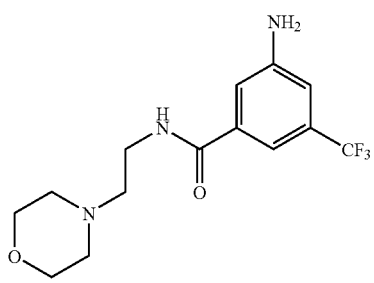

3-amino-N-(2-morpholinoethyl)-5-(trifluoromethyl) benzamide

Step 1: N-(2-morpholinoethyl)-3-nitro-5-(trifluoromethyl)benzamide

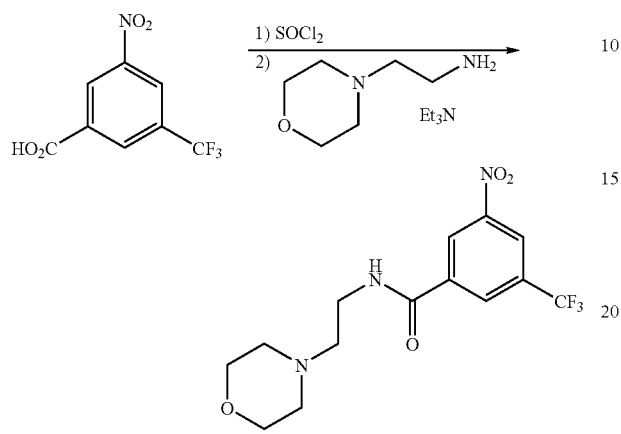

A mixture of 3-nitro-5-(trifluoromethyl)benzoic acid (300 mg, 1.29 mmol, 1.0 equiv) and thionyl chloride (2.0 ml) was heated at 75° C. for 1 h. The solvent was removed in vacuo and the residue taken up in $CH_2Cl_2$ (5.0 ml). To the solution was added 2-morpholinoethanamine (185 mg, 1.42 mmol, 1.1 equiv) and triethylamine (0.54 ml, 3.86 mmol, 3.0 equiv). After the reaction was complete, the solution was diluted with $CH_2Cl_2$ (ca. 10 ml) and washed with water and brine. After drying with $Na_2SO_4$ and concentration in vacuo, the resulting N-(2-morpholinoethyl)-3-nitro-5-(trifluoromethyl)benzamide was advanced without further purification. MS m/z: 348 (M+H$^+$); Calculated for $C_{14}H_{16}F_3N_3O_4$: 347.1

Step 2: 3-amino-N-(2-morpholinoethyl)-5-(trifluoromethyl)benzamide

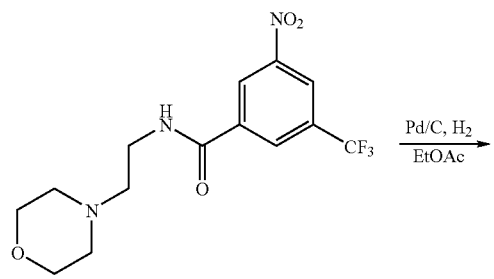

A mixture of N-(2-morpholinoethyl)-3-nitro-5-(trifluoromethyl)benzamide (300 mg, 0.865 mmol, 1.0 equiv) and 10% Pd/C (20 mg) in EtOAc (25 ml) and MeOH (2 mL) was exposed to an atmosphere of $H_2$ (balloon). Upon completion of the reduction, the reaction mixture was filtered through celite and concentrated in vacuo to afford 3-amino-N-(2-morpholinoethyl)-5-(trifluoromethyl)benzamide, which was advanced without further purification. MS m/z: 318 (M+H$^+$); Calculated for $C_{14}H_{18}F_3N_3O_2$: 317.1

Example 149

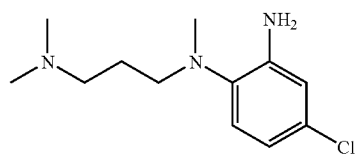

4-chloro-N1-(3-(dimethylamino)propyl)-N1-methyl-benzene-1,2-diamine

Step 1: Preparation of 4-chloro-N-(3-(dimethylamino)propyl)-N-methyl-2-nitrobenzenamine To 2,5-dichloronitrobenzene (3.0 g, 16 mmol) was added N1,N1,N3-trimethylpropane-1,3-diamine (2.2 g, 19 mmol). The mixture was stirred for 2.5 days at RT, diluted with 0.01 N HCl and extracted with EtOAc. The aqueous layer was made basic with $Na_2CO_3$ and extracted with EtOAc. The organic layer was dried over anhydrous $Na_2SO_4$, filtered and concentrated to yield 4-chloro-N-(3-(dimethylamino)propyl)-N-methyl-2-nitrobenzenamine as an orange oil. MS m/z=272 [M+H]$^+$. Calc'd for $C_{12}H_{18}ClN_3O_2$: 271.75.

Step 2: Preparation of 4-chloro-N1-(3-(dimethylamino)propyl)-N-1-methylbenzene-1,2-diamine To 4-chloro-N-(3-(dimethylamino)propyl)-N-methyl-2-nitrobenzenamine (4.0 g, 15 mmol) in EtOH (80 ml) and water (10 ml) was added Raney-Ni (10 g). The mixture was stirred for 5 hours at RT, filtered through a pad of Celite and concentrated to yield 4-chloro-N1-(3-(dimethylamino)propyl)-N1-methylbenzene-1,2-diamine as a deep red oil. MS m/z=242 [M+H$^+$. Calc'd for $C_{12}H_{20}ClN_3$: 241.77.

Example 150

3-amino-4-deuteromethoxy(-d$_3$)benzotrifluoride

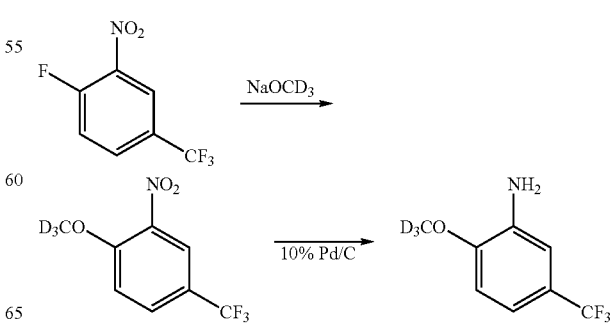

Step 1: To 10 g of deuterated methanol over an ice bath was added sodium metal until a cloudy solution formed. 4-Chloro-3-nitrobenzotrifluoride (2.25 g, 1.46 mL, 0.01 mol), was added to the solution dropwise over an ice bath. The reaction mixture was allowed to stir 24 hours at room temperature. The orange solution is brought to pH 6 (turns yellow) with acetic acid added dropwise over an ice bath.

Step 2: 10% Palladium on carbon (0.05 g) was added to a reaction mixture of the nitroaniline (0.01 mol) allowed to stir at room temperature under a $H_2(g)$ atmosphere (via balloon). The reaction mixture was then filtered through celite. The filtrate was concentrated to afford a yellow oil that was reconstituted in dichloromethane (5 ml) and purified by flash silica column using isocratic 90/10/1 $CH_2Cl_2/CH_3OH/NH_4OH$. A very pale yellow solid is isolated. LC-MS(+) revealed a mass of 195 (M+H$^+$); calc'd for $C_8H_5D_3F_3NO$: 194.17.

Example 151

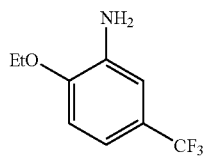

3-amino-4-ethoxybenzotrifluoride

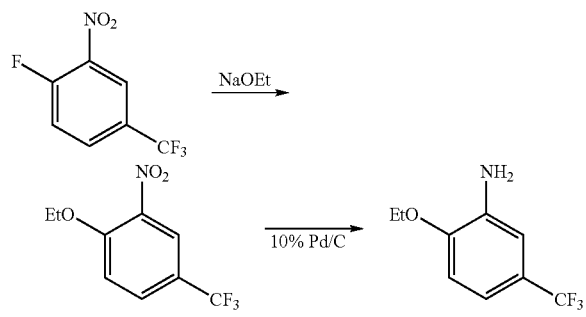

The title compound was prepared by a method similar to Example 150, using ethanol in place of deuteromethanol and purified by flash silica column using isocratic 90/10/1: $CH_2Cl_2/CH_3OH/NH_4OH$. A very pale yellow solid was isolated. LC-MS(+) revealed a mass of 206 (M+H$^+$); calc'd for $C_9H_{10}F_3NO$: 205.18.

Example 152

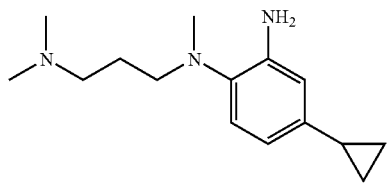

4-cyclopropyl-N1-(3-(dimethylamino)propyl)-N1-methylbenzene-1,2-diamine

Step 1: N-(4-Bromo-2-nitro-phenyl)-N,N',N'-trimethylpropane-1,3-diamine

To a round bottom flask at 0° C. was added 4-Bromo-1-fluoro-2-nitrobenzene (10 g, 45.46 mmol) and N,N,N'-Trimethyl-propane-1,3-diamine (6.99 ml, 47.73 mmol). The reaction was allowed to warm to RT and stirred for 16 h. The reaction was extracted into EtOAc, washed once with saturated aqueous $NaHCO_3$, twice with water, and then dried over $Mg_2SO_4$. The organic layer was filtered and concentrated to yield the title compound as a bright orange solid.
MS (M+H$^+$)=316, 318; Calc'd for $C_{12}H_{18}BrN_3O_2$=316.19.

Step 2: 4-cyclopropyl-N-(3-(dimethylamino)propyl)-N-methyl-2-nitrobenzenamine

To a pressure vessel was added 2-cyclopropyl-4,4,5,5-tetramethyl-1,3,2-dioxaborolane (900 mg, 5.36 mmol), potassium phosphate (3.0 g, 14.42 mmol), and 0.82 mL water. After stirring at RT for 15 minutes, N-(4-Bromo-2-nitrophenyl)-N,N',N'-trimethyl-propane-1,3-diamine (Step 1, 1.30 g, 4.12 mmol), palladium acetate (92 mg, 0.412 mmol), tricyclohexylphosphine (231 mg 0.824 mmol), and 21 ml toluene were added. The reaction was sealed and stirred at 80° C. for 19 h. The reaction was then cooled to RT, quenched with EtOAc and extracted into water, washed once with brine, and then dried over $Mg_2SO_4$. The crude mixture was then purified by reverse phase chromatography to yield the title compound as a dark red-brown oil. MS (M+H$^+$)=278; Calc'd for $C_{15}H_{23}N_3O_2$=277.36.

Step 3: 4-cyclopropyl-N-1-(3-(dimethylamino)propyl)-N-1-methylbenzene-1,2-diamine 4-cyclopropyl-N-(3-(dimethylamino)propyl)-N-methyl-2-nitrobenzenamine (Step 2, 600 mg, 2.16 mmol) was dissolved in 22 mL MeOH. Palladium (115 mg, 0.108 mmol, 10% w/w on carbon) was added, a balloon containing hydrogen was inserted, and the reaction was stirred at RT for 18 h. The solution was then filtered through a pad of Celite and concentrated, yielding the title compound as viscous red-brown oil. MS (M+H$^+$)=248; Calc'd for $C_{15}H_{25}N_3$=247.38.

Example 153

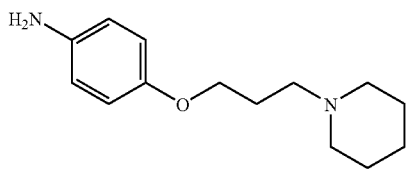

4-(3-Piperidin-1-yl-propoxy)aniline

Step 1: 1-(3-Chloropropyl)piperidine

A mixture of 1-bromo-3-chloropropane (65.6 g, 0.417 mol) and piperidine (62 ml, 0.625 mol) in anhydrous THF (200 ml) was heated to reflux for 24 h. The mixture was cooled to RT and filtered to remove solids. The organics were concentrated under in vacuo. The resultant residue was taken up in 2N HCl and washed twice with ethyl acetate. The aqueous layer was basicified with 2N NaOH to pH 14. The compound was extracted three times with ethyl acetate and the combined organics dried over anhydrous magnesium sulfate. The solution was then concentrated under reduced pressure to give the desired compound as a yellowish oil.

Step 2: 1-[3-(4-nitrophenoxy)propyl]piperidine

In a three-necked flask fitted with an overhead mechanical stirrer, a mixture of 1-(3-chloropropyl)piperidine (49.8 g, 0.308 mol), 4-nitrophenol (42.8 g, 0.308 mol) and potassium carbonate (212 g, 1.53 mol), in anhydrous DMF (200 mL) was heated to 94° C. and stirred for 18 h. The mixture was cooled to room temperature, then diluted with 2 L water. The organics were taken up in ethyl acetate and washed twice with 2N sodium hydroxide and then brine. The combined organics were dried over magnesium sulfate then concentrated under reduced pressure to give the title compound as a yellowish oil.

Step 3: 4-(3-Piperidin-1-ylpropoxy)aniline

A mixture of 1-[3-(4-nitrophenoxy)propyl]piperidine (15.5 g, 58.6 mmol) and 10% Pd/C (12.5 g) in 150 mL of EtOH was placed under a balloon of $H_2$. The mixture was stirred for 18 h. The catalyst was removed by suction filtration and the organics concentrated to give the title compound as a yellowish oil. MS (m/z)=235.2 (M+H$^+$); Calc'd for $C_{14}H_{22}N_2O$=234.34.

Example 154

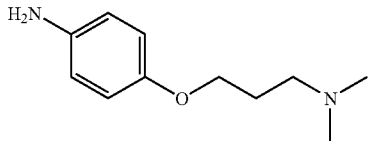

4-(3-(dimethylamino)propoxy)aniline

Step 1: 1-(3-chloropropoxy)-4-nitrobenzene

A solution of 4-Nitrophenol (10 g, 72 mmol) dissolved in acetonitrile (100 ml was charged with potassium carbonate (24.9 g, 180 mmol) and 1-bromo-3-chloropropane (113.2 g, 720 mmol). The mixture was heated and stirred at reflux overnight. The reaction was cooled to room temperature, the solids filtered off and the solvent evaporated under reduced pressure to give the title compound.

Step 2: 4-(3-(dimethylamino)propoxy)nitrobenzene

A mixture of 1-(3-chloropropoxy)-4-nitrobenzene (2 g, 9.27 mmol), potassium carbonate (7.69 g, 46.4 mmol) and acetonitrile (15 ml) was prepared and stirred in a tube. To the stirring solution dimethylamine hydrochloride (3.78 g, 46.4 mmol) was added quickly. The tube was sealed and the mixture was stirred while heating overnight at 80° C. The mixture was cooled well before opening the pressure tube, then water and dichloromethane were added and the aqueous layer was extracted with dichloromethane. The combined organics were dried and evaporated giving the title product.

Step 3: 4-(3-(dimethylamino)propoxy)aniline 4-(3-(dimethylamino)propoxy)nitrobenzene (4.4 g, 19.6 mmol) was hydrogenated over Pd (10% on C, 0.4 g) in ethanol (50 ml) for 16 h. The catalyst was filtered off and the solvent removed under reduced pressure to afford the title compound as a brown oil. MS (m/z)=195.3 (M+H$^+$); Calc'd for $C_{11}H_{18}N_2O$=194.28.

Example 155

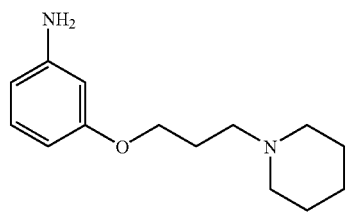

3-(3-Piperidin-1-yl-propoxy)aniline

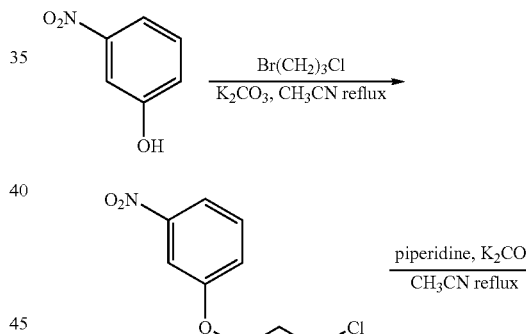

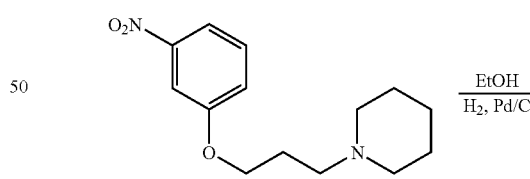

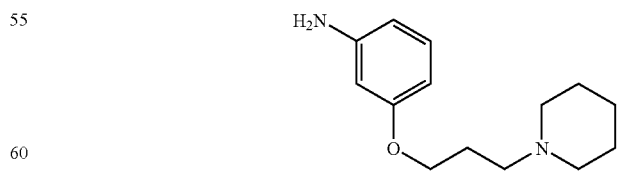

The title compound was prepared by a method similar to that described in Example 154 above, wherein 3-nitrophenol was substituted for 4-nitrophenol in Step 1 and piperidine for dimethylamine hydrochloride in Step 2. MS (m/z)=235.2 (M+H$^+$); Calc'd for $C_{14}H_{23}N_2O$=234.34.

Example 156

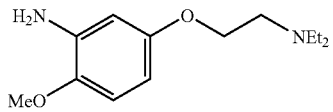

5-(2-(diethylamino)ethoxy)-2-methoxyaniline

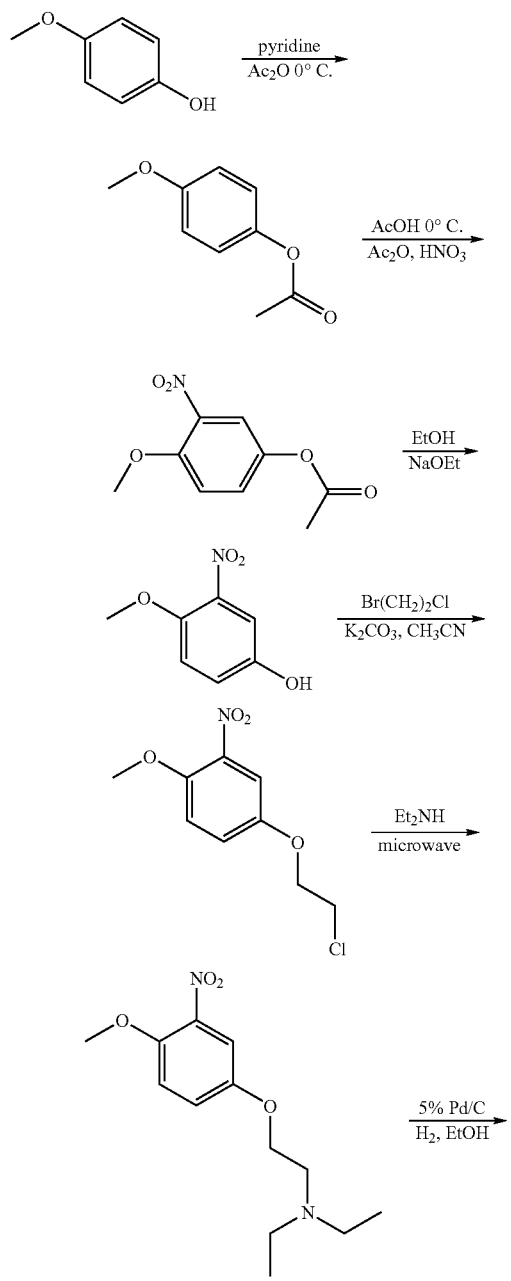

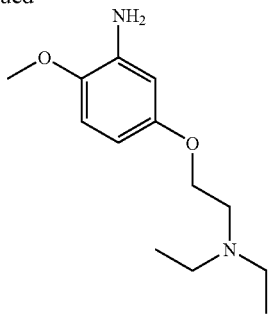

Step 1: 4-Methoxyphenylacetate

4-Methoxyphenol (2 g, 16 mmol) was dissolved in anhydrous pyridine (6.5 ml) and stirred while cooling at 0° C. under a nitrogen atmosphere. Acetic anhydride (7.5 ml, 80 mmol) was added. The reaction was allowed to warm to room temperature, where it was stirred for 16 h. The reaction was cooled in an ice bath before quenching with ice. The solution was neutralized with saturated aqueous sodium bicarbonate solution and then extracted with ethyl acetate. The combined organic extracts were washed twice with 2M HCl, then with saturated aqueous copper sulfate solution to remove residual pyridine. The organic extract was further washed with 5M aqueous sodium hydroxide solution and brine, then dried over sodium sulfate and concentrated under reduced pressure to afford a clear oil, which crystallized to give the title compound as a white solid.

Step 2: 4-Methoxy-3-nitrophenylacetate

4-Methoxyphenylacetate (2.37 g, 14.3 mmol) was dissolved in glacial acetic acid (4 ml) and cooled to 5-10° C. A chilled mixture of glacial acetic acid (1.3 ml), fuming nitric acid (0.9 ml) and acetic anhydride (1.3 ml) was added dropwise as the temperature gradually increased to 25° C. The reaction was stirred for 1 h, then quenched with ice and diluted with water. The resulting precipitate was isolated by filtration, rinsed with water and dried in vacuo to afford the title compound as a fine crystalline yellow solid.

Step 3: 4-Methoxy-3-nitrophenol

4-Methoxy-3-nitrophenylacetate (2.46 g, 11.7 mmol) was dissolved in anhydrous ethanol (80 ml) and sodium ethoxide (1.19 g, 17.5 mmol) was added. The reaction was stirred at room temperature for 0.5 h. The dark red solution was acidified with 2M HCl and concentrated under reduced pressure. The residue was taken up into water and extracted with dichloromethane. The combined organics were washed with 2M HCl and brine, then dried over sodium sulfate. Evaporation of the solvent under reduced pressure gave the title compound as a yellow solid.

Step 4: 4-(2-chloroethoxy)-1-methoxy-2-nitrobenzene

4-Methoxy-3-nitrophenol (0.8 g, 4.7 mmol) was dissolved in acetonitrile (13 ml). Potassium carbonate (1.63 g, 11.8 mmol) was added, followed by 1-bromo-2-chloroethane (3.93 ml, 47.2 mmol). The reaction was heated and stirred at reflux for 20 h. The reaction was cooled to room temperature, the solid was then filtered off and the solvent evaporated under reduced pressure to give the title compound.

Step 5: N,N-Diethyl-2-(4-methoxy-3-nitrophenoxy)ethylamine 4-(2-chloroethoxy)-1-methoxy-2-nitrobenzene (0.15 g, 0.67 mmol) was dissolved in acetonitrile (1 ml). Excess diethylamine (1.5 ml, 17.7 mmol) was added and the reaction heated in the microwave (T=120° C., 40 min) to complete conversion. The reaction mixture was diluted with dichloromethane, then washed with 5M sodium hydroxide and brine, then dried over sodium sulfate. Evaporation of the solvent under reduced pressure gave the title compound as an orange oil.

Step 6: 5-(2-(diethylamino)ethoxy)-2-methoxyphenylamine

N,N-diethyl-2-(4-methoxy-3-nitrophenoxy)ethylamine (0.29 g, 1.1 mmol) was hydrogenated over Pd (5% on C, 50% wet, 0.12 g) in ethanol (5 ml) for 16 hours. The catalyst was filtered off and the solvent removed under reduced pressure to afford the title compound as a red oil. MS (m/z)=239(M+H$^+$); Calc'd for $C_{13}H_{22}N_2O_2$=238.33.

Example 157

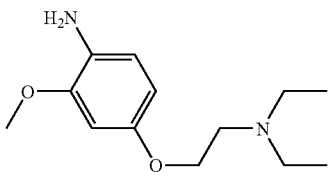

4-(2-(diethylamino)ethoxy)-2-methoxyaniline

Step 1: 4-Fluoro-2-methoxynitrobenzene

5-Fluoro-2-nitrophenol (6 g, 38.2 mmol) was dissolved in anhydrous DMF (20 ml). Potassium carbonate (5.3 g, 38.2 mmol) was added, followed by iodomethane (2.28 ml, 38.2 mmol). The reaction was stirred at room temperature for 16 h, then partitioned between dichloromethane and water. The organic layer was washed three times with 1M sodium hydroxide and once with brine, then dried over sodium sulfate. Removal of the solvent in vacuo afforded the title compound as a yellow oil, which solidified upon standing.

Step 2: 3-Methoxy-4-nitrophenol

4-Fluoro-2-methoxynitrobenzene (4.68 g, 27.4 mmol) was suspended in a 5M potassium hydroxide solution (50 ml) and heated to 90° C. for 5 h. The red solution was cooled to room temperature and acidified to pH 6 with 1M HCl. The aqueous solution was extracted three times with ethyl acetate and the combined organics were washed with brine and dried over sodium sulfate. Removal of the solvent under reduced pressure, followed by purification by flash column chromatography (1:1 hexane/ethyl acetate) afforded the title compound as a yellow solid.

Step 3: 4-(2-chloroethoxy)-2-methoxy-1-nitrobenzene

3-Methoxy-4-nitrophenol (0.6 g, 3.6 mmol) was dissolved in acetonitrile (15 ml). Potassium carbonate (1.3 g, 9.1 mmol) was added, followed by 1-bromo-2-chloroethane (5.1 g, 35.5 mmol). The reaction was stirred in a sealed pressure tube at 80° C. for 20 h. The reaction was cooled to room temperature, the solid was then filtered off and the solvent evaporated under reduced pressure. The residue was then taken up into ethyl acetate and washed with 1M sodium hydroxide, brine, and then dried over sodium sulfate. Evaporation of the solvent afforded the title compound as a yellow solid.

Step 4: N,N-Diethyl-2-(3-methoxy-4-nitrophenoxy)ethylamine 4-(2-Chloroethoxy)-2-methoxy-1-nitrobenzene (0.22 g, 0.9 mmol) was dissolved in acetonitrile (1 ml). Diethylamine (0.14 ml, 2.6 mmol) and potassium carbonate (0.31 g, 2.2 mmol) were added and the reaction was heated in a sealed pressure tube to 80° C. for 20 h. The reaction mixture was diluted with dichloromethane, then washed with 1M sodium hydroxide and brine, then dried over sodium sulfate. Evaporation of the solvent under reduced pressure gave the title compound as a brown oil.

Step 5: N,N-Diethyl-2-(4-amino-3-methoxyphenoxy)ethylamine

N,N-Diethyl-2-(3-methoxy-4-nitrophenoxy)ethylamine (140 mg, 0.5 mmol) was hydrogenated over Pd (5% on C, 50% wet, 40 mg) in ethanol (5 ml) for 16 hours. The catalyst was filtered off and the solvent removed under reduced pressure to afford the title compound as a brown oil. MS (m/z)= 239 (M+H$^+$); Calc'd for $C_{13}H_{22}N_2O_2$=238.33

Example 158

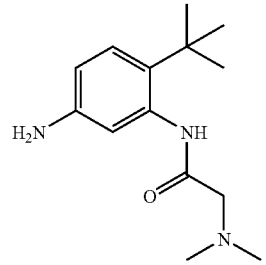

N-(5-amino-2-tert-butylphenyl)-2-dimethylamino) acetamide

Step 1: 2-tert-butyl-5-nitrobenzenamine

Concentrated sulfuric acid (1 L) was cooled to −10° C. with a dry ice-isopropanol bath in a 2 L 3-necked round bottom flask fitted with a mechanical stirrer and temperature probe. The 2-t-butylaniline (109 g, 730 mmol) was added, giving a clumpy solid. Once the temperature of the mixture was stabilized at −10° C., the potassium nitrate (101 g, 1001 mmol) was added portion wise, as a solid, over a 4-hour period, maintaining the temperature between −20 and −5° C. Once all of the potassium nitrate was added, the reaction was left to stir overnight with gradual warming to room temperature. The reaction was quenched by diluting with water and then extracting three times with EtOAc. Each of the EtOAc extracts was washed multiple times with saturated NaHCO$_3$, until gas evolution ceased, and with brine. The ethyl acetate extracts were combined, dried over anhydrous Na$_2$SO$_4$, filtered and concentrated under reduced pressure giving a black oil. The oil was eluted through a 36 x & cm column of silica gel with EtOAc: hexanes gradient 5-50%. Solvent evaporation afforded 2-tert-butyl-5-nitrobenzenamine as a red solid.

Step 2:
2-bromo-N-(2-tert-butyl-5-nitrophenyl)acetamide 2-tert-Butyl-5-nitrobenzenamine (70 g, 359 mmol) and a catalytic amount of DMAP were dissolved into THF (1.5 L) under N$_2$. Triethylamine (109 g, 1077 mmol) was added and the solution was cooled to 0° C. Bromoacetyl bromide (207 g, 1023 mmol) was then added and the reaction was stirred at room temperature for 16 hours. The reaction was then partially concentrated under reduced pressure, treated with water, and extracted three times with EtOAc. The EtOAc extracts were washed with brine, combined, dried over Na$_2$SO4 and concentrated to a black oil. The oil was purified using silica chromatography, 95:5:0.5 CH$_2$Cl$_2$:MeOH:NH$_4$OH, giving 2-bromo-N-(2-tert-butyl-5-nitrophenyl)acetamide as a brown solid.

Step 3: N-(2-tert-butyl-5-nitrophenyl)-2-(dimethylamino)acetamide

2-Bromo-N-(2-tert-butyl-5-nitrophenyl)acetamide (80 g, 253, mmol) and potassium carbonate (70 g, 506 mmol) were combined in THF (1.75 L), and the mixture was cooled to 0° C. N,N-Dimethylamine (40 mL of a 2 M solution in THF, 800 mmol) was then added to the mixture through an addition funnel over a 30-minute period. The mixture was then stirred at room temperature for 16 hours. The mixture was filtered and the filtrate concentrated. The crude material was purified by silica chromatography eluting with 50% EtOAc:hexanes to give N-(2-tert-butyl-5-nitrophenyl)-2-(dimethylamino)acetamide as a brown solid.

Step 4: N-(5-amino-2-tert-butylphenyl)-2-dimethylamino)acetamide

To a solution of N-(2-tert-butyl-5-nitrophenyl)-2-(dimethylamino)acetamide (25.8 g, O$_2$ mmol) in 1,4-dioxane (200 mL) was added 10% Pd/C (2.5 g) as a slurry in a minimal amount of EtOH. The mixture was evacuated and purged with H$_2$, and stirred at room temperature for 16 hours. The reaction was then purged with N$_2$ and filtered through celite. The filtrate was concentrated and purified using silica chromatography, 97.5:2.5:0.25 to 95:5:0.5 CH$_2$Cl$_2$:MeOH:NH$_4$OH, to afford N-(5-amino-2-tert-butylphenyl)-2-dimethylamino)acetamide as a brown solid.

Example 159

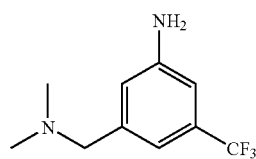

3-((dimethylamino)methyl)-5-(trifluoromethyl)benzenamine

The title compound was synthesized using a procedure similar to that described in Example 95. MS m/z=219 [M+H]$^+$. Calc'd for C$_{10}$H$_{13}$F$_3$N$_2$: 218.

Example 160

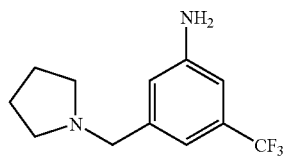

3-(pyrrolidin-1-ylmethyl)-5-(trifluoromethyl)benzenamine

The title compound was synthesized using a procedure similar to that described in Example 95. MS m/z=245 [M+H]$^+$. Calc'd for C$_{12}$H$_{15}$F$_3$N$_2$: 244.

Example 161

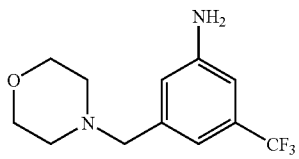

3-(pyrrolidin-1-ylmethyl)-5-(trifluoromethyl)benzenamine

The title compound was synthesized using a procedure similar to that described in Example 95. MS m/z=261 [M+H]$^+$. Calc'd for $C_{12}H_{15}F_3N_2O$: 260.

Example 162

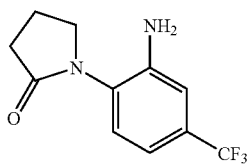

1-(2-amino-4-(trifluoromethyl)phenyl)pyrrolidin-2-one

A resealable tube was charged with 2-bromo-5-(trifluoromethyl)aniline (1.00 g, 4.16 mmol), 2-pyrrolidinone (0.425 g, 5.00 mmol), N,N'-ethylene diamine (0.037 g, 0.42 mmol), potassium carbonate (1.15 g, 8.32 mmol), copper iodide (0.80 mg, 0.42 mmol) and toluene (1.0 mL). The tube was sealed and the mixture was heated at 80° C. for 24 h. The resulting mixture was partitioned between ethyl acetate and water. The organic phase was separated, dried over anhydrous sodium sulfate, filtered, and concentrated. The residue was purified via column chromatography on silica gel (gradient elution with 0-100% ethyl acetate-hexane) to afford 1-(2-amino-4-(trifluoromethyl)phenyl)pyrrolidin-2-one as a gray solid. MS m/z=245 [M+H]$^+$. Calc'd for $C_{11}H_{11}F_3N_2O$: 244.

Example 163

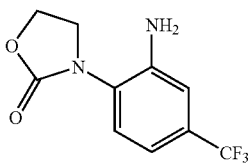

3-(2-amino-4-(trifluoromethyl)phenyl)oxazolidin-2-one

The title compound was synthesized using a procedure similar to that described in Example 162. MS m/z=247 [M+H]$^+$. Calc'd for $C_{10}H_9F_3N_2O_2$: 246.

Example 164

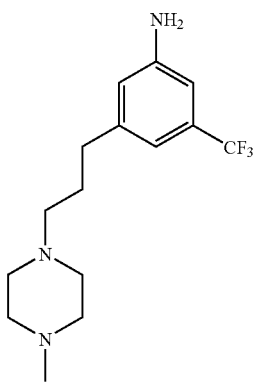

3-(3-(4-methylpiperazin-1-yl)propyl)-5-(trifluoromethyl)benzenamine

A solution of 1-allyl-4-methylpiperazine (2.12 g, 14.0 mmol) and 9-BBN (0.5 M in THF, 1.7 g, 28 mL, 14.0 mmol) was heated at reflux for 3 h and then cooled to RT. The solution was added to a mixture of 3-bromo-5-(trifluoromethyl)aniline (3.0 o g, 12.5 mmol), potassium carbonate (8.64 g, 62.5 mmol), PdCl$_2$(PPh$_3$)$_2$—CH$_2$Cl$_2$ adduct (0.457 g, 0.6 mmol), DMF (30 mL) and water (2 mL). The mixtre was heated to 75° C. for 24. The mixture was concentrated, triturated with dichloromethane, and filtered. The filtrate was concentrated and the residue was purified via column chromatography on silica gel (gradient elution with 0-20% methanol-dichloromethane) to afford 3-(3-(4-methylpiperazin-1-yl)propyl)-5-(trifluoromethyl)benzenamine as a brown oil. MS m/z=302 [M+H]$^+$. Calc'd for $C_{15}H_{22}F_3N_3$: 301.

Example 165

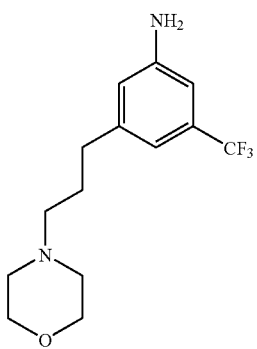

3-(3-morpholinopropyl)-5-(trifluoromethyl)benzenamine

The title compound was synthesized using a procedure similar to that described in Example 164. MS m/z=289 [M+H]$^+$. Calc'd for $C_{14}H_{19}F_3N_2O$: 288.

Example 166

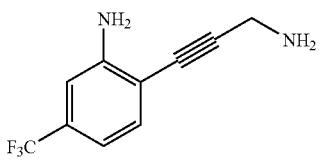

2-(3-dimethylamino-1-propynyl)-5-(trifluoromethyl) aniline

A resealable tube was charged with 2-bromo-5-(trifluoromethyl)aniline (1.00 g, 4.16 mmol), 1-dimethylamino-2-propyne (0.520 g, 6.20 mmol), PdCl$_2$(PPh$_3$)$_2$ (0.15 g, 0.21 mmol), copper iodide (0.80 mg, 0.42 mmol), diisopropylethylamine (1.0 mL) and acetonitrile (3.0 mL). The system was purged with argon, the tube sealed and the mixture stirred at room temperature for 20 h. The reaction mixture was filtered through celite and concentrated. The residue was purified via column chromatography on silica gel (gradient elution with 0-10% methanol-dichloromethane) to afford 2-(3-dimethylamino-1-propynyl)-5-(trifluoromethyl)aniline as a brown oil. MS m/z=243 [M+H]$^+$. Calc'd for $C_{12}H_{13}F_3N_2$: 242.

Example 167

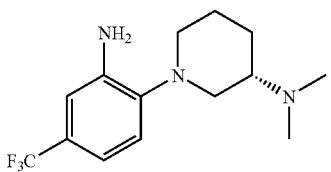

(S)-1-(2-amino-4-(trifluoromethyl)phenyl)-N,N-dimethylpiperidin-3-amine

Step 1: (S)-tert-butyl 1-(2-nitro-4-(trifluoromethyl) phenyl)piperidin-3-ylcarbamate To a 200-mL RBF was added (s)-3-n-boc-amino piperidine (10.9 g, 54.4 mmol), Sodium bicarbonate (11.4 g, 136 mmol), THF, and 1-fluoro-2-nitro-4-(trifluoromethyl)benzene (7.62 ml, 54.4 mmol). The yellow mixture was heated to 70° C. with a water-cooled reflux condenser. The orange mixture was allowed to stir for 14 h, and was then cooled to ambient temperature, and filtered through a glass frit, rinsing with EtOAc. Concentration in vacuo afforded an orange oil, which crystallized on standing to an orange solid. The material was treated with 250 mL hexanes and heated on the rotovap (no vacuum) to 60° C. Small amounts of EtOAc were added until all solid dissolved, total volume of EtOAc was approx 10 mL. The solution was allowed to cool overnight, resulting in the formation of orange crystals. The liquid was decanted and the crystals rinsed twice with 50 mL hexanes. The crystals were collected to give (S)-tert-butyl 1-(2-nitro-4-(trifluoromethyl) phenyl)piperidin-3-ylcarbamate as orange crystals. The filtrate was concentrated to an orange solid. This material was treated with 150 mL hexanes and was heated to 65° C. Almost all of the material had dissolved. The hot liquid was decanted into a flask and allowed to cool overnight, resulting in an orange solid. The liquid was discarded, and additional crystals of (S)-tert-butyl 1-(2-nitro-4-(trifluoromethyl)phenyl)piperidin-3-ylcarbamate were collected. MS m/z=390 [M+H]$^+$. Calc'd for $C_{17}H_{20}F_3N_3$: 389.

Step 2: (S)-1-(2-nitro-4-(trifluoromethyl)phenyl) piperidin-3-amine dihydrochloride A solution of (S)-tert-butyl 1-(2-nitro-4-(trifluoromethyl) phenyl)piperidin-3-ylcarbamate (15.64 g, 40 mmol) was cooled to 7° C. and hydrochloric acid 4.0 M dioxane (80 ml, 321 mmol) was added and the mixture allowed to warm to ambient temperature. The orange solution was allowed to stir for 14 h, at which point it was concentrated in vacuo to give (S)-1-(2-nitro-4-(trifluoromethyl)phenyl)piperidin-3-amine dihydrochloride as a yellow solid. MS m/z=290 [M+H]$^+$. Calc'd for $C_{12}H_{14}F_3N_3O_2$: 289.

Step 3: (S)-N,N-dimethyl-1-(2-nitro-4-(trifluoromethyl)phenyl)piperidin-3-amine To a yellow solution of (S)-1-(2-nitro-4-(trifluoromethyl) phenyl)piperidin-3-amine dihydrochloride (13.39 g, 37 mmol) in 123 mL MeOH under nitrogen at 0° C. was added formaldehyde (37% solution) (14 ml, 185 mmol), Acetic acid (11 ml, 185 mmol), and sodium cyanoborohydride (4.6 g, 74 mmol) in portions over 5 min. The cloudy mixture was warmed to ambient temperature. After 10 min, the reaction became quite hot and was cooled with an ice bath. After 1.5 h, the reaction was complete by LCMS. The solvent was removed in vacuo, and the flask cooled to 0° C. Water was added, and the mixture was basified with 1N NaOH, and 6N NaOH. The mixture was extracted with 1×200 mL EtOAc, 1×100 mL EtOAc, and the combined organics were dried over anhydrous Na$_2$SO$_4$ and concentrated in vacuo to give (S)-N,N-dimethyl-1-(2-nitro-4-(trifluoromethyl)phenyl)piperidin-3-amine as an orange oil. MS m/z=318 [M+H]$^+$. Calc'd for $C_{14}H_{18}F_3N_3O_2$: 317.

Step 4: (S)-1-(2-amino-4-(trifluoromethyl)phenyl)-N,N-dimethylpiperidin-3-amine A 500 mL parr pressure bottle was charged with palladium, 10 wt. % on activated carbon, 50% water wet (9.1 g, 8.6 mmol) under nitrogen. (S)-N,N-dimethyl-1-(2-nitro-4-(trifluoromethyl)phenyl)piperidin-3-amine (13.6 g, 43 mmol) was added as a solution in methanol via syringe, rinsing in with multiple methanol washes until the final volume was approximately 100 mL. The vessel was placed in a parr shaker, and treated with 2 atm H$_2$ and shaken overnight. The reaction was flushed with nitrogen, and filtered through a pad of celite rinsing with 1.3 L of methanol and concentrated in vacuo. The oil was taken up in CH$_2$Cl$_2$, dried over Na$_2$SO$_4$, filtered, and concentrated in vacuo to give (S)-1-(2-amino-4-(trifluoromethyl)phenyl)-N,N-dimethylpiperidin-3-amine as a red oil. MS m/z=288 [M+H]$^+$. Calc'd for $C_{14}H_{20}F_3N_3$: 287.

Example 167 was also made by a different method as described in Example 125 herein.

Example 168

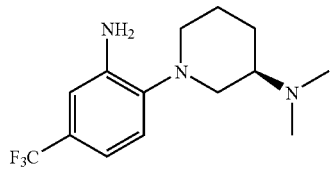

(R)-1-(2-amino-4-(trifluoromethyl)phenyl)-N,N-dimethylpiperidin-3-amine

The title compound was synthesized using a procedure similar to that described in Example 167. MS m/z=288 [M+H]$^+$. Calc'd for $C_{14}H_{20}F_3N_3$: 287.

Example 169

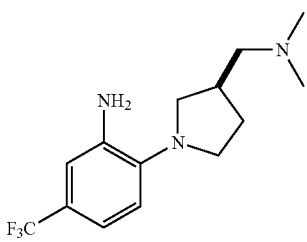

(R)-2-(3-((dimethylamino)methyl)pyrrolidin-1-yl)-5-(trifluoromethyl)benzenamine

The title compound was synthesized using a procedure similar to that described in Example 167. MS m/z=288 [M+H]$^+$. Calc'd for $C_{14}H_{20}F_3N_3$: 287.

Example 170

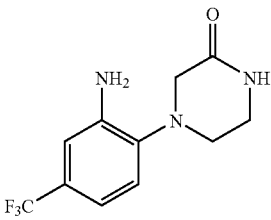

(4-(2-amino-4-(trifluoromethyl)phenyl)piperazin-2-one

The title compound was synthesized using a procedure similar to that described in pending U.S. Patent Application No. 60/569,193. MS m/z=260 [M+H]$^+$. Calc'd for $C_{11}H_{12}F_3N_3O$: 259.

Example 171

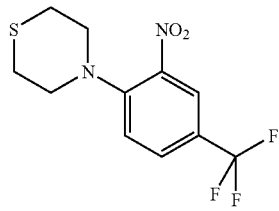

Synthesis of 4-(2-nitro-4-(trifluoromethyl)phenyl)thiomorpholine

To a solution of 1-fluoro-2-nitro-4-(trifluoromethyl)benzene (7.00 g, 33.48 mmol) in THF (250 ml) at room temperature was added thiomorpholine (3.45 g, 33.48 mmol) and sodium bicarbonate (3.66 g, 43.52 mmol). The vessel was purged with nitrogen and stirred at room temperature for 48 hours. After removal of solvent under reduced pressure, the mixture was taken up in ethyl acetate and filtered. The organics were washed with water, then brine and dried with magnesium sulfate. Filtration and concentration provided the title compound as a bright orange solid. MS m/z: 293.1 (M+H$^+$); calc MW=292.28.

Example 172

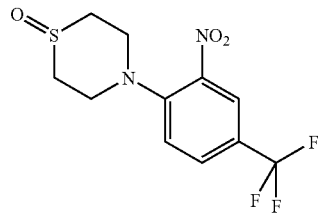

Synthesis of the sulfoxide of 4-(2-nitro-4-(trifluoromethyl)phenyl)thiomorpholine To a solution of 4-(2-nitro-4-(trifluoromethyl)phenyl)thiomorpholine (2.0 g, 6.84 mmol) in methanol (60 ml) and water (15 ml) was added NaIO$_4$ (1.61 g, 7.53 mmol). The mixture was allowed to stir at room temperature for 12 hours, at which time it was filtered to remove white solid precipitates. Concentration afforded the title compound as an orange solid. MS m/z: 309 (M+H$^+$); calc'd MW=308.28.

Example 173

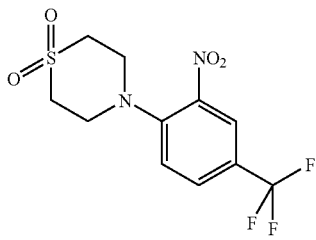

Synthesis of the sulfone of 4-(2-nitro-4-(trifluoromethyl)phenyl)thiomorpholine To a solution of the sulfoxide of 4-(2-nitro-4-(trifluoromethyl)phenyl)thiomorpholine (170 mg, 0.55 mmol) in methanol (50 ml) was added KMNO$_4$ (96 mg, 0.61 mmol). The reaction was stirred at room temperature for 15 minutes and then quenched by the addition of aqueous saturated sodium bisulfate (20 ml). The reaction was filtered and concentrated to provide the sulfone product. MS m/z: 325 (M+H$^+$); calc'd MW=324.28.

The nitro groups of Examples 173-175 were reduced to the corresponding amine by conventional methods, such as be hydrogenation in the presence of a palladium catalyst. The reduction product of Example 173 was found to have a MS (m/z)=263.1 (M+H$^+$); calc'd MW=262.30, and the reduction product of Example 175 was found to have a MS (m/z)=295.1 (M+H$^+$); Calc'd MW=294.30.

Example 176

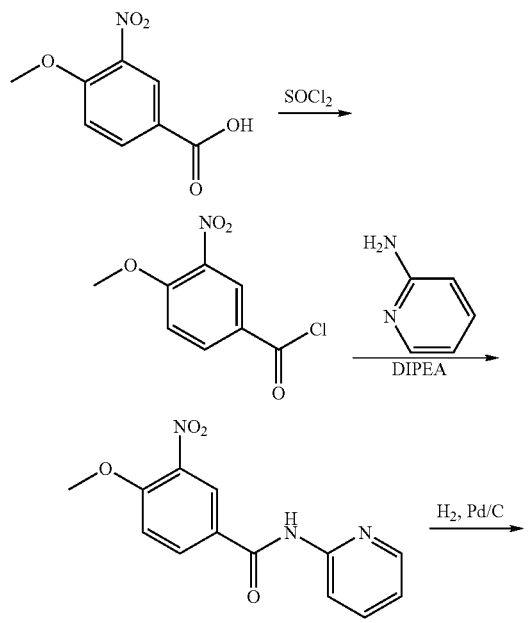

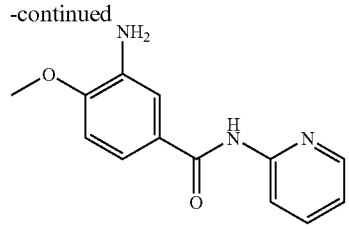

Synthesis of 3-amino-4-methoxy-N-(pyridine-3-yl)benzamide

Step 1: 4-methoxy-3-nitrobenzoic acid (10.0 g, 0.051 mol), and thionyl chloride (25 g, 0.212 mol), were refluxed together for 24 hours. The reaction mixture was cooled to room temperature and concentrated. The off-white solid was carried onto the next step.

Step 2: 4-methoxy-3-nitrobenzoyl chloride (1.08 g, 0.005 mol), 2-aminopyridine (0.94 g, 0.01 mol) and DIPEA (1.8 mL, 0.01 mol) were allowed to stir in dichloromethane (10 mL) for 48 hours to form 4-methoxy-3-nitro-N-(pyridin-2-yl)benzamide. Intermediate was purified via silica column chromatography using 0 to 100% ethyl acetate in hexane.

Step 3: Into a 100 mL round bottom flask was placed 4-methoxy-3-nitro-N-(pyridin-2-yl)benzamide (0.735 g, 2.69 mmol), 10% Palladium on carbon (250 mg), ethanol (50 mL), and acetic acid (10 mL) under inert atmosphere. Atmosphere then exchanged with hydrogen (via balloon) and allowed to stir 24 hours at room temperature. Reaction mixture was filtered through celite, concentrated under reduced pressure, then purified via silica column chromatography using 0 to 100% ethyl acetate in hexane. MS m/z=244 [M+H]$^+$. Calc'd for C$_{13}$H$_{13}$N$_3$O$_2$: 243.3.

Various different B rings (R$^2$ groups), which are contemplated herein, may be commercially purchased or made by various methods, as represented by Examples 177-182a.

Example 177

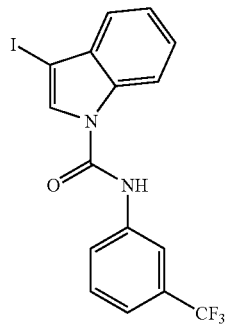

Synthesis of 3-iodo-N-(3-(trifluoromethyl)phenyl)-1H-indole-1-carboxamide

To a solution of 3-iodoindole (583 mg, 2.4 mmol) (Witulski, B.; Buschmann, N.; Bergstrasser, U. *Tetrahedron* 2000, 56, 8473-8480.) in DMF (10 mL) at 0° C. was added NaH (125 mg, 3.1 mmol, 60% dispersion in mineral oil). The reaction mixture was allowed to warm to room temperature and stir for 0.5 h. Then 1-isocyanato-3-(trifluoromethyl)benzene (0.38 mL, 2.64 mmol) was added and allowed to stir for an additional 0.5 h. Sat. aq. NH₄Cl (20 mL) was added and the mixture was poured onto water (50 mL). The aqueous layer was extracted with Et₂O (3×25 mL). The combined organics were washed with brine (10 mL), dried over anhydrous sodium sulfate, filtered and concentrated under reduced pressure. The crude concentrate was purified via automated flash chromatography (silica gel, 0 to 50% EtOAc in hexanes, gradient elution) to afford 3-iodo-N-(3-(trifluoromethyl)phenyl)-1H-indole-1-carboxamide.

Example 178

5-Bromothiophene-3-carboxylic acid was prepared by a method similar to that described in Campaigne, E. E.; Bourgeois, R. C. *J. Am. Chem. Soc.* 1954, 76, 2445-7. MS (m/z)= 206 (M−H⁺)

Example 179

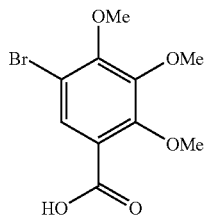

Synthesis of 5-bromo-2,3,4-trimethoxybenzoic acid

To a solution of 2,3,4-trimethoxybenzoic acid (4.7 g, 22 mmol) and NaOAc (5.5 g, 40 mmol) in 35 ml AcOH was added a solution of bromine (1.5 ml, 29 mmol) in 35 ml AcOH. The reaction became red in color, which quickly faded. The mixture was heated to 80° C. for 1 h, at which point it was cooled to ambient temperature. The material was partitioned between dichloromethane and water. The organic layer was removed and the aqueous layer was extracted once with dichloromethane. The combined organic layers were dried with Na₂SO₄, filtered, and concentrated to give an oil which solidified on standing. The material was dissolved in diethyl ether and hexanes. Concentration to ½ the volume resulted in precipitation of a white solid. Filtration provided the title compound as a white solid. MS m/z: 293 (M+H⁺); calc'd for C₁₀H₁₁BrO₅: 291.1

Example 180

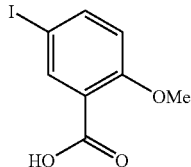

Synthesis of 5-iodo-2-methoxybenzoic acid

Step 1. Synthesis of methyl 5-iodo-2-methoxy benzoate

To a solution of 5-iodosalicylic acid (10.0 g, 38 mmol) in 189 ml acetone was added potassium carbonate (23 g, 169 mmol). The mixture was cooled to 0° C. and dimethyl sulfate (7.7 ml, 80 mmol) was added. The mixture was heated to reflux overnight and was cooled to ambient temperature and concentrated under reduced pressure. The residue was partitioned between EtOAc and water, and the aqueous layer was extracted three times with EtOAc. The combined organic layers were dried with Na₂SO₄, filtered, and concentrated to give a white solid. This material was heated with hexanes and allowed to stand for 60 h, resulting in the formation of crystals. Filtration provided the title compound as white needles. MS (ES⁺): 292.9 (M+H)⁺. Calc'd for C₉H₉IO₃: 292.07.

Step 2. Synthesis of 5-iodo-2-methoxybenzoic acid

A mixture of methyl 5-iodo-2-methoxy benzoate (6.0 g, 21 mmol) and 23 ml each MeOH and 1N NaOH was heated with a water-cooled reflux condensor to 90° C. for 2 h. The reaction was cooled to ambient temperature, 100 mL water was added, and the solution adjusted to pH 1 with 6N HCl. A thick white precipitate formed which was collected by filtration to give the title compound as a white solid. MS (m/z): 278.9 (M+H)⁺. Calc'd for C₈H₇IO₃: 278.04.

Example 181

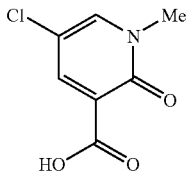

Synthesis of 5-chloro-1-methyl-2-oxo-1,2-dihydropyridine-3-carboxylic acid

Step 1. Synthesis of methyl 5-chloro-1-methyl-2-oxo-1,2-dihydropyridine-3-carboxylate To a suspension of 5-chloro-2-hydroxynicotinic acid (2.0 g, 12 mmol) and cesium carbonate (8.2 g, 26 mmol) in 50 mL DMF was added MeI (1.6 ml, 26 mmol). The reaction was allowed to stir for approximately 12 h. The cloudy yellow mixture was added to EtOAc/water. The organic layer was removed and the aqueous layer was extracted three times with EtOAc. The combined organic layers were washed once with water and brine, dried with Na$_2$SO$_4$, filtered, and concentrated to give an orange-yellow solid. The material was partitioned between 1N HCl and EtOAc. The organic layer was washed twice with 1N HCl, dried with Na$_2$SO$_4$, filtered, and concentrated to give the desired product as an orange solid. MS (m/z): 202.0 (M+H)$^+$. Calc'd for C$_8$H$_8$ClNO$_3$: 201.61.

Step 2. Synthesis of 5-chloro-1-methyl-2-oxo-1,2-dihydropyridine-3-carboxylic acid A mixture of methyl-5-chloro-1-methyl-2-oxo-1,2-dihydropyridine-3-carboxylate (0.36 g, 1.8 mmol) and 2.0 mL each MeOH and 1N NaOH was heated in a sealed vial to 80° C. for 1 h. The reaction was cooled to ambient temperature, and the methanol was removed by a stream of nitrogen. Water (2 ml) was added and the solution was adjusted to pH 1 with 6N HCl. A thick white precipitate formed which was partitioned between water and dichloromethane. The organic layer was removed and the aqueous layer was extracted twice with dichloromethane. The combined organic layers were dried with Na$_2$SO$_4$, filtered, and concentrated to give an orange-yellow solid. The material was partitioned between 1N HCl and EtOAc. The organic layer was washed twice with 1N HCl, dried with Na$_2$SO$_4$, filtered, and concentrated to give the desired product as a light orange solid. MS (m/z): 188.0 (M+H)$^+$. Calc'd for C$_7$H$_6$ClNO$_3$: 187.58.

Example 182

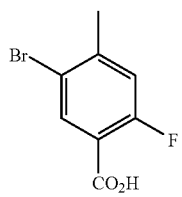

5-bromo-2-fluoro-4-methylbenzoic acid was prepared by a method described in PCT Patent Publication WO 2003/032972.

Example 182a

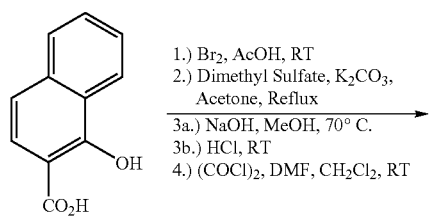

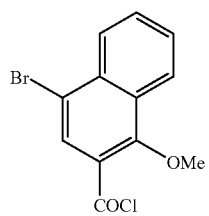

The title compound was prepared according to a literature procedure published in *J. Med. Chem.* 2001, 44, 1815.

Various different A-B linked ring intermediates (substituted R$^2$ groups), which are contemplated herein, may be made by various methods, such as with A-B amide linked rings, as represented by Examples 183-191.

Example 183

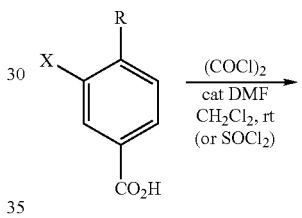

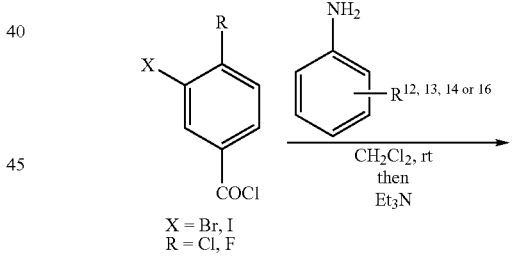

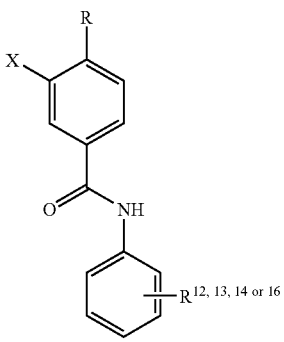

Synthesis of 3-bromo-4-fluoro-N-(2-fluoro-3-(trifluoromethyl)phenyl)benzamide

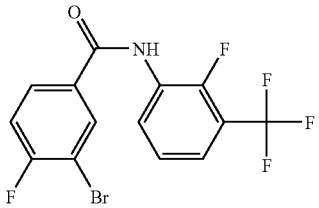

Step 1: 3-Bromo-4-fluorobenzoyl chloride

Oxalyl chloride (1.739 g, 1.20 ml, 13.7 mmol) was added dropwise to a solution of 3-bromo-4-fluorobenzoic acid (0.600 mg, 2.74 mmol) and dichloromethane (9 ml). N,N-Dimethylformamide (1 drop) was added and the colorless solution stirred at rt for 1 h. The solution was concentrated to afford 3-bromo-4-fluorobenzoyl chloride an off-white solid which was used directed without purification.

Step 2: 3-Bromo-4-fluoro-N-(2-fluoro-3-(trifluoromethyl)phenyl)benzamide

2-Fluoro-3-(trifluromethyl)aniline (0.515 g, 0.37 mL, 2.88 mmol) was added to a solution of 3-bromo-4-fluorobenzoyl chloride (0.650 g, 2.74 mmol) in dichloromethane (5 ml), and the mixture stirred at room temperature for 30 min. Triethylamine (0.360 g, 0.50 ml, 3.56 mmol) was added and the solution stirred at room temperature for 1 h. The reaction mixture was partitioned between dichloromethane and saturated aqueous sodium bicarbonate solution. The aqueous phase was separated and extracted with dichloromethane. The combined organic phases were washed with water, brine, dried over anhydrous sodium sulfate, filtered, and concentrated to afford a light yellow solid. Trituration with dichloromethane and filtering afforded 3-bromo-4-fluoro-N-(2-fluoro-3-(trifluoromethyl)phenyl)benzamide as a white solid. MS (M−H$^+$) 377.9; Calculated for $C_{14}H_7BrF_5NO$: 379.

Example 184

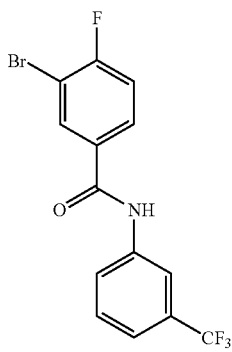

Synthesis of 3-Bromo-4-fluoro-N-(3-(trifluoromethyl)phenyl)benzamide

3-Bromo-4-fluoro-N-(3-(trifluoromethyl)phenyl)benzamide was synthesized from 3-trifluoromethylaniline and 3-bromo-4-fluorobenzoyl chloride according to the procedure described in Example 183, affording the title compound as a white solid. MS (M−H$^+$) 360.0; Calculated for $C_{14}H_8BrF_4NO$: 361.

Example 185

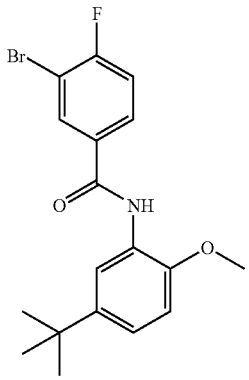

Synthesis of 3-Bromo-N-(5-tert-butyl-2-methoxyphenyl)-4-fluorobenzamide

3-Bromo-N-(5-tert-butyl-2-methoxyphenyl)-4-fluorobenzamide was synthesized from 5-tert-butyl-o-anisidine and 3-bromo-4-fluorobenzoyl chloride according to the procedure described in Example 183, affording the title compound as an off-white solid. MS (M+H$^+$) 380.0; Calculated for $C_{18}H_{19}BrFNO_2$: 379.

Example 186

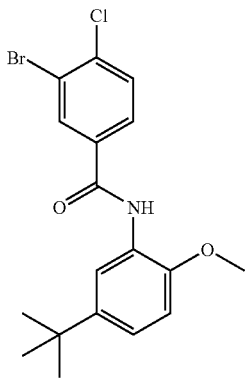

Synthesis of 3-Bromo-N-(5-tert-butyl-2-methoxyphenyl)-4-chlorobenzamide

Step 1: 3-Bromo-4-chlorobenzoyl chloride

3-Bromo-4-chlorobenzoyl chloride was prepared from 3-bromo-4-chlorobenzoic acid according to the procedure described in Example 183 for the synthesis of 3-bromo-4-fluorobenzoyl chloride.

Step 2: 3-Bromo-N-(5-tert-butyl-2-methoxyphenyl)-4-chlorobenzamide

3-Bromo-N-(5-tert-butyl-2-methoxyphenyl)-4-chlorobenzamide was synthesized from 5-tert-butyl-o-anisidine and 3-bromo-4-chlorobenzoyl chloride according to the procedure described in Example 183, step 2. 3-Bromo-N-(5-tert-butyl-2-methoxyphenyl)-4-chlorobenzamide was obtained as an off-white solid. MS (M–H$^+$) 394.0; Calculated for $C_{18}H_{19}BrClNO_2$: 395.

Example 187

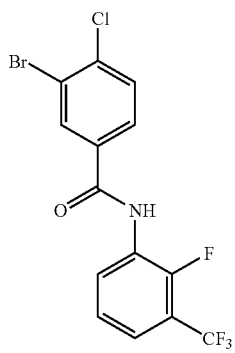

Synthesis of 3-Bromo-4-chloro-N-(2-fluoro-3-(trifluoromethyl)phenyl)benzamide 3-Bromo-4-chloro-N-(2-fluoro-3-(trifluoromethyl)phenyl)benzamide was synthesized from 2-fluoro-3-(triflurom-ethyl)aniline and 3-bromo-4-chlorobenzoyl chloride according to the procedure described in Example 183. 3-Bromo-4-chloro-N-(2-fluoro-3-(trifluoromethyl)phenyl)benzamide was obtained as a red-orange solid. MS (M–H$^+$) 393.9; Calc'd for $C_{14}H_7BrClF_4NO$: 395.

Example 188

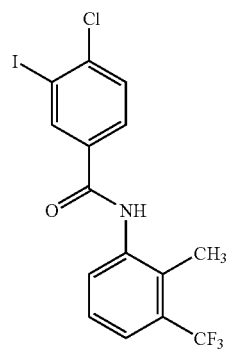

Synthesis of 4-Chloro-3-iodo-N-(2-methyl-3-(trifluoromethyl)phenyl)benzamide

Step 1: 4-Chloro-3-iodobenzoylchloride

4-Chloro-3-iodobenzoylchloride was prepared from 4-chloro-3-iodobenzoic acid according to the procedure described in Example 183 for the synthesis of 3-bromo-4-fluorobenzoyl chloride.

Step 2: 4-Chloro-3-iodo-N-(2-methyl-3-(trifluoromethyl)phenyl)benzamide

4-Chloro-3-iodo-N-(2-methyl-3-(trifluoromethyl)phenyl)benzamide was synthesized from 2-methyl-3-(triflurom-ethyl)aniline and 4-chloro-3-iodobenzoyl chloride according to the procedure dscribed in Example 183. 4-Chloro-3-iodo-N-(2-methyl-3-(trifluoromethyl)phenyl)benzamide was obtained as a white solid. MS (M–H$^+$) 437.8; Calculated for $C_{15}H_{10}ClF_3INO$: 439.

Example 189

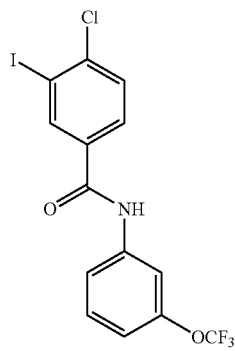

Synthesis of 4-Chloro-3-iodo-N-(3-(trifluoromethoxy)phenyl)benzamide

4-Chloro-3-iodo-N-(3-(trifluoromethoxy)phenyl)benzamide was synthesized from 3-(trifluoromethoxy)aniline and 4-chloro-3-iodobenzoylchloride according to the procedure described in Example 183, affording the title compound as a white solid. MS (M–H$^+$) 439.8; Calculated for $C_{14}H_8ClF_3INO_2$: 441.

The following A-B amide linked ring intermediates, Examples 190-270, were made by methods similar to that described in Example 183.

| Example No. | Structure |
|---|---|
| 190 | 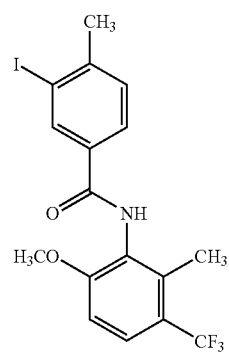 |
| 191 | 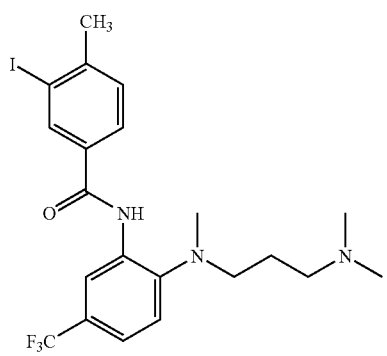 |
| 192 | 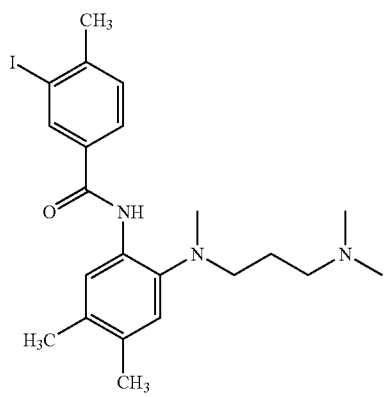 |
| 193 | 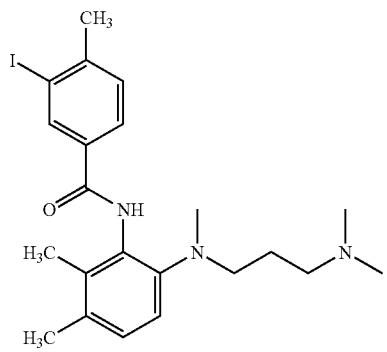 |
-continued
| Example No. | Structure |
|---|---|
| 194 | 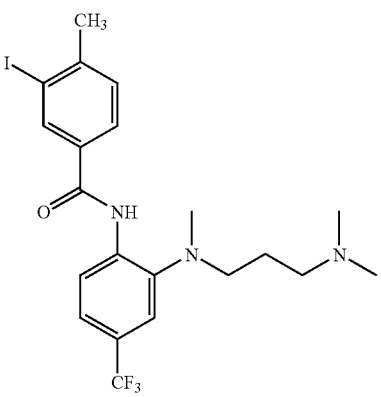 |
| 195 | 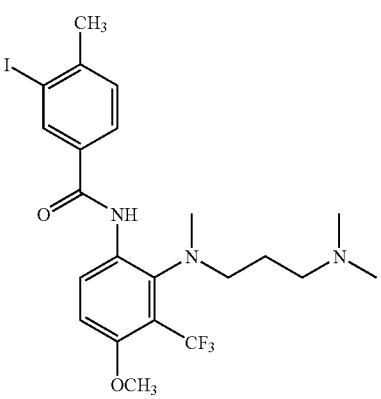 |
| 196 | 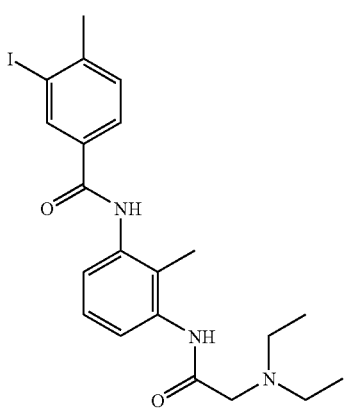 |

-continued
| Example No. | Structure |
|---|---|
| 197 | 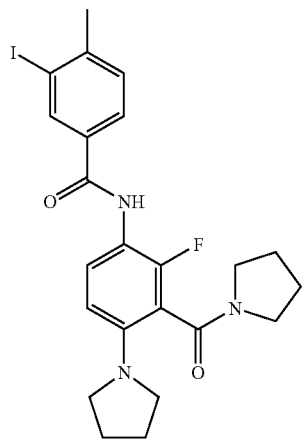 |
| 198 | 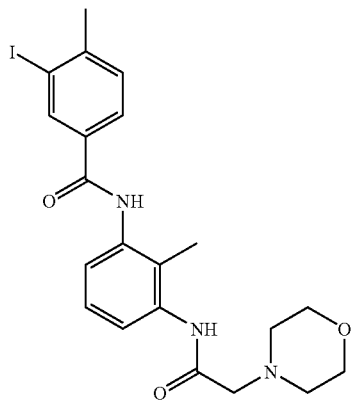 |
| 199 | 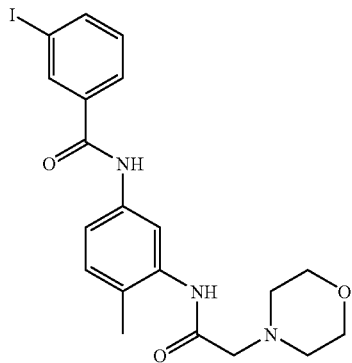 |
-continued
| Example No. | Structure |
|---|---|
| 200 | 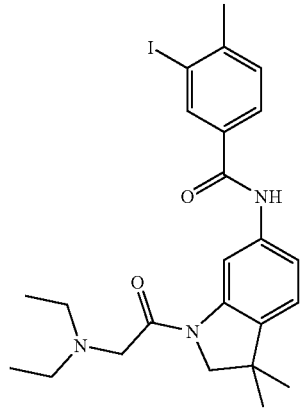 |
| 201 | 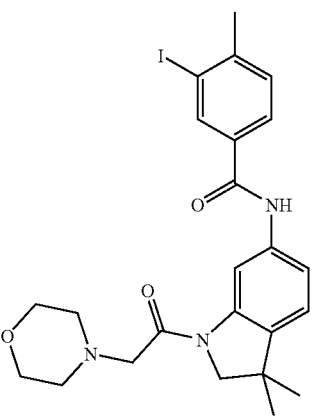 |
| 202 | 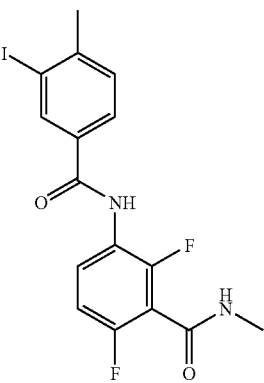 |
| 203 | 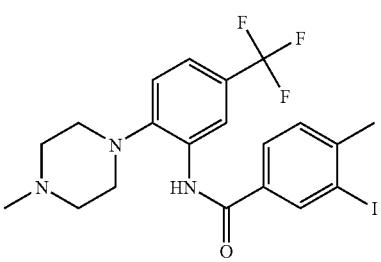 |

-continued
| Example No. | Structure |
|---|---|
| 204 | 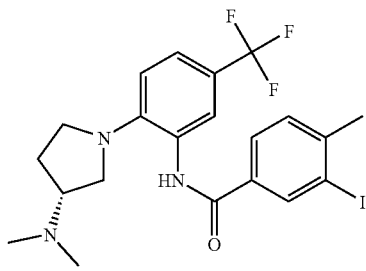 |
| 205 | 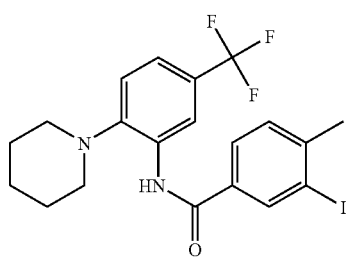 |
| 206 | 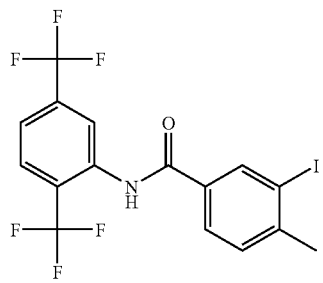 |
| 207 | 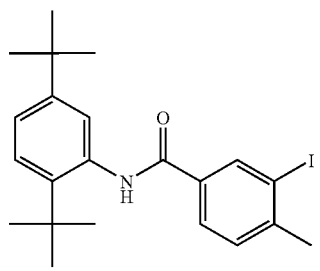 |
| 208 | 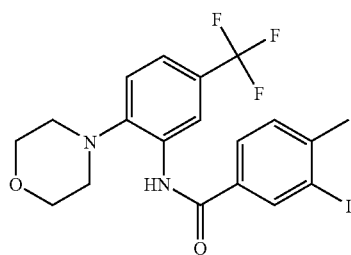 |
-continued
| Example No. | Structure |
|---|---|
| 209 | 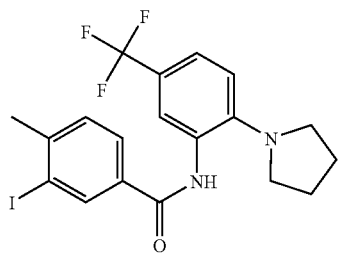 |
| 210 | 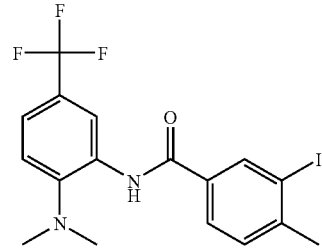 |
| 211 | 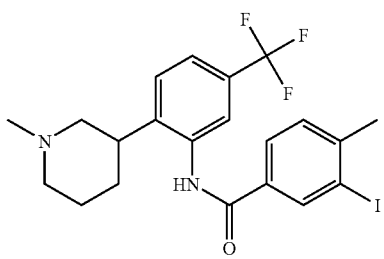 |
| 212 | 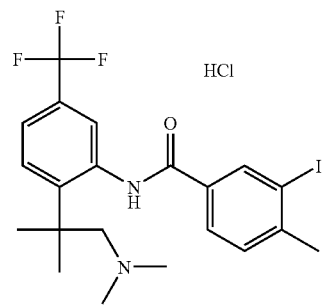 |
| 213 | 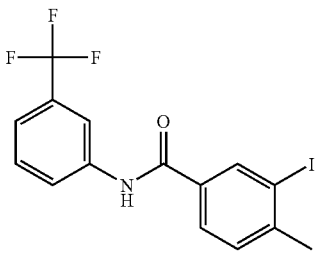 |

| Example No. | Structure |
|---|---|
| 214 | 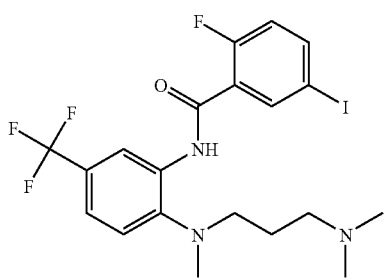 |
| 215 | 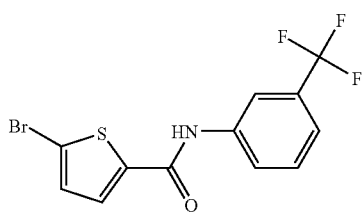 |
| 216 | 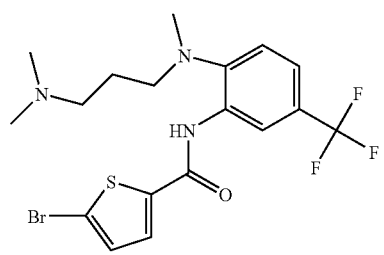 |
| 217 | 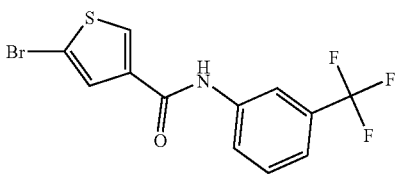 |
| 218 | 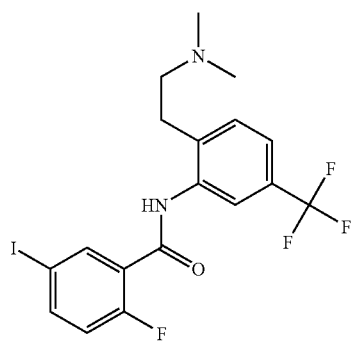 |
| 219 | 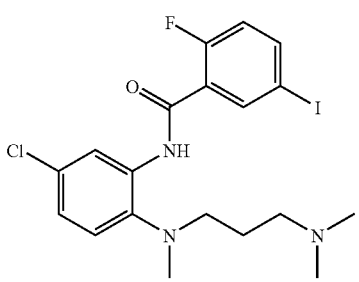 |
| Example No. | Structure |
|---|---|
| 220 | 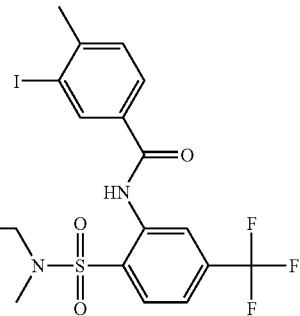 |
| 221 | 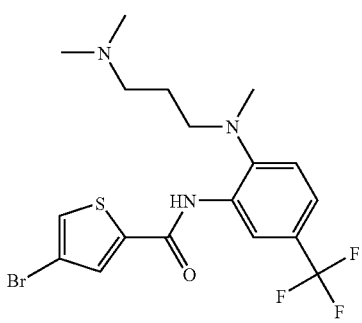 |
| 222 | 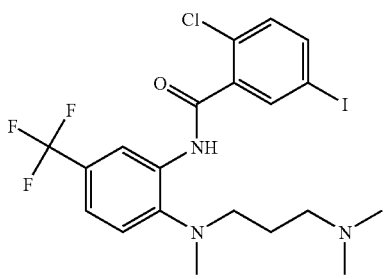 |
| 223 | 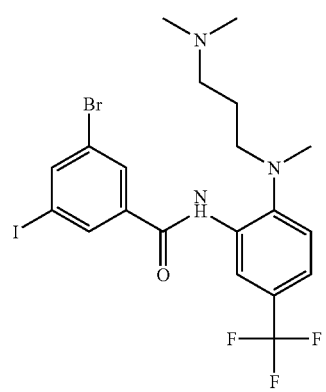 |

-continued
| Example No. | Structure |
|---|---|
| 224 | 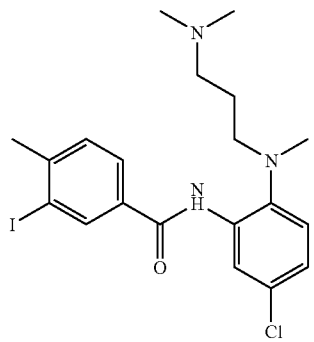 |
| 225 | 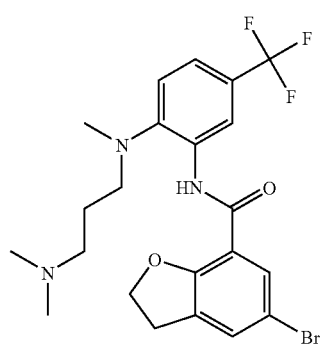 |
| 226 | 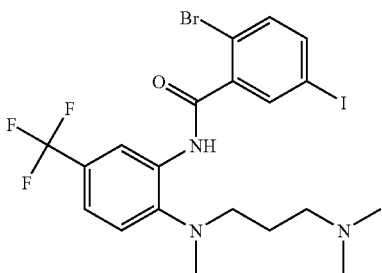 |
| 227 | 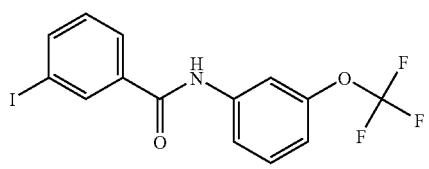 |
| 228 | 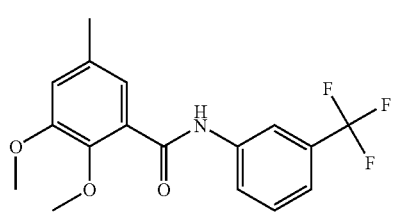 |
-continued
| Example No. | Structure |
|---|---|
| 229 | 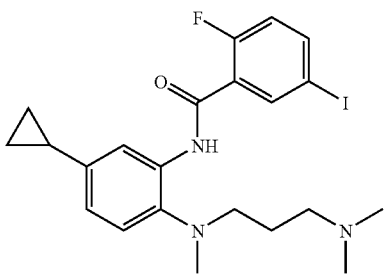 |
| 230 | 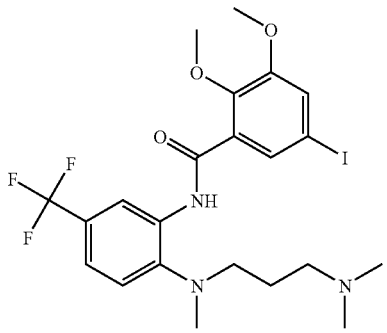 |
| 231 | 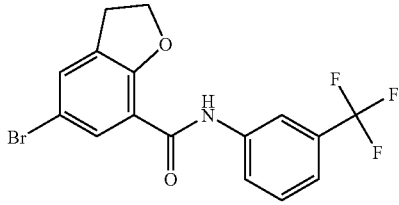 |
| 232 | 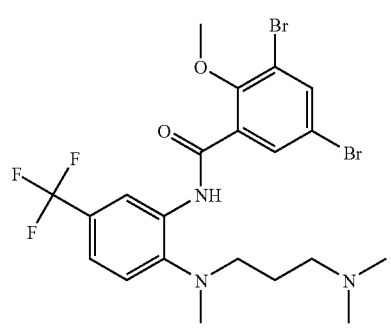 |
| 233 | 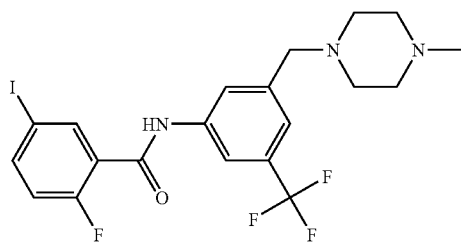 |

-continued
| Example No. | Structure |
|---|---|
| 234 | 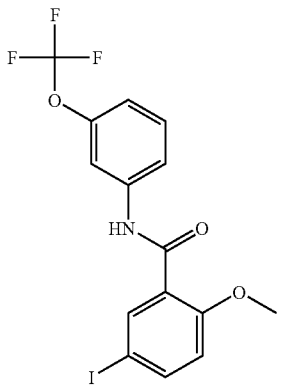 |
| 235 | 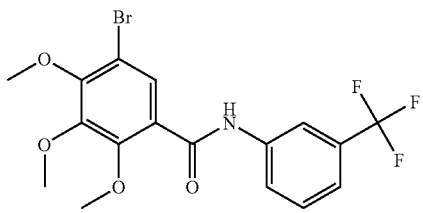 |
| 236 | 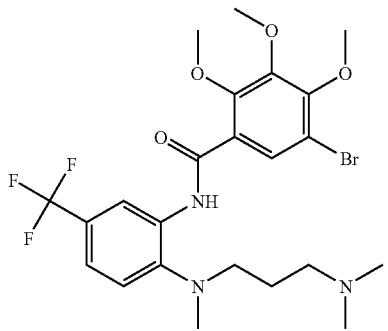 |
| 237 | 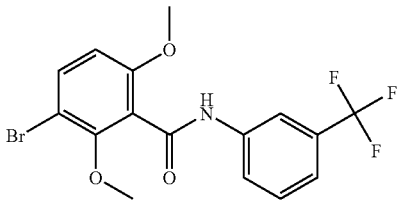 |
| 238 | 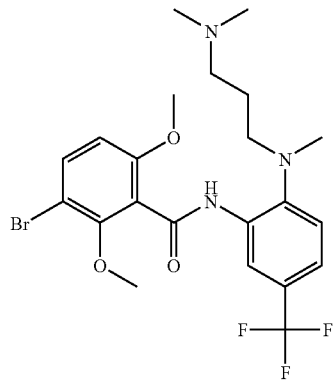 |
-continued
| Example No. | Structure |
|---|---|
| 239 | 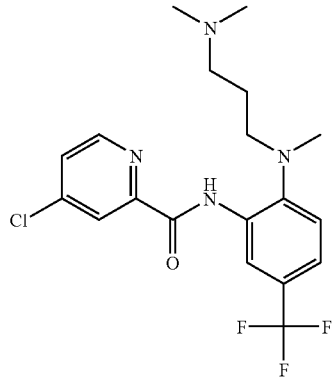 |
| 240 | 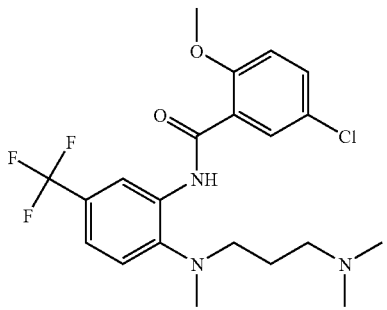 |
| 241 | 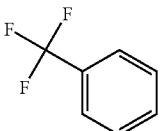 |
| 242 | 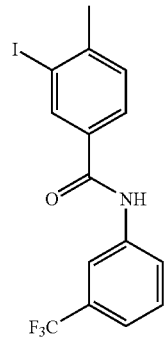 |

-continued
| Example No. | Structure |
|---|---|
| 243 | 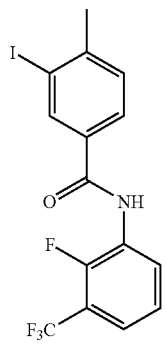 |
| 244 | 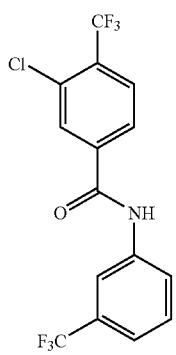 |
| 245 | 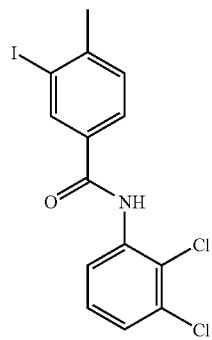 |
| 246 | 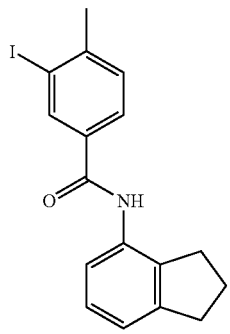 |
-continued
| Example No. | Structure |
|---|---|
| 247 | 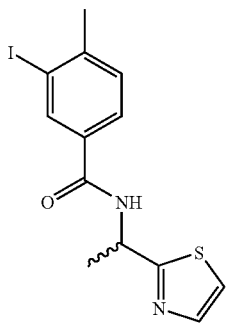 |
| 248 | 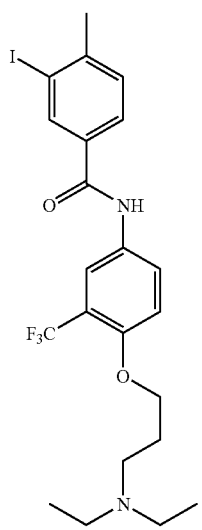 |
| 249 | 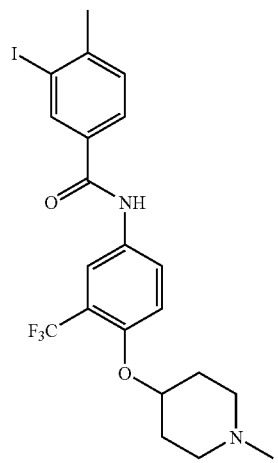 |

-continued
| Example No. | Structure |
|---|---|
| 250 | 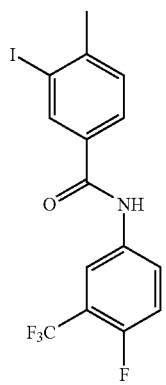 |
| 251 | 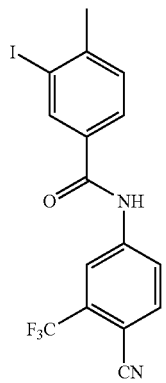 |
| 252 | 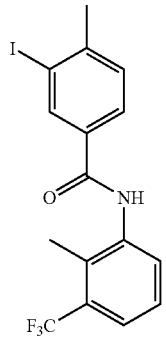 |
| 253 | 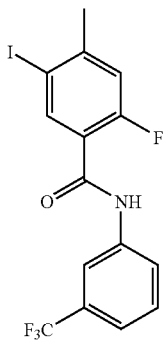 |
-continued
| Example No. | Structure |
|---|---|
| 254 | 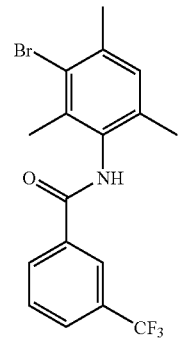 |
| 255 | 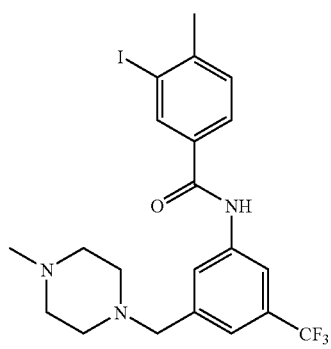 |
| 256 | 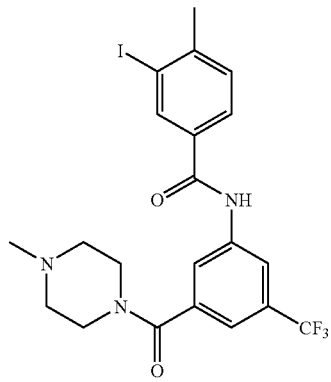 |
| 257 | 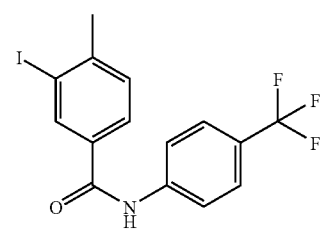 |
| 258 | 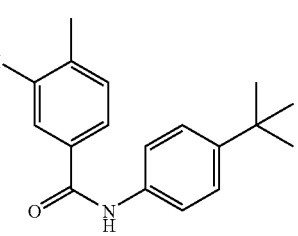 |

-continued
| Example No. | Structure |
|---|---|
| 259 | 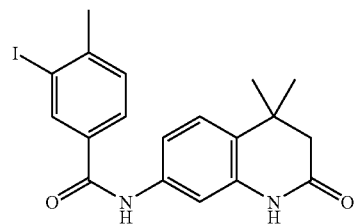 |
| 260 | 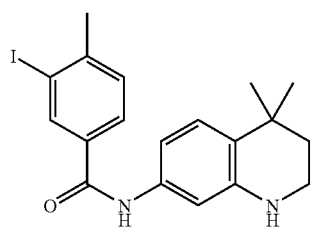 |
| 261 | 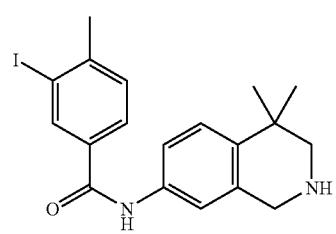 |
| 262 | 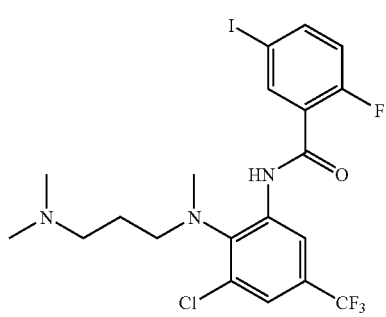 |
| 263 | 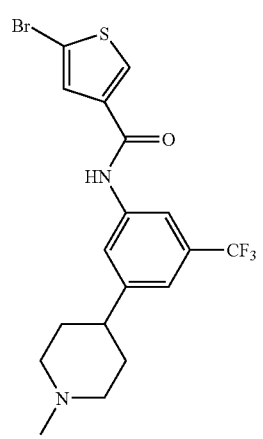 |
-continued
| Example No. | Structure |
|---|---|
| 264 | 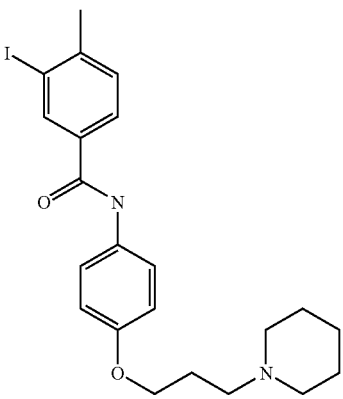 |
| 265 | 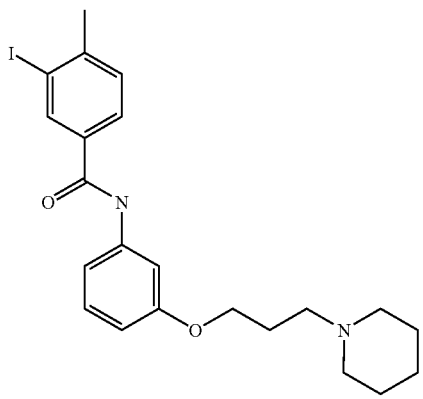 |
| 266 | 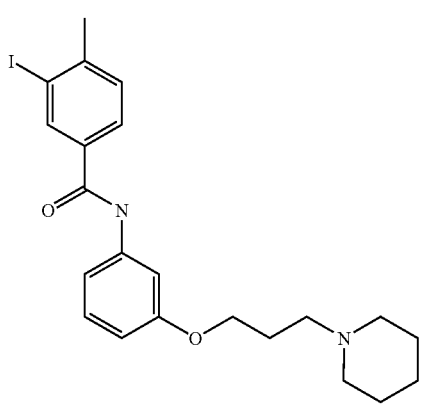 |

-continued

| Example No. | Structure |
|---|---|
| 267 | 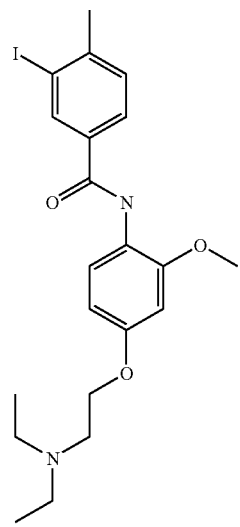 |
| 268 | 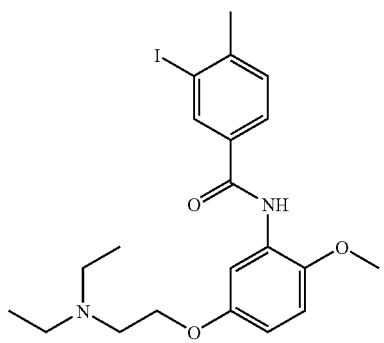 |
| 269 | 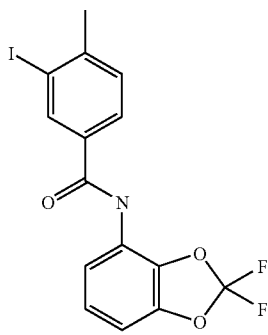 |
| 270 | 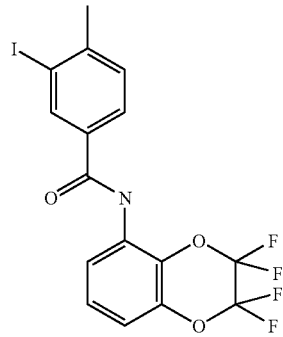 |

Various different alkyne-substituted heteroaryl C ring (pyridines, pyrimidines, quinolines, quinazolines, imidazolo-pyridines, and the like), which are contemplated herein, may be made by various methods, as represented by Examples 271-275.

Example 271

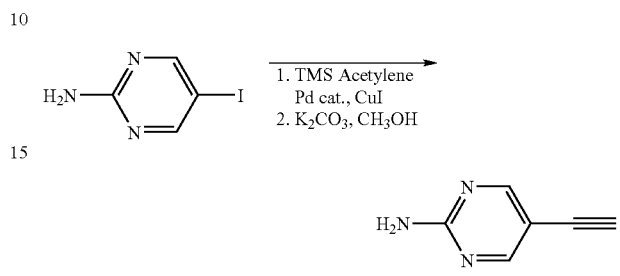

Synthesis of 2-amino-5-ethynylpyrimidine

Into a 1 L round bottom flask was placed the 2-amino-5-iodopyrimidine (8.0 g, 36.2 mmol), acetonitrile (300 mL), triethylamine (30 mL), TMS acetylene (7.68 g, 78.2 mmol), palladium dichloro-bis-triphenylphosphine (1.26 g, 1.8 mmol), and copper(I) iodide (0.342 g, 1.8 mmol). The vessel was filled with argon gas and allowed to stir at room temperature for 3 hours. The solvent was evaporated and the crude was taken up in methanol (400 mL). Then excess potassium carbonate (10 eq) was added, and the mixture was stirred at room temperature for 1.5 hours. Activated charcoal was added and the mixture was filtered through celite. The filtrate was concentrated under reduced pressure to afford a tan solid, which was added to a solution of 10% methanol in water (200 mL). The resulting precipitate was isolated by filtration, dried in a vacuum oven to constant mass and afforded the title compound as a tan solid. MS m/z=120 [M+H]$^+$. Calc'd for $C_6H_5N_3$: 119.

Example 272

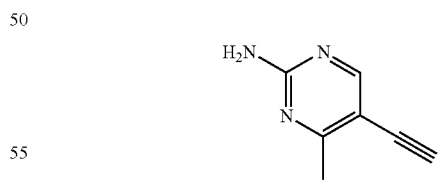

Synthesis of 5-ethynyl-4-methylpyrimidin-2-amine

The title compound was prepared from 5-iodo-4-methylpyrimidin-2-amine (prepared according to the method described in Sakamoto, T.; Kondo, Y.; Yamanaka, H. *Synthesis,* 1984, 3, 252-4) in a manner similar to that described in Example 271 above. MS (m/z): 236 (M+H$^+$)

Example 273

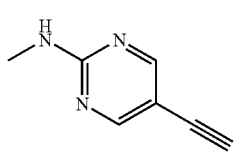

5-ethynyl-N-methylpyrimidin-2-amine

Step 1: 5-bromo-N-methylpyrimidin-2-amine

A mixture of 2-chloro-5-bromopyrimidine (2.5 g, 13 mmol), methylamine hydrochloride (7.9 g, 116 mmol), and diisopropylethylamine (18 mL, 103 mmol) in 43 mL acetonitrile was heated in a sealed vessel for 16 h. The reaction was partitioned between EtOAc and water. The organic layer was washed once with brine, dried over anhydrous sodium sulfate, filtered, and concentrated to give 5-bromo-N-methylpyrimidin-2-amine. MS m/z=188 [M+H]$^+$. Calc'd for $C_5H_6BrN_3$: 187.

Step 2: N-methyl-5-(2-(trimethylsilyl)ethynyl)pyrimidin-2-amine

A 100 mL round bottom flask was charged with palladium (bisbenzonitrile)dichloride (0.23 g, 0.61 mmol), trit-butylphosphonium tetrafluoroborate (0.35 g, 1.2 mmol) and copper (I) iodide (0.11 g, 0.61 mmol) under argon. 20 mL dioxane was added, followed by diisopropylethylamine (2.6 mL, 18 mmol), 5-bromo-N-methylpyrimidin-2-amine (2.3 g, 12 mmol), and trimethylsilyl acetylene (3.4 mL, 24 mmol). The reaction was allowed to stir overnight. The cloudy brown mixture was diluted with EtOAc and filtered through a pad of silica gel and concentrated in vacuo to give a brown solid. This was further purified by silica gel chromatography, eluting with 0-50% EtOAc/dichloromethane to give N-methyl-5-(2-(trimethylsilyl)ethynyl)pyrimidin-2-amine as a yellow solid. MS m/z=206 [M+H]$^+$. Calc'd for $C_{10}H_{15}N_3Si$: 205.

Step 3: 5-ethynyl-N-methylpyrimidin-2-amine

To a slurry of N-methyl-5-(2-(trimethylsilyl)ethynyl)pyrimidin-2-amine (2.4 g, 12 mmol) in 60 mL methanol was added potassium carbonate (4.8 g, 35 mmol). The cloudy mixture was allowed to stir rapidly for 4 h. The mixture was then concentrated to a small volume and partitioned between water and dichloromethane. The aqueous layer was extracted 5× with dichloromethane and 2× with EtOAc. The combined organic layers were dried over anhydrous sodium sulfate, filtered, and concentrated in vacuo to give N-methyl-5-(2-(trimethylsilyl)ethynyl)pyrimidin-2-amine as a brown solid. MS m/z=134 [M+H]$^+$. Calc'd for $C_7H_7N_3$: 133.

Example 274

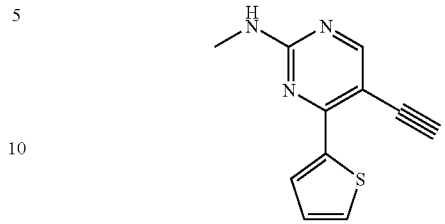

5-ethynyl-N-methyl-4-(thiophen-2-yl)pyrimidin-2-amine

Step 1: 5-bromo-2-chloro-4-(thiophen-2-yl)pyrimidine

A solution of thiophene (3.3 g, 39 mmol) in THF (100 mL) was cooled to −78° C. n-Butyllithium (2.5 M in hexane, 24 mL, 59 mmol) was added and the mixture stirred at −78° C. for 1 h. 2-Chloro-5-bromopyrimidine (7.5 g, 39 mmol) was added and the mixture stirred at −78° C. for 1 h. DDQ (17.7 g, 78 mmol) was added with stirring, followed by the addition of methanol (5 mL). The mixture stirred for 1 h and was then warmed to 0° C. and then to RT. The reaction mixture was poured into 0.5 M sodium ascorbate (aq) solution (100 mL), and allowed to stir for 1 h. The mixture was treated with saturated aqueous potassium carbonate solution (50 mL), and extracted with ethyl acetate. The combined organic layers were dried over anhydrous sodium sulfate, filtered and concentrated. The residue was purified via column chromatography on silica gel (eluting with 100% dichloromethane) to afford 5-bromo-2-chloro-4-(thiophen-2-yl)pyrimidine as a yellow solid. MS m/z=276 [M+H]$^+$. Calc'd for $C_8H_4BrClN_2S$: 275.

Step 2: 5-bromo-N-methyl-4-(thiophen-2-yl)pyrimidin-2-amine

A 16 by 100 mm vial was charged with 5-bromo-2-chloro-4-(thiophen-2-yl)pyrimidine (1.00 g, 3.6 mmol), THF (4 mL), triethylamine (1.5 ml, 11 mmol), and methylamine hydrochloride (0.49 g, 7.3 mmol), and water (0.4 mL). The vial was capped and heated to 85° C. with stirring for 20 hours. The reaction was cooled to room temperature and concentrated. The residue was purified via column chromatography on silica gel (gradient elution with 0 to 4% methanol in dichloromethane) to afford 5-bromo-N-methyl-4-(thiophen-2-yl)pyrimidin-2-amine. MS m/z=271 [M+H]$^+$. Calc'd for $C_9H_8BrN_3S$: 270.

Step 3: N-methyl-4-(thiophen-2-yl)-5-(2-(trimethylsilyl)ethynyl)pyrimidin-2-amine A 75 mL thick wall glass tube with a teflon screw cap was charged with 5-bromo-N-methyl-4-(thiophen-2-yl)pyrimidin-2-amine (0.995 g, 3.68 mmol), acetonitrile (9 mL), triethylamine (3.00 ml, 3.68 mmol), dichlorobistriphenylphosphine palladium(II) (0.259 g, 0.368 mmol), copper(I) iodide (0.0351 g, 0.184 mmol), and ethynyltrimethylsilane (0.362 g, 3.68 mmol). The tube was capped and heated to 90° C. for 2 hours. The reaction mixture was cooled to room temperature and concentrated. The residue was purified via column chromatography on silica gel (gradient elution with 0-100% ethyl acetate-hexane) to afford N-methyl-4-(thiophen-2-yl)-5-(2-(trimethylsilyl)ethynyl)pyrimidin-2-amine. MS m/z=288 [M+H]$^+$. Calc'd for $C_{14}H_{17}N_3SSi$: 287.

Step 4: 5-ethynyl-N-methyl-4-(thiophen-2-yl)pyrimidin-2-amine

A 25 mL round bottom flask was charged with N-methyl-4-(thiophen-2-yl)-5-(2-(trimethylsilyl)ethynyl)pyrimidin-2-amine (0.518 g, 1.80 mmol), methanol (20 mL), and potassium carbonate (0.747 g, 5.41 mmol), and the reaction mixture stirred at room temperature for 24 hours. The reaction mixture was concentrated and the residue was purified via column chromatography on silica gel (gradient elution with 0-100% ethyl acetate-hexane) to 5-ethynyl-N-methyl-4-(thiophen-2-yl)pyrimidin-2-amine. MS m/z=216 [M+H]$^+$. Calc'd for $C_{11}H_9N_3S$: 215.

Example 275

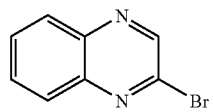

2-Bromoquinoxaline was prepared in a manner similar to that described in Kato, Y.; Okada, S.; Tomimoto, K.; Mase, Tetrahedron Let. 2001, 42, 4849-4851. MS (m/z): 210 (M+H$^+$)

Example 276

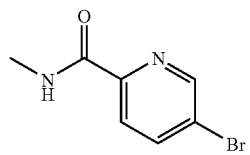

5-Bromo-N-methylpicolinamide was prepared in a manner similar to that described in Markevitch, D. Y.; Rapta, M.; Hecker, S. J.; Renau, T. E. Synthetic Commun. 2003, 33, 3285-3289. MS (m/z): 217 (M+H$^+$)

Example 277

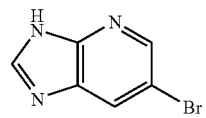

6-Bromo-3H-imidazo[4,5-b]pyridine was prepared in a manner similar to that described in Yutilov, Y. M.; Lopatinskaya, K. Y.; Smolyar, N. N.; Korol, I. V. Russian Journal of Organic Chemistry 2003, 39, 280-281. MS (m/z): 199 (M+H$^+$)

Example 278

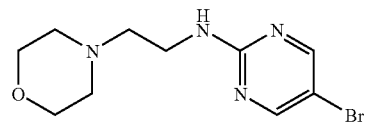

5-bromo-N-(2-morpholinoethyl)pyrimidin-2-amine

A resealable tube was charged with a solution of 2-chloro-5-bromopyrimidine (1.00 g, 5.17 mmol), N-(2-aminoethyl)morpholine (0.808 g, 6.20 mmol), diisopropylethylamine (0.801 g, 1.1 mL, 6.20 mmol), and THF (40 mL). The mixture was heated at 85° C. for 20 h. The reaction mixture was concentrated and then purified via column chromatography on silica gel (gradient elution with 0-100% (90:10:1, dichloromethane/methanol/ammonium hydroxide)-dichloromethane) to afford 5-bromo-N-(2-morpholinoethyl)pyrimidin-2-amine as a light yellow solid. MS m/z=288 [M+H]$^+$. Calc'd for $C_{10}H_{15}BrN_4O$: 287.

Example 278a

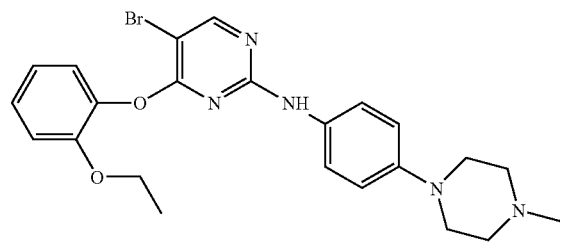

5-bromo-4-(2-ethoxyphenoxy)-N-(4-(4-methylpiperazin-1-yl)phenyl)pyrimidin-2-amine Step 1.
5-bromo-2-chloro-4-(2-ethoxyphenoxy)pyrimidine To a suspension of NaH (0.42 g 60% in mineral oil, 10.5 mmol) in DMF (8.0 mL) was slowly added 2-ethoxylphenol (1.34 g, 9.7 mmol) in MeCN (4.0 mL) at 0° C. under $N_2$. After the addition, the reaction mixture was allowed to warm up to room temperature for 0.5 hour. 5-bromo-2,4-dichloropyrimidine (2.0 g, 8.8 mmol) in MeCN (16.0 mL) was slowly added and then the resulting reaction mixture was stirred at room temperature for 24 hour. EtOAc (120 mL) was added and washed with NaOH (30 mL, 0.5N) and brine (25×2 mL). The organic layer was dried with $MgSO_4$, and concentrated under reduced pressure. The residue was purified by silica gel chromatography (10% to 30% EtOAc in Hexanes, gradient elution) to provide the 5-bromo-2-chloro-4-(2-ethoxyphenoxy)pyrimidine. MS m/z=330 [M+1]$^+$. Calc'd for: $C_{12}H_{10}BrClN_2O_2$: 329

Step 2. 5-bromo-4-(2-ethoxyphenoxy)-N-(4-(4-methylpiperazin-1-yl)phenyl)pyrimidin-2-amine To a solution of 5-bromo-2-chloro-4-(2-ethoxy)pyrimidine (0.8 g, 2.4 mmol) and 4-(2-(pyrrolidin-1-yl)ethoxy)benzenamine (0.51 g, 2.7 mmol) in 1,4-dioxane (5.0 mL) was added trifluoroacetic acid (0.1 mL). The resulting reaction mixture was stirred at 90° C. overnight. The reaction mixture was allowed to cool to room temperature, diluted with $CH_2Cl_2$ (200 mL) and washed with sat. aq. $NaHCO_3$ (20×2 mL) and brine (20×3 mL). The organic layer was dried with $MgSO_4$, and concentrated under reduced pressure. The residue was purified by silica gel chromatography (10% to 50% EtOAc in Hexanes, gradient elution) to get the 5-bromo-4-(2-ethoxyphenoxy)-N-(4-(4-methylpiperazin-1-yl)phenyl)pyrimidin-2-amine. MS m/z=485 [M+1]$^+$. Calc'd for: $C_{23}H_{26}BrN_5O_2$: 484

Example 278b

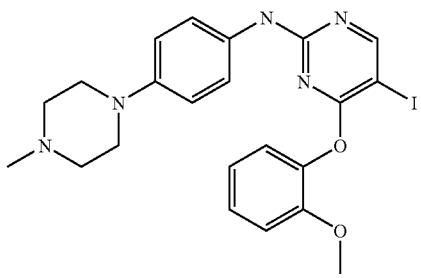

The compound above, 5-iodo-4-(2-methoxyphenoxy)-N-(4-(4-methylpiperazin-1-yl)phenyl)pyrimidin-2-amine, was prepared by a method similar to that described in Example 278a. MS m/z=517 [M+H]$^+$; Calc'd for: $C_{22}H_{24}IN_5O_2$; 517.36

Example 278c

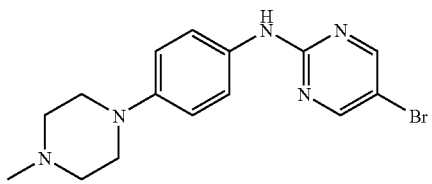

5-bromo-N-(4-(4-methylpiperazin-1-yl)phenyl)pyrimidin-2-amine

A resealable tube was charged with 2-chloro-5-bromopyrimidine (1.00 g, 5.21 mmol), 4-(N-methylpiperazine)aniline (1.20 g, 6.25 mmol), trifluoroacetic acid (1.78 g, 1.20 mL, 15.6 mmol), and isopropanol (50 mL). The tube was sealed and the mixture stirred at 100° C. for 20 h. The reaction mixture was concentrated and the residue was purified via column chromatography on silica gel (gradient elution with 0-100% (90:10:1, dichloromethane/methanol/ammonium hydroxide)-dichloromethane) to afford 5-bromo-N-(4-(4-methylpiperazin-1-yl)phenyl)pyrimidin-2-amine. MS m/z=348, 350 [M+H]$^+$. Calc'd for $C_{15}H_{18}BrN_5$: 348.

General Synthesis of Acid Chlorides

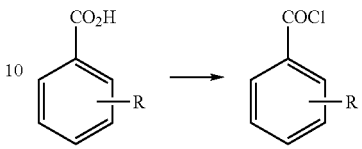

While persons of ordinary skill in the art readily appreciate how to make an acid chloride, the following Examples 279 and 280 represent methods utilized in making representative compounds of Formulas I-III.

Example 279

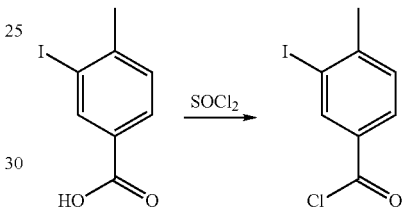

3-iodo-4-methylbenzoyl acid chloride

Into a 100 mL round bottom flask is placed 3-iodo-4-methyl benzoic acid (10 g, 38.175 mmol) and thionyl chloride (25 mL, 344 mmol). The reaction was allowed to stir at reflux for 2 hours. The reaction was cooled to room temperature and concentrated under reduced pressure. The concentrate was placed under high vacuum for about 24 hr and afforded the title acid chloride as a light yellow solid.

Example 280

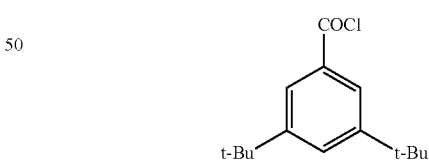

3,5-ditert-butyl benzoyl chloride

Oxalyl chloride (0.542 g, 0.37 ml, 4.27 mmol) was added dropwise to a solution of 3,5-di-tert-butylbenzoic acid (0.200 g, 0.853 mmol) and dichloromethane (4 ml). N,N-Dimethylformamide (1 drop) was added and the colorless solution stirred at RT for 3 h. The solution was concentrated to afford 3,5-di-tert-butylbenzoyl chloride as a yellow oil.

The following acid chlorides were prepared according to the methods described in Example 280 above. 1-methyl-1H- indole-2-carbonyl chloride, 2-chloro-3-(trifluoromethyl) benzoyl chloride, 4-chloro-3-(trifluoromethyl)benzoyl chloride, 2-chloro-3-methylbenzoyl chloride, and 2-chloro-3-fluorobenzoyl chloride.

The following Examples 281-351, made using many of the building blocks described above, should assist in understanding the present invention and should not be construed as limiting the scope of the invention.

| Ex. No. | Structure | Compound Name | MW | MS: M+H | Method |
|---|---|---|---|---|---|
| 281 | 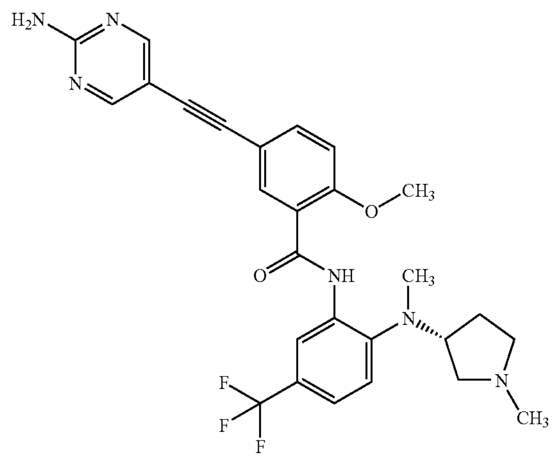 | 5-((2-amino-5-pyrimidinyl)ethynyl)-N-(2-(methyl((3R)-1-methyl-3-pyrrolidinyl)amino)-5-(trifluoromethyl)phenyl)-2-(methyloxy)benzamide | 524.544 | 525 | A1 |
| 282 | 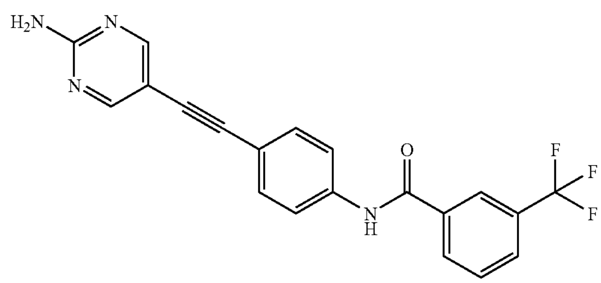 | N-(4-((2-amino-5-pyrimidinyl)ethynyl)phenyl)-3-(trifluoromethyl)benzamide | 382.344 | 383 | B1 |
| 283 | 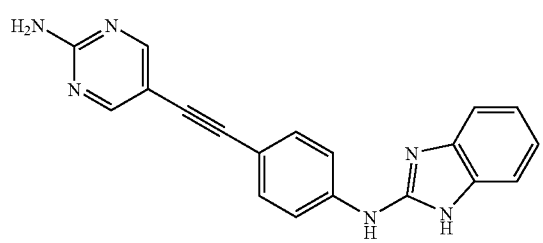 | N-(4-((2-amino-5-pyrimidinyl)ethynyl)phenyl)-1H-benzimidazol-2-amine | 326.362 | 327 | C2 |
| 284 | 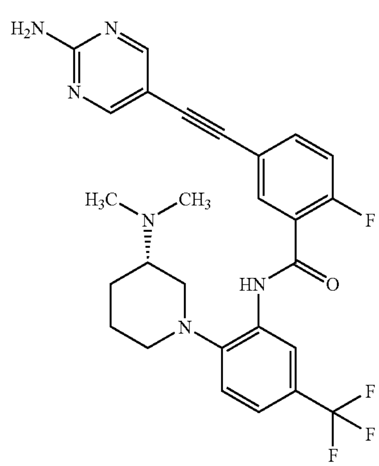 | 5-((2-amino-5-pyrimidinyl)ethynyl)-N-(2-((3S)-3-dimethylamino)-1-piperidinyl)-5-(trifluoromethyl)phenyl)-2-fluorobenzamide | 526.535 | 527 | A1 |

-continued

| Ex. No. | Structure | Compound Name | MW | MS: M + H | Method |
|---|---|---|---|---|---|
| 285 | 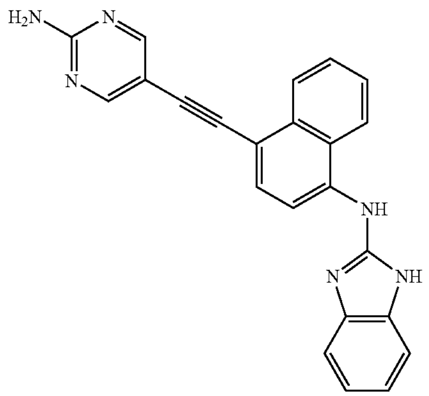 | N-(4-((2-amino-5-pyrimidinyl)ethynyl)-1-naphthalenyl)-1H-benzimidazol-2-amine | 376.421 | 377 | C2 |
| 286 | 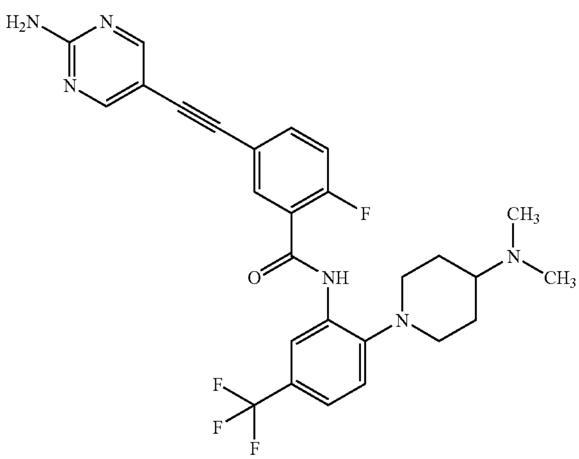 | 5-((2-amino-5-pyrimidinyl)ethynyl)-N-(2-(4-(dimethylamino)-1-piperidinyl)-5-(trifluoromethyl)phenyl)-2-fluorobenzamide | 526.535 | 527 | A1 |
| 287 | 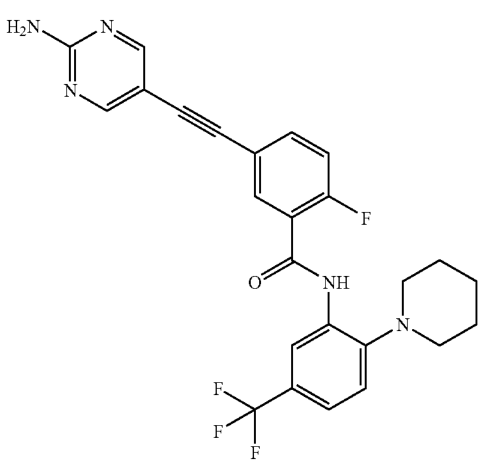 | 5-((2-amino-5-pyrimidinyl)ethynyl)-2-fluoro-N-(2-(1-(trifluoromethyl)phenyl)benzamide | 483.467 | 484 | A1 |

| Ex. No. | Structure | Compound Name | MW | MS: M + H | Method |
|---|---|---|---|---|---|
| 288 | 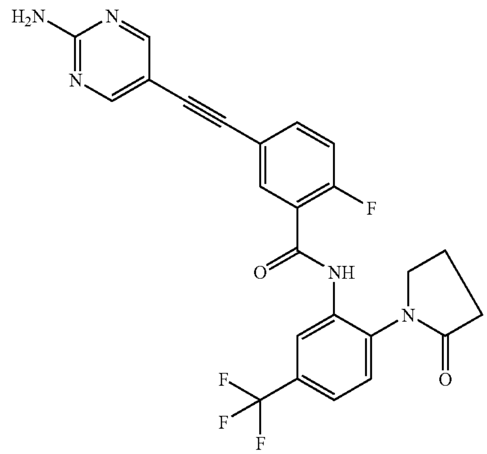 | 5-((2-amino-5-pyrimidinyl)ethynyl)-2-fluoro-N-(2-(2-oxo-1-pyrrolidinyl)-5-(trifluoromethyl)phenyl)benzamide | 483.423 | 484 | A1 |
| 289 | 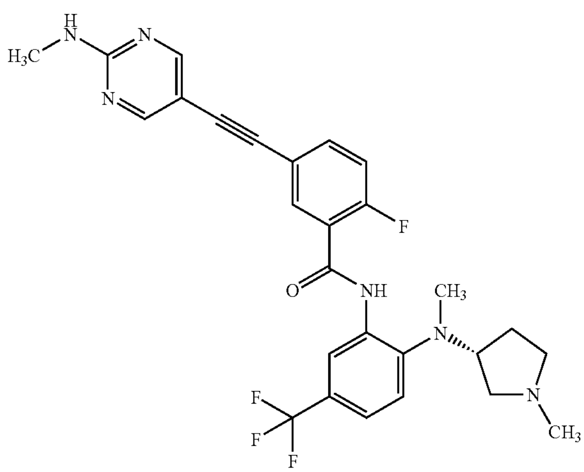 | 2-fluoro-5-((2-(methylamino)-5-pyrimidinyl)ethynyl)-N-(2-(methyl((3R)-1-methyl-3-pyrrolidinyl)amino)-5-(trifluoromethyl)phenyl)benzamide | 526.535 | 527 | A1 |
| 290 | 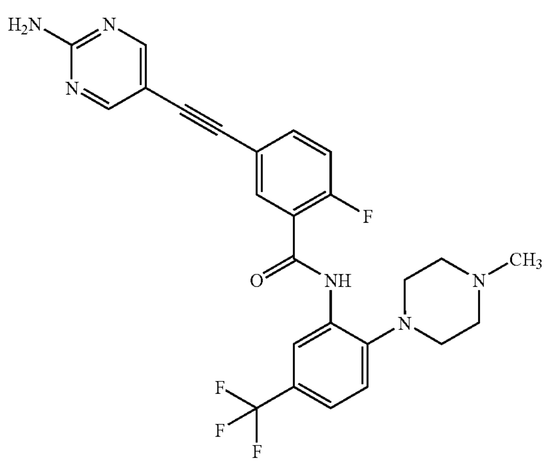 | 5-((2-amino-5-pyrimidinyl)ethynyl)-2-fluoro-N-(2-(4-methyl-1-piperazinyl)-5-(trifluoromethyl)phenyl)benzamide | 498.482 | 499 | A1 |

-continued

| Ex. No. | Structure | Compound Name | MW | MS: M + H | Method |
|---|---|---|---|---|---|
| 291 | 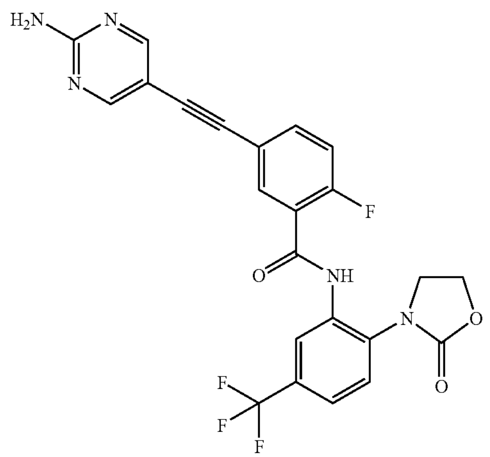 | 5-((2-amino-5-pyrimidinyl)ethynyl)-2-fluoro-N-(2-(2-oxo-1,3-oxazolidin-3-yl)-5-(trifluoromethyl)phenyl)benzamide | 485.396 | 486 | A1 |
| 292 | 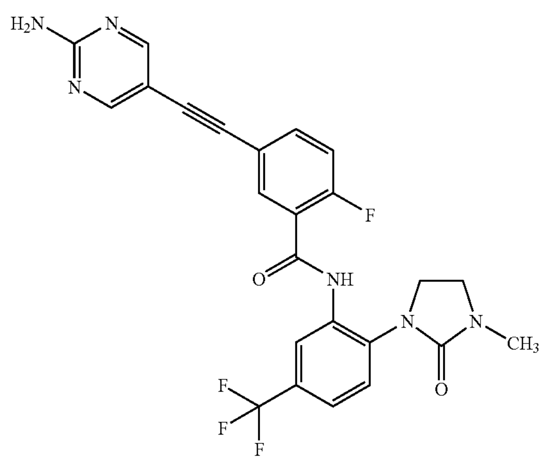 | 5-((2-amino-5-pyrimidinyl)ethynyl)-2-fluoro-N-(2-(3-methyl-2-oxo-1-imidazolidinyl)-5-(trifluoromethyl)phenyl)benzamide | 498.438 | 499 | A1 |
| 293 | 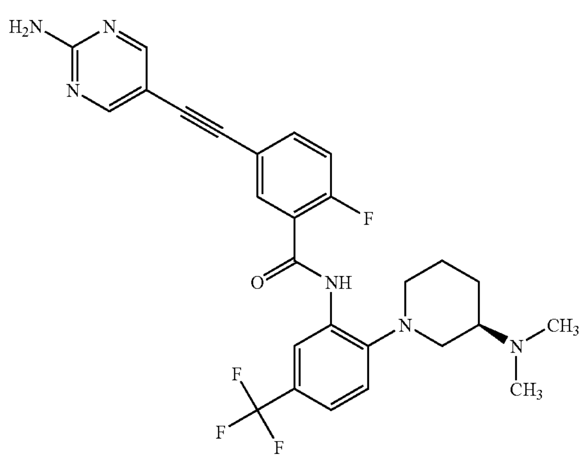 | 5((2-amino-5-pyrimidinyl)ethynyl)-N-(2-((3R)-3-(dimethylamino)-1-piperidinyl)-5-(trifluoromethyl)phenyl)-2-fluorobenzamide | 526.535 | 527 | A1 |

| Ex. No. | Structure | Compound Name | MW | MS: M + H | Method |
|---|---|---|---|---|---|
| 294 | 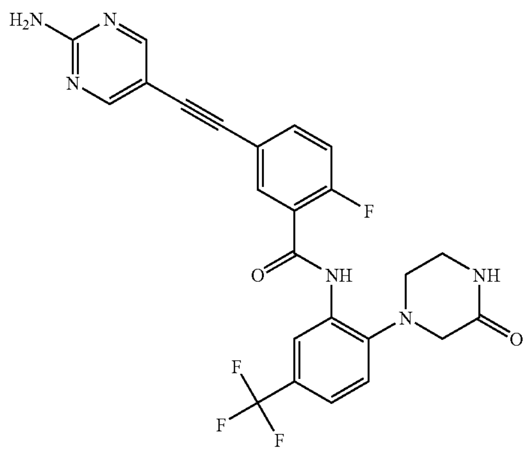 | 5-((2-amino-5-pyrimidinyl)ethynyl)-2-fluoro-N-(2-(3-oxo-1-piperazinyl)-5-(trifluoromethyl)phenyl)benzamide | 498.438 | 499 | A1 |
| 295 | 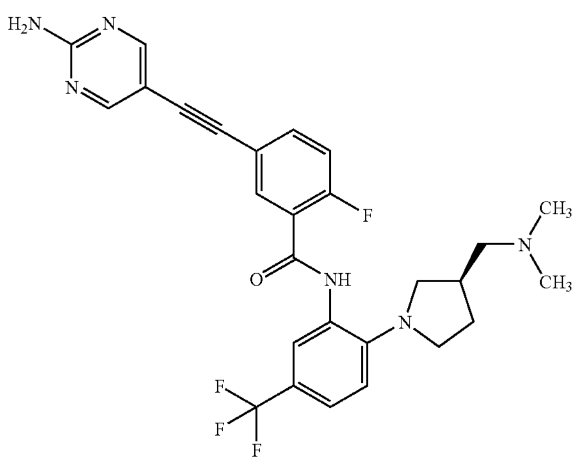 | 5-((2-amino-5-pyrimidinyl)ethynyl)-N-(2-((3R)-3-((dimethylamino)methyl)-1-pyrrolidinyl)-5-(trifluoromethyl)phenyl)-2-fluorobenzamide | 526.535 | 527 | A1 |
| 296 | 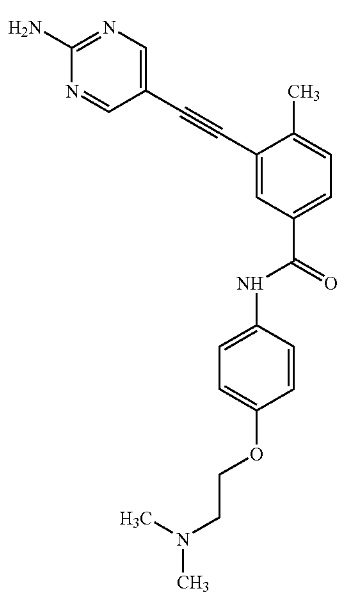 | 3-((2-amino-5-pyrimidinyl)ethynyl)-N-(4-((2-(dimethylamino)ethyl)oxy)phenyl)-4-methylbenzamide | 415.495 | 416 | A1 |

| Ex. No. | Structure | Compound Name | MW | MS: M + H | Method |
|---|---|---|---|---|---|
| 297 | 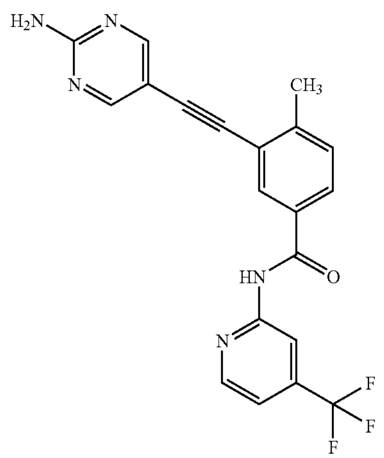 | 3-((2-amino-5-pyrimidinyl)ethynyl)-4-methyl-N-(4-(trifluoromethyl)-2-pyridinyl)benzamide | 397.359 | 398 | A1 |
| 298 | 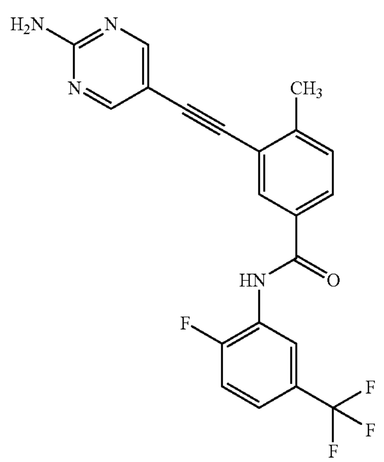 | 3-((2-amino-5-pyrimidinyl)ethynyl)-N-(2-fluoro-5-(trifluoromethyl)phenyl)-4-methylbenzamide | 414.361 | 415 | A1 |
| 299 | 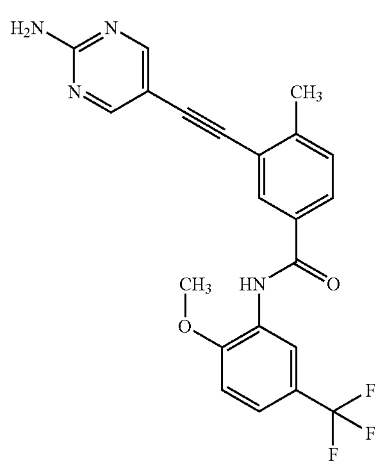 | 3-((2-amino-5-pyrimidinyl)ethynyl)-4-methyl-N-(2-(methyloxy)-5-(trifluoromethyl)phenyl)benzamide | 426.396 | 427 | A1 |

-continued

| Ex. No. | Structure | Compound Name | MW | MS: M + H | Method |
|---|---|---|---|---|---|
| 300 | 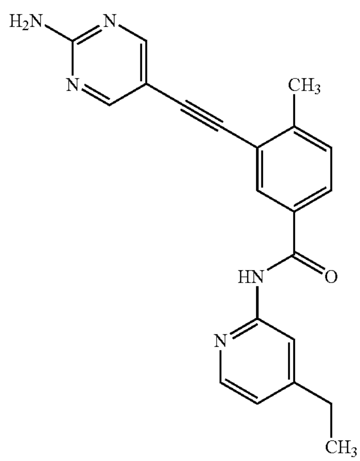 | 3-((2-amino-5-pyrimidinyl)ethynyl)-N-(4-ethyl-2-pyridinyl)-4-methylbenzamide | 357.415 | 358 | A1 |
| 301 | 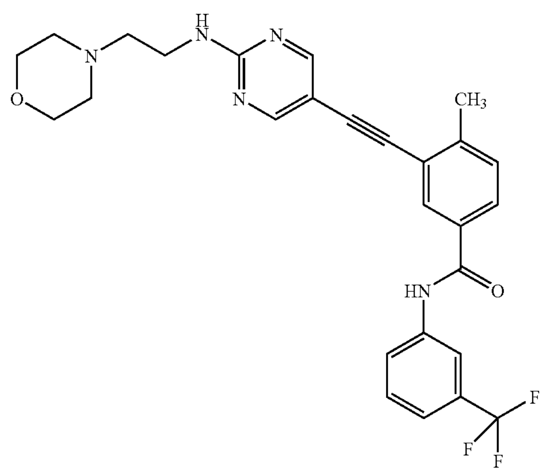 | 4-methyl-3-((2-((2-(4-morpholinyl)ethyl)amino)-5-pyrimidinyl)ethynyl)-N-(3-(trifluoromethyl)phenyl)benzamide | 509.529 | 510 | D1 |
| 302 | 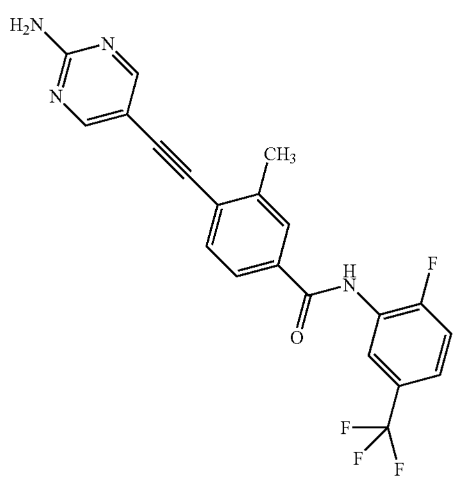 | 4-((2-amino-5-pyrimidinyl)ethynyl)-N-(2-fluoro-5-(trifluoromethyl)phenyl)-3-methylbenzamide | 414.361 | 415 | A1 |

| Ex. No. | Structure | Compound Name | MW | MS: M + H | Method |
|---|---|---|---|---|---|
| 303 | 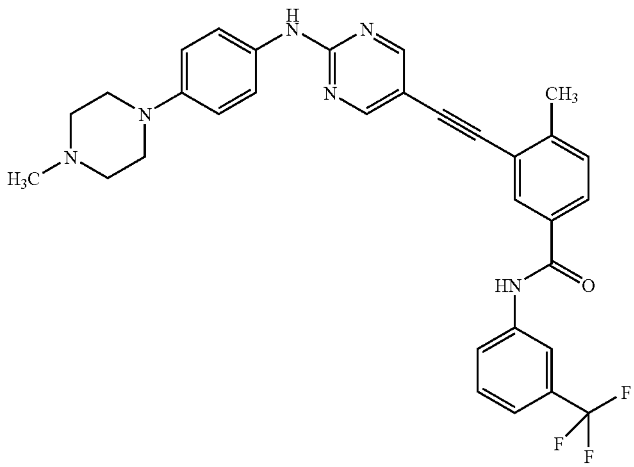 | 4-methyl-3-((2-((4-(4-methyl-1-piperazinyl)phenyl)amino)-5-pyrimidinyl)ethynyl)-N-(3-(trifluoromethyl)phenyl)benzamide | 570.616 | 571 | D1 |
| 304 | 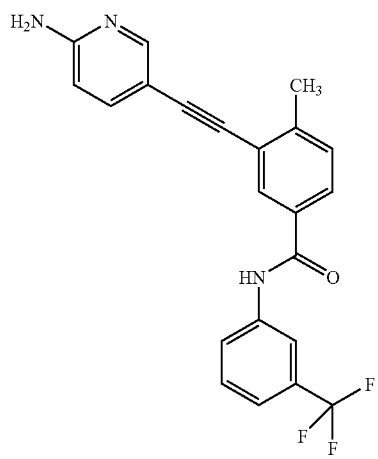 | 3-((6-amino-3-pyridinyl)ethynyl)-4-methyl-N-(3-(trifluoromethyl)phenyl)benzamide | 395.382 | 396 | D1 |
| 305 | 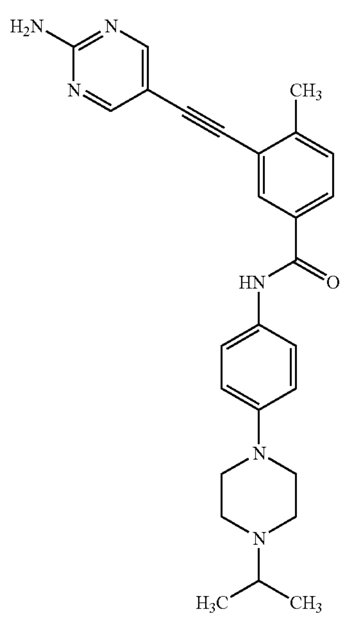 | 3-((2-amino-5-pyrimidinyl)ethynyl)-4-methyl-N-(4-(4-(1-methylethyl)-1-piperazinyl)phenyl)benzamide | 454.575 | 455 | A1 |

| Ex. No. | Structure | Compound Name | MW | MS: M + H | Method |
|---|---|---|---|---|---|
| 306 | 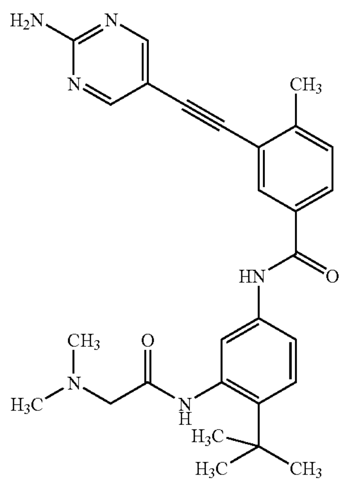 | 3-((2-amino-5-pyrimidinyl)ethynyl)-N-(4-(1,1-dimethyl-ethyl)-3-((N,N-dimethylglycyl)amino)phenyl)-4-methylbenzamide | 484.601 | 485 | A1 |
| 307 | 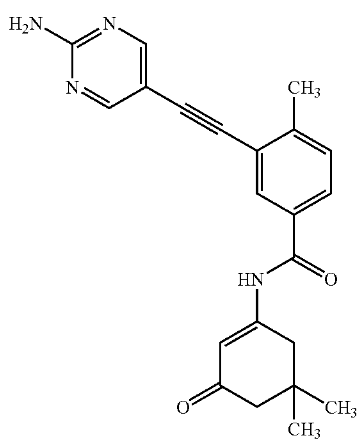 | 3-((2-amino-5-pyrimidinyl)ethynyl)-N-(5,5-dimethyl-3-oxo-1-cyclohexen-1-yl)-4-methylbenzamide | 374.442 | 375 | A1 |
| 308 | 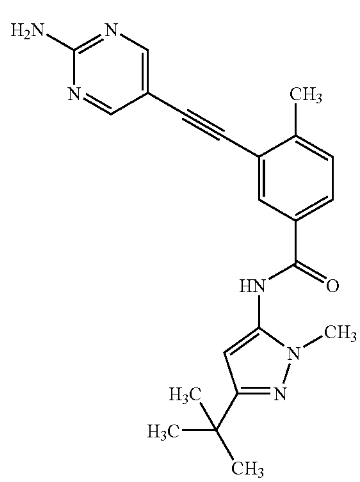 | 3-((2-amino-5-pyrimidinyl)ethynyl)-N-(3-(1,1-dimethylethyl)-1-methyl-1H-pyrazol-5-yl)-4-methylbenzamide | 388.473 | 389 | A1 |

-continued

| Ex. No. | Structure | Compound Name | MW | MS: M + H | Method |
|---|---|---|---|---|---|
| 309 | 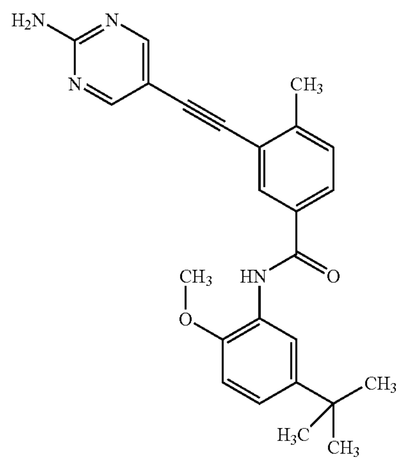 | 3-((2-amino-5-pyrimidinyl)ethynyl)-N-(5-(1,1-dimethylethyl)-2-(methyloxy)phenyl)-4-methylbenzamide | 414.506 | 415 | A1 |
| 310 | 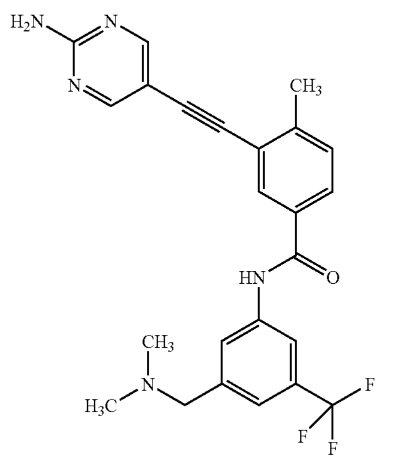 | 3-((2-amino-5-pyrimidinyl)ethynyl)-N-(3-((dimethylamino)methyl)-5-(trifluoromethyl)phenyl)-4-methylbenzamide | 453.466 | 454 | A1 |
| 311 | 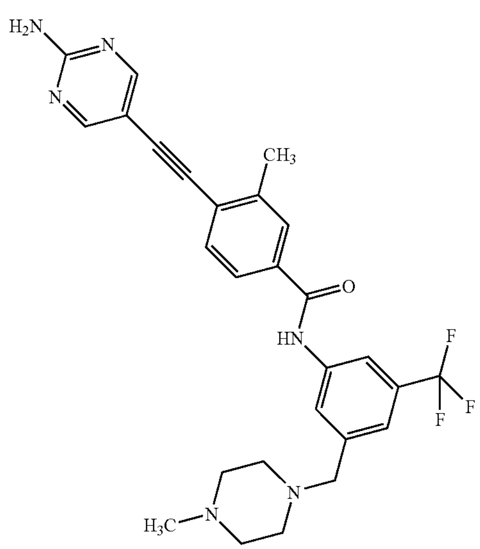 | 4-((2-amino-5-pyrimidinyl)ethynyl)-3-methyl-N-(3-((4-methyl-1-piperazinyl)methyl)-5-(trifluoromethyl)phenyl)benzamide | 508.545 | 509 | A1 |

-continued

| Ex. No. | Structure | Compound Name | MW | MS: M + H | Method |
|---|---|---|---|---|---|
| 312 | 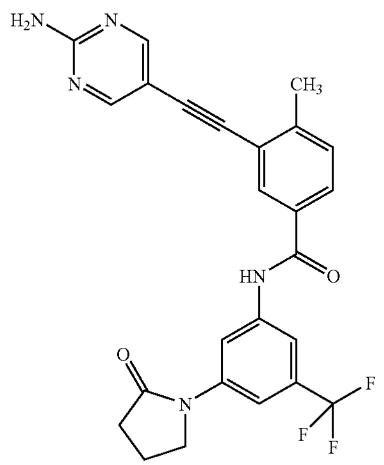 | 3-((2-amino-5-pyrimidinyl)ethynyl)-4-methyl-N-(3-(2-oxo-1-pyrrolidinyl)-5-(trifluoromethyl)phenyl)benzamide | 479.46 | 480 | A1 |
| 313 | 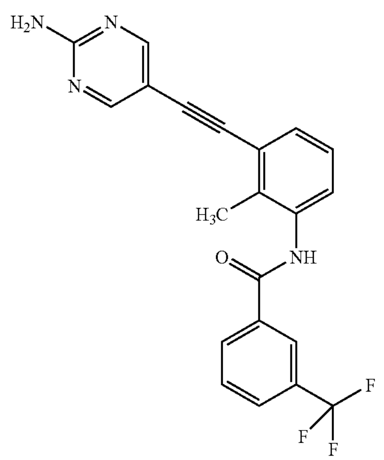 | N-(3-((2-amino-5-pyrimidinyl)ethynyl)-2-methylphenyl)-3-(trifluoromethyl)benzamide | 396.371 | 397 | A1 |
| 314 | 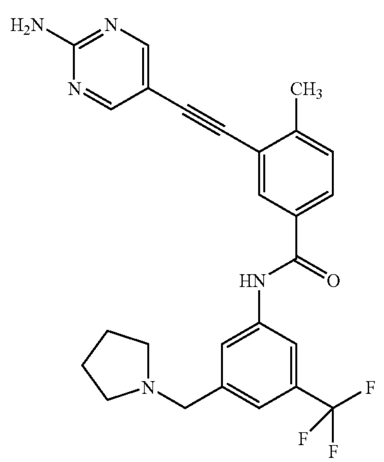 | 3-((2-amino-5-pyrimidinyl)ethynyl)-4-methyl-N-(3-(1-pyrrolidinyl-methyl)-5-(trifluoromethyl)phenyl)benzamide | 479.504 | 480 | A1 |

-continued

| Ex. No. | Structure | Compound Name | MW | MS: M + H | Method |
|---|---|---|---|---|---|
| 315 | 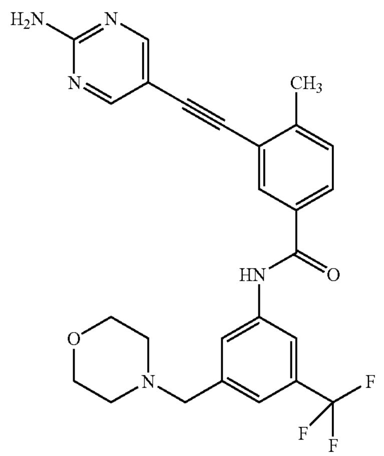 | 3-((2-amino-5-pyrimidinyl)ethynyl)-4-methyl-N-(3-(4-morpholinylmethyl)-5-(trifluoromethyl)phenyl)benzamide | 495.503 | 496 | A1 |
| 316 | 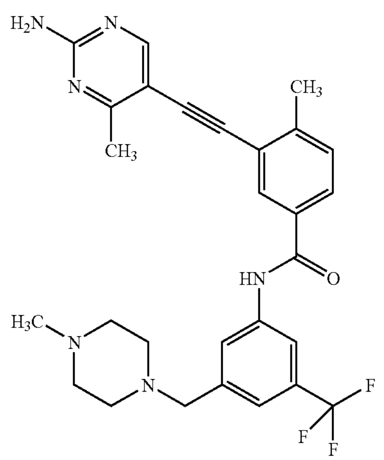 | 3-((2-amino-4-methyl-5-pyrimidinyl)ethynyl)-4-methyl-N-(3-((4-methyl-1-piperazinyl)methyl)-5-(trifluoromethyl)phenyl)benzamide | 522.572 | 523 | A1 |
| 317 | 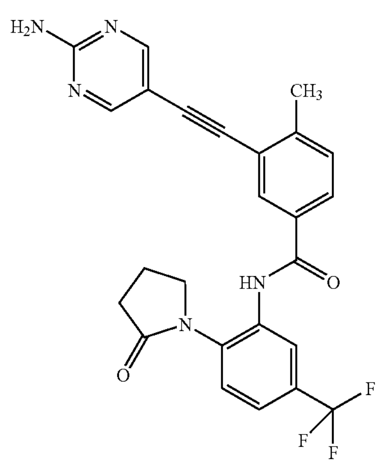 | 3-((2-amino-5-pyrimidinyl)ethynyl)-4-methyl-N-(2-(2-oxo-1-pyrrolidinyl)-5-(trifluoromethyl)phenyl)benzamide | 479.46 | 480 | A1 |

-continued
| Ex. No. | Structure | Compound Name | MW | MS: M + H | Method |
|---|---|---|---|---|---|
| 318 | 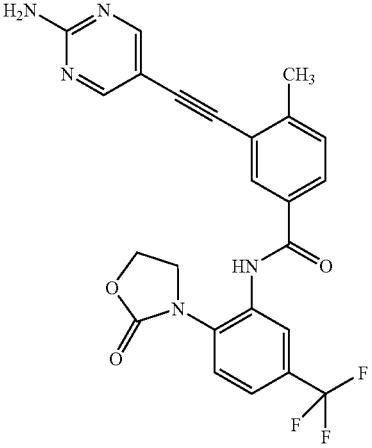 | 3-((2-amino-5-pyrimidinyl)ethynyl)-4-methyl-N-(2-(2-oxo-1,3-oxazolidin-3-yl)-5-(trifluoromethyl)phenyl)benzamide | 481.432 | 482 | A1 |
| 319 | 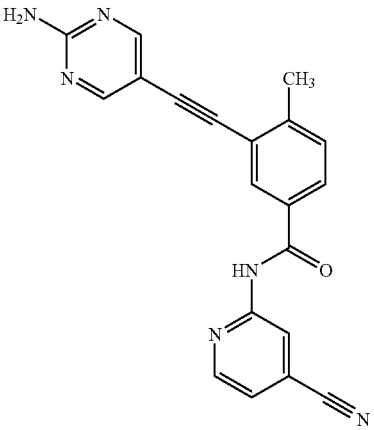 | 3-((2-amino-5-pyrimidinyl)ethynyl)-N-(4-cyano-2-pyridinyl)-4-methylbenzamide | 354.372 | 355 | A1 |
| 320 | 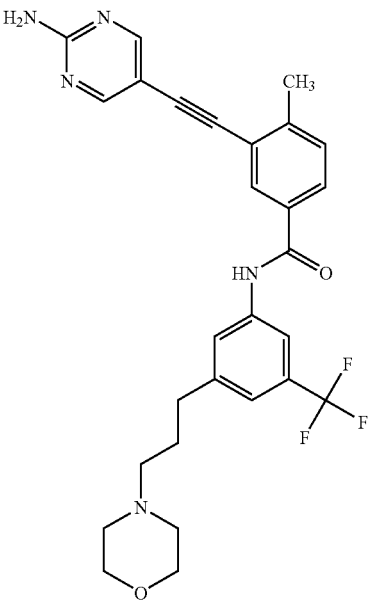 | 3-((2-amino-5-pyrimidinyl)ethynyl)-(4-methyl-N-(3-(3-(4-morpholinyl)propyl)-5-(trifluoromethyl)phenyl)benzamide | 523.556 | 524 | A1 |

| Ex. No. | Structure | Compound Name | MW | MS: M + H | Method |
|---|---|---|---|---|---|
| 321 | 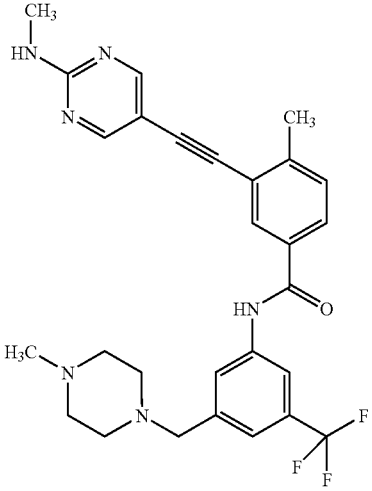 | 4-methyl-3-((2-(methylamino)-5-pyrimidinyl)ethynyl)-N-(3-((4-methyl-1-piperazinyl)methyl)-5-(trifluoromethyl)phenyl)benzamide | 522.572 | 523 | A1 |
| 322 | 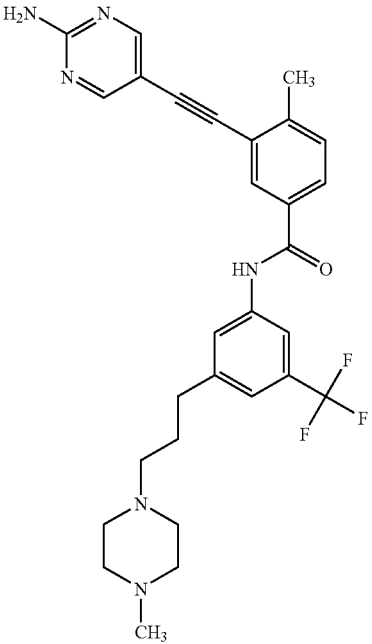 | 3-((2-amino-5-pyrimidinyl)ethynyl)-4-methyl-N-(3-(3-(4-methyl-1-piperazinyl)propyl)-5-(trifluoromethyl)phenyl)benzamide | 536.599 | 537 | A1 |

-continued

| Ex. No. | Structure | Compound Name | MW | MS: M + H | Method |
|---|---|---|---|---|---|
| 323 | 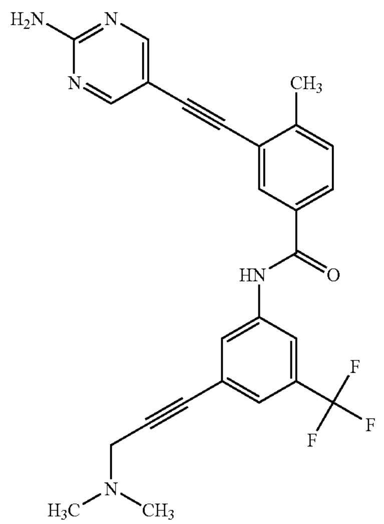 | 3-((2-amino-5-pyrimidinyl)ethynyl)-N-(3-(3-(dimethylamino)-1-propyn-1-yl)-5-(trifluoromethyl)phenyl)-4-methylbenzamide | 477.488 | 478 | A1 |
| 324 | 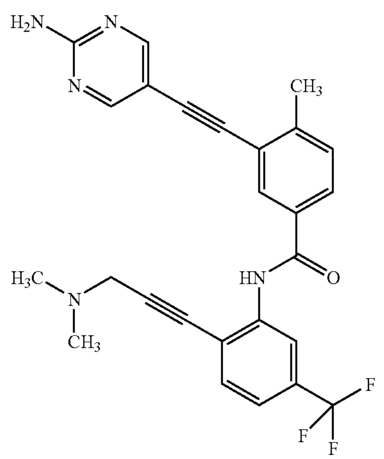 | 3-((2-amino-5-pyrimidinyl)ethynyl)-N-(2-(3-(dimethylamino)-1-propyn-1-yl)-5-(trifluoromethyl)phenyl)-4-methylbenzamide | 477.488 | 478 | A1 |
| 325 | 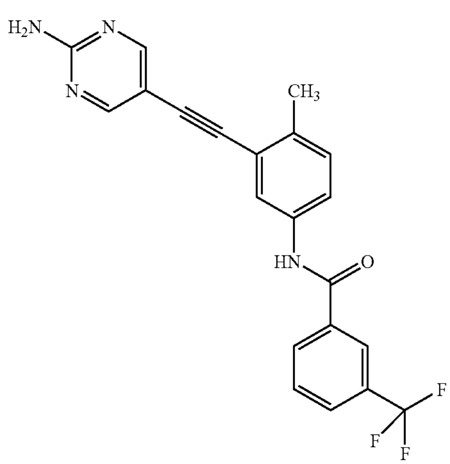 | N-(3-((2-amino-5-pyrimidinyl)ethynyl)-4-methylphenyl)-3-(trifluoromethyl)benzamide | 396.371 | 397 | A1 |

-continued

| Ex. No. | Structure | Compound Name | MW | MS: M + H | Method |
|---|---|---|---|---|---|
| 326 | 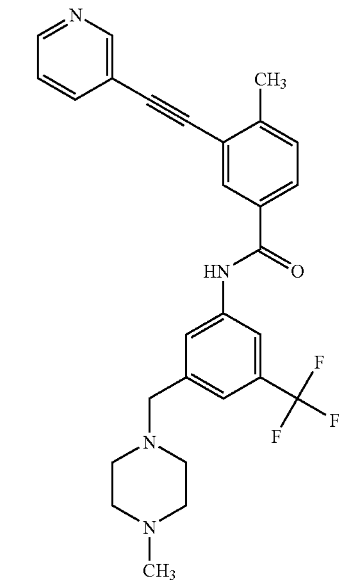 | 4-methyl-N-(3-((4-methyl-1-piperazinyl)methyl)-5-(trifluoromethyl)phenyl)-3-(3-pyridinylethynyl)benzamide | 492.542 | 493 | A1 |
| 327 | 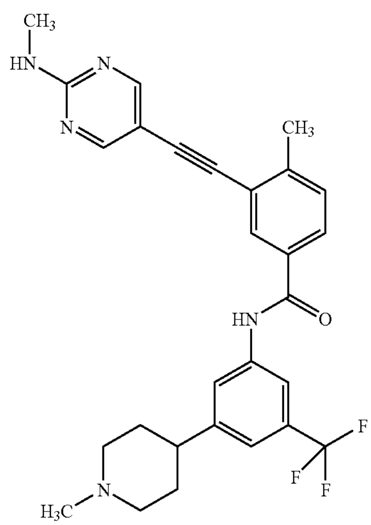 | 4-methyl-3-((2-(methylamino)-5-pyrimidinyl)ethynyl)-N-(3-(1-methyl-4-piperidinyl)-5-(trifluoromethyl)phenyl)benzamide | 507.557 | 508 | A1 |
| 328 | 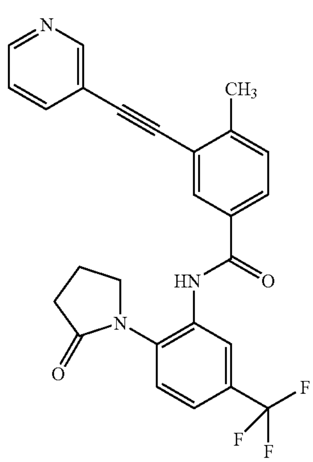 | 4-methyl-N-(2-(2-oxo-1-pyrrolidinyl)-5-(trifluoromethyl)phenyl)-3-(3-pyridinylethynyl)benzamide | 463.457 | 464 | A1 |

-continued

| Ex. No. | Structure | Compound Name | MW | MS: M + H | Method |
|---|---|---|---|---|---|
| 329 | 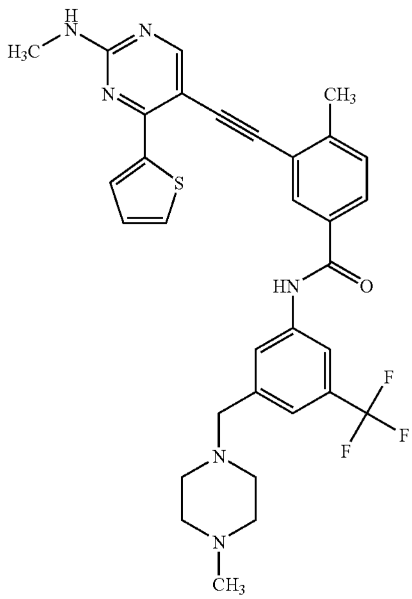 | 4-methyl-3-((2-(methylamino)-4-(2-thienyl)-5-pyrimidinyl)ethynyl)-N-(3-((4-methyl-1-piperazinyl)methyl)-5-(trifluoromethyl)phenyl)benzamide | 604.698 | 605 | A1 |
| 330 | 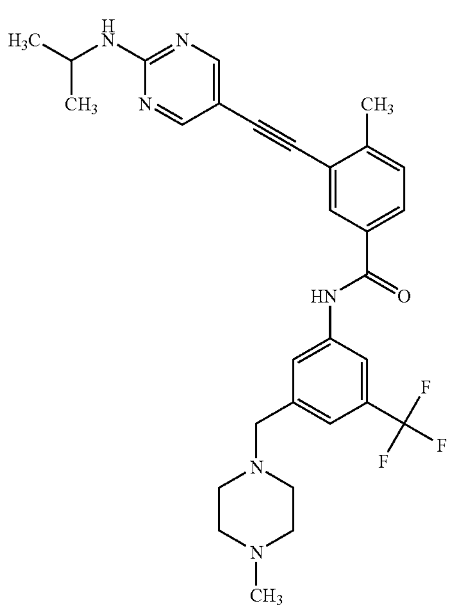 | 4-methyl-3-((2-((1-methylethyl)amino)-5-pyrimidinyl)ethynyl)-N-(3-((4-methyl-1-piperazinyl)methyl)-5-(trifluoromethyl)phenyl)benzamide | 550.626 | 551 | A1 |

-continued

| Ex. No. | Structure | Compound Name | MW | MS: M + H | Method |
|---|---|---|---|---|---|
| 331 | 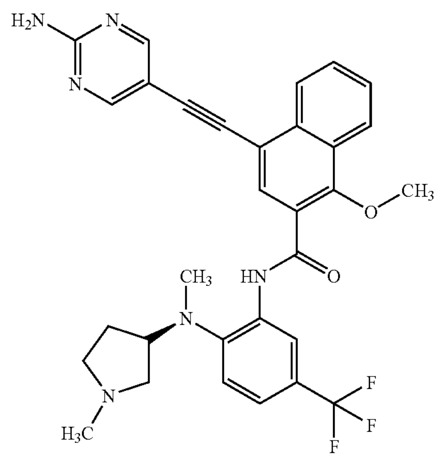 | 4-((2-amino-5-pyrimidinyl)ethynyl)-N-(2-(methyl((3R)-1-methyl-3-pyrrolidinyl)amino)-5-(trifluoromethyl)phenyl)-1-(methyloxy)-2-naphthalenecarboxamide | 574.604 | 575 | A1 |
| 332 | 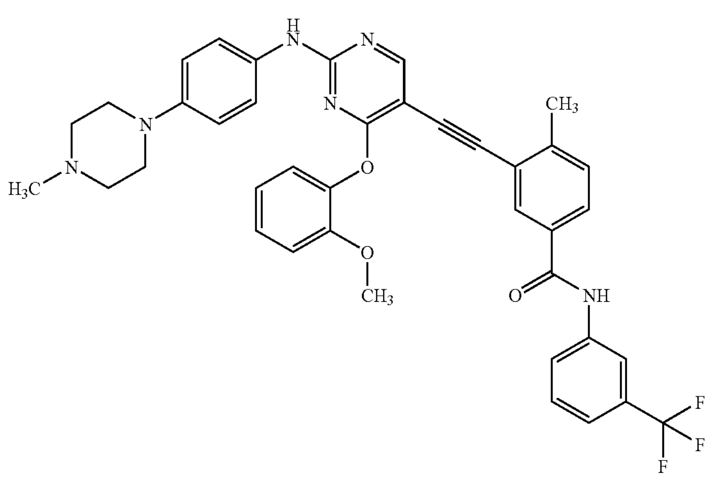 | 4-methyl-3-((4-((2-(methyloxy)phenyl)oxy)-2-((4-(4-methyl-1-piperazinyl)phenyl)amino)-5-pyrimidinyl)ethynyl)-N-(3-(trifluoromethyl)phenyl)benzamide | 692.739 | 693 | D1 |
| 333 | 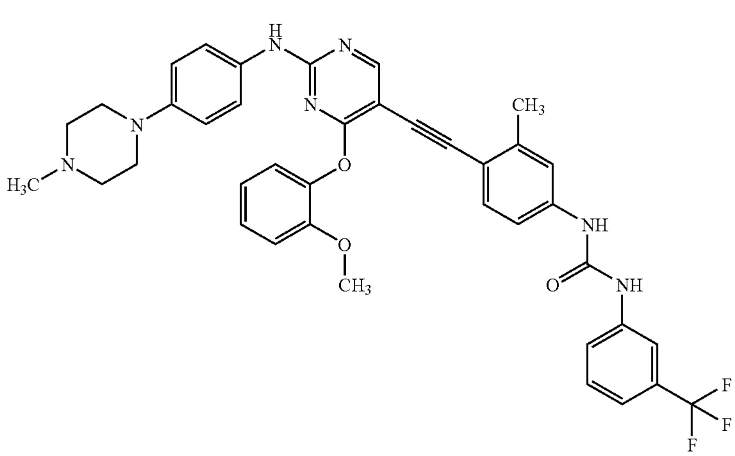 | N-(3-methyl-4-((4-((2-(methyloxy)phenyl)oxy)-2-((4-(4-methyl-1-piperazinyl)phenyl)amino)-5-pyrimidinyl)ethynyl)phenyl)-N'-(3-(trifluoromethyl)phenyl)urea | 707.753 | 708 | D1 |

-continued

| Ex. No. | Structure | Compound Name | MW | MS: M + H | Method |
|---|---|---|---|---|---|
| 334 | 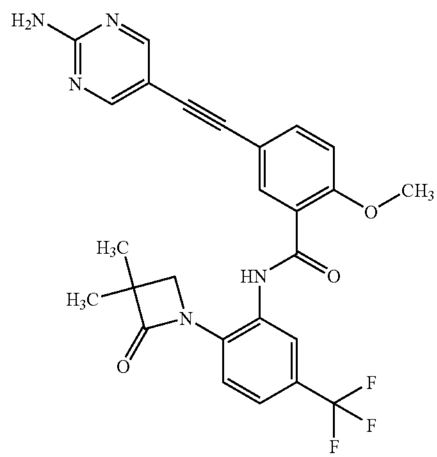 | 5-((2-amino-5-pyrimidinyl)ethynyl)-N-(2-(3,3-dimethyl-2-oxo-1-azetidinyl)-5-(trifluoromethyl)phenyl)-2-(methyloxy)benzamide | 509.486 | 510 | A1 |
| 335 | 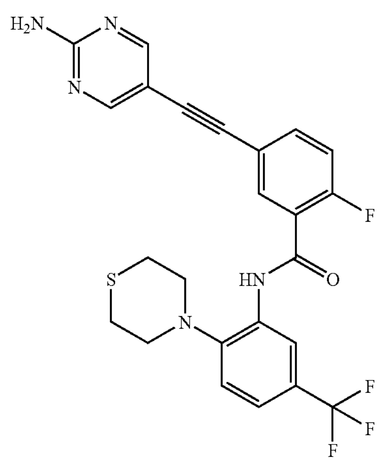 | 5-((2-amino-5-pyrimidinyl)ethynyl)-2-fluoro-N-(2-(4-thiomorpholinyl)-5-(trifluoromethyl)phenyl)benzamide | 501.506 | 502 | A1 |
| 336 | 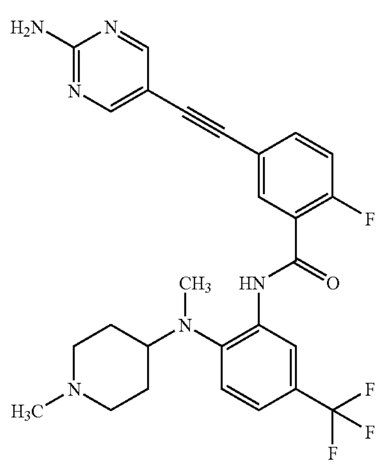 | 5-((2-amino-5-pyrimidinyl)ethynyl)-2-fluoro-N-(2-(methyl(1-methyl-4-piperidinyl)amino)-5-(trifluoromethyl)phenyl)benzamide | 526.535 | 527 | A1 |

-continued

| Ex. No. | Structure | Compound Name | MW | MS: M + H | Method |
|---|---|---|---|---|---|
| 337 | 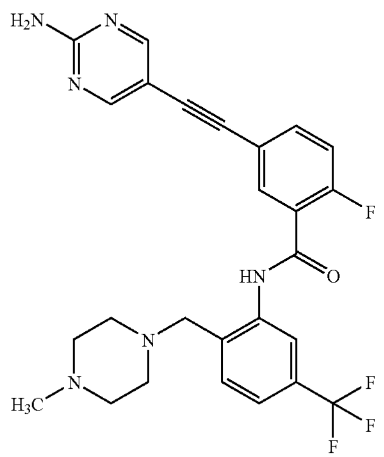 | 5-((2-amino-5-pyrimidinyl)ethynyl)-2-fluoro-N-(2-((4-methyl-1-piperazinyl)methyl)-5-(trifluoromethyl)phenyl)benzamide | 512.509 | 513 | 1 |
| 338 | 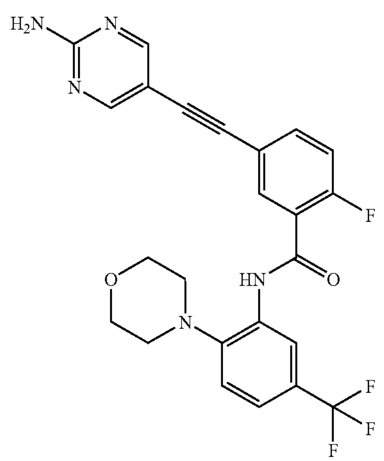 | 5-((2-amino-5-pyrimidinyl)ethynyl)-2-fluoro-N-(2-(4-morpholinyl)-5-(trifluoromethyl)phenyl)benzamide | 485.439 | 486 | A1 |
| 339 | 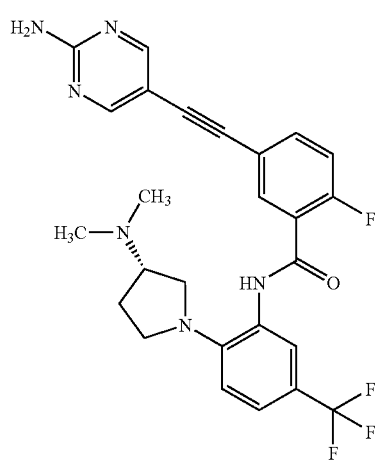 | 5-((2-amino-5-pyrimidinyl)ethynyl)-N-(2-((3S)-3-(dimethylamino)-1-pyrrolidinyl)-5-(trifluoromethyl)phenyl)-2-fluorobenzamide | 512.509 | 513 | A1 |

-continued

| Ex. No. | Structure | Compound Name | MW | MS: M + H | Method |
|---|---|---|---|---|---|
| 340 | 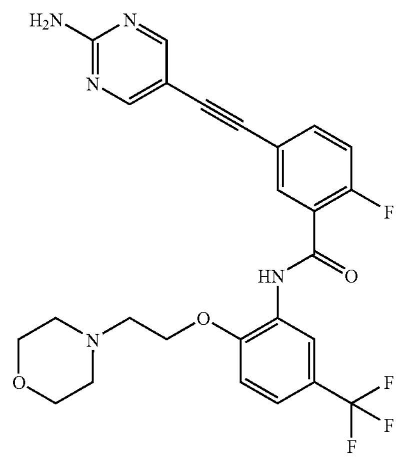 | 5-((2-amino-5-pyrimidinyl)ethynyl)-2-fluoro-N-(2-((2-(4-morpholinyl)ethyl)oxy)-5-(trifluoromethyl)phenyl)benzamide | 529.492 | 530 | A1 |
| 341 | 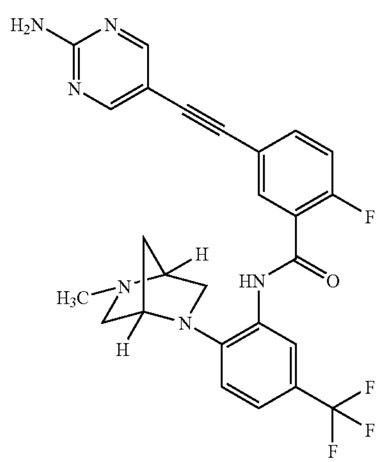 | 5-((2-amino-5-pyrimidinyl)ethynyl)-2-fluoro-N-(2-((1S,4R)-5-methyl-2,5-diazabicyclo[2.2.1]hept-2-yl)-5-(trifluoromethyl)phenyl)benzamide | 510.493 | 511 | A1 |
| 342 | 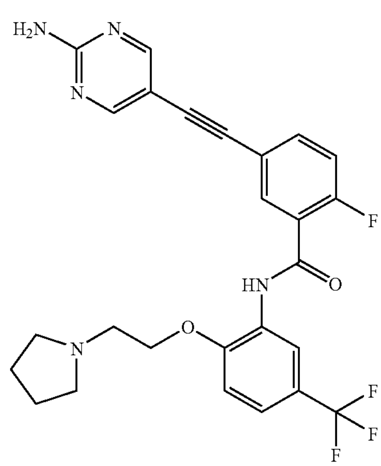 | 5-((2-amino-5-pyrimidinyl)ethynyl)-2-fluoro-N-(2-((2-(1-pyrrolidinyl)ethyl)oxy)-5-(trifluoromethyl)phenyl)benzamide | 513.493 | 514 | A1 |

| Ex. No. | Structure | Compound Name | MW | MS: M + H | Method |
|---|---|---|---|---|---|
| 343 | 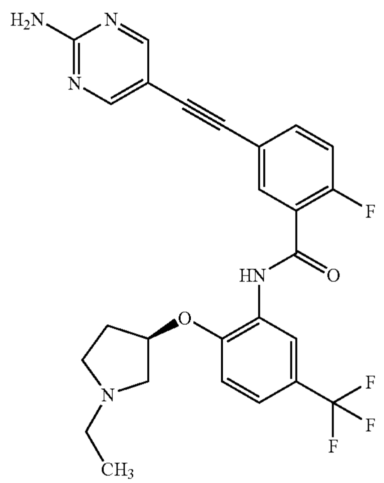 | 5-((2-amino-5-pyrimidinyl)ethynyl)-N-(2-(((3S)-1-ethyl-3-pyrrolidinyl)oxy)-5-(trifluoromethyl)phenyl)-2-fluorobenzamide | 513.495 | 514 | A1 |
| 344 | 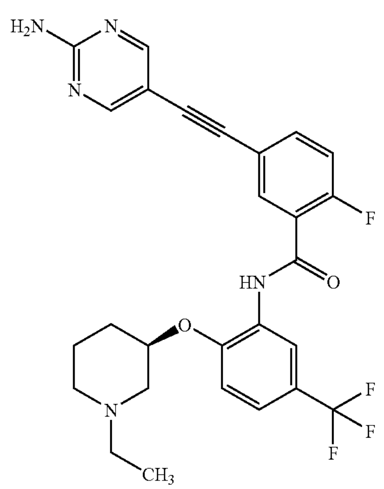 | 5-((2-amino-5-pyrimidinyl)ethynyl)-N-(2-(((3S)-1-ethyl-3-piperidinyl)oxy)-5-(trifluoromethyl)phenyl)-2-fluorobenzamide | 527.52 | 528 | A1 |

-continued

| Ex. No. | Structure | Compound Name | MW | MS: M + H | Method |
|---|---|---|---|---|---|
| | | | | | |
| 345 | 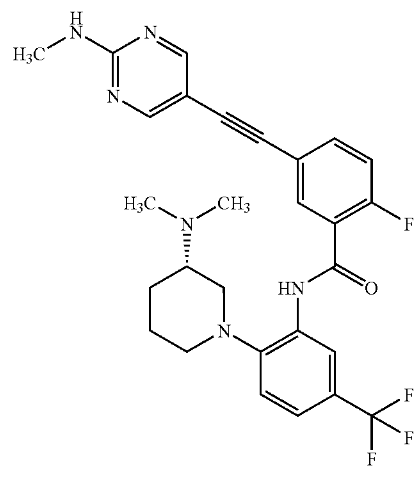 | N-(2-((3S)-3-(dimethylamino)-1-piperidinyl)-5-(trifluoromethyl)phenyl)-2-fluoro-5-((2-(methyl-amino)-5-pyrimidinyl)ethynyl)benzamide | 540.562 | 541 | A1 |
| 346 | 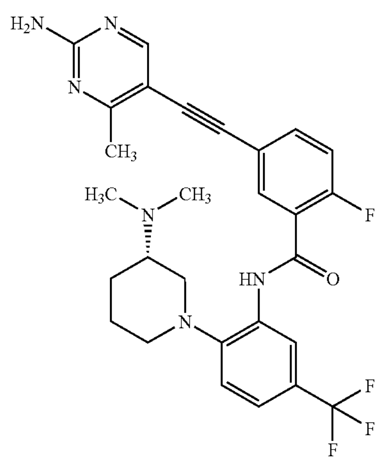 | 5-((2-amino-4-methyl-5-pyrimidinyl)ethynyl)-N-(2-((3S)-3-(dimethylamino)-1-piperidinyl)-5-(trifluoromethyl)phenyl)-2-fluorobenzamide | 540.562 | 541 | A1 |

-continued

| Ex. No. | Structure | Compound Name | MW | MS: M + H | Method |
|---|---|---|---|---|---|
| 347 | 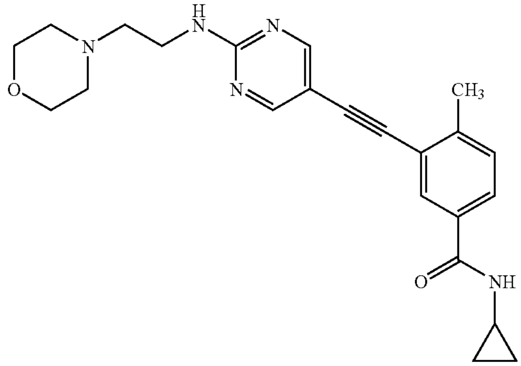 | N-cyclopropyl-4-methyl-3-((2-((2-(4-morpholinyl)ethyl)amino)-5-pyrimidinyl)ethynyl)benzamide | 405.499 | 406 | A1 |
| 348 | 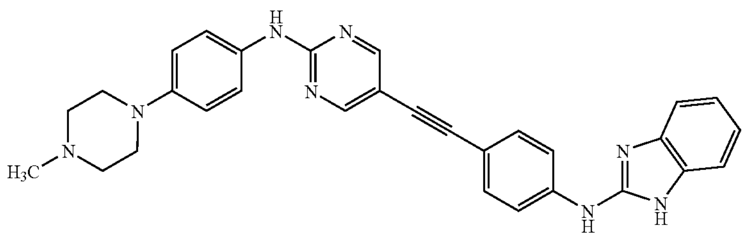 | N-(4-((2-((4-(4-methyl-1-piperazinyl)phenyl)amino)-5-pyrimidinyl)ethynyl)phenyl)-1H-benzimidazol-2-amine | 500.607 | 501 | C2 |
| 349 | 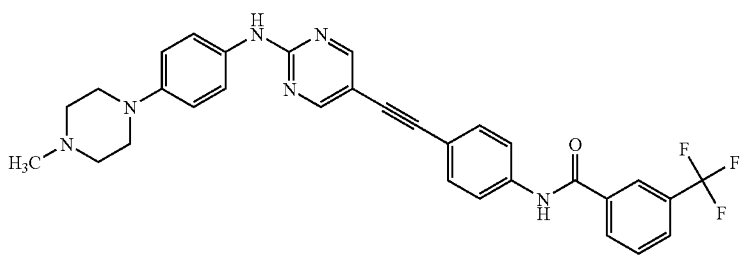 | N-(4-((2-((4-(4-methyl-1-piperazinyl)phenyl)amino)-5-pyrimidinyl)ethynyl)-phenyl)-3-(trifluoromethyl)benzamide | 556.589 | 557 | B1 |
| 350 | 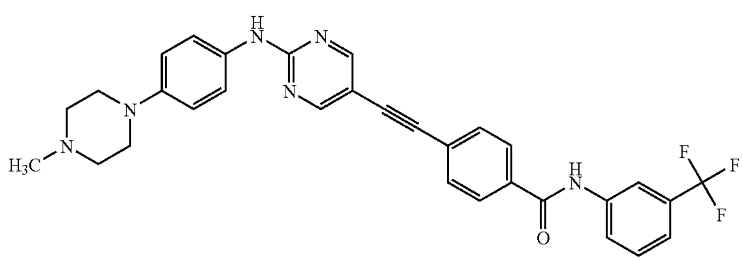 | 4-((2-((4-(4-methyl-1-piperazinyl)phenyl)amino)-5-pyrimidinyl)ethynyl)-N-(3-trifluoromethyl)phenyl)benzamide | 556.589 | 557 | A1 |
| 351 | 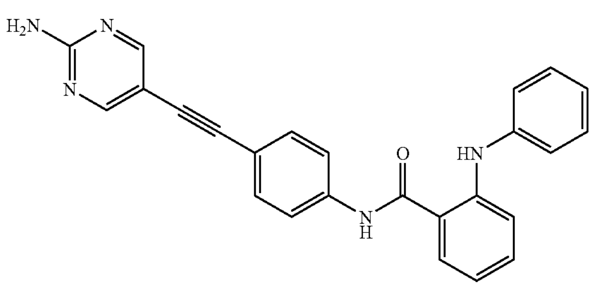 | N-(4-((-amino-5-pyrimidinyl)ethynyl)phenyl)-2-(phenylamino)benzamide | 405.459 | 406 | B1 |

Biological Evaluation

The following assays can be employed to determine the degree of activity of a compound as a protein kinase inhibitor. Compounds described herein have been tested in one or more of these assays, and have shown activity. Representative compounds of the invention were tested and found to exhibit $IC_{50}$ values of 25 μM or less in any one of the described assays, thereby demonstrating and confirming the utility of the compounds of the invention as protein kinase inhibitors and in the prophylaxis and treatment of immune diseases, proliferative disorders, angiogenic diseases, etc.

TIE-2-Homogenous Time Resolved Flourescent (HTRF) Kinase Assay $IC_{50}$'s for the inhibition of the Tie-2 kinase enzyme for individual compounds were measured using an HTRF assay, utilizing the following procedure:

In a 96 well plate (available from Costar Co.) was placed 1 uL of each test and standard compound per well in 100% DMSO having a 25 uM final compound concentration (3-fold, 10 point dilution). To each well was added 20 uL of a reaction mix formed from Tie-2 (4.0 uL; of a 10 mm stock solution available from Gibco), 0.05% BSA (0.1 uL; from a 10% stock solution available from Sigma-Aldrich Co.), 0.002 mM of BLC HER-2 KKK (Biotinylated Long chain peptide; 0.04 uL; from a 0.002 mM stock solution), 0.01 mM concentration of ATP (0.02 uL; commercially available from Sigma-Aldrich Co.) and the remaining solution was water (15.84 uL) to make to a total volume of 20 uL/well.

The reaction was initiated in each well by adding 20 uL per well of an enzyme preparation consisting of a 50 mM concentration of Hepes (1.0 uL; from a 1000 mM stock solution commercially available from Gibco Co.), 0.05% concentration of BSA (0.1 uL), 4 mM of DTT (0.08 uL; from a 1000 mM stock solution available from Sigma-Aldrich Co.), a $2.4 \times 10^{-7}$ concentration of Tie-2 (0.02 uL, from a 4 mM concentration stock), with the remaining volume being water (18.8 uL) to dilute the enzyme preparation to a total volume of 20 uL. The plate was incubated for about 90 minutes at RT. After incubation, a 160 uL of a filtered detection mixture, prepared from 0.001 mg/ml of SA-APC (0.0765 uL; available as a 2.09 mg/ml stock solution from Gibco), 0.03125 nM concentration of Eu-Ab (0.1597 uL; available in a 31.3 nM stock solution from Gibco), with the remaining volume being Detection buffer (159.73 uL), was added to each well to stop the reaction therein. The plate was then allowed to equilibrate for about 3 hr and read on a Ruby Star fluorescent reader (available from BMG Technologies, Inc.) using a 4 parameter fit using activity base to calculate the corresponding $IC_{50}$'s for the test and standard compounds in each well. The following exemplary compounds were found to have $IC_{50}$'s for the inhibition of Tie-2 as measured by the HTRF assay of less than or equal to 10 uM: Examples 1-44, 46-64, 66-67, 69-77, 79 and 81-92.

TIE-2 Cell-Based Delfia Assay

Day 1—Plate Preparation

Three 175 ml flasks of EAHY926 cells were obtained from the University of N. Carolina. All cells were trypsinized (i.e., washed with 20 mL of PBS followed by 3 mL of trypsin-EDTA obtained from Gibco Co., cat. no. 25300-054, for 5 min at RT), then cultured in a growth medium solution containing DMEM (High glucose, Gibco Co., cat. no. 1965-092), 10% FBS serum (Gibco Co., cat. no. 10099-141) and P/S (Penicillin-Streptomycin-Glutamine; Gibco Co., cat. no. 10378-016) culture media. The cells were counted using a Z2® Coulter® counter. The cells were plated in four 24-well tissue culture plates (Costar Co., cat. no. 353047) to initially contain $4 \times 10^5$ cells/ml per well, and then loaded to 500 uL volume having a final cell density of $2 \times 10^5$ cells/well. The cells were incubated for 5 or more hours at 37° C. under 5% $CO_2$. The DMEM+10% serum+P/S culture media was removed and the cells washed twice with 500 uL of PBS (without Ca+ and Mg++; Gibco Co., cat. no. 14190-136) at RT. 500 uL of 0.5% FBS+F12 (F12 nutrient mixture; Gibco Co., cat. no. 11765-054) was added to each well and the cells were incubated at 37° C. overnight (about 15 hr).

100 ug of anti-hTie2 antibody (R & D Systems, Inc., Cat. No. AF313) was diluted with 10 mL of ice-cold PBS to prepare a 10 ug/mL antibody concentration stock. A 96-well microplate (Perkin-Elmer Wallac, cat. no. AAAND-0001) was coated with 100 uL of the anti-Tie2 antibody stock and the coated plate was stored at 4° C. overnight.

Day 2—Compound Plate Preparation

The media in the microplate was replaced with a preparation of 500 uL DMEM+1% BSA (Bovine Serum Albumin; ICN Biomedicals, Inc., cat. no. 160069). 20 uL of a selected Tie2 reference compound was placed in a selected well of the 96-well plate, and diluted 1:4 with 100% DMSO from an initial concentration of about 10 mM to a final concentration of about 2.5 mM, then diluted 1:3 with 100% DMSO for a 10 point dilution to a final concentration of about 0.128 uM.

Test compounds (10 uL of a 10 mM concentration) were similarly diluted 1:4 with 100% DMSO to obtain a sample concentration of about 2.5 mM, then diluted 1:3 for a 10 point dilution to finally obtain a concentration of about 0.128 uM for each test compound. 20 uL of 100% DMSO served as positive controls, while and 10 uL of the 2.5 mM concentration of the reference compound served as the negative control.

A 2 uL aliquot from each well (test compounds, positive and negative controls) in the 96-well plate was added to designated wells in the 24-well cell culture plate (1:250). The culture plate was incubated for 2.5 at 37° C. in an atmosphere of about 5% $CO_2$.

The Tie-2 ligand was stimulated with the following series of preparations: (1) about 0.5 mL of a protease inhibitor cocktail (Sigma-Aldrich Co., cat. no. P8340) was thawed; (2) to prepare the phosphatase inhibitor, a 300 mM $NaVO_4$ (Sigma-Aldrich Chem. Co., cat. no. S6508-10G) stock solution in PBS was made and stored at RT. Two 1 mL aliquots of the $NaVO_4$ solution was prepared in separate two vials by adding 100 uL of the $NaVO_4$ stock solution to 900 uL RT PBS and each solution was activated by adding 6 uL of $H_2O_2$ to each vial. Both $NaVO_4$ solutions were mixed, wrapped in aluminum foil and stored at RT for 15 min.

The Delfia plates, containing 200 uL of PBS+0.1% TWEEN20, were washed three times and blocked by adding 200 uL of a diluted solution of 5% BSA (16 mL of stock 7.5% BSA solution, available from Perkin-Elmer Wallac, Cat. No. $CR^{84}$-100, was diluted with 8 mL of room temperature PBS). The plates were then stored at room temperature for about one hour.

100 uL of 35% BSA solution was diluted with 3.4 mL of ice cold PBS to make a 1% BSA/PBS solution. 100 uL of this 1% BSA/PBS solution was diluted with 900 uL of ice cold PBS. hAng1 was reconstituted with 250 uL of ice cold PBS+0.1% BSA to make a 100 ug/mL concentration in solution. The solution was separated into 70 uL aliquots and stored at −80° C.

1 mL of the 30 mM solution of NaVO$_4$/PBS was diluted with 99 mL of ice cold PBS to form a 300 uM concentration. The solution was kept cold on ice. 210 uL of the activated NaVO$_4$ and 280 uL of the protease inhibitor preparation was added to 21 mL of RIPA buffer and kept cold on ice.

Dilute hAng1 and Stimulate Cells:

70 uL of the 100 ug/mL stock solution was added to 700 uL in 1% BSA/DMEM (1:10) to 10 ug/mL concentration, and it was stored on ice. 5 uL of this 10 ug/mL hAng1 preparation was added to each well of the 24-well plate. The plate was shaken at 700 rpm at 37° C. for about 2.5 minutes.

After shaking, the wells were incubated for 7.5 min at 37° C. The media was removed and 400 uL of ice cold PBS+300 uM NaVO$_4$ was added. The wells were kept on ice for at least 5 min and washed 1× with ice cold PBS+300 uM NaVO$_4$. The wells were tapped against a dry paper towel. The cells were lysed with 150 uL of RIPA, 300 uM of NaVO$_4$, and 100 uL/1*10$^7$ cells protease inhibitor cocktail (purchased from Sigma-Aldrich, Cat. No. P8340). The solution was incubated, then shaken on ice for 30 min.

The BSA blocking solution was removed from the 96-well plates, which were then tapped dry. 140 uL of cell lysate was added to the antibody-coated plate and the plate was incubated at 4° C. for 2 hours.

Delfia 25× Wash Buffer Concentrate (purchased from Perkin-Elmer Wallac, Cat. No. 1244-114) was diluted with 24 parts DDI water to obtain a washing solution. The lysate was removed and the plate was washed three times each with 400 uL of Delfia washing solution. The plate was tap dried with a paper towel.

The Anti-Phosphotyrosine clone 4G10 (purchased from Upstatebiotech Co., Cat. No. 05-321) was diluted with Delfia Assay Buffer (purchased from Perkin-Elmer Wallac, cat. no. 1244-1111) to make a solution of about 1 ug/mL in concentration. 100 uL of antibody was added to the plate and the plate was incubated at room temperature for one hour. The plate was again washed three times with 400 uL pre-time of the Delfia Washing solution.

The Eu-N1 labeled anti-mouse antibody (purchased from Perkin-Elmer Wallac, cat. no. AD0124) was diluted with Delfia Assay Buffer to make a solution of about 0.1 ug/mL in concentration.

100 uL of antibody was added to the plate and the plate was incubated at room temperature for one hour. The plate was again washed with Delfia Wash Buffer three times as described above. 100 uL of Delfia Enhancement Solution (purchased from Perkin-Elmer Wallac, Cat. No. 1244-105) was added to each well and the plate was incubated at room temperature for 5 min in the dark.

The Europium signal was measured with a Victor multilabel counter (Wallac Model 1420) while shaking (shake fast, linear, 0.10 mm for 1 s) using a Europium protocol.

Raw data was analyzed using a fit equation in XLFit. IC$_{50}$ values were then determined using Grafit software. A majority of the compounds of Examples 1-92 were found to have an IC$_{50}$ of less than 25 µM in the Tie-2 cell-based Delfia assay.

The compounds of the invention also were found to have inhibitory activity with respect to other kinase enzymes as well. For example, the compounds were found to be inhibitors of Lck. The exemplary assays described as follows were used to make such determination.

LCK-Homogenous Time Resolved Flourescent (HTRF) Kinase Assay

The LCK HTRF assay begins with LCK in the presence of ATP phosphorylating the biotinylated peptide Gastrin. The reaction incubates for 90 min. To quench the assay detection reagents are added which both stop the reaction by diluting out the enzyme and chelating the metals due to the presence of EDTA. Once the detection reagents are added the assay incubates for 30 min to allow for equilibration of the detection reagents.

The LCK HTRF assay is comprised of 10 µL of compound in 100% DMSO, 15 µL of ATP and biotinylated Gastrin, and 15 µL of LCK KD GST (225-509) for a final volume of 40 µL. The final concentration of gastrin is 1.2 µM. The final concentration of ATP is 0.5 µm (Km app=0.6 µM+/−0.1) and the final concentration of LCK is 250 µM. Buffer conditions are as follows: 50 mM HEPES pH 7.5, 50 mM NaCl, 20 mM MgCl, 5 mM MnCl, 2 mM DTT, 0.05% BSA.

The assay is quenched and stopped with 160 µL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.0004 mg/mL, and europilated anti-phosphotyrosine Ab (Eu-anti-PY) at a final conc of 0.025 nM.

The assay plate is read in either a Discovery or a RubyStar. The eu-anti-PY is excited at 320 nm and emits at 615 nm to excite the SA-APC which in turn emits at 655 nm. The ratio of SA-APC at 655 nm (excited due to close proximity to the Eu-anti-PY because of phosphorylation of the peptide) to free Eu-anti-PY at 615 nm will give substrate phosphorylation.

Assays for other kinases are done in a similar way as described above, varying the concentrations of enzyme, peptide substrate, and ATP added to the reaction, depending on the specific activity of the kinase and measured Km's for the substrates.

Human Mixed Lymphocyte Reaction (huMLR):

The purpose of this assay is to test the potency of T cell activation inhibitors in an in vitro model of allogeneic T cell stimulation. Human peripheral blood lymphocytes (hPBL; 2×10$^5$/well) are incubated with mitomycin C-treated B lymphoblastoid cells (JY cell line; 1×10$^5$/well) as allogeneic stimulators in the presence or absence of dilutions of potential inhibitor compound in 96-well round-bottom tissue culture plates. These cultures are incubated at 37° C. in 5% CO$_2$ for 6 days total. The proliferative response of the hPBL is measured by $^3$H-thymidine incorporation overnight between days 5 and 6 after initiation of culture. Cells are harvested onto glass fiber filters and $^3$H-thymidine incorporation into DNA is analyzed by liquid scintillation counter.

Jurkat Proliferation/Survival Assay:

The purpose of this assay is to test the general anti-proliferative/cytotoxic effect of compounds on the Jurkat human T cell line. Jurkat cells (1×10$^5$/well) are plated in 96-well flat-bottom tissue culture plates with or without compound dilutions and cultured for 72 h at 37° C. in 5% CO$_2$. Viable cell number is determined during the last 4 h of culture by adding 10 µL/well WST-1 dye. WST-1 dye conversion relies on active mitochondrial electron transport for reduction of the tetrazolium dye. The dye conversion was read by OD at 450-600 nm.

Anti-CD3/CD28-Induced T Cell IL-2 Secretion and Proliferation Assay:

The purpose of this assay is to test the potency of T cell receptor (TCR; CD3) and CD28 signaling pathway inhibitors in human T cells. T cells are purified from human peripheral blood lymphocytes (hPBL) and pre-incubated with or without compound prior to stimulation with a combination of an anti-CD3 and an anti-CD28 antibody in 96-well tissue culture plates (1×10$^5$ T cells/well). Cells are cultured for ~20 h at 37°

C. in 5% $CO_2$, then secreted IL-2 in the supernatants is quantified by cytokine ELISA (Pierce/Endogen). The cells remaining in the wells are then pulsed with $^3$H-thymidine overnight to assess the T cell proliferative response. Cells are harvested onto glass fiber filters and $^3$H-thymidine incorporation into DNA is analyzed by liquid scintillation counter. For comparison purposes, phorbol myristic acid (PMA) and calcium ionophore can be used in combination to induce IL-2 secretion from purified T cells. Potential inhibitor compounds can be tested for inhibition of this response as described above for anti-CD3 and -CD28 antibodies.

Assays for other kinases are done in a similar way as described above, varying the concentrations of enzyme, peptide substrate, and ATP added to the reaction, depending on the specific activity of the kinase and measured Km's for the substrates.

Exemplary compounds 1-23, 25-54, 56-64, 66-67, 69-77, 81-83 and 85-92 exhibited an average $IC_{50}$ value of 10 uM or less in the human HTRF assay for the inhibition of the Lck kinase enzyme.

Indications

Accordingly, compounds of the invention are useful for, but not limited to, the prevention or treatment of inflammation, cancer and related diseases. The compounds of the invention have kinase modulatory activity in general, and kinase inhibitory activity in particular. In one embodiment of the invention, there is provided a method of modulating a protein kinase enzyme in a subject, the method comprising administering to the subject an effective dosage amount of a compound of a compound of Formulae I and II. In another embodiment, the kinase enzyme is ab1, Akt, bcr-ab1, Blk, Brk, Btk, c-kit, c-Met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes or Zap70.

Various of the compounds of the invention have selective inhibitory activity for specific kinase receptor enzymes, including Tie-2, Lck, p38 and VEGFR/KDR. Accordingly, the compounds of the invention would be useful in therapy as antineoplasia agents, anti-inflammatory agents or to minimize deleterious effects of Tie-2, Lck; VEGF and/or p38.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma). The compounds are useful for the treatment of neoplasia selected from lung cancer, colon cancer and breast cancer.

The compounds would also be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

Based on the ability to modulate kinases impacting angiogenesis, the compounds of the invention are also useful in treatment and therapy of proliferative diseases. Particularly, these compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermatomyositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof. An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, consequential to or associated with disease or further (in a broader sense of the invention) with surgical intervention, including, in particular conditions such as insertion endopathy, myofasciale syndrome and tendomyosis. The present invention is further applicable to the treatment of inflammation, e.g. inflammatory disease or condition, of connective tissues including dermatomyositis and myositis.

The compounds of the invention can also be used as active agents against such disease states as arthritis, atherosclerosis, psoriasis, hemangiomas, myocardial angiogenesis, coronary and cerebral collaterals, ischemic limb angiogenesis, wound healing, peptic ulcer *Helicobacter* related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

The compounds of the invention can also be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease.

The compounds will also be useful in treating disorders in which protein extravasation leads to the deposition of fibrin and extracellular matrix, promoting stromal proliferation (e.g. fibrosis, cirrhosis and carpal tunnel syndrome).

The compounds of the invention are also useful in the treatment of ulcers including bacterial, fungal, Mooren ulcers and ulcerative colitis.

The compounds of the invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of sub-cutaneous fat and for the treatment of obesity. The compounds of the invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration. The compounds of the invention are also useful in the treatment of cardiovascular conditions such as atherosclerosis, restenosis, arteriosclerosis, vascular occlusion and carotid obstructive disease.

The compounds of the invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the invention are also useful in the treatment of diabetic conditions such as diabetic retinopathy and microangiopathy.

The compounds of the present invention are also capable of inhibiting other protein kinases, including for example, Src, fgf, c-Met, ron, ckit and ret, and thus may be effective in the treatment of diseases associated with other protein kinases. More specifically, the compounds of the present invention inhibit the Src-family of protein tyrosine kinases such as Lck, Fyn(B), Fyn(T), Lyn, Src, Yes, Hck, Fgr and Blk, and are thus useful in the treatment, including prevention and therapy, of protein tyrosine kinase-associated disorders such as immunologic disorders. "Protein tyrosine kinase-associated disorders" are those disorders which result from aberrant tyrosine kinase activity, and/or which are alleviated by the inhibition of one or more of these enzymes. For example, Lck inhibitors are of value in the treatment of a number of such disorders (for example, the treatment of autoimmune diseases), as Lck inhibition blocks T cell activation. The treatment of T cell mediated diseases, including inhibition of T cell activation and proliferation, is a preferred embodiment of the present invention. Compounds of the present invention which selectively block T cell activation and proliferation are preferred. Also, compounds of the present invention which may block the activation of endothelial cell protein tyrosine kinase by oxidative stress, thereby limiting surface expression of adhesion molecules that induce neutrophil binding, and which can inhibit protein tyrosine kinase necessary for neutrophil activation would be useful, for example, in the treatment of ischemia and reperfusion injury.

The present invention also provides methods for the treatment of protein tyrosine kinase-associated disorders, comprising the step of administering to a subject in need thereof at least one compound of the Formula I or of Formula II in an amount effective therefor. Other therapeutic agents such as those described below may be employed with the inventive compounds in the present methods. In the methods of the present invention, such other therapeutic agent(s) may be administered prior to, simultaneously with or following the administration of the compound(s) of the present invention.

Use of the compound(s) of the present invention in treating protein tyrosine kinase-associated disorders is exemplified by, but is not limited to, treating a range of disorders such as: arthritis (such as rheumatoid arthritis, psoriatic arthritis or osteoarthritis); transplant (such as organ transplant, acute transplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; multiple sclerosis; inflammatory bowel disease, including ulcerative colitis and Crohn's disease; lupus (systemic lupus erythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers where Lck or other Src-family kinases such as Src are activated or overexpressed, such as colon carcinoma and thymoma, or cancers where Src-family kinase activity facilitates tumor growth or survival; glomerulonephritis, serum sickness; uticaria; allergic diseases such as respiratory allergies (asthma, hayfever, allergic rhinitis) or skin allergies; scleracielma; mycosis fungoides; acute inflammatory responses (such as acute respiratory distress syndrome and ishchemia/reperfusion injury); dermatomyositis; alopecia greata; chronic actinic dermatitis; eczema; Behcet's disease; Pustulosis palmoplanteris; Pyoderma gangrenum; Sezary's syndrome; atopic dermatitis; systemic schlerosis; and morphea. The present invention also provides for a method for treating the aforementioned disorders such as atopic dermatitis by administration of a therapeutically effective amount of a compound of the present invention, which is an inhibitor of protein tyrosine kinase, to a patient in need of such treatment.

Src-family kinases other than Lck, such as Hck and Fgr are important in the Fcγ receptor induced respiratory burst of neutrophils as well as the Fcγ receptor responses of monocytes and macrophages. The compounds of the present invention may inhibit the Fcγ induced respiratory burst response in neutrophils, and may also inhibit the Fcγ dependent production of TNFα. The ability to inhibit Fcγ receptor dependent neutrophil, monocyte and macrophage responses would result in additional anti-inflammatory activity for the present compounds in addition to their effects on T cells. This activity would be especially of value, for example, in the treatment of inflammatory diseases, such as arthritis or inflammatory bowel disease.

The present compounds may also be of value for the treatment of autoimmune glomerulonephritis and other instances of glomerulonephritis induced by deposition of immune complexes in the kidney that trigger Fcγ receptor responses and which can lead to kidney damage.

In addition, certain Src family kinases, such as Lyn and Fyn(B), may be important in the Fcε receptor induced degranulation of mast cells and basophils that plays an important role in asthma, allergic rhinitis, and other allergic disease. Fcε receptors are stimulated by IgE-antigen complexes. The compounds of the present invention may inhibit the Fcε induced degranulation responses. The ability to inhibit Fcε receptor dependent mast cell and basophil responses may result in additional anti-inflammatory activity for the present compounds beyond their effect on T cells.

The combined activity of the present compounds towards monocytes, macrophages, T cells, etc. may prove to be a valuable tool in the treatment of any of the aforementioned disorders.

In a particular embodiment, the compounds of the present invention are useful for the treatment of the aforementioned exemplary disorders irrespective of their etiology, for example, for the treatment of rheumatoid arthritis, transplant rejection, multiple sclerosis, inflammatory bowel disease, lupus, graft v. host disease, T cell mediated hypersensitivity disease, psoriasis, Hashimoto's thyroiditis, Guillain-Barre syndrome, cancer, contact dermatitis, allergic disease such as allergic rhinitis, asthma, ischemic or reperfusion injury, or atopic dermatitis whether or not associated with PTK.

In another embodiment, the compounds are useful for the treatment of rheumatoid spondylitis, gouty arthritis, adult respiratory distress syndrome (ARDS), anaphylaxis, muscle degeneration, cachexia, Reiter's syndrome, type II diabetes, bone resorption diseases, graft vs. host reaction, Alzheimer's disease, atherosclerosis, brain trauma, multiple sclerosis, cerebral malaria, sepsis, septic shock, toxic shock syndrome, fever, and myalgias due to infection, or which subject is infected by HIV-1, HIV-2, HIV-3, cytomegalovirus (CMV), influenza, adenovirus, the herpes viruses (including HSV-1, HSV-2), or herpes zoster in a subject, the method comprising administering to the subject a pharmaceutical composition comprising an effective dosage amount of a compound of the invention.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation, cancer and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable carrier, which includes diluents, excipients, adjuvants and the like (collectively referred to herein as "carrier" materials) as described herein, and, if desired, other active ingredients. A pharmaceutical composition of the invention may comprise an effective amount of a compound of the invention or an effective dosage amount of a compound of the invention. An effective dosage amount of a compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, and typically from about 1 to 500 mg. A suitable daily dose for a human or other mammal may vary widely depending on the condition of the patient and other factors, but, once again, can be determined using routine methods and practices.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, and more advantageously about 0.01 and about 30 mg/kg body weight may be appropriate. The daily dose can be administered in one to four doses per day.

For therapeutic purposes, the active compounds of this invention are ordinarily combined with one or more adjuvants or "excipients" appropriate to the indicated route of administration. If administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, pastes, suspensions and the like) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include, for example, Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables. The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formulas I-III may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents, which may be used in combination with compounds of the invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents, which may be used in combination with compounds of the invention consists of alkylating-type antineoplastic agents. Suitable alkylating-type antineoplastic agents may be selected from but not limited to the group consisting of Shionogi 254-S, aldophosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SR[1] International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the compounds of the invention may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit anti-thymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the compounds of the invention may also be used in co-therapies with other anti-neoplastic agents, such as other kinase inhibitors including p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors.

The invention also provides processes for making compounds for Formula I, the method comprising the step of A process of making a compound of Formula I, the process comprising the step of reacting a compound of Formula A,

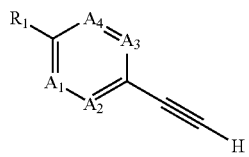

A wherein $A^1$, $A^2$, $A^3$, $A^4$ and $R^1$ are as defined in claim 1, with a compound of Formula B, X—$R^2$ wherein X is a halogen selected from bromine and iodine and $R^2$ is as defined in claim 1, to form a compound of formula I.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:

1. A compound of Formula I:

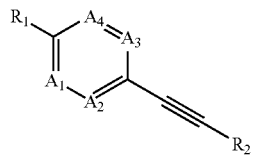

I or a pharmaceutically acceptable salt, thereof, wherein
either each of $A^1$ and $A^4$, independently, is N, $A^2$ is $CR^4$ and $A^3$ is $CR^5$ or each of $A^2$ and $A^3$, independently, is N, $A^1$ is $CR^3$ and $A^4$ is $CR^6$;

$R^1$ is $NR^7R^7$, $NR^7R^8$, $C(O)R^7$, $COOR^7$, $C(O)R^8$, $COOR^8$, $C(O)NR^7R^7$, $NR^7C(O)R^7$, $C(O)NR^7R^8$, $NR^7C(O)R^8$, $S(O)_2NR^7R^7$, $NR^7S(O)_2R^7$, $S(O)_2R^8$, $S(O)_2NR^7R^8$ or $NR^7S(O)_2R^8$;

$R^2$ is a phenyl, naphthyl, pyridyl, pyrimidinyl, quinolinyl, isoquinolinyl, quinazolinyl, isoquinazolinyl, thiophenyl, imidazolyl, thiazolyl, oxazolyl, isoxazolyl, isothiazolyl, indolyl, benzofuranyl, dihydrobenzofuranyl, benzothiophenyl or benzimidazolyl ring substituted with 1-5 substituents of $R^{16}$, $C(O)R^{10}$, $COOR^{10}$, $C(O)R^{11}$, $COOR^{11}$, $C(O)NR^{10}R^{10}$, $C(O)NR^{10}R^{11}$, $NR^{10}C(O)R^{10}$, $NR^{10}C(O)R^{11}$, $NR^{10}C(O)NR^{10}R^{10}$, $NR^{10}C(O)NR^{10}R^{11}$, $S(O)_2NR^{10}R^{10}$, $S(O)_2NR^{10}R^{11}$, $NR^{10}S(O)_2R^{10}$ or $NR^{10}S(O)_2R^{11}$, provided that one substituent on $R^2$ is $C(O)NR^{10}R^{11}$, $NR^{10}C(O)R^{11}$, $NR^{10}C(O)NR^{10}R^{10}$, $NR^{10}C(O)NR^{10}R^{11}$, $S(O)_2NR^{10}R^{10}$, $S(O)_2NR^{10}R^{11}$, $NR^{10}S(O)_2R^{10}$ or $NR^{10}S(O)_2R^{11}$;

$R^3$ is H, halo, haloalkyl, $OR^7$, $SR^7$ or $C_{1-10}$-alkyl, the $C_{1-10}$-alkyl optionally substituted with 1-3 substituents of $R^9$;

$R^4$ is H $R^5$ is H $R^6$ is H, halo, haloalkyl or $C_{1-10}$-alkyl optionally substituted with 1-3 substituents of $R^9$;

$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^9$, oxo, $NR^9R^9$, $OR^9$, $SR^9$, $C(O)R^9$ or a partially or fully saturated or unsaturated 5-6 membered ring of carbon atoms optionally including 1-3 heteroatoms selected from O, N, or S, and optionally substituted independently with 1-5 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H, halo, haloalkyl, CN, $NO_2$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $R^{11}$, $R^{12}$ or $R^{16}$, $NR^{11}R^{12}$, $NR^{12}R^{12}$, $OR^{11}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, $NR^{12}(COOR^{12})$, $OC(O)NR^{11}R^{12}$, $OC(O)NR^{12}R^{12}$, $S(O)_2R^{11}$, $S(O)_2R^{12}$, $S(O)_2NR^{11}R^{12}$, $S(O)_2NR^{12}R^{12}$, $NR^{12}S(O)_2NR^{11}R^{12}$, $NR^{12}S(O)_2NR^{12}R^{12}$, $NR^{12}S(O)_2R^{11}$, $NR^{12}S(O)_2R^{12}$, $NR^{12}S(O)_2R^{11}$ or $NR^{12}S(O)_2R^{12}$;

$R^{11}$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is substituted independently with 1-5 substituents of $R^{12}$, $R^{13}$, $R^{14}$ or $R^{16}$;

alternatively, $R^{10}$ and $R^{11}$ taken together form a partially or fully saturated or unsaturated 5-6 membered ring of carbon atoms optionally including 1-3 heteroatoms selected from O, N, or S, and the ring optionally substituted independently with 1-5 substituents of $R^{12}$, $R^{13}$, $R^{14}$ or $R^{16}$;

$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-5 substituents of $R^{13}$, $R^{14}$, $R^{15}$ or $R^{16}$;

$R^{13}$ is $NR^{14}R^{15}$, $NR^{15}R^{15}$, $OR^{14}$, $SR^{14}$, $OR^{15}$, $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is a partially or fully saturated or unsaturated 5-8 membered or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-5 substituents of $R^{16}$;

$R^{16}$ is H, halo, haloalkyl, CN, OH, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, oxo, acetyl, benzyl, phenyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl;

and provided that (1) when said at least one substituent on said $R^2$ ring system is $C(O)NR^{10}R^{10}$ or $C(O)NR^{10}R^{11}$, then $R^{10}$ and $R^{11}$, independently, are not —$CH_2$-L-Q or —$C(C_{1-6}alkyl)(C_{1-6}alkyl)$-L-Q, wherein L is —O—, —NH—, —NHC(O)—, —NHC(O)N—, NHC(=NH)N— or —$CO_2$— and Q is H, substituted or unsubstituted $C_{1-6}$alkyl, substituted or unsubstituted aryl, substituted or unsubstituted heterocyclyl, substituted or unsubstituted hetearyl or $C_{1-6}$alkyl substituted with aryl, heterocyclyl or heteroaryl; or (2) when $R^2$ is a pyrimidyl ring substituted with $NR^7R^8$, then the $NR^7R^8$ substitution is not ortho to the alkynyl group of Formula I.

2. The compound of claim 1 wherein each of $A^2$ and $A^3$, independently, is N, $A^1$ is $CR^3$ and $A^4$ is $CR^6$.

3. The compound of claim 1 wherein each of $A^1$ and $A^4$, independently, is N, $A^2$ is $CR^4$ and $A^3$ is $CR^5$.

4. The compound of claim 3 wherein $R^2$ is a phenyl, naphthyl, pyridyl, thiophenyl, indolyl, benzofuranyl, dihydrobenzofuranyl, benzothiophenyl or benzimidazolyl ring and one of the 1-5 substituents on $R^2$ is $C(O)NR^{10}R^{11}$, or $NR^{10}C(O)R^{11}$.

5. The compound of claim 1 wherein
$A^1$ and $A^4$, independently, are N;
$A^2$ is CH;
$A^3$ is CH;
$R^1$ is $NR^7R^7$, $NR^7R^8$, $C(O)R^7$, $COOR^7$, $C(O)R^8$, $COOR^8$, $C(O)NR^7R^7$, $NR^7C(O)R^7$, $C(O)NR^7R^8$, $NR^7C(O)R^8$, $S(O)_2NR^7R^7$, $NR^7S(O)_2R^7$, $S(O)_2R^8$, $S(O)_2NR^7R^8$ or $NR^7S(O)_2R^8$;
$R^2$ is a phenyl, naphthyl, pyridyl, thiophenyl, furyl, pyrrolyl, indolyl, isoindolyl, benzofuranyl, dihydrobenzofuranyl, benzothiophenyl or benzimidazolyl ring, said ring substituted independently with 1-5 substituents of $R^{16}$ and one substituent of $C(O)NR^{10}R^{11}$, or $NR^{10}C(O)R^{11}$;
$R^7$ is H or $C_{1-10}$-alkyl optionally substituted with 1-3 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2$ $NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;
$R^8$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein said ring system is optionally substituted independently with 1-5 substituents of $R^9$, oxo, $NR^9R^9$, $OR^9$, $SR^9$, $C(O)R^9$ or a partially or fully saturated or unsaturated 5-6 membered ring of carbon atoms optionally including 1-3 heteroatoms selected from O, N, or S, and optionally substituted independently with 1-3 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H, halo, haloalkyl, CN, $NO_2$, $C_{1-10}$-alkyl or $C_{3-10}$-cycloalkyl, each of the $C_{1-10}$-alkyl and $C_{3-10}$-cycloalkyl optionally substituted with 1-5 substituents of $R^{16}$, $NR^{11}R^{12}$, $NR^{12}R^{12}$, $OR^{11}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, $NR^{12}(COOR^{12})$, $C(O)NR^{11}R^{12}$, $OC(O)NR^{12}R^{12}$, $S(O)_2R^{11}$, $S(O)_2R^{12}$, $S(O)_2NR^{11}R^{12}$, $S(O)_2NR^{12}R^{12}$, $NR^{12}S(O)_2NR^{11}R^{12}$, $NR^{12}S(O)_2NR^{12}R^{12}$, $NR^{12}S(O)_2R^{11}$, $NR^{12}S(O)_2R^{12}$, $NR^{12}S(O)_2R^{11}$ or $NR^{12}S(O)_2R^{12}$;

$R^{11}$ is a partially or fully saturated or unsaturated 5-8 membered monocyclic, or 6-12 membered bicyclic ring system, said ring system formed of carbon atoms optionally including 1-3 heteroatoms if monocyclic or 1-6 heteroatoms if bicyclic, said heteroatoms selected from O, N, or S, and wherein each ring of said ring system is substituted independently with 1-5 substituents of $R^{12}$, $R^{13}$, $R^{14}$ or $R^{16}$;

alternatively, $R^{10}$ and $R^{11}$ taken together form a partially or fully saturated or unsaturated 5-6 membered ring of carbon atoms optionally including 1-3 heteroatoms selected from O, N, or S, and the ring optionally substituted independently with 1-5 substituents of $R^{12}$, $R^{13}$, $R^{14}$ or $R^{16}$;

$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-5 substituents of $R^{13}$, $R^{14}$, $R^{15}$ or $R^{16}$;

$R^{13}$ is $NR^{14}R^{15}$, $NR^{15}R^{15}$, $OR^{14}$, $SR^{14}$, $OR^{15}$; $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is a partially or fully saturated or unsaturated 5-8 membered or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-5 substituents of $R^{16}$;

$R^{16}$ is H, halo, haloalkyl, CN, OH, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, oxo, acetyl, benzyl, phenyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl;

and provided that (1) when said at least one substituent on said $R^2$ ring system is $C(O)NR^{10}R^{10}$ or $C(O)NR^{10}R^{11}$, then $R^{10}$ and $R^{11}$, independently, are not —$CH_2$-L-Q or —$C(C_{1-6}alkyl)(C_{1-6}alkyl)$-L-Q, wherein L is —O—, —NH—, —NHC(O)—, —NHC(O)N—, NHC(=NH)N— or —$CO_2$— and Q is H, substituted or unsubstituted $C_{1-6}$alkyl, substituted or unsubstituted aryl, substituted or unsubstituted heterocyclyl, substituted or unsubstituted heteraryl or $C_{1-6}$alkyl substituted with aryl, heterocyclyl or heteroaryl.

6. The compound of claim 1, having a general Formula II

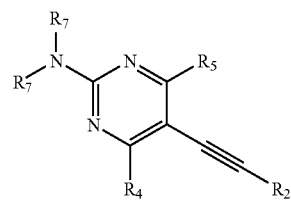

wherein
$R^2$ is

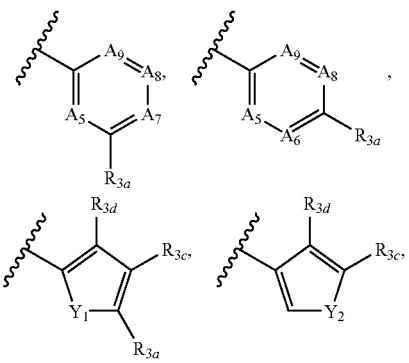

-continued

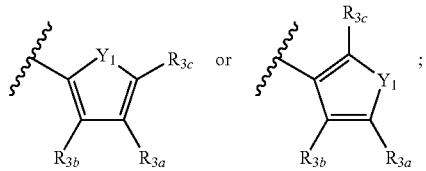

wherein
each of $A^5$, $A^6$, and $A^7$ is, independently, $CR^{3b}$ or N;
$A^8$ is $CR^{3c}$ or N; and
$A^9$ is $CR^{3d}$ or N, provided no more than two of $A^5$, $A^6$, $A^7$, $A^8$ and $A^9$ is N;
$Y^1$ is O or S;
$Y^2$ is $NR^{3a}$;
$R^{3a}$ is $C(O)NR^{10}R^{11}$, $NR^{10}C(O)R^{11}$, $NR^{10}C(O)NR^{10}R^{10}$ or $NR^{10}C(O)NR^{10}R^{11}$;
$R^{3b}$ is H, halo, haloalkyl, CN, $NO_2$, $NH_2$, $C_{1-10}$-alkyl, $C_{2-10}$-alkenyl, $C_{2-10}$-alkynyl or $C_{3-10}$-cycloalkyl;
$R^{3c}$ is H, halo, haloalkyl, CN, $NO_2$, $NH_2$, $C_{1-10}$-alkyl, $C_{2-10}$-alkenyl, $C_{2-10}$-alkynyl or $C_{3-10}$-cycloalkyl;
$R^{3d}$ is H, halo, haloalkyl, CN, $NO_2$, $NH_2$, $C_{1-10}$-alkyl, $C_{2-10}$-alkenyl, $C_{2-10}$-alkynyl or $C_{3-10}$-cycloalkyl; and
alternatively, $R^{3c}$ and $R^{3d}$ taken together with the atoms to which they are attached form a phenyl or tetrahydrofuranyl ring system, optionally substituted with 1-3 substituents of halo, haloalkyl, CN, $NO_2$, $NH_2$, $C_{1-10}$-alkyl, $C_{2-10}$-alkenyl, $C_{2-10}$-alkynyl or $C_{3-10}$-cycloalkyl, provided that when $R^{3a}$ is $NR^{10}C(O)NR^{10}R^{10}$ or $NR^{10}C(O)NR^{10}R^{11}$, then $R^2$ is

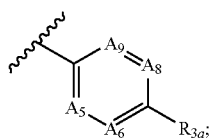

$R^4$ is H;
$R^5$ is H;
$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with 1-5 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;
$R^8$ is a phenyl, naphthyl, pyridyl, piperazinyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl or cycloheptyl ring system, said ring system optionally substituted independently with 1-3 substituents of $R^9$, oxo, $NR^9R^9$, $OR^9$; $SR^9$, $C(O)R^9$, phenyl, pyridyl, piperidyl, piperazinyl or morpholinyl;
$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{1-10}$-alkoxyl, $C_{1-10}$-thioalkoxyl or a ring system selected from phenyl, naphthyl, pyridyl, piperazinyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl and dioxozinyl, each of the $C_{1-10}$-alkyl, $C_{2-10}$-alkenyl, $C_{2-10}$-alkynyl, $C_{3-10}$-cycloalkyl, $C_{1-10}$-alkylamino-, $C_{1-10}$-dialkylamino-, $C_{1-10}$-alkoxyl, $C_{1-10}$-thioalkoxyl and ring system optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamino, dimethylamino, ethylamino, diethylamino, propylamine, isopropylamine, dipropylamine, diisopropylamine, benzyl or phenyl;
$R^{10}$ is H, halo, haloalkyl, CN, $NO_2$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^{11}$, $R^{12}$ or $R^{16}$, $NR^{11}R^{12}$, $NR^{12}R^{12}$, $OR^{11}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, $NR^{12}(COOR^{12})$, $OC(O)NR^{11}R^{12}$, $OC(O)NR^{12}R^{12}$, $S(O)_2R^{11}$, $S(O)_2R^{12}$, $S(O)_2NR^{11}R^{12}$, $S(O)_2NR^{12}R^{12}$, $NR^{12}S(O)_2NR^{11}R^{12}$, $NR^{12}S(O)_2NR^{12}R^{12}$, $NR^{12}S(O)_2R^{11}$, $NR^{12}S(O)_2R^{12}$, $NR^{12}S(O)_2R^{11}$ or $NR^{12}S(O)_2R^{12}$;
$R^{11}$ is a phenyl, naphthyl, 5,6,7,8-tetrahydronaphthyl, dihydro-indenyl, pyridyl, pyrimidinyl, triazinyl, quinolinyl, tetrahydroquinolinyl, oxo-tetrahydroquinolinyl, isoquinolinyl, oxo-tetrahydroisoquinolinyl, tetrahydroisoquinolinyl, quinazolinyl, isoquinazolinyl, thiophenyl, furyl, tetrahydrofuranyl, pyrrolyl, pyrazolyl, thieno-pyrazolyl, tetrahydropentapyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, aza-indolyl, 2,3-dihydroindolyl, isoindolyl, indazolyl, benzofuranyl, benzothiophenyl, benzimidazolyl, imidazopyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl or cycloheptyl ring system, said ring system substituted independently with 1-3 substituents of $R^{12}$, $R^{13}$, $R^{14}$ or $R^{16}$;
alternatively, $R^{10}$ and $R^{11}$ taken together form a partially or fully saturated or unsaturated 5-6 membered ring of carbon atoms optionally including 1-3 heteroatoms selected from O, N, or S, and the ring optionally substituted independently with 1-3 substituents of $R^{12}$, $R^{13}$, $R^{14}$ or $R^{16}$;

R$^{12}$ is H, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl or C$_{1-10}$-thioalkyl, each of which is optionally substituted independently with 1-3 substituents of R$^{13}$, R$^{14}$, R$^{15}$ or R$^{16}$;

R$^{13}$ is NR$^{14}$R$^{15}$, NR$^{15}$R$^{15}$, OR$^{14}$; SR$^{14}$, OR$^{15}$; SR$^{15}$, C(O)R$^{14}$, OC(O)R$^{14}$, COOR$^{14}$, C(O)R$^{15}$, OC(O)R$^{15}$, COOR$^{15}$, C(O)NR$^{14}$R$^{15}$, C(O)NR$^{15}$R$^{15}$, NR$^{14}$C(O)R$^{14}$, NR$^{15}$C(O)R$^{14}$, NR$^{14}$C(O)R$^{15}$, NR$^{15}$C(O)R$^{15}$, NR$^{15}$C(O)NR$^{14}$R$^{15}$, NR$^{15}$C(O)NR$^{15}$R$^{15}$, NR$^{15}$(COOR$^{14}$), NR$^{15}$(COOR$^{15}$), OC(O)NR$^{14}$R$^{15}$, OC(O)NR$^{15}$R$^{15}$, S(O)$_2$R$^{14}$, S(O)$_2$R$^{15}$, S(O)$_2$NR$^{14}$R$^{15}$, S(O)$_2$NR$^{15}$R$^{15}$, NR$^{14}$S(O)$_2$NR$^{14}$R$^{15}$, NR$^{15}$S(O)$_2$NR$^{15}$R$^{15}$, NR$^{14}$S(O)$_2$R$^{14}$ or NR$^{15}$S(O)$_2$R$^{15}$;

R$^{14}$ is phenyl, pyridyl, pyrimidinyl, thiophenyl, furyl, tetrahydrofuryl, pyrrolyl, pyrazolyl, thieno-pyrazolyl, imidazolyl, triazolyl, thiazolyl, thiadiazolyl, benzothiazolyl, oxazolyl, oxadiazolyl, benzoxazolyl, benzoxadiazolyl, isoxazolyl, isothiazolyl, indolyl, aza-indolyl, isoindolyl, indazolyl, benzofuranyl, benzothiophenyl, benzimidazolyl, pyrrolidinyl, pyrazolinyl, morpholinyl, piperidinyl, piperazinyl, 2,3-dihydro-1,4-benzoxazinyl, 1,3-benzodioxolyl, cyclopropyl, cyclobutyl, azetidinyl, cyclopentyl and cyclohexyl, each of which is optionally substituted independently with 1-3 substituents of R$^{15}$ or R$^{16}$;

R$^{15}$ is H or C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl or C$_{1-10}$-thioalkoxyl, each of which is optionally substituted independently with 1-5 substituents of R$^{16}$; and R$^{16}$ is H, halo, haloalkyl, CN, OH, NO$_2$, NH$_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, oxo, acetyl, benzyl, phenyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, NO$_2$, NH$_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

7. The compound of claim 6 wherein
R$^2$ is

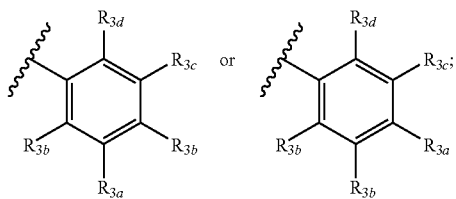

wherein
R$^{3a}$ is C(O)NR$^{10}$R$^{11}$, or NR$^{10}$C(O)R$^{11}$;
each of R$^{3b}$, R$^{3c}$ and R$^{3d}$, independently, is H, F, Cl, Br, I, CF$_3$, CF$_2$CF$_3$, OCF$_3$, OCF$_2$CF$_3$, CN, NO$_2$, NH$_2$, methyl, ethyl, propyl, isopropyl, n-butyl, sec-butyl, tert-butyl, acetylenyl, cyclopropyl, cyclobutyl, cyclopentyl, cyclohexyl, OH, methoxyl, ethoxyl, propoxyl, SH, thiomethyl or thioethyl;

each of R$^4$ and R$^5$, independently, is H or methyl;

each R$^7$, independently, is H or C$_{1-10}$-alkyl;

R$^{10}$ is H, methyl, ethyl, propyl, isopropyl, n-butyl, sec-butyl, tert-butyl, acetylenyl, cyclopropyl, cyclobutyl, cyclopentyl, cyclohexyl, OH, methoxyl, ethoxyl, propoxyl, SH, thiomethyl or thioethyl; each of which is optionally substituted with one or more substituents of R$^{11}$, R$^{12}$ or R$^{16}$;

R$^{11}$ is a phenyl, naphthyl, 5,6,7,8-tetrahydronaphthyl, dihydro-indenyl, pyridyl, pyrimidinyl, triazinyl, quinolinyl, tetrahydroquinolinyl, oxo-tetrahydroquinolinyl, isoquinolinyl, oxo-tetrahydroisoquinolinyl, tetrahydroisoquinolinyl, quinazolinyl, isoquinazolinyl, thiophenyl, furyl, tetrahydrofuranyl, pyrrolyl, pyrazolyl, thieno-pyrazolyl, tetrahydropentapyrazolyl, imidazolyl, triazolyl, tetrazolyl, thiazolyl, thiadiazolyl, benzothiazolyl, oxazolyl, oxadiazolyl, benzoxazolyl, benzoxadiazolyl, isoxazolyl, isothiazolyl, indolyl, aza-indolyl, 2,3-dihydroindolyl, isoindolyl, indazolyl, benzofuranyl, benzothiophenyl, benzimidazolyl, imidazo-pyridinyl, purinyl, benzotriazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl, cyclopropyl, cyclobutyl, azetidinyl, cyclopentyl, cyclohexyl or cycloheptyl ring system, said ring system substituted independently with 1-3 substituents of R$^{12}$, R$^{13}$, R$^{14}$ or R$^{16}$;

alternatively, R$^{10}$ and R$^{11}$ taken together form a partially or fully saturated or unsaturated 5-6 membered ring of carbon atoms optionally including 1-3 heteroatoms selected from O, N, or S, and the ring optionally substituted independently with 1-3 substituents of R$^{12}$, R$^{13}$, R$^{14}$ or R$^{16}$;

R$^{12}$ is H, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl or C$_{1-10}$-thioalkyl, each of which is optionally substituted independently with 1-3 substituents of R$^{13}$, R$^{14}$, R$^{15}$ or R$^{16}$;

R$^{13}$ is NR$^{14}$R$^{15}$, NR$^{15}$R$^{15}$, OR$^{14}$; SR$^{14}$, OR$^{15}$; SR$^{15}$, C(O)R$^{14}$, OC(O)R$^{14}$, COOR$^{14}$, C(O)R$^{15}$, OC(O)R$^{15}$, COOR$^{15}$, C(O)NR$^{14}$R$^{15}$, C(O)NR$^{15}$R$^{15}$, NR$^{14}$C(O)R$^{14}$, NR$^{15}$C(O)R$^{14}$, NR$^{14}$C(O)R$^{15}$, NR$^{15}$C(O)R$^{15}$, NR$^{15}$C(O)NR$^{14}$R$^{15}$, NR$^{15}$C(O)NR$^{15}$R$^{15}$, NR$^{15}$(COOR$^{14}$), NR$^{15}$(COOR$^{15}$), OC(O)NR$^{14}$R$^{15}$, OC(O)NR$^{15}$R$^{15}$, S(O)$_2$R$^{14}$, S(O)$_2$R$^{15}$, S(O)$_2$NR$^{14}$R$^{15}$, S(O)$_2$NR$^{15}$R$^{15}$, NR$^{14}$S(O)$_2$NR$^{14}$R$^{15}$, NR$^{15}$S(O)$_2$NR$^{15}$R$^{15}$, NR$^{14}$S(O)$_2$R$^{14}$ or NR$^{15}$S(O)$_2$R$^{15}$;

R$^{14}$ is phenyl, pyridyl, pyrimidinyl, thiophenyl, furyl, tetrahydrofuryl, pyrrolyl, pyrazolyl, thieno-pyrazolyl, imidazolyl, triazolyl, thiazolyl, thiadiazolyl, benzothiazolyl, oxazolyl, oxadiazolyl, benzoxazolyl, benzoxadiazolyl, isoxazolyl, isothiazolyl, indolyl, aza-indolyl, isoindolyl, indazolyl, benzofuranyl, benzothiophenyl, benzimidazolyl, pyrrolidinyl, pyrazolinyl, morpholinyl, piperidinyl, piperazinyl, 2,3-dihydro-1,4-benzoxazinyl, 1,3-benzodioxolyl, cyclopropyl, cyclobutyl, azetidinyl, cyclopentyl and cyclohexyl, each of which is optionally substituted independently with 1-3 substituents of R$^{15}$ or R$^{16}$;

R$^{15}$ is H or C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl or C$_{1-10}$- thioalkoxyl, each of which is optionally substituted independently with 1-3 substituents of $R^{16}$; and $R^{16}$ is H, halo, haloalkyl, CN, OH, NO$_2$, NH$_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, oxo, acetyl, benzyl, phenyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, NO$_2$, NH$_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

8. A compound, or a pharmaceutically acceptable salt thereof, selected from:

3-((2-amino-5-pyrimidinyl)ethynyl)-4-methyl-N-(3-(trifluoromethyl)phenyl)benzamide;

6-((2-amino-5-pyrimidinyl)ethynyl)-N-(3-(trifluoromethyl)phenyl)-2-pyridinecarboxamide;

5-((2-amino-5-pyrimidinyl)ethynyl)-N-(3-(trifluoromethyl)phenyl)-3-pyridinecarboxamide;

2-((2-amino-5-pyrimidinyl)ethynyl)-N-(3-(trifluoromethyl)phenyl)-4-pyridinecarboxamide;

5-((2-amino-5-pyrimidinyl)ethynyl)-2-fluoro-N-(3-(trifluoromethyl)phenyl)benzamide;

3-((2-amino-5-pyrimidinyl)ethynyl)-4-methyl-N-(2-(4-methyl-1-piperazinyl)-5-(trifluoromethyl)phenyl)benzamide;

3-((2-amino-5-pyrimidinyl)ethynyl)-N-(2-((3-(dimethylamino)propyl)(methyl)amino)-5-(trifluoromethyl)phenyl)-4-methylbenzamide;

3-((2-amino-5-pyrimidinyl)ethynyl)-N-(2-(dimethylamino)-5-(trifluoromethyl)phenyl)-4-methylbenzamide;

3-((2-amino-5-pyrimidinyl)ethynyl)-N-(2-((3R)-3-(dimethylamino)-1-pyrrolidinyl)-5-(trifluoromethyl)phenyl)-4-methylbenzamide;

3-((2-amino-5-pyrimidinyl)ethynyl)-4-methyl-N-(2-(methyl(1-methyl-4-piperidinyl)amino)-5-(trifluoromethyl)phenyl)benzamide;

3-((2-amino-5-pyrimidinyl)ethynyl)-4-methyl-N-(2-(methyl((3R)-1-methyl-3-pyrrolidinyl)amino)-5-(trifluoromethyl)phenyl)benzamide;

3-((2-amino-5-pyrimidinyl)ethynyl)-N-(2-(2-(dimethylamino)-1,1-dimethylethyl)-5-(trifluoromethyl)phenyl)-4-methylbenzamide;

3-((2-amino-5-pyrimidinyl)ethynyl)-N-(2-((3S)-3-(dimethylamino)-1-piperidinyl)-5-(trifluoromethyl)phenyl)-4-methylbenzamide;

5-((2-amino-5-pyrimidinyl)ethynyl)-2-fluoro-N-(2-(methyl((3S)-1-methyl-3-pyrrolidinyl)amino)-5-(trifluoromethyl)phenyl)benzamide;

5-((2-amino-5-pyrimidinyl)ethynyl)-2-fluoro-N-(2-(methyl((3R)-1-methyl-3-pyrrolidinyl)amino)-5-(trifluoromethyl)phenyl)benzamide;

5-((2-amino-5-pyrimidinyl)ethynyl)-N-(2-((3-(dimethylamino)propyl)(methyl)amino)-5-(trifluoromethyl)phenyl)-2-fluorobenzamide;

5-((2-amino-5-pyrimidinyl)ethynyl)-N-(2-((3R)-3-(dimethylamino)-1-pyrrolidinyl)-5-(trifluoromethyl)phenyl)-2-fluorobenzamide;

3-((2-amino-5-pyrimidinyl)ethynyl)-N-(5-cyclohexyl-2-(methyloxy)phenyl)-4-methylbenzamide;

5-((2-methyl-5-((6-(trifluoromethyl)-2,3-dihydro-1H-indol-1-yl)carbonyl)phenyl)ethynyl)-2-pyrimidinamine;

5-((2-methyl-5-((7-(trifluoromethyl)-3,4-dihydro-1(2H)-quinolinyl)carbonyl)phenyl)ethynyl)-2-pyrimidinamine;

3-((2-amino-5-pyrimidinyl)ethynyl)-N-(2-(4-(hydroxymethyl)-1H-imidazol-1-yl)-5-(trifluoromethyl)phenyl)-4-methylbenzamide;

5-((2-amino-5-pyrimidinyl)ethynyl)-N-(2-((3-(dimethylamino)propyl)(methyl)amino)-5-(trifluoromethyl)-3-pyridinyl)-2-fluorobenzamide;

3-((2-amino-5-pyrimidinyl)ethynyl)-N-(2-((3-(dimethylamino)propyl)(methyl)amino)-5-(trifluoromethyl)-3-pyridinyl)-4-methylbenzamide;

3-((2-amino-5-pyrimidinyl)ethynyl)-N-(3-(trifluoromethyl)phenyl)-1H-indole-1-carboxamide;

3-((2-amino-5-pyrimidinyl)ethynyl)-4-methyl-N-(3-(1,2,3,6-tetrahydro-4-pyridinyl)-5-(trifluoromethyl)phenyl)benzamide;

N-(3-((2-amino-5-pyrimidinyl)ethynyl)-5-(trifluoromethyl)phenyl)-3-(trifluoromethyl)benzamide;

3-((2-amino-5-pyrimidinyl)ethynyl)-4-methyl-N-(3-(1-methyl-4-piperidinyl)-5-(trifluoromethyl)phenyl)benzamide;

5-((2-amino-5-pyrimidinyl)ethynyl)-N-(3-(trifluoromethyl)phenyl)-2-thiophenecarboxamide;

5-((2-amino-5-pyrimidinyl)ethynyl)-N-(2-((3-(dimethylamino)propyl)(methyl)amino)-5-(trifluoromethyl)phenyl)-2-thiophenecarboxamide;

3-((2-amino-5-pyrimidinyl)ethynyl)-N-(4-(1,1-dimethylethyl)phenyl)-4-methylbenzamide;

3-((2-amino-5-pyrimidinyl)ethynyl)-N-(2-((3-(dimethylamino)propyl)(methyl)amino)-5-(1,1-dimethylethyl)phenyl)-4-methylbenzamide;

5-((2-amino-5-pyrimidinyl)ethynyl)-N-(2-((3-(dimethylamino)propyl)(methyl)amino)-5-(1,1-dimethylethyl)phenyl)-2-thiophenecarboxamide;

3-((2-amino-5-pyrimidinyl)ethynyl)-N-(3,5-bis(trifluoromethyl)phenyl)-4-methylbenzamide;

3-((2-amino-5-pyrimidinyl)ethynyl)-4-chloro-N-(3-(trifluoromethyl)phenyl)benzamide;

3-((2-amino-5-pyrimidinyl)ethynyl)-N-(3-chloro-2-((3-(dimethylamino)propyl)(methyl)amino)-5-(trifluoromethyl)phenyl)-4-methylbenzamide;

3-((2-amino-5-pyrimidinyl)ethynyl)-4-chloro-N-(3-methyl-4-(1-methylethyl)phenyl)benzamide;

3-((2-amino-5-pyrimidinyl)ethynyl)-4-chloro-N-(4-(1,1-dimethylethyl)phenyl)benzamide;

3-((2-amino-4-methyl-5-pyrimidinyl)ethynyl)-N-(2-((3-(dimethylamino)propyl)(methyl)amino)-5-(trifluoromethyl)phenyl)-4-methylbenzamide;

3-((2-amino-5-pyrimidinyl)ethynyl)-N-(2-(((3-(dimethylamino)propyl)(methyl)amino)sulfonyl)-5-(trifluoromethyl)phenyl)-4-methylbenzamide;

5-((2-amino-5-pyrimidinyl)ethynyl)-N-(3-(trifluoromethyl)phenyl)-3-thiophenecarboxamide;

5-((2-amino-4-methyl-5-pyrimidinyl)ethynyl)-2-fluoro-N-(2-(methyl((3R)-1-methyl-3-pyrrolidinyl)amino)-5-(trifluoromethyl)phenyl)benzamide;

5-((2-amino-4-methyl-5-pyrimidinyl)ethynyl)-2-fluoro-N-(2-(methyl((3S)-1-methyl-3-pyrrolidinyl)amino)-5-(trifluoromethyl)phenyl)benzamide;

3-((2-amino-5-pyrimidinyl)ethynyl)-N-(5-chloro-2-((3-(dimethylamino)propyl)(methyl)amino)phenyl)-4-methylbenzamide;

3-((2-amino-5-pyrimidinyl)ethynyl)-N-(4-chloro-3-(trifluoromethyl)phenyl)-4-methylbenzamide;
3-((2-amino-5-pyrimidinyl)ethynyl)-4-methyl-N-(3-methyl-4-(1-methylethyl)phenyl)benzamide;
3-((2-amino-5-pyrimidinyl)ethynyl)-5-fluoro-N-(2-(methyl((3S)-1-methyl-3-pyrrolidinyl)amino)-5-(trifluoromethyl)phenyl)benzamide;
3-((2-amino-5-pyrimidinyl)ethynyl)-5-fluoro-N-(2-(methyl((3R)-1-methyl-3-pyrrolidinyl)amino)-5-(trifluoromethyl)phenyl)benzamide;
5-((2-amino-5-pyrimidinyl)ethynyl)-2-fluoro-N-(3-((4-methyl-1-piperazinyl)methyl)-5-(trifluoromethyl)phenyl)benzamide;
5-((2-amino-5-pyrimidinyl)ethynyl)-2-fluoro-N-(3-((4-methyl-1-piperazinyl)methyl)-5-(trifluoromethyl)phenyl)benzamide;
3-((2-amino-5-pyrimidinyl)ethynyl)-4-methyl-N-(3-((4-methyl-1-piperazinyl)methyl)-5-(trifluoromethyl)phenyl)benzamide;
3-((2-amino-5-pyrimidinyl)ethynyl)-4-methyl-N-(3-((4-methyl-1-piperazinyl)carbonyl)-5-(trifluoromethyl)phenyl)benzamide;
5-((2-amino-5-pyrimidinyl)ethynyl)-2-fluoro-N-(3-((4-methyl-1-piperazinyl)carbonyl)-5-(trifluoromethyl)phenyl)benzamide;
3-((2-amino-5-pyrimidinyl)ethynyl)-4-(methyloxy)-N-(2-methyl-3-(trifluoromethyl)phenyl)benzamide;
3-((2-amino-5-pyrimidinyl)ethynyl)-4-methyl-N-(2-((4-methyl-1-piperazinyl)sulfonyl)-5-(trifluoromethyl)phenyl)benzamide;
5-((2-amino-5-pyrimidinyl)ethynyl)-N-(3-(1-methyl-4-piperidinyl)-5-(trifluoromethyl)phenyl)-3-thiophenecarboxamide;
5-((2-amino-5-pyrimidinyl)ethynyl)-N-(3-chloro-2-((3-(dimethylamino)propyl)(methyl)amino)-5-(trifluoromethyl)phenyl)-2-fluorobenzamide;
5-((2-amino-5-pyrimidinyl)ethynyl)-N-(2-(((3-(dimethylamino)propyl)(methyl)amino)sulfonyl)-5-(trifluoromethyl)phenyl)-2-fluorobenzamide;
5-((2-amino-5-pyrimidinyl)ethynyl)-2-fluoro-N-(2-((4-methyl-1-piperazinyl)sulfonyl)-5-(trifluoromethyl)phenyl)benzamide;
3-((2-amino-5-pyrimidinyl)ethynyl)-4-methyl-N-(2-methyl-3-(trifluoromethyl)phenyl)benzamide;
3-((2-amino-5-pyrimidinyl)ethynyl)-4-methyl-N-(3-((trifluoromethyl)oxy)phenyl)benzamide;
3-((2-amino-5-pyrimidinyl)ethynyl)-4-(methyloxy)-N-(3-((trifluoromethyl)oxy)phenyl)benzamide;
5-((2-amino-5-pyrimidinyl)ethynyl)-N-(2-((3-(dimethylamino)propyl)(methyl)amino)-5-(trifluoromethyl)phenyl)-3-thiophenecarboxamide;
4-((2-amino-5-pyrimidinyl)ethynyl)-N-(2-((3-(dimethylamino)propyl)(methyl)amino)-5-(trifluoromethyl)phenyl)-2-thiophenecarboxamide;
5-((2-amino-5-pyrimidinyl)ethynyl)-N-(3-((1,1-dioxido-4-thiomorpholinyl)carbonyl)-5-(trifluoromethyl)phenyl)-2-fluorobenzamide;
5-((2-amino-4-methyl-5-pyrimidinyl)ethynyl)-N-(3-chloro-2-((3-(dimethylamino)propyl)(methyl)amino)-5-(trifluoromethyl)phenyl)-2-fluorobenzamide;
5-((2-amino-5-pyrimidinyl)ethynyl)-2-fluoro-N-(2-(1H-1,2,4-triazol-1-yl)-5-(trifluoromethyl)phenyl)benzamide;
3-((2-amino-5-pyrimidinyl)ethynyl)-4-methyl-N-((1R)-1-phenylethyl)benzamide;
5-((2-amino-5-pyrimidinyl)ethynyl)-N-(2-((dimethylamino)methyl)-5-(trifluoromethyl)phenyl)-2-fluorobenzamide;
3-((2-amino-5-pyrimidinyl)ethynyl)-4-methyl-N-(3-methyl-5-isoxazolyl)benzamide;
5-((2-amino-5-pyrimidinyl)ethynyl)-N-(5-cyclopropyl-2-((3-(dimethylamino)propyl)(methyl)amino)phenyl)-2-fluorobenzamide;
5-((2-amino-5-pyrimidinyl)ethynyl)-N-(3-((((2S)-1-methyl-2-pyrrolidinyl)methyl)oxy)-5-(trifluoromethyl)phenyl)-3-thiophenecarboxamide;
3-((2-amino-5-pyrimidinyl)ethynyl)-4-methyl-N-((1S)-1-(1,3-thiazol-2-yl)ethyl)benzamide;
3-((2-amino-5-pyrimidinyl)ethynyl)-4-methyl-N-((1R)-1-(1,3-thiazol-2-yl)ethyl)benzamide;
3-((2-amino-5-pyrimidinyl)ethynyl)-N-(3-methyl-5-isoxazolyl)-4-(methyloxy)benzamide;
3-((2-amino-5-pyrimidinyl)ethynyl)-4-methyl-N-(2-(4-thiomorpholinyl)-5-(trifluoromethyl)phenyl)benzamide;
3-((2-amino-5-pyrimidinyl)ethynyl)-N-(3,4-dimethyl-5-isoxazolyl)-4-methylbenzamide;
3-((2-amino-5-pyrimidinyl)ethynyl)-N-(3,4-dimethyl-5-isoxazolyl)-4-(methyloxy)benzamide;
3-((2-amino-5-pyrimidinyl)ethynyl)-4-(methyloxy)-N-(3-(1-methyl-4-piperidinyl)-5-(trifluoromethyl)phenyl)benzamide;
5-((2-amino-5-pyrimidinyl)ethynyl)-2-fluoro-N-(2-(methyl((3S)-1-methyl-3-pyrrolidinyl)amino)-5-(trifluoromethyl)phenyl)benzamide;
5-((2-amino-5-pyrimidinyl)ethynyl)-2-fluoro-N-(2-(methyl((3R)-1-methyl-3-pyrrolidinyl)amino)-5-(trifluoromethyl)phenyl)benzamide;
3-((2-amino-5-pyrimidinyl)ethynyl)-4-methyl-N-(3-(4-methyl-1-piperazinyl)-5-(trifluoromethyl)phenyl)benzamide;
5-((2-amino-5-pyrimidinyl)ethynyl)-2-(methyloxy)-N-(3-((4-methyl-1-piperazinyl)methyl)-5-(trifluoromethyl)phenyl)benzamide;
N-(4-((2-amino-5-pyrimidinyl)ethynyl)-3-methylphenyl)-N'-(3-(trifluoromethyl)phenyl)urea;
N-(4-((2-amino-5-pyrimidinyl)ethynyl)-3-methylphenyl)-N'-(3-fluorophenyl)urea;
N-(4-((2-amino-5-pyrimidinyl)ethynyl)-3-methylphenyl)-3-(trifluoromethyl)benzamide;
N-(4-((2-amino-5-pyrimidinyl)ethynyl)-3-methylphenyl)-4-(trifluoromethyl)benzamide;
5-((2-amino-5-pyrimidinyl)ethynyl)-N-(2-((3-(dimethylamino)propyl)(methyl)amino)-5-(trifluoromethyl)phenyl)-2,3-dihydro-1-benzofuran-7-carboxamide;
5-((2-amino-5-pyrimidinyl)ethynyl)-N-(2-(methyl((3R)-1-methyl-3-pyrrolidinyl)amino)-5-(trifluoromethyl)phenyl)-2-(methyloxy)benzamide;
N-(4-((2-amino-5-pyrimidinyl)ethynyl)phenyl)-3-(trifluoromethyl)benzamide;
N-(4-((2-amino-5-pyrimidinyl)ethynyl)phenyl)-1H-benzimidazol-2-amine;
5-((2-amino-5-pyrimidinyl)ethynyl)-N-(2-((3S)-3-(dimethylamino)-1-piperidinyl)-5-(trifluoromethyl)phenyl)-2-fluorobenzamide;
N-(4-((2-amino-5-pyrimidinyl)ethynyl)-1-naphthalenyl)-1H-benzimidazol-2-amine;
5-((2-amino-5-pyrimidinyl)ethynyl)-N-(2-(4-(dimethylamino)-1-piperidinyl)-5-(trifluoromethyl)phenyl)-2-fluorobenzamide;
5-((2-amino-5-pyrimidinyl)ethynyl)-2-fluoro-N-(2-(1-piperidinyl)-5-(trifluoromethyl)phenyl)benzamide;

5-((2-amino-5-pyrimidinyl)ethynyl)-2-fluoro-N-(2-(2-oxo-1-pyrrolidinyl)-5-(trifluoromethyl)phenyl)benzamide;

5-((2-amino-5-pyrimidinyl)ethynyl)-2-(methyloxy)-N-(2-(1-piperidinyl)-5-(trifluoromethyl)phenyl)benzamide;

2-fluoro-5-((2-(methylamino)-5-pyrimidinyl)ethynyl)-N-(2-(methyl((3R)-1-methyl-3-pyrrolidinyl)amino)-5-(trifluoromethyl)phenyl)benzamide;

5-((2-amino-5-pyrimidinyl)ethynyl)-2-fluoro-N-(2-(4-methyl-1-piperazinyl)-5-(trifluoromethyl)phenyl)benzamide;

5-((2-amino-5-pyrimidinyl)ethynyl)-2-fluoro-N-(2-(2-oxo-1,3-oxazolidin-3-yl)-5-(trifluoromethyl)phenyl)benzamide;

5-((2-amino-5-pyrimidinyl)ethynyl)-2-fluoro-N-(2-(3-methyl-2-oxo-1-imidazolidinyl)-5-(trifluoromethyl)phenyl)benzamide;

5-((2-amino-5-pyrimidinyl)ethynyl)-N-(2-((3R)-3-(dimethylamino)-1-piperidinyl)-5-(trifluoromethyl)phenyl)-2-fluorobenzamide;

5-((2-amino-5-pyrimidinyl)ethynyl)-2-fluoro-N-(2-((3S)-3-(methylamino)-1-piperidinyl)-5-(trifluoromethyl)phenyl)benzamide;

N-(2-((3S)-3-amino-1-piperidinyl)-5-(trifluoromethyl)phenyl)-5-((2-amino-5-pyrimidinyl)ethynyl)-2-fluorobenzamide;

5-((2-amino-5-pyrimidinyl)ethynyl)-2-fluoro-N-(2-(3-oxo-1-piperazinyl)-5-(trifluoromethyl)phenyl)benzamide;

5-((2-amino-5-pyrimidinyl)ethynyl)-N-(2-((3R)-3-((dimethylamino)methyl)-1-pyrrolidinyl)-5-(trifluoromethyl)phenyl)-2-fluorobenzamide;

5-((2-amino-5-pyrimidinyl)ethynyl)-2-fluoro-N-(2-((3R)-3-hydroxy-1-piperidinyl)-5-(trifluoromethyl)phenyl)benzamide;

4-((2-(ethyloxy)phenyl)oxy)-5-(phenylethynyl)-N-(4-((2-(1-pyrrolidinyl)ethyl)oxy)phenyl)-2-pyrimidinamine;

5-((2,6-dimethylphenyl)ethynyl)-4-((2-(ethyloxy)phenyl)oxy)-N-(4-((2-(1-pyrrolidinyl)ethyl)oxy)phenyl)-2-pyrimidinamine;

5-((2,6-dimethylphenyl)ethynyl)-4-((2-(ethyloxy)phenyl)oxy)-N-(4-(4-methyl-1-piperazinyl)phenyl)-2-pyrimidinamine;

3-((2-amino-5-pyrimidinyl)ethynyl)-N-(4-((2-(dimethylamino)ethyl)oxy)phenyl)-4-methylbenzamide;

3-((2-amino-5-pyrimidinyl)ethynyl)-4-methyl-N-(4-(trifluoromethyl)-2-pyridinyl)benzamide;

3-((2-amino-5-pyrimidinyl)ethynyl)-N-(2-fluoro-5-(trifluoromethyl)phenyl)-4-methylbenzamide;

3-((2-amino-5-pyrimidinyl)ethynyl)-4-methyl-N-(2-(methyloxy)-5-(trifluoromethyl)phenyl)benzamide;

3-((2-amino-5-pyrimidinyl)ethynyl)-N-(4-ethyl-2-pyridinyl)-4-methylbenzamide;

4-methyl-3-((2-((2-(4-morpholinyl)ethyl)amino)-5-pyrimidinyl)ethynyl)-N-(3-(trifluoromethyl)phenyl)benzamide;

4-((2-amino-5-pyrimidinyl)ethynyl)-N-(2-fluoro-5-(trifluoromethyl)phenyl)-3-methylbenzamide;

4-methyl-3-((2-((4-(4-methyl-1-piperazinyl)phenyl)amino)-5-pyrimidinyl)ethynyl)-N-(3-(trifluoromethyl)phenyl)benzamide;

3-((2-amino-5-pyrimidinyl)ethynyl)-4-methyl-N-(4-(4-(1-methylethyl)-1-piperazinyl)phenyl)benzamide;

3-((2-amino-5-pyrimidinyl)ethynyl)-N-(4-(1,1-dimethylethyl)-3-((N,N-dimethylglycyl)amino)phenyl)-4-methylbenzamide;

3-((2-amino-5-pyrimidinyl)ethynyl)-N-(5,5-dimethyl-3-oxo-1-cyclohexen-1-yl)-4-methylbenzamide;

3-((2-amino-5-pyrimidinyl)ethynyl)-N-(3-(1,1-dimethylethyl)-1-methyl-1H-pyrazol-5-yl)-4-methylbenzamide;

3-((2-amino-5-pyrimidinyl)ethynyl)-N-(5-(1,1-dimethylethyl)-2-(methyloxy)phenyl)-4-methylbenzamide;

3-((2-amino-5-pyrimidinyl)ethynyl)-N-(3-((dimethylamino)methyl)-5-(trifluoromethyl)phenyl)-4-methylbenzamide;

4-((2-amino-5-pyrimidinyl)ethynyl)-3-methyl-N-(3-((4-methyl-1-piperazinyl)methyl)-5-(trifluoromethyl)phenyl)benzamide;

3-((2-amino-5-pyrimidinyl)ethynyl)-4-methyl-N-(3-(2-oxo-1-pyrrolidinyl)-5-(trifluoromethyl)phenyl)benzamide;

N-(3-((2-amino-5-pyrimidinyl)ethynyl)-2-methylphenyl)-3-(trifluoromethyl)benzamide;

3-((2-amino-5-pyrimidinyl)ethynyl)-4-methyl-N-(3-(1-pyrrolidinylmethyl)-5-(trifluoromethyl)phenyl)benzamide;

3-((2-amino-5-pyrimidinyl)ethynyl)-4-methyl-N-(3-(4-morpholinylmethyl)-5-(trifluoromethyl)phenyl)benzamide;

3-((2-amino-4-methyl-5-pyrimidinyl)ethynyl)-4-methyl-N-(3-((4-methyl-1-piperazinyl)methyl)-5-(trifluoromethyl)phenyl)benzamide;

3-((2-amino-5-pyrimidinyl)ethynyl)-4-methyl-N-(2-(2-oxo-1-pyrrolidinyl)-5-(trifluoromethyl)phenyl)benzamide;

3-((2-amino-5-pyrimidinyl)ethynyl)-4-methyl-N-(2-(2-oxo-1,3-oxazolidin-3-yl)-5-(trifluoromethyl)phenyl)benzamide;

3-((2-amino-5-pyrimidinyl)ethynyl)-N-(4-cyano-2-pyridinyl)-4-methylbenzamide;

3-((2-amino-5-pyrimidinyl)ethynyl)-4-methyl-N-(3-(3-(4-morpholinyl)propyl)-5-(trifluoromethyl)phenyl)benzamide;

4-methyl-3-((2-(methylamino)-5-pyrimidinyl)ethynyl)-N-(3-((4-methyl-1-piperazinyl)methyl)-5-(trifluoromethyl)phenyl)benzamide;

3-((2-amino-5-pyrimidinyl)ethynyl)-4-methyl-N-(3-(3-(4-methyl-1-piperazinyl)propyl)-5-(trifluoromethyl)phenyl)benzamide;

3-((2-amino-5-pyrimidinyl)ethynyl)-N-(3-(3-(dimethylamino)-1-propyn-1-yl)-5-(trifluoromethyl)phenyl)-4-methylbenzamide;

3-((2-amino-5-pyrimidinyl)ethynyl)-N-(2-(3-(dimethylamino)-1-propyn-1-yl)-5-(trifluoromethyl)phenyl)-4-methylbenzamide;

N-(3-((2-amino-5-pyrimidinyl)ethynyl)-4-methylphenyl)-3-(trifluoromethyl)benzamide;

4-methyl-N-(3-((4-methyl-1-piperazinyl)methyl)-5-(trifluoromethyl)phenyl)-3-(3-pyridinylethynyl)benzamide;

4-methyl-3-((2-(methylamino)-5-pyrimidinyl)ethynyl)-N-(3-(1-methyl-4-piperidinyl)-5-(trifluoromethyl)phenyl)benzamide;

4-methyl-N-(2-(2-oxo-1-pyrrolidinyl)-5-(trifluoromethyl)phenyl)-3-(3-pyridinylethynyl)benzamide;

4-methyl-3-((2-(methylamino)-4-(2-thienyl)-5-pyrimidinyl)ethynyl)-N-(3-((4-methyl-1-piperazinyl)methyl)-5-(trifluoromethyl)phenyl)benzamide;

4-methyl-3-((2-((1-methylethyl)amino)-5-pyrimidinyl)ethynyl)-N-(3-((4-methyl-1-piperazinyl)methyl)-5-(trifluoromethyl)phenyl)benzamide;

4-((2-amino-5-pyrimidinyl)ethynyl)-N-(2-(methyl((3R)-1-methyl-3-pyrrolidinyl)amino)-5-(trifluoromethyl)phenyl)-1-(methyloxy)-2-naphthalenecarboxamide;

4-methyl-3-((4-((2-(methyloxy)phenyl)oxy)-2-((4-(4-methyl-1-piperazinyl)phenyl)amino)-5-pyrimidinyl)ethynyl)-N-(3-(trifluoromethyl)phenyl)benzamide;

4-((2-(methyloxy)phenyl)oxy)-N-(4-(4-methyl-1-piperazinyl)phenyl)-5-(phenylethynyl)-2-pyrimidinamine;

N-(3-methyl-4-((4-((2-(methyloxy)phenyl)oxy)-2-((4-(4-methyl-1-piperazinyl)phenyl)amino)-5-pyrimidinyl)ethynyl)phenyl)-N'-(3-(trifluoromethyl)phenyl)urea;

5-((2-amino-5-pyrimidinyl)ethynyl)-N-(2-(3,3-dimethyl-2-oxo-1-azetidinyl)-5-(trifluoromethyl)phenyl)-2-(methyloxy)benzamide;

5-((2-amino-5-pyrimidinyl)ethynyl)-2-fluoro-N-(2-(4-thiomorpholinyl)-5-(trifluoromethyl)phenyl)benzamide;

5-((2-amino-5-pyrimidinyl)ethynyl)-2-fluoro-N-(2-(methyl(1-methyl-4-piperidinyl)amino)-5-(trifluoromethyl)phenyl)benzamide;

5-((2-amino-5-pyrimidinyl)ethynyl)-2-fluoro-N-(2-((4-methyl-1-piperazinyl)methyl)-5-(trifluoromethyl)phenyl)benzamide;

5-((2-amino-5-pyrimidinyl)ethynyl)-2-fluoro-N-(2-(4-morpholinyl)-5-(trifluoromethyl)phenyl)benzamide;

5-((2-amino-5-pyrimidinyl)ethynyl)-N-(2-((3S)-3-(dimethylamino)-1-pyrrolidinyl)-5-(trifluoromethyl)phenyl)-2-fluorobenzamide;

5-((2-amino-5-pyrimidinyl)ethynyl)-2-fluoro-N-(2-((2-(4-morpholinyl)ethyl)oxy)-5-(trifluoromethyl)phenyl)benzamide;

5-((2-amino-5-pyrimidinyl)ethynyl)-2-fluoro-N-(2-((1S,4R)-5-methyl-2,5-diazabicyclo[2.2.1]hept-2-yl)-5-(trifluoromethyl)phenyl)benzamide;

5-((2-amino-5-pyrimidinyl)ethynyl)-2-fluoro-N-(2-((2-(1-pyrrolidinyl)ethyl)oxy)-5-(trifluoromethyl)phenyl)benzamide;

5-((2-amino-5-pyrimidinyl)ethynyl)-N-(2-(((3S)-1-ethyl-3-pyrrolidinyl)oxy)-5-(trifluoromethyl)phenyl)-2-fluorobenzamide;

5-((2-amino-5-pyrimidinyl)ethynyl)-N-(2-(((3S)-1-ethyl-3-piperidinyl)oxy)-5-(trifluoromethyl)phenyl)-2-fluorobenzamide;

N-(2-((3S)-3-(dimethylamino)-1-piperidinyl)-5-(trifluoromethyl)phenyl)-2-fluoro-5-((2-(methylamino)-5-pyrimidinyl)ethynyl)benzamide;

5-((2-amino-4-methyl-5-pyrimidinyl)ethynyl)-N-(2-((3S)-3-(dimethylamino)-1-piperidinyl)-5-(trifluoromethyl)phenyl)-2-fluorobenzamide;

N-cyclopropyl-4-methyl-3-((2-((2-(4-morpholinyl)ethyl)amino)-5-pyrimidinyl)ethynyl)benzamide;

N-(4-((2-((4-(4-methyl-1-piperazinyl)phenyl)amino)-5-pyrimidinyl)ethynyl)phenyl)-1H-benzimidazol-2-amine;

N-(4-((2-((4-(4-methyl-1-piperazinyl)phenyl)amino)-5-pyrimidinyl)ethynyl)phenyl)-3-(trifluoromethyl)benzamide;

4-((2-((4-(4-methyl-1-piperazinyl)phenyl)amino)-5-pyrimidinyl)ethynyl)-N-(3-(trifluoromethyl)phenyl)benzamide; and N-(4-((2-amino-5-pyrimidinyl)ethynyl)phenyl)-2-(phenylamino)benzamide.

9. A pharmaceutical composition comprising a pharmaceutically acceptable carrier and a compound according to claim 1.

10. A pharmaceutical composition comprising a pharmaceutically acceptable carrier and a compound according to claim 8.

11. A method of treating a rheumatoid arthritis in a subject, the method comprising administering to the subject an effective dosage amount of a compound of claim 1.

12. A method of treating breast cancer in a subject, the method comprising administering to the subject an effective dosage amount of a compound according to claim 1.

13. A method of treating breast cancer in a subject, the method comprising administering to the subject an effective dosage amount of the pharmaceutical composition according to claim 9.

14. A method of reducing blood flow in a tumor selected from breast cancer, colon carcinoma and thymoma in a subject, said method comprising administering to the subject an effective dosage amount of a compound according to claim 1.

15. A method of treating colon carcinoma or thymoma in a subject, the method comprising administering to the subject an effective dosage amount of a compound according to claim 1.

* * * * *